(12) United States Patent
Barany et al.

(10) Patent No.: US 9,670,540 B2
(45) Date of Patent: Jun. 6, 2017

(54) METHODS AND DEVICES FOR DNA SEQUENCING AND MOLECULAR DIAGNOSTICS

(75) Inventors: Francis A. Barany, New York, NY (US); Steven A. Soper, Baton Rouge, LA (US); George Grills, Trumansburg, NY (US); Yu-wei Cheng, Beachwood, OH (US); Jianmin Huang, Elmhurst, NY (US); Hong Wang, Mesa, AZ (US); Malgorzata A. Witek, Chapel Hill, NC (US); Daniel Sang-won Park, Baton Rouge, LA (US); Michael C. Murphy, Baton Rouge, LA (US); Robin Lindsey McCarley, Prairieville, LA (US); Mateusz L. Hupert, Chapel Hill, NC (US)

(73) Assignees: Cornell University, Ithaca, NY (US); Board of Supervisors of Louisiana State University and Agricultural and Mechanical College, Baton Rouge, LA (US)

(*) Notice: Subject to any disclaimer, the term of this patent is extended or adjusted under 35 U.S.C. 154(b) by 350 days.

(21) Appl. No.: 14/234,011

(22) PCT Filed: Jul. 23, 2012

(86) PCT No.: PCT/US2012/000329
§ 371 (c)(1),
(2), (4) Date: Jul. 7, 2014

(87) PCT Pub. No.: WO2013/012440
PCT Pub. Date: Jan. 24, 2013

(65) Prior Publication Data
US 2015/0099642 A1 Apr. 9, 2015

Related U.S. Application Data

(60) Provisional application No. 61/572,755, filed on Jul. 21, 2011.

(51) Int. Cl.
*C12Q 1/68* (2006.01)
*G01N 33/58* (2006.01)
*C07H 21/04* (2006.01)

(52) U.S. Cl.
CPC ......... *C12Q 1/6874* (2013.01); *C12Q 1/6806* (2013.01); *G01N 33/585* (2013.01)

(58) Field of Classification Search
CPC ............ C12Q 1/6806; C12Q 2525/197; C12Q 2525/313; C12Q 2535/122; C12Q 2563/131; C12Q 2565/543; C12Q 1/6874
USPC .............................................. 435/6.12, 91.2
See application file for complete search history.

(56) References Cited

U.S. PATENT DOCUMENTS

| | | |
|---|---|---|
| 2003/0219792 A1 | 11/2003 | Armes et al. |
| 2004/0191703 A1 | 9/2004 | Soper et al. |
| 2007/0042419 A1 | 2/2007 | Barany et al. |
| 2008/0044864 A1 | 2/2008 | Jeong et al. |
| 2009/0111089 A1 | 4/2009 | Lindstrom et al. |
| 2009/0226975 A1 | 9/2009 | Sabot et al. |
| 2009/0298128 A1 | 12/2009 | Chun |
| 2010/0022412 A1 | 1/2010 | Rigatti et al. |
| 2010/0108519 A1 | 5/2010 | Soper et al. |

FOREIGN PATENT DOCUMENTS

| | | | |
|---|---|---|---|
| WO | WO 98/44151 | * | 10/1998 |
| WO | 2009/140326 A2 | | 11/2009 |

OTHER PUBLICATIONS

PCT International Search Report and Written Opinion for PCT/US2012/000329, filed Jul. 23, 2012 (mailed Mar. 7, 2013).
Guo et al., "Four-color DNA Sequencing with 3'-O-modified Nucleotide Reversible Terminators and Chemically Cleavable Fluorescent Dideoxynucleotides," Proc Natl Acad Sci USA 105(27):9145-50 (2008).
Ju et al., "Four-color DNA Sequencing by Synthesis Using Cleavable Fluorescent Nucleotide Reversible Terminators," Proc Natl Acad Sci USA 103(52):19635-40 (2006).
Metzker et al., "Termination of DNA Synthesis by Novel 3'-modified-deoxyribonucleoside 5'-triphosphates," Nucleic Acids Res. 22(20):4259-67 (1994).
Turcatti et al., "A New Class of Cleavable Fluorescent Nucleotides: Synthesis and Optimization as Reversible Terminators for DNA Sequencing by Synthesis," Nucleic Acids Res. 36(4):e25 (2008).
Wu et al., "3'-O-modified Nucleotides as Reversible Terminators for Pyrosequencing," Proc Natl Acad Sci USA 104 (42):16462-7 (2007).
Shendure and Ji, "Next-generation DNA Sequencing," Nat Biotechnol 26(10):1135-45 (2008).
Mardis, "The Impact of Next-generation Sequencing Technology on Genetics," Trends Genet 24(3):133-41 (2008).
Bentley et al., "Accurate Whole Human Genome Sequencing Using Reversible Terminator Chemistry," Nature 456 (7218):53-9 (2008).
Leary et al., "Development of Personalized Tumor Biomarkers Using Massively Parallel Sequencing," Sci Transl Med 2(20):20ra14 (2010).
Tucker et al., "Massively Parallel Sequencing: The Next Big Thing in Genetic Medicine," Am J Hum Genet 85 (2):142-54 (2009).
Gnirke et al., "Solution Hybrid Selection with Ultra-long Oligonucleotides for Massively Parallel Targeted Sequencing," Nat Biotechnol 27(2):182-9 (2009).

(Continued)

*Primary Examiner* — Teresa Strzelecka
(74) *Attorney, Agent, or Firm* — LeClairRyan, a Professional Corporation

(57) ABSTRACT

The present invention is directed to methods for capturing, amplifying and identifying one or more of a plurality of target nucleotide sequences in a sample. The present invention is further directed to a device comprising a solid support having a plurality of wells or pillars and a plurality of oligonucleotides attached to the wells or pillars. Other aspects of the invention are directed to methods of making such devices.

24 Claims, 168 Drawing Sheets

(56) References Cited

OTHER PUBLICATIONS

Yi et al., "Sequencing of 50 Human Exomes Reveals Adaptation to High Altitude," Science 329(5987):75-8 (2010).
Rothberg et al., "An Integrated Semiconductor Device Enabling Non-optical Genome Sequencing," Nature 475 (7356):348-52 (2011).
Dharmasiri et al., "High-throughput Selection, Enumeration, Electrokinetic Manipulation, and Molecular Profiling of Low-abundance Circulating Tumor Cells Using a Microfluidic System," Anal Chem 83(6):2301-9 (2011).
Adams et al., "Highly Efficient Circulating Tumor Cell Isolation from Whole Blood and Label-free Enumeration Using Polymer-based Microfluidics with an Integrated Conductivity Sensor," J Am Chem Soc 130(27):8633-41 (2008).
Witek et al., "Purification and Preconcentration of Genomic DNA from Whole Cell Lysates Using Photoactivated Polycarbonate (PPC) Microfluidic Chips," Nucleic Acids Res 34(10):e74 (2006).
Wang et al., "Microarrays Assembled in Microfluidic Chips Fabricated from Poly(methyl methacrylate) for the Detection of Low-abundant DNA Mutations," Anal Chem 75(5):1130-40 (2003).
Chen et al., "Temperature Distribution Effects on Micro-CFPCR Performance," Biomed Microdevices 10:141-52 (2008).
Hashimoto et al., "Rapid PCR in a Continuous Flow Device," Lab Chip 4:638-45 (2004).
Chen et al., "Electrokinetically Synchronized Polymerase Chain Reaction Microchip Fabricated in Polycarbonate," Anal Chem 77(2):658-66 (2005).
Ku et al., "Polymer Microfluidic Chips with Integrated Waveguides for Reading Microarrays," Anal Chem 79 (23):9007-13 (2007).
Xu et al., "Solid-phase Reversible Immobilization in Microfluidic Chips for the Purification of Dye-labeled DNA Sequencing Fragments," Anal Chem 75(13):2975-84 (2003).

\* cited by examiner

**Genomic Sequencing.
Generating clusters v5.2, l.**

1. Anneal amplicons to surface such that single molecules are sufficiently far apart. Using a polymerase ◆ with no 5'→3' or strand displacement activity, extend primer A on surface to make full length copies.

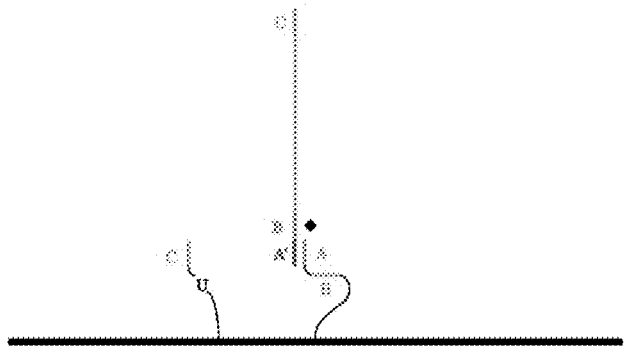

2. Denature original strands and wash away.

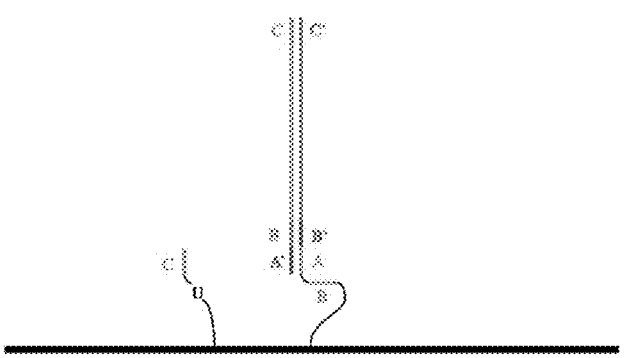

3. Liberated 3' ends containing sequence C' will hybridize to primer C on surface. Add thermophilic polymerase ◆ with strand displacing activity.

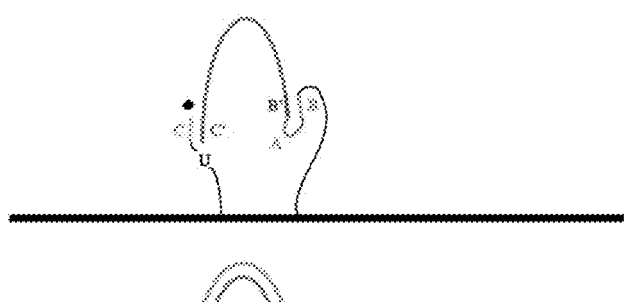

4. Polymerase will make full length copy and displace sequence B.

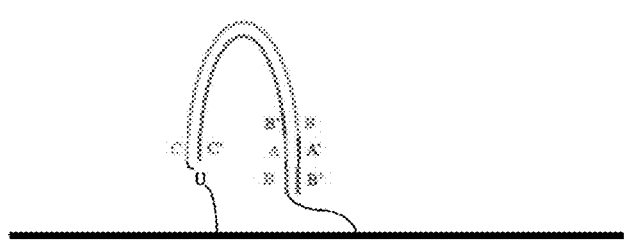

Figure 2A

Genomic Sequencing.
Generating clusters v5.2, II.

5. Denature strands. B' sequences hybridize to B sequences, but free 3' end has a mismatch to prevent extension.

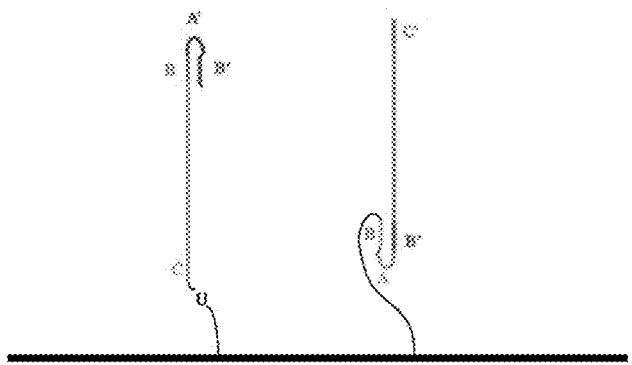

6. Sequence A' will hybridize to a new primer A on the surface. Polymerase ◆ will bind to 3' end of primer A and start extending, immediately displacing sequence B', which will hybridize back to sequence B on the primer. Meanwhile, sequence C' will hybridize to a new primer C on surface. Polymerase ◆ will bind to 3' end of primer C and start extending.

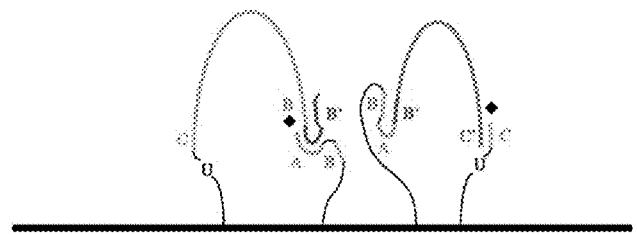

7. The first polymerase will continue to extend, making a full length copy ending in sequence C'. The second polymerase will make full length copy, displacing, and finally copying sequence B.

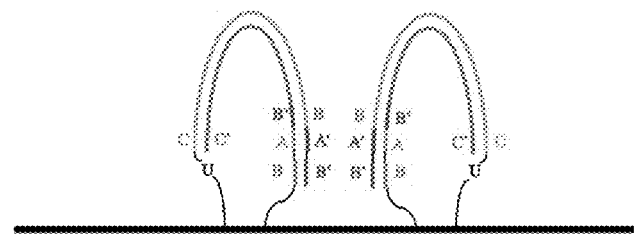

Figure 2B

**Genomic Sequencing.
Generating clusters v5.2, III.**

8. Denature strands. B' sequences hybridize to B sequences, but free 3' ends have mismatched bases to prevent extension.

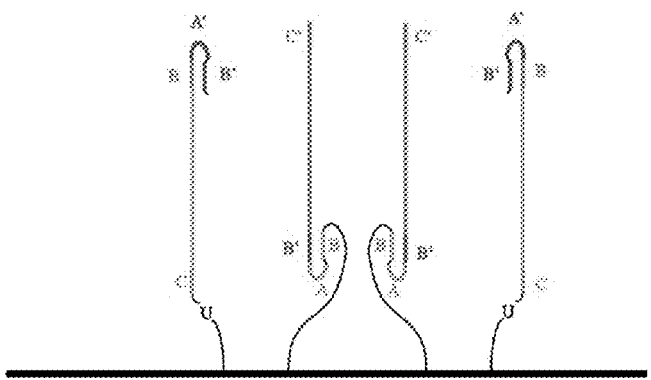

9. Sequences A' will hybridize to new primers A on the surface. Polymerases ♦ will bind to 3' end of primer A and start extending, immediately displacing sequence B', which will hybridize back to sequence B on the primer. Meanwhile, sequences C' will hybridize to new primers C on surface. Polymerases ♦ will bind to 3' end of primer C and start extending.

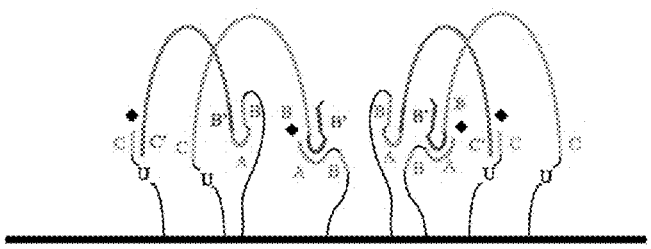

10. The first polymerases will continue to extend, making full length copies ending in sequence C'. The second polymerases will make full length copies, displacing, and finally copying sequences B.

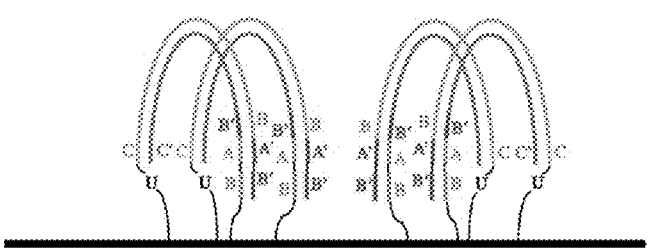

Figure 2C

Genomic Sequencing.
Generating clusters v5.2, IV.

11. After strand displacement amplification is completed, liberate the C primers from the surface. In this example, the C primers contained a Uracil (U), which may be cut using UDG and EndoVIII. Denature and wash away liberated strands.

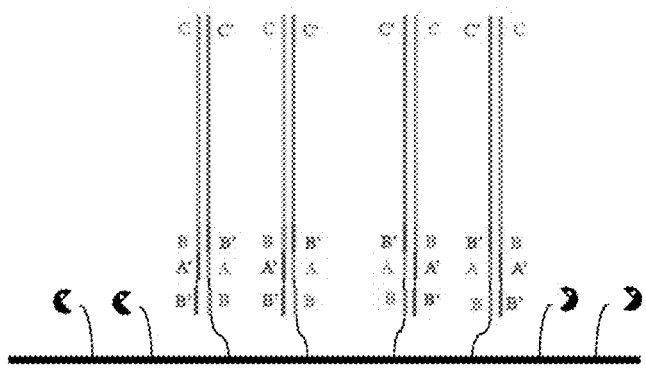

12. Remaining single stranded target sequences are all in the same orientation and suitable for solid-phase sequencing.

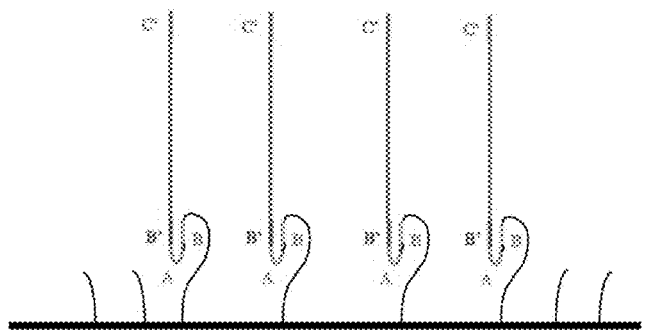

Figure 2D

Genomic Sequencing.
Generating clusters v5.2, V. Example of sequencing by synthesis.

13. Hybridize primer C to amplified strands. Extend a single base with fluorescently labeled (*) nucleotide, which is blocked on the 3' side (.). Image to determine base added at each cluster.

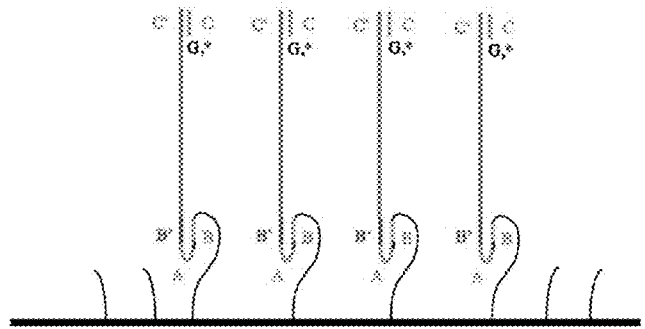

14. Cleave off fluorescent and 3' blocking groups. Extend the next base and image.

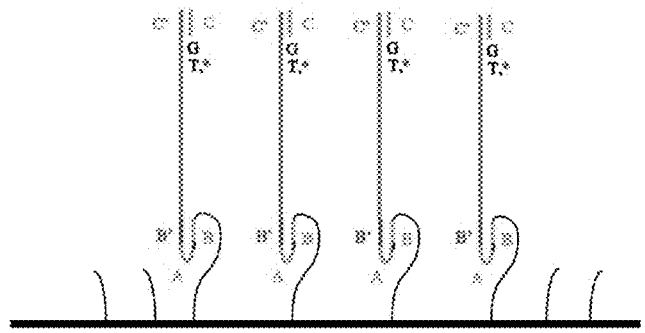

15. Continue the process of base addition, imaging, and cleaving of blocking groups to build a linear sequence at each cluster.

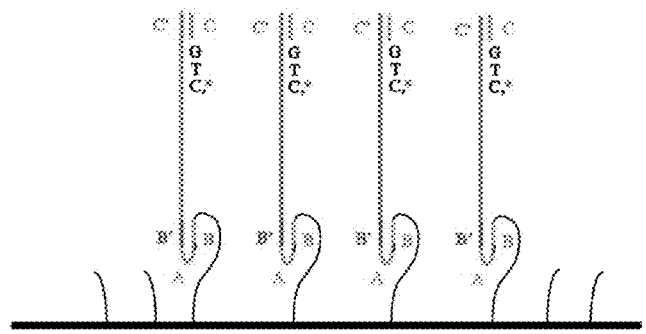

Figure 2E

**Genomic Sequencing.
Generating clusters v5.3, L**

1. Anneal amplicons to surface such that single molecules are sufficiently far apart. Using a polymerase ◆ with no 5'→3' or strand displacement activity, extend primer A on surface to make full length copies.

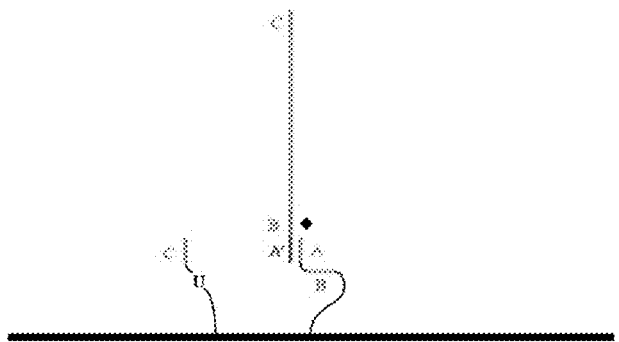

2. Denature original strands and wash away.

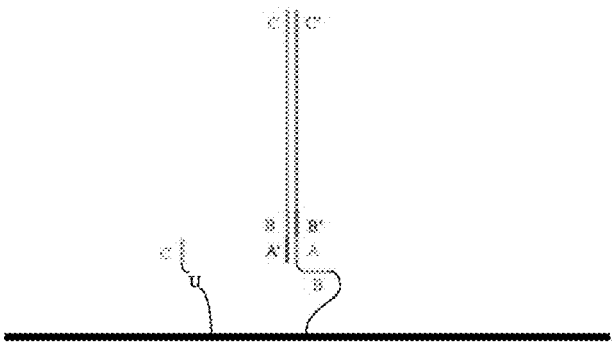

3. Liberated 3' ends containing sequence C' will hybridize to primer C on surface. Add thermophilic polymerase ◆ with strand displacing activity.

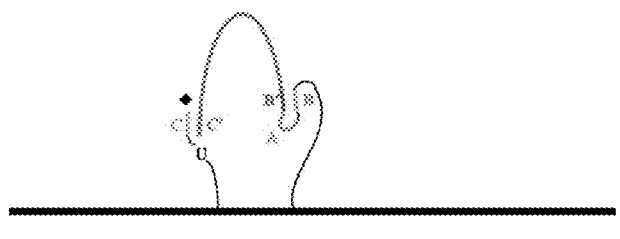

4. Polymerase will make full length copy and displace sequence B.

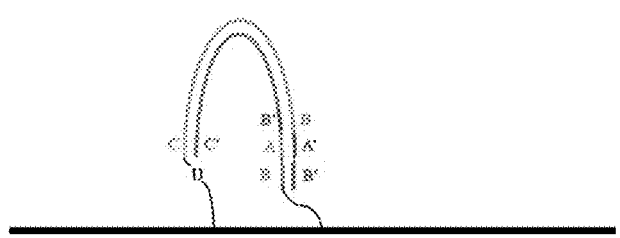

Figure 3A

**Genomic Sequencing.
Generating clusters v5.3, II.**

5. Denature strands. B' sequences hybridize to B sequences. Polymerase ♦ will bind to the free 3' end of B' and extend to form full-length hairpined double-stranded DNA.

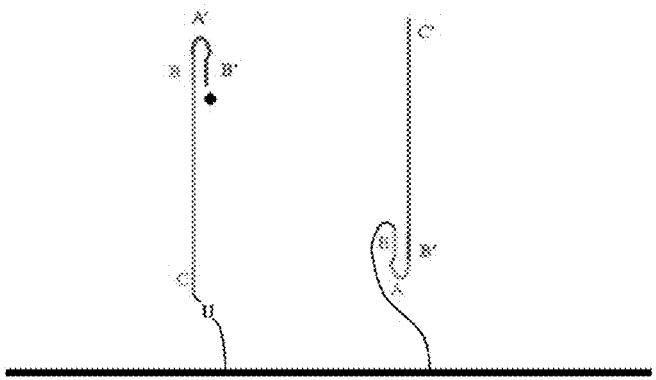

6. Sequence A' at the turn of the full-length hairpin will hybridize to a new primer A on the surface. Strand-displacing polymerase ♦ will bind to 3' end of primer A and start extending, displacing the B' sequence as it unwinds the hairpin. Meanwhile, sequence C' will hybridize to a new primer C on surface. Polymerase ♦ will bind to 3' end of primer C and start extending.

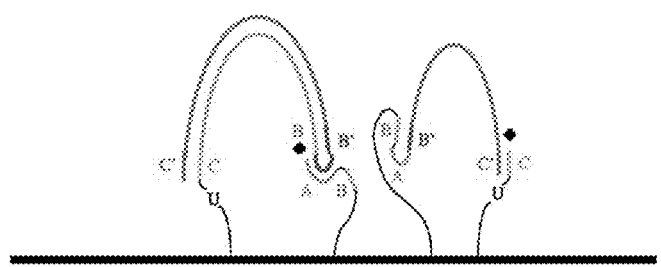

7. The first polymerase will continue to extend, making a full length copy ending in sequence C' and displacing the full length sequence, which becomes single-stranded. This displaced single strand may snap back to regenerate the full-length hairpin and liberate the newly synthesized A primer strand. The second polymerase will make full length copy, displacing, and finally copying sequence B.

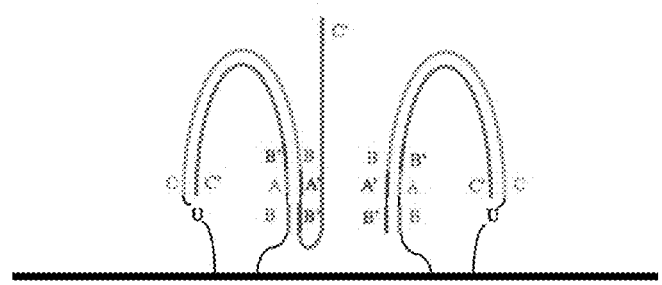

Figure 3B

**Genomic Sequencing.
Generating clusters v5.3, III.**

8. Denature strands. C' products containing boths strands will snap back to form full-length hairpins. B' sequences hybridize to B sequences. Polymerases ♦ will bind to the free 3' ends of B' and extend to form full-length hairpined double-stranded DNA. (Partial denaturation or natural separation of DNA strands under given buffer and temperature conditions may be sufficient to initiate strand-dispacing extension of free B' sequences, as well as strand-displacing snap back to form full-length hairpins, liberating full-length single-stranded A primer containing target.)

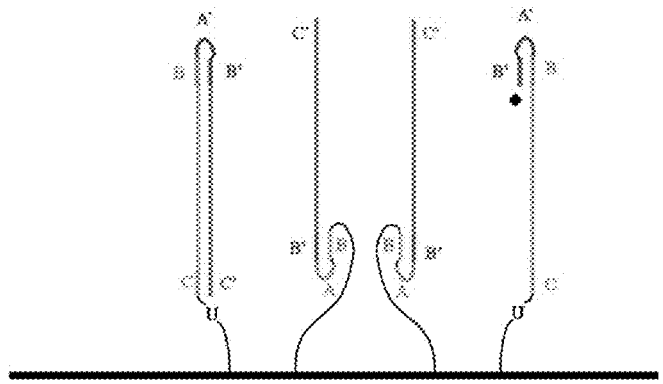

9. Sequences A' will hybridize to new primers A on the surface. Strand-displacing polymerases ♦ will bind to 3' ends of primer A and start extending, displacing the B' sequences, unwinding the hairpins. Meanwhile, sequences C' will hybridize to new primers C on surface. Polymerases ♦ will bind to 3' ends of primer C and start extending.

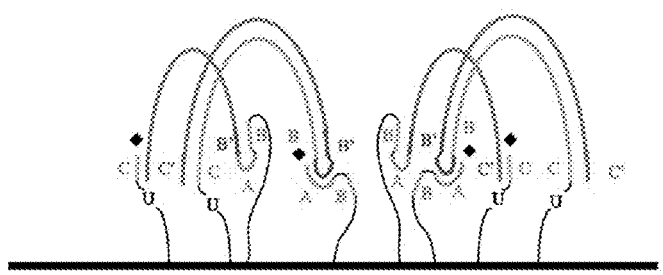

10. The first polymerases will continue to extend, making full length copies ending in sequence C' and displacing the full length sequences, which becomes single-stranded. These displaced single strands may snap back to regenerate the full-length hairpins and liberate the newly synthesized A primer strands. The second polymerases will make full length copy, displacing, and finally copying sequence B.

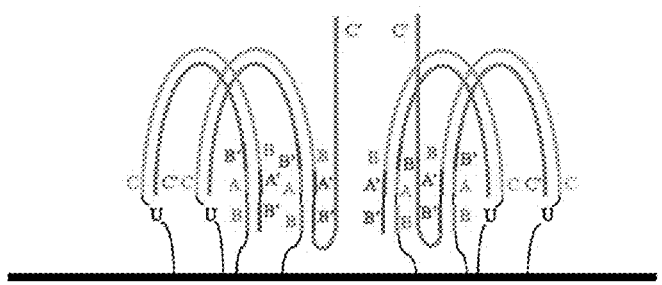

Figure 3C

Genomic Sequencing.
Generating clusters v5.3, IV.

11. After strand displacement amplification is completed, liberate the C primers from the surface. In this example, the C primers contained a Uracil (U), which may be cut using UDG and EndoVIII. C' products containing boths strands will snap back to form full-length hairpins and dissociate from surface. Denature and wash away remaining liberated strands.

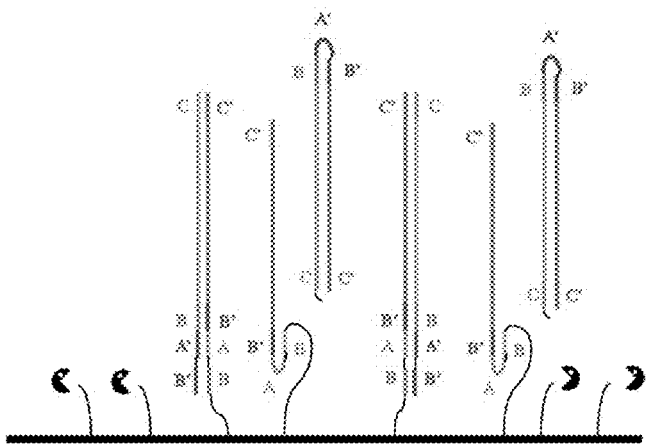

12. Remaining single stranded target sequences are all in the same orientation and suitable for solid-phase sequencing.

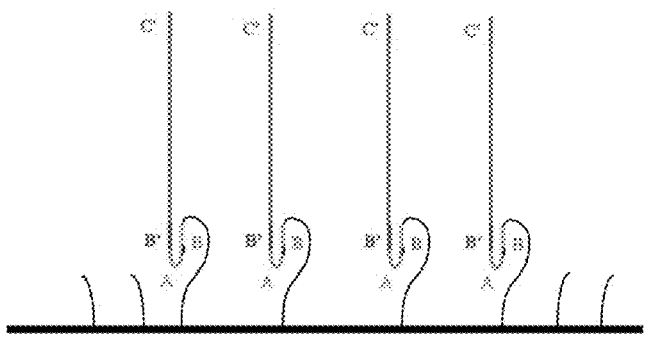

Figure 3D

Genomic Sequencing.
Generating clusters v5.3, V. Example of sequencing by synthesis.

13. Hybridize primer C to amplified strands. Extend a single base with fluorescently labeled (*) nucleotide, which is blocked on the 3' side (,). Image to determine base added at each cluster.

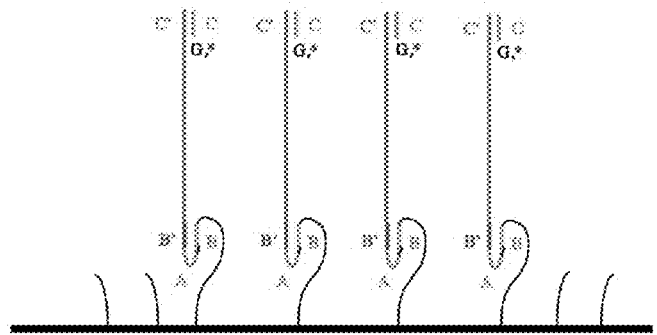

14. Cleave off fluorescent and 3' blocking groups. Extend the next base and image.

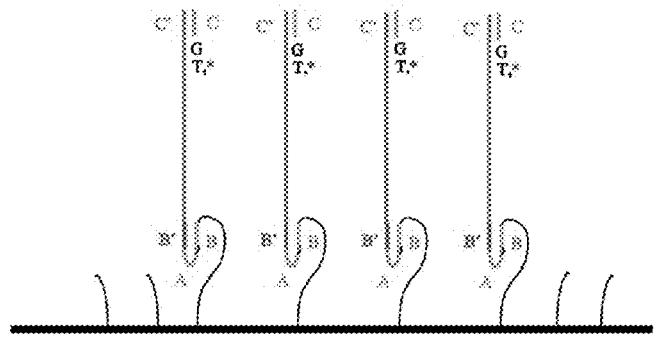

15. Continue the process of base addition, imaging, and cleaving of blocking groups to build a linear sequence at each cluster.

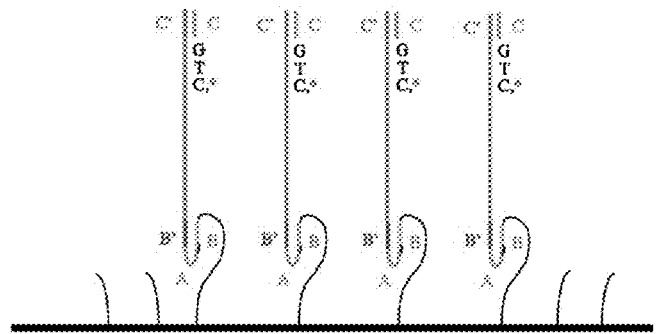

Figure 3E

Genomic Sequencing.
Generating clusters v5.3, VI. Sequencing the opposite strand.

16. Hybridize primer C to amplified strands. Extend with polymerase ◆ lacking 5'-3' exonuclease and strand-displacing activity.

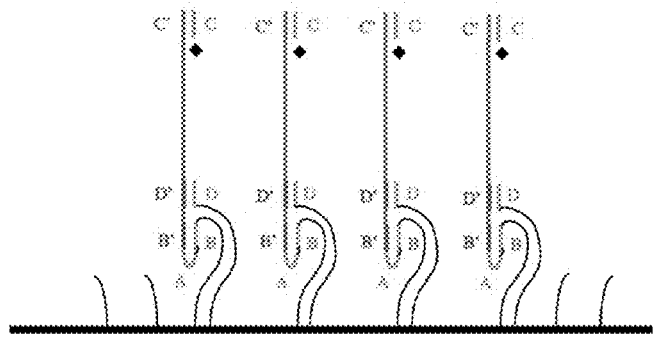

17. Covalently link extended strand to sequence D using ligase. ●
Cleave B primer or it's attachment to the surface/A primer. For example, the B primer could contain an 8-oxoguanine instead of a guanine, and this could be cleaved with Fpg. ★

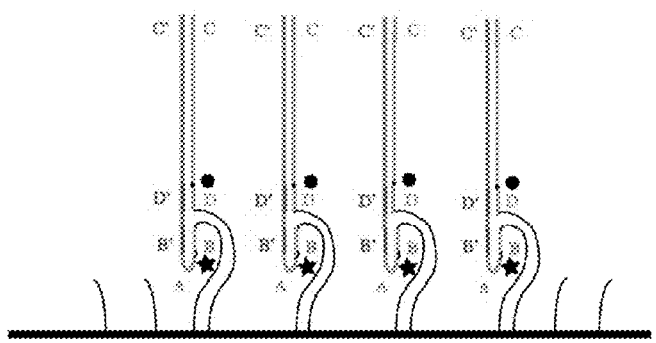

18. Denature away original strands. Remaining single stranded target sequences are all in the same orientation and suitable for solid-phase sequencing.

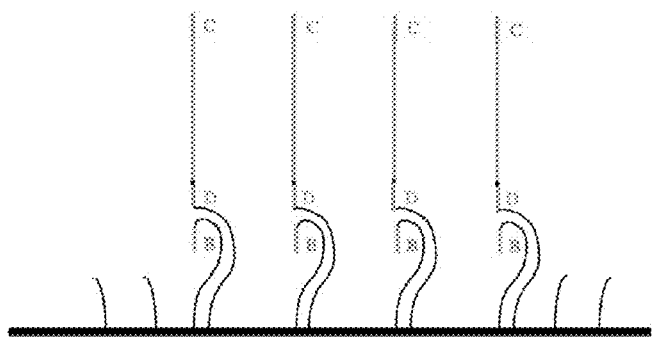

Figure 3F

Genomic Sequencing.
Generating clusters v5.3, VII. Sequencing the opposite strand.

19. Hybridize primer D' to amplified strands. Extend a single base with fluorescently labeled (*) nucleotide, which is blocked on the 3' side ('). Image to determine base added at each cluster.

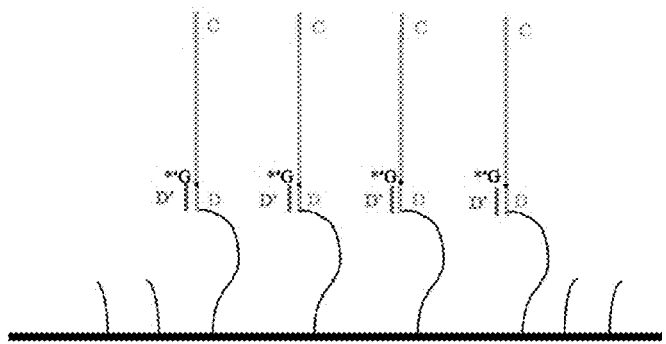

20. Cleave off fluorescent and 3' blocking groups. Extend the next base and image.

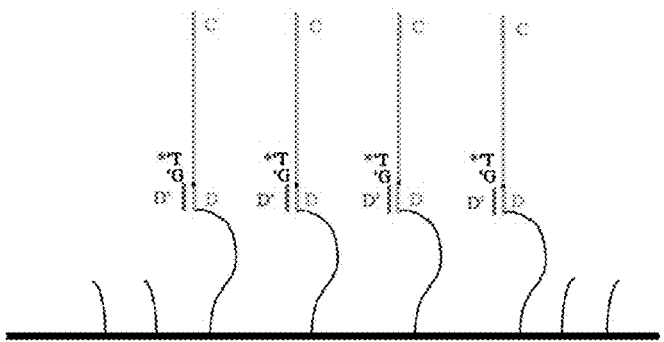

21. Continue the process of base addition, imaging, and cleaving of blocking groups to build a linear sequence at each cluster.

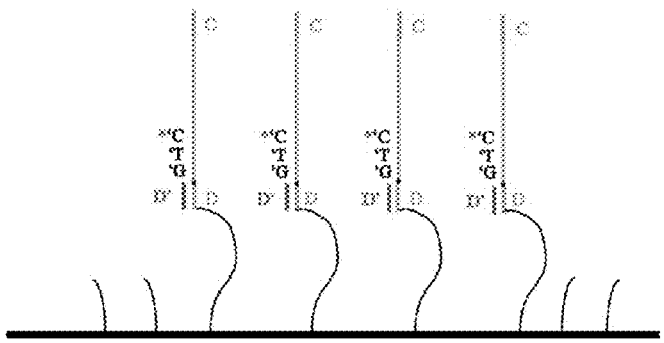

Figure 3G

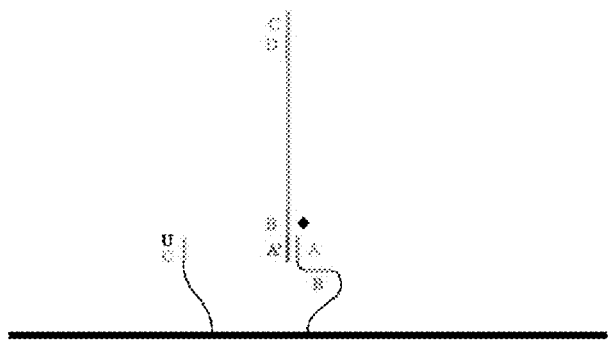
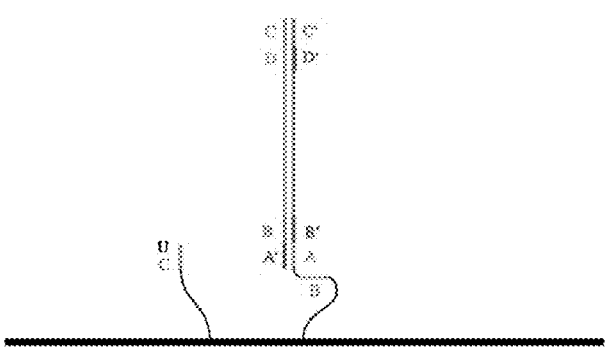
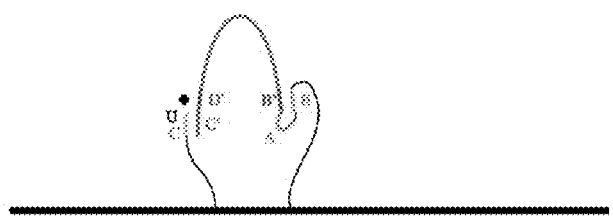
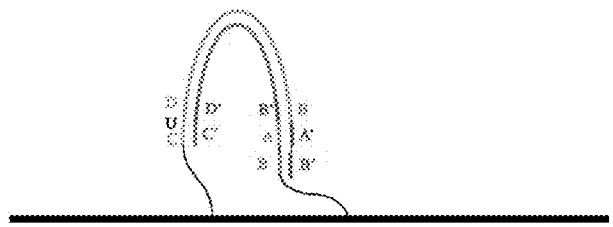
Figure 4A

Genomic Sequencing.
Generating clusters v5.4, II.

5. Denature strands. B' sequences hybridize to B sequences. Polymerase ◆ will bind to the free 3' end of B' and extend to form full-length hairpined double-stranded DNA.

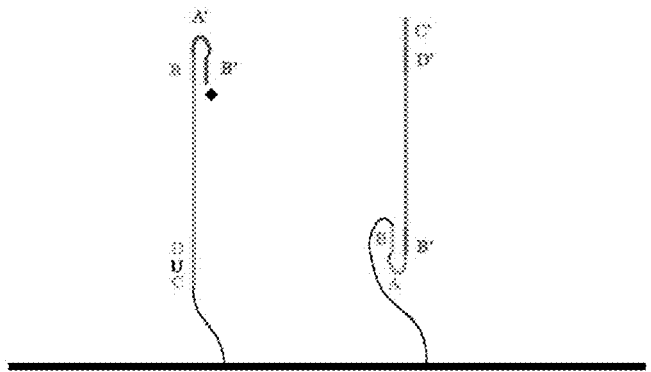

6. Sequence A' will hybridize to a new primer A on the surface. Strand-displacing polymerase ◆ will bind to 3' end of primer A and start extending, displacing the B' sequence as it unwinds the hairpin. Meanwhile, sequence C' will hybridize to a new primer C on surface. Polymerase ◆ will bind to 3' end of primer C and start extending.

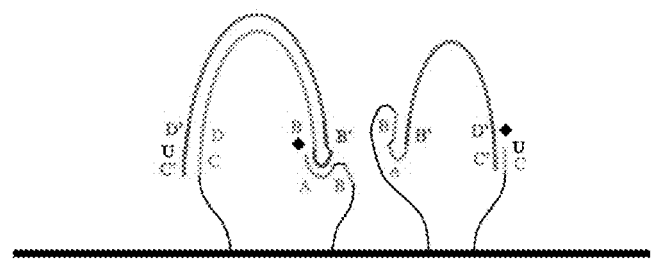

7. The first polymerase will continue to extend, making a full length copy ending in sequence C' and displacing the full length sequence, which becomes single-stranded. The second polymerase will make full length copy, displacing, and finally copying sequence B.

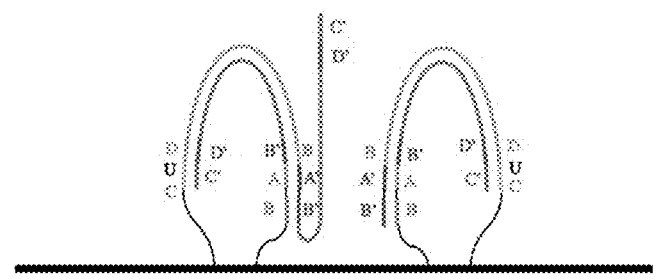

Figure 4B

**Genomic Sequencing.
Generating clusters v5.4, III.**

8. Denature strands. C' products containing boths strands will snap back to form full-length hairpins. B' sequences hybridize to B sequences. Polymerases ◆ will bind to the free 3' ends of B' and extend to form full-length hairpined double-stranded DNA. (Partial denaturation or natural separation of DNA strands under given buffer and temperature conditions may be sufficient to initiate strand-dispacing extension of free B' sequences, as well as strand-displacing snap back to form full-length hairpins, liberating full-length single-stranded A primer containing target.)

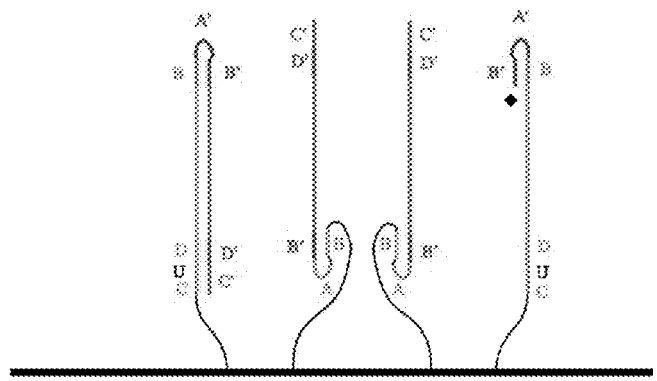

9. Sequences A' will hybridize to new primers A on the surface. Strand-displacing polymerases ◆ will bind to 3' ends of primer A and start extending, displacing the B' sequences, unwinding the hairpins. Meanwhile, sequences C' will hybridize to new primers C on surface. Polymerases ◆ will bind to 3' ends of primer C and start extending.

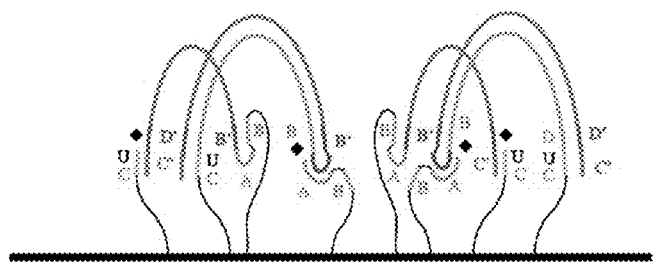

10. The first polymerases will continue to extend, making full length copies ending in sequence C' and displacing the full length sequences, which becomes single-stranded. These displaced single strands may snap back to regenerate the full-length hairpins and liberate the newly synthesized A primer strands. The second polymerases will make full length copy, displacing, and finally copying sequence B.

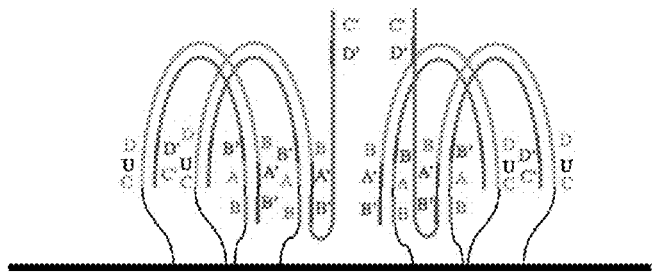

Figure 4C

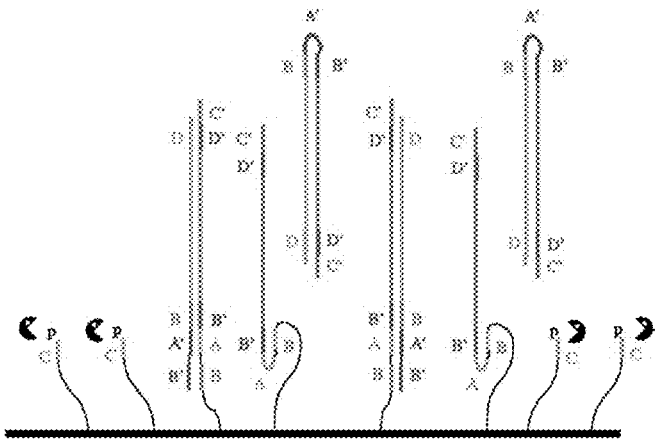
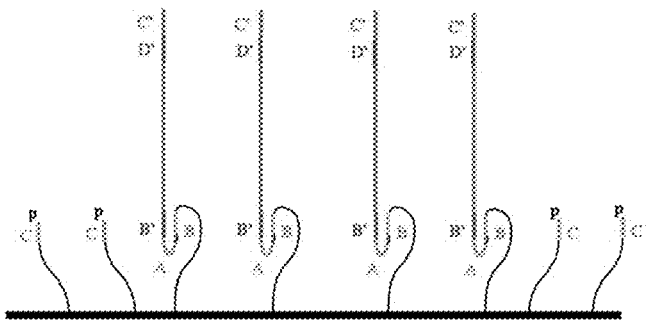
Figure 4D

Genomic Sequencing.
Generating clusters v5.4, V. Example of sequencing by synthesis.

13. Hybridize primer D to amplified strands. Extend a single base with fluorescently labeled (*) nucleotide, which is blocked on the 3' side (,). Image to determine base added at each cluster. (Note that primer DNA may contain all or a portion of primer C sequence to minimize hybridization of portion of primer C on surface to template. Even if it hybridizes, it is blocked on the 3' end and will not extend.)

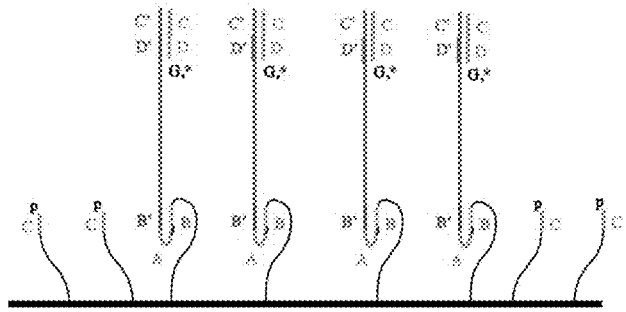

14. Cleave off fluorescent and 3' blocking groups. Extend the next base and image.

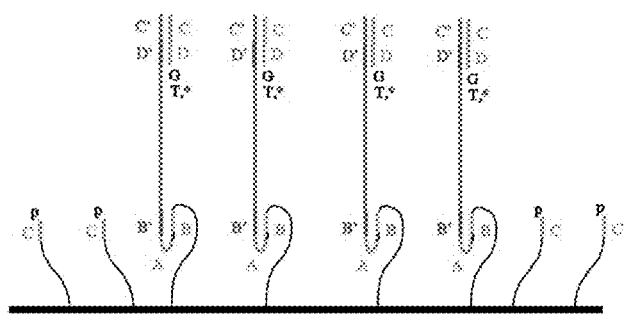

15. Continue the process of base addition, imaging, and cleaving of blocking groups to build a linear sequence at each cluster.

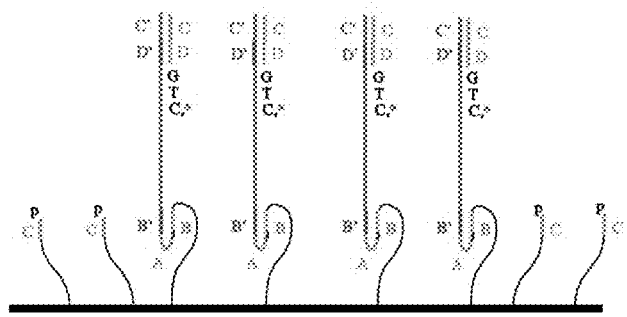

Figure 4E

Genomic Sequencing.
Generating clusters v5.4, VI. Sequencing the opposite strand.

16. Cleave the 3' phosphate from the remaining portion of primer C, for example by using the phosphatase activity of T4 kinase ★, to liberate a free 3' end. Hybridize remaining portion of primer C to amplified strands. Extend with polymerase ◆ that contains 5'-3' exonuclease activity, and lacks strand-displacing activity.

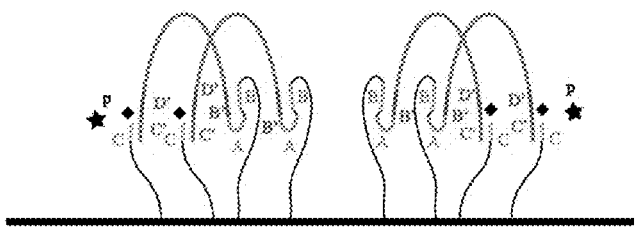

17. As polymerase extends through the template, it reaches the B sequence hybridized to B' sequence. The 5'-3' exonuclease activity digests the B sequence, liberating that strand from the solid surface. Polymerase ◆ continues extending through the A sequence.

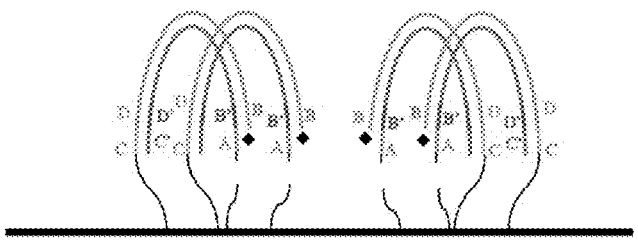

18. Denature away original strands. Remaining single stranded target sequences are all in the same orientation and suitable for solid-phase sequencing.

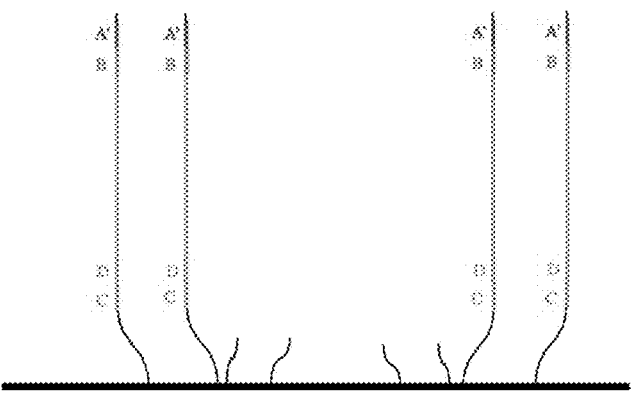

Figure 4F

Genomic Sequencing.
Generating clusters v5.4, VII. Sequencing the opposite strand.

19. Hybridize primer B' to amplified strands. Extend a single base with fluorescently labeled (*) nucleotide, which is blocked on the 3' side ('). Image to determine base added at each cluster. (Note that primer B' may contain all or a portion of primer A sequence on the 5' end.)

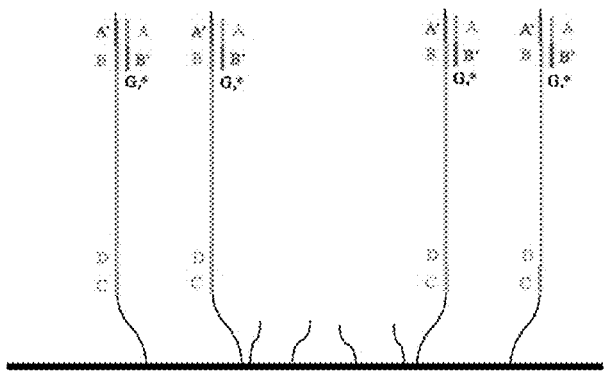

20. Cleave off fluorescent and 3' blocking groups. Extend the next base and image.

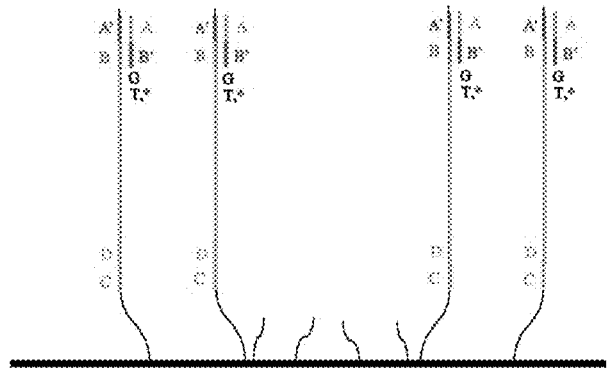

21. Continue the process of base addition, imaging, and cleaving of blocking groups to build a linear sequence at each cluster.

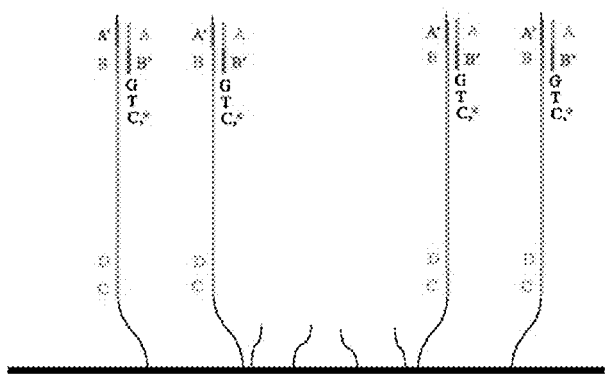

Figure 4G

Genomic Sequencing.
Generating clusters v5.5, I.

1. Anneal amplicons to surface such that single molecules are sufficiently far apart. Using a polymerase ♦ with no 5'->3' or strand displacement activity, extend primer A on surface to make full length copies.

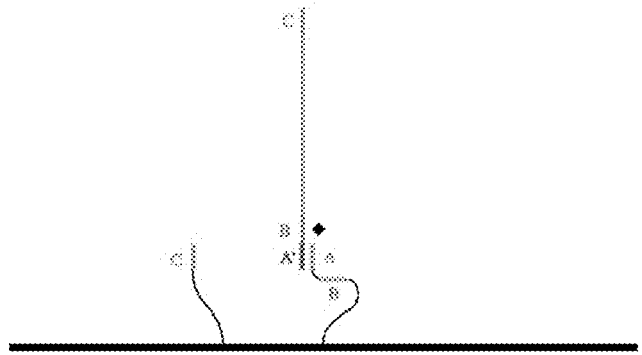

2. Denature original strands and wash away.

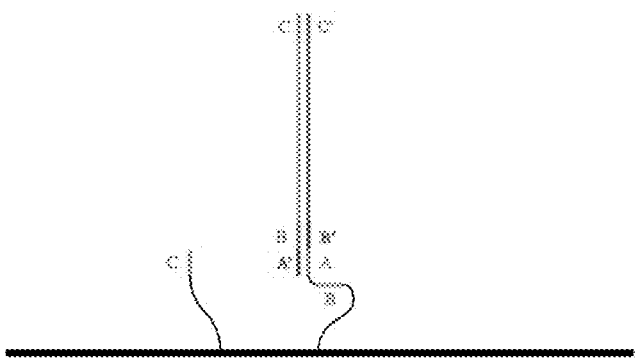

3. Liberated 3' ends containing sequence C' will hybridize to primer C on surface. Add thermophilic polymerase ♦ with strand displacing activity.

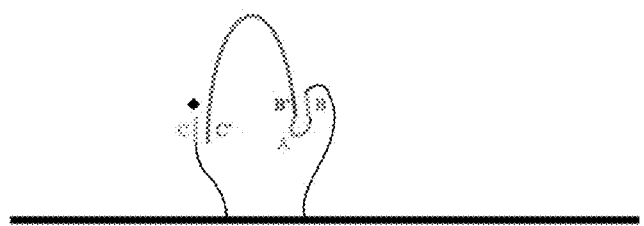

4. Polymerase will make full length copy and displace sequence B.

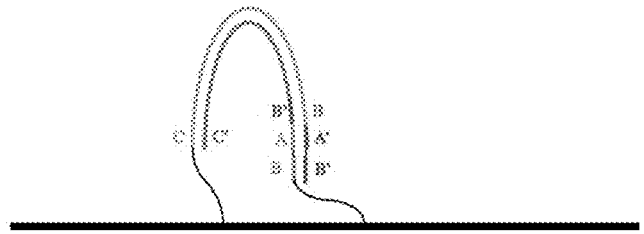

Figure 5A

Genomic Sequencing.
Generating clusters v5.5, II.

5. Denature strands. B' sequences hybridize to B sequences. Polymerase ◆ will bind to the free 3' end of B' and extend to form full-length hairpined double-stranded DNA.

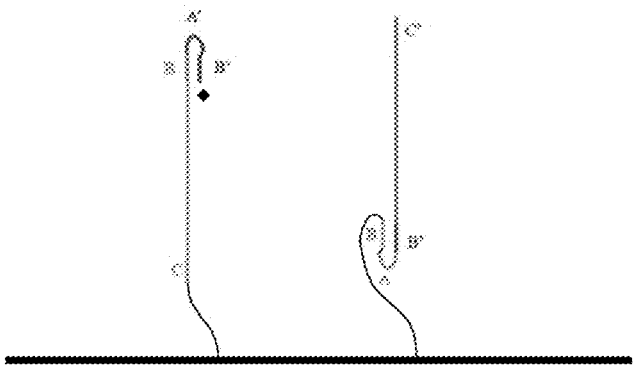

6. Sequence A' at the turn of the full-length hairpin will hybridize to a new primer A on the surface. Strand-displacing polymerase ◆ will bind to 3' end of primer A and start extending, displacing the B' sequence as it unwinds the hairpin. Meanwhile, sequence C' will hybridize to a new primer C on surface. Polymerase ◆ will bind to 3' end of primer C and start extending.

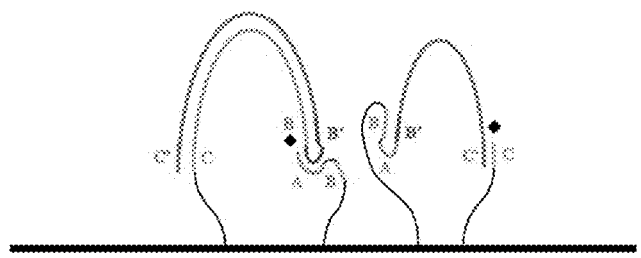

7. The first polymerase will continue to extend, making a full length copy ending in sequence C' and displacing the full length sequence, which becomes single-stranded. This displaced single strand may snap back to regenerate the full-length hairpin and liberate the newly synthesized A primer strand. The second polymerase will make full length copy, displacing, and finally copying sequence B.

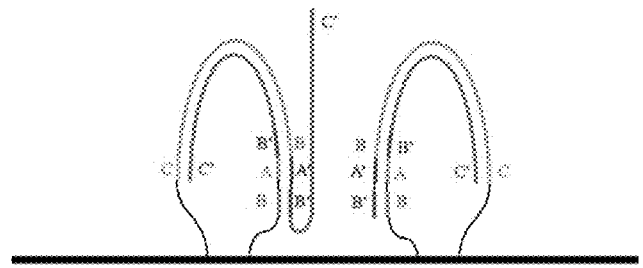

Figure 5B

Genomic Sequencing.
Generating clusters v5.5, III.

8. Denature strands. C' products containing boths strands will snap back to form full-length hairpins. B' sequences hybridize to B sequences. Polymerases ♦ will bind to the free 3' ends of B' and extend to form full-length hairpined double-stranded DNA. (Partial denaturation or natural separation of DNA strands under given buffer and temperature conditions may be sufficient to initiate strand-displacing extension of free B' sequences, as well as strand-displacing snap back to form full-length hairpins, liberating full-length single-stranded A primer containing target.)

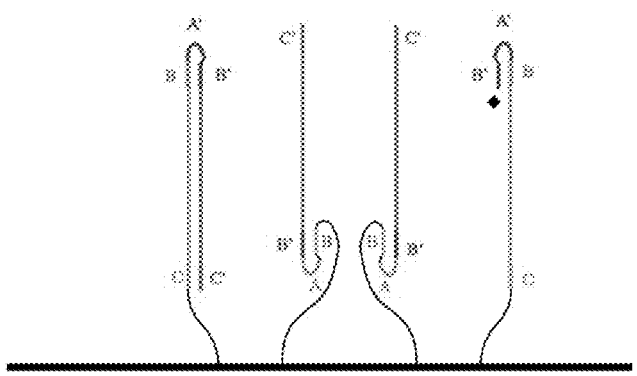

9. Sequences A' will hybridize to new primers A on the surface. Strand-displacing polymerases ♦ will bind to 3' ends of primer A and start extending, displacing the B' sequences, unwinding the hairpins. Meanwhile, sequences C' will hybridize to new primers C on surface. Polymerases ♦ will bind to 3' ends of primer C and start extending.

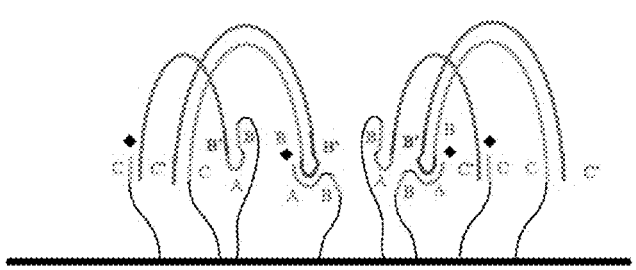

10. The first polymerases will continue to extend, making full length copies ending in sequence C' and displacing the full length sequences, which becomes single-stranded. These displaced single strands may snap back to regenerate the full-length hairpins and liberate the newly synthesized A primer strands. The second polymerases will make full length copy, displacing, and finally copying sequence B.

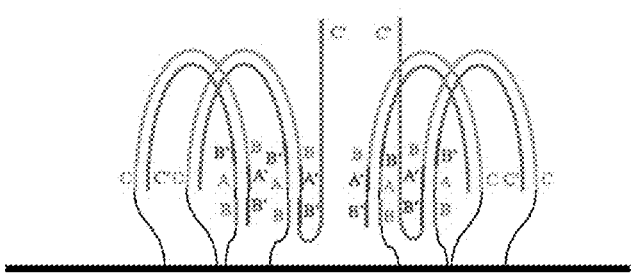

Figure 5C

Genomic Sequencing.
Generating clusters v5.5, IV.

11. Denature strands. C' products containing boths strands will snap back to form full-length hairpins. B' sequences hybridize to B sequences. Polymerases ◆ will bind to the free 3' ends of B' and extend to form full-length hairpined double-stranded DNA. (Partial denaturation or natural separation of DNA strands under given buffer and temperature conditions may be sufficient to initiate strand-dispacing extension of free B' sequences, as well as strand-displacing snap back to form full-length hairpins, liberating full-length single-stranded A primer containing target.) Repeat cycles as needed.

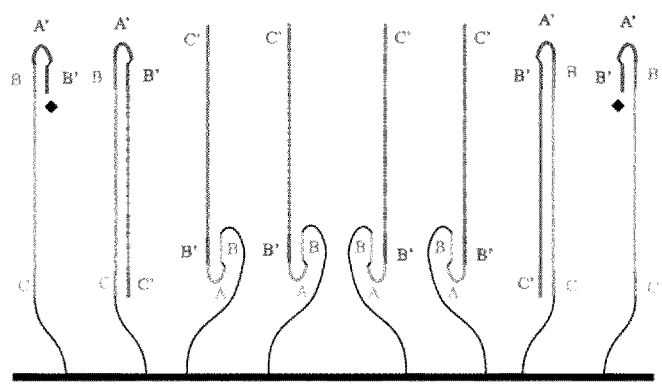

12. After C primer products are extended to form hairpins, remaining single stranded target sequences are all in the same orientation and suitable for solid-phase sequencing.

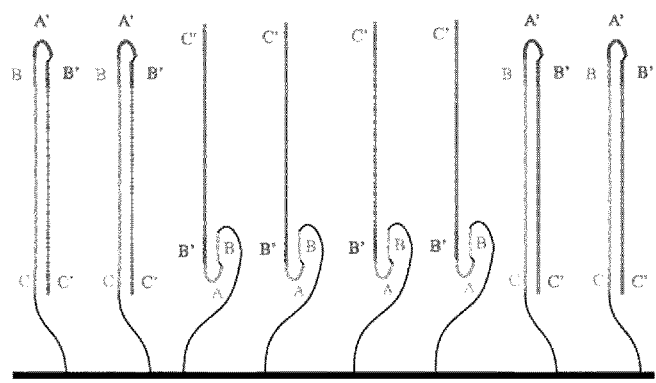

Figure 5D

Genomic Sequencing.
Generating clusters v5.5, V. Example of sequencing by synthesis.

13. Hybridize primer C to amplified strands. Extend a single base with fluorescently labeled (*) nucleotide, which is blocked on the 3' side (.). Image to determine base added at each cluster.

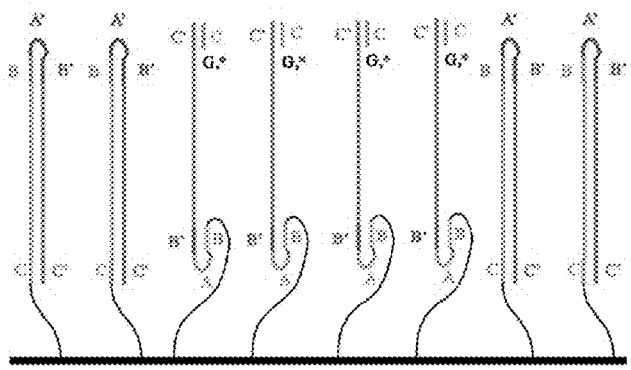

14. Cleave off fluorescent and 3' blocking groups. Extend the next base and image.

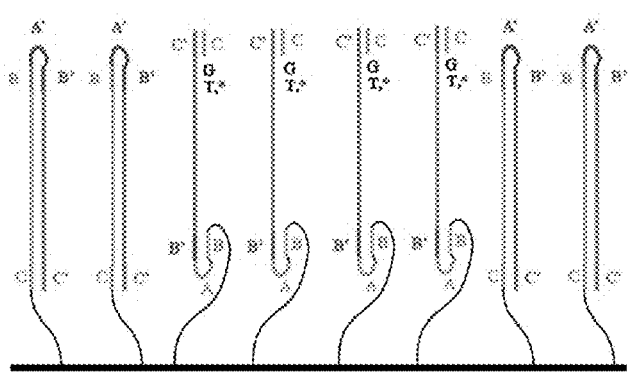

15. Continue the process of base addition, imaging, and cleaving of blocking groups to build a linear sequence at each cluster.

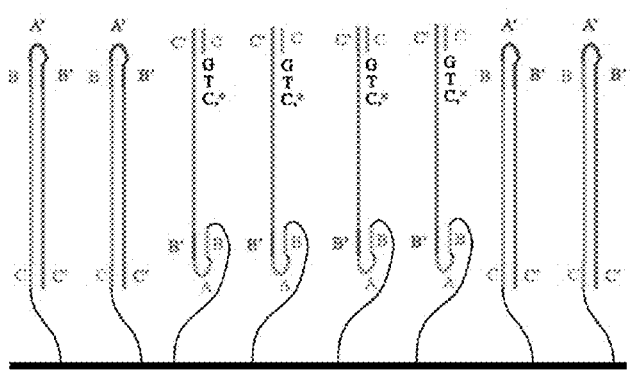

Figure 5E

Genomic Sequencing.
Generating clusters v5.5, VI. Sequencing the opposite strand.

16. Hybridize primer A" to A' regions in hairpinned strands. Primer A" is modified such that it protects the A' region from exonuclease digestion when hybridized to A'. Add Exonuclease I to digest single-stranded DNA from the 3' end. Add Exonuclease III to digest double-stranded DNA until digestion is blocked by the A" primer.

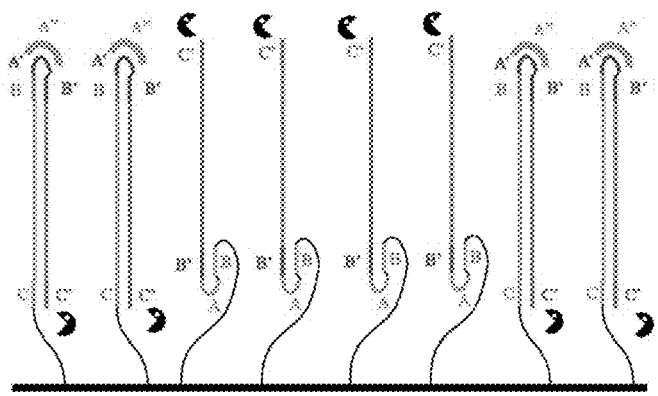

17. Inactivate or wash away enzymes, and denature away A" primer. Remaining single stranded target sequences are all in the same orientation and suitable for solid-phase sequencing.

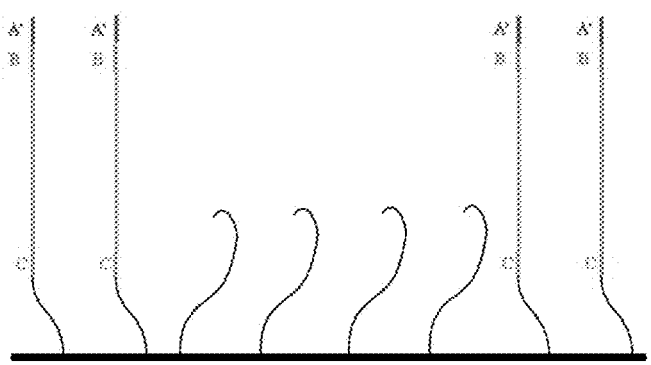

Figure 5F

Genomic Sequencing.
Generating clusters v5.5, VII. Sequencing the opposite strand.

18. Hybridize primer B' to amplified strands. Extend a single base with fluorescently labeled (*) nucleotide, which is blocked on the 3' side ('). Image to determine base added at each cluster. (Note that primer B' may contain all or a portion of primer A sequence on the 5' end.)

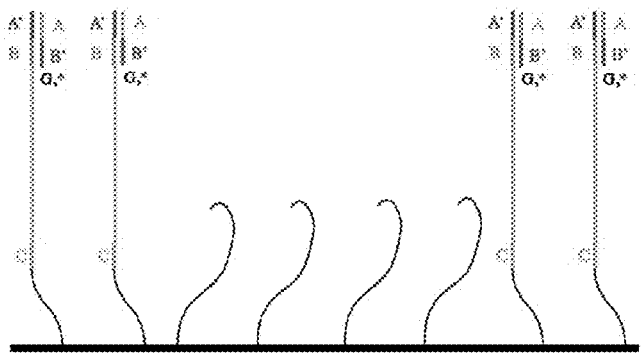

19. Cleave off fluorescent and 3' blocking groups. Extend the next base and image.

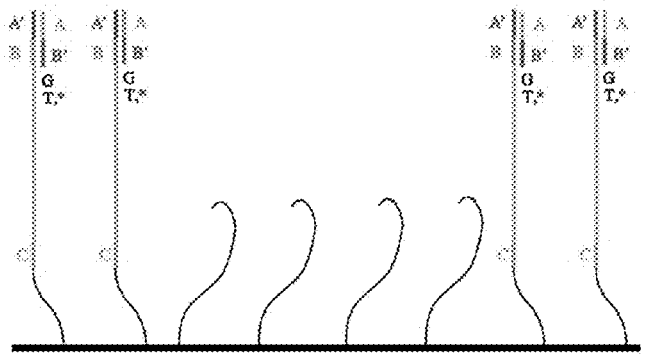

20. Continue the process of base addition, imaging, and cleaving of blocking groups to build a linear sequence at each cluster.

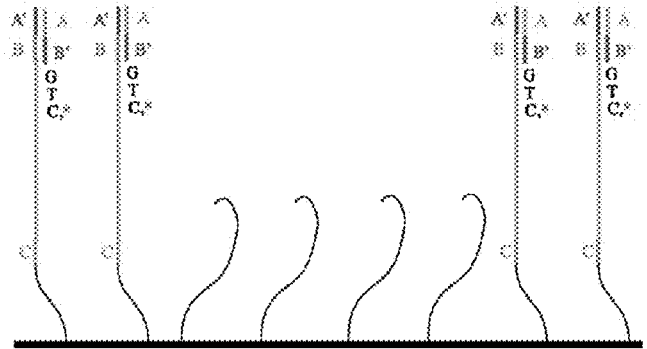

Figure 5G

Gene-Specific Sequencing.
Generating clusters v5.6, I.

1. Anneal genomic DNA to surface such that a desired region is captured by primers C and B. Using a polymerase ◆ with either 5'→3' exonuclease or strand displacement activity, extend primer C on surface to make full length copies.

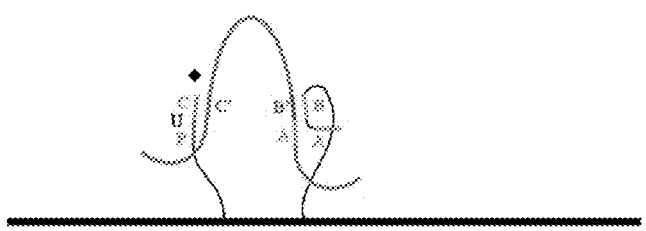

2. Denature original strands and wash away.

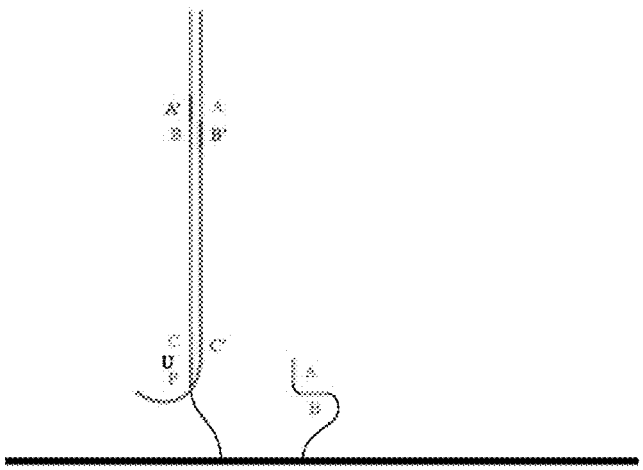

3. Strands containing sequence A' will hybridize to primer A on surface. Add thermophilic polymerase ◆ with strand displacing activity.

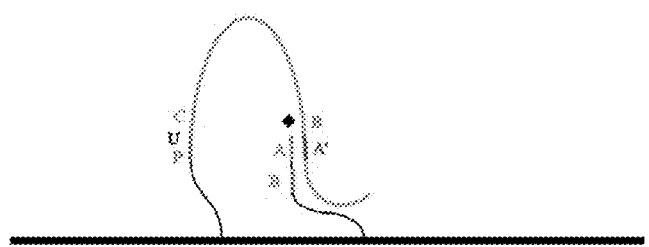

4. Polymerase will make full length copy including universal primer sequence P'.

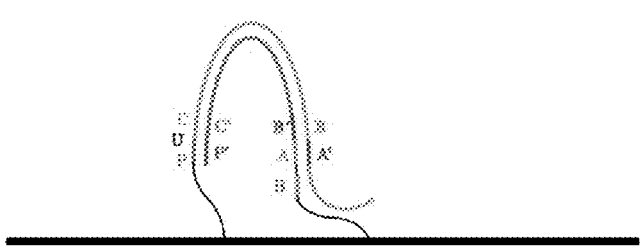

Figure 6A

**Genomic Sequencing.
Generating clusters v5.6, II.**

5. Denature strands. B' sequences hybridize to B sequences.

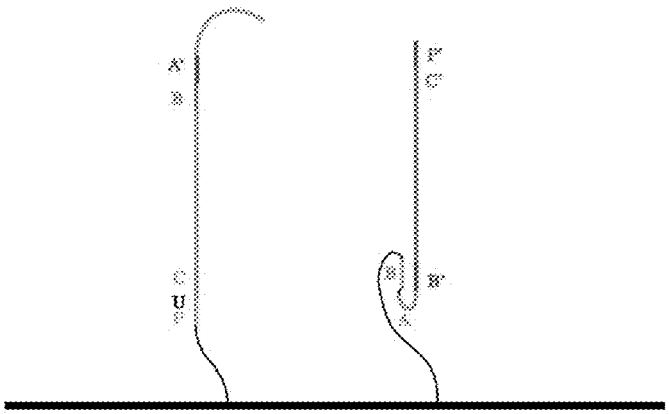

6. Sequence A' will hybridize to a new primer A on the surface. Strand-displacing polymerase ◆ will bind to 3' end of primer A and start extending. Meanwhile, sequence P'C' will hybridize to a new primer PC on surface. Polymerase ◆ will bind to 3' end of primer PC and start extending.

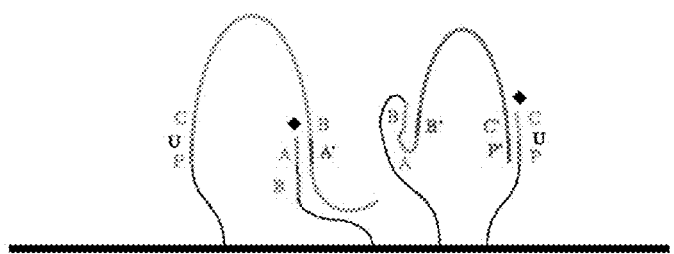

7. The first polymerase will continue to extend, making a full length copy ending in sequence C'P'. The second polymerase will make full length copy, displacing, and finally copying sequence B.

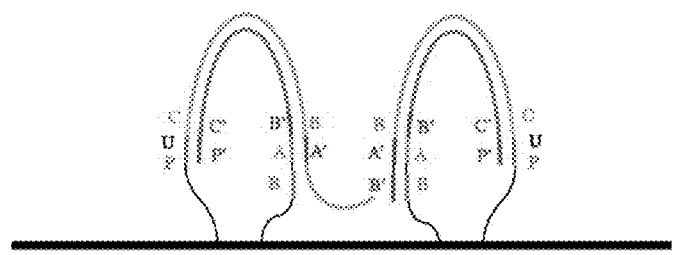

Figure 6B

**Genomic Sequencing.
Generating clusters v5.6, III.**

8. Denature strands. P'C' products containing boths strands will snap back to form full-length hairpins. B' sequences hybridize to B sequences. Polymerases ♦ will bind to the free 3' ends of B' and extend to form full-length hairpined double-stranded DNA. (Partial denaturation or natural separation of DNA strands under given buffer and temperature conditions may be sufficient to initiate strand-dispacing extension of free B' sequences, as well as strand-displacing snap back to form full-length hairpins, liberating full-length single-stranded A primer containing target.)

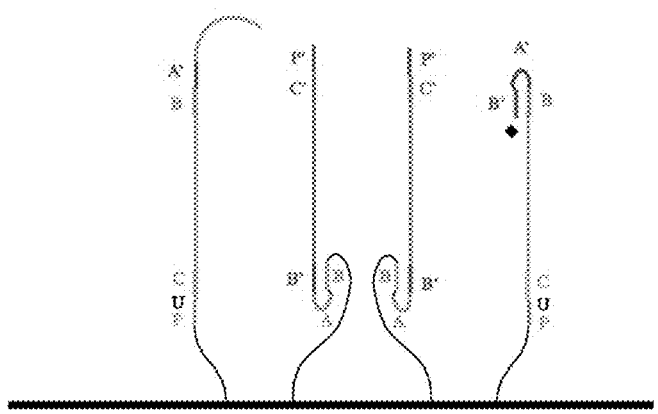

9. Sequences A' will hybridize to new primers A on the surface. Strand-displacing polymerases ♦ will bind to 3' ends of primer A and start extending, displacing the B' sequences, unwinding the hairpins. Meanwhile, sequences P'C' will hybridize to new primers PC on surface. Polymerases ♦ will bind to 3' ends of primer PC and start extending.

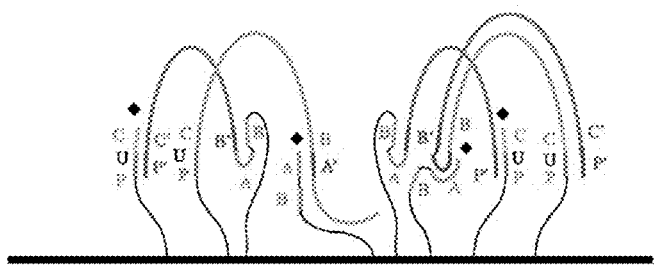

10. The first polymerases will continue to extend, making full length copies ending in sequence P'C' and displacing the full length sequences, which becomes single-stranded. These displaced single strands may snap back to regenerate the full-length hairpins and liberate the newly synthesized A primer strands. The second polymerases will make full length copy, displacing, and finally copying sequence B.

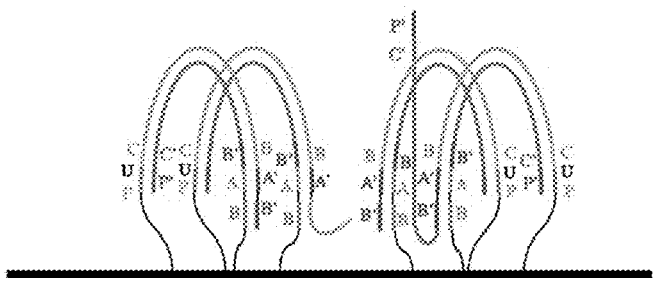

Figure 6C

Genomic Sequencing.
Generating clusters v5.6, IV.

11. After strand displacement amplification is completed, liberate the PC primers from the surface. In this example, the PC primers contained a Uracil (U), which may be cut using UDG and EndoVIII. P'C' products containing both strands will snap back to form full-length hairpins and dissociate from surface. Denature and wash away remaining liberated strands. EndoVIII leaves a 3' phosphate on the ends of the remaining portion of the C sequence still on the surface, so it will not extend with polymerase.

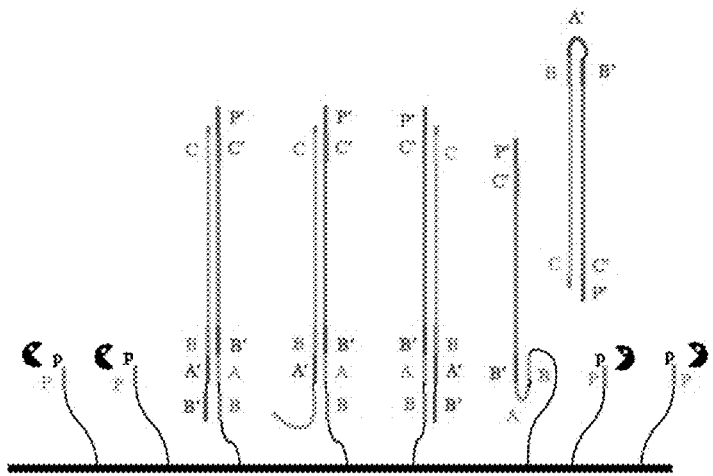

12. Remaining single stranded target sequences are all in the same orientation and suitable for solid-phase sequencing.

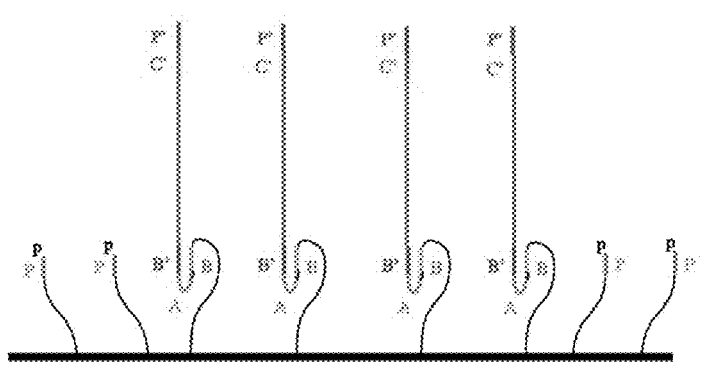

Figure 6D

Genomic Sequencing.
Generating clusters v5.6, V. Example of sequencing by synthesis.

13. Hybridize primer P to amplified strands. Extend a single base with fluorescently labeled (*) nucleotide, which is blocked on the 3' side (,). Image to determine base added at each cluster.

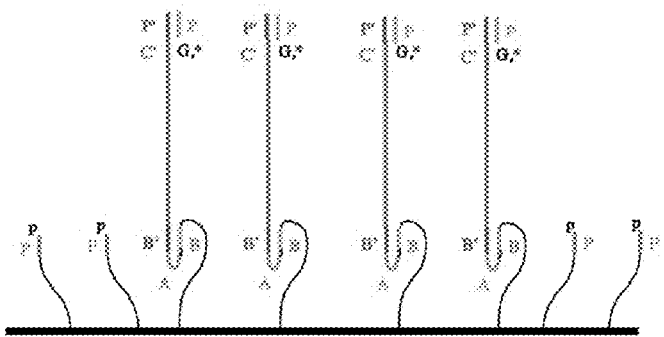

14. Cleave off fluorescent and 3' blocking groups. Extend the next base and image.

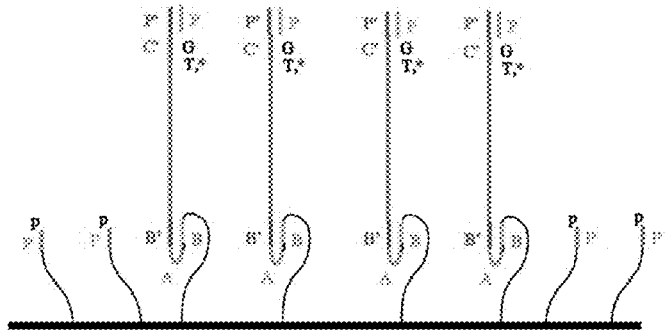

15. Continue the process of base addition, imaging, and cleaving of blocking groups to build a linear sequence at each cluster. If desired, one can avoid reading through the C primer seuqence by running the initial approximately 20 reactions without fluorescent reading. Alternatively, the primer may be extended by sequential rounds of adding 3 dNTPs.

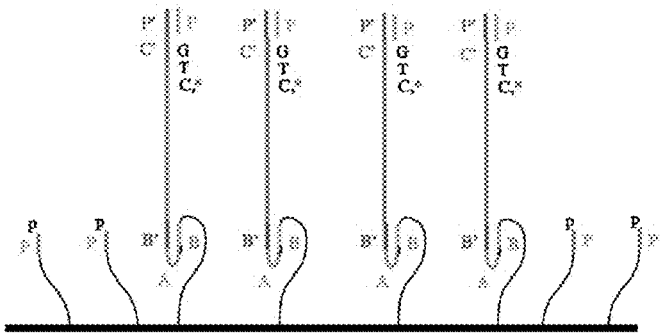

Figure 6E

Genomic Sequencing.
Generating clusters v5.6, VI. Sequencing the opposite strand.

16. Cleave the 3' phosphate from the remaining portion of primer P, for example by using the phosphatase activity of T4 kinase ★, to liberate a free 3' end. Hybridize remaining portion of primer P to amplified strands. Extend with polymerase ♦ that contains 5'-3' exonuclease activity, and lacks strand-displacing activity.

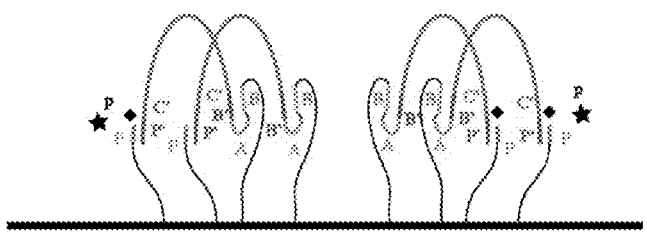

17. As polymerase extends through the template, it reaches the B sequence hybridized to B' sequence. The 5'-3' exonuclease activity digests the B sequence, liberating that strand from the solid surface. Polymerase ♦ continues extending through the A sequence.

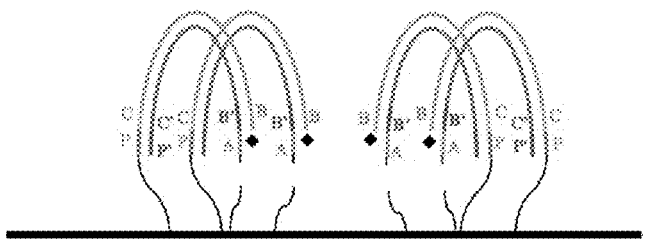

18. Denature away original strands. Remaining single stranded target sequences are all in the same orientation and suitable for solid-phase sequencing.

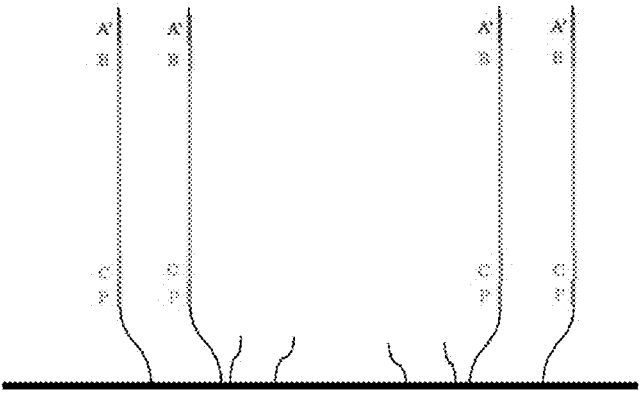

Figure 6F

Genomic Sequencing.
Generating clusters v5.6, VII. Sequencing the opposite strand.

19. Hybridize primer B' to amplified strands. Extend a single base with fluorescently labeled (*) nucleotide, which is blocked on the 3' side ('). Image to determine base added at each cluster. (Note that primer B' may contain all or a portion of primer A sequence on the 5' end.)

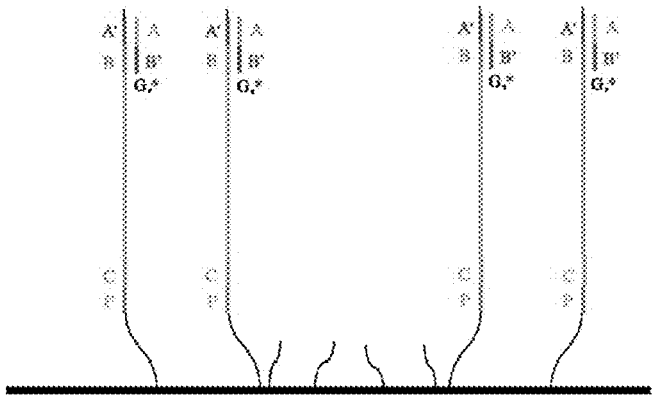

20. Cleave off fluorescent and 3' blocking groups. Extend the next base and image.

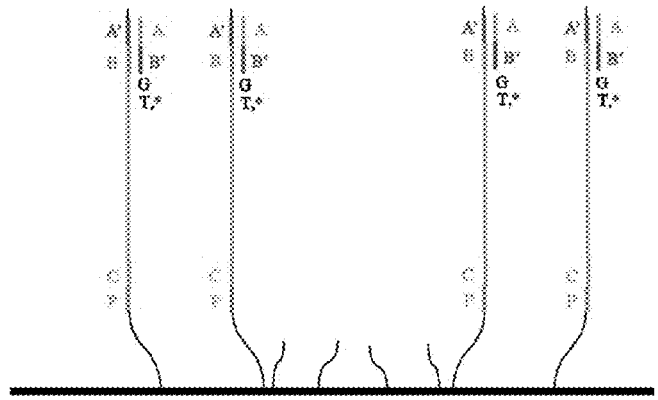

21. Continue the process of base addition, imaging, and cleaving of blocking groups to build a linear sequence at each cluster.

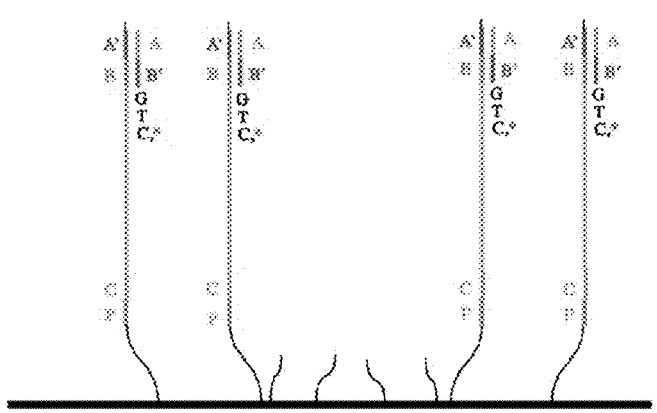

Figure 6G

Gene-Specific Sequencing.
Generating clusters v5.7, I.

1. Anneal genomic DNA to surface such that a desired region is captured by primers C and B. Using a polymerase ◆ with either 5'→3' exonuclease or strand displacement activity, extend primer C on surface to make full length copies.

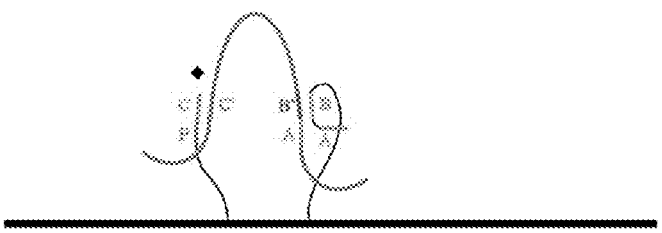

2. Denature original strands and wash away.

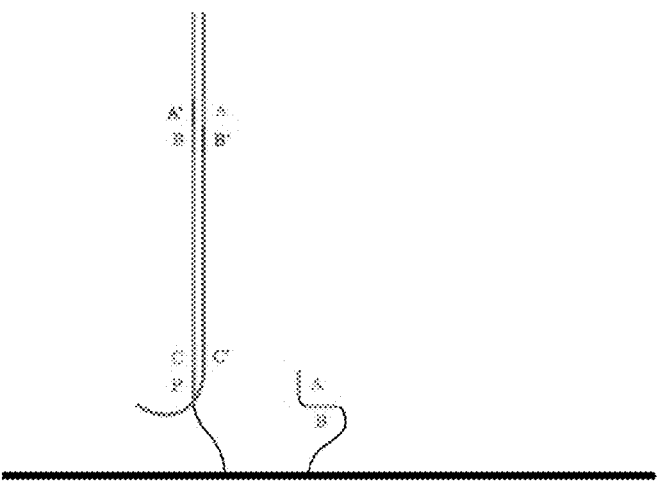

3. Strands containing sequence A' will hybridize to primer A on surface. Add thermophilic polymerase ◆ with strand displacing activity.

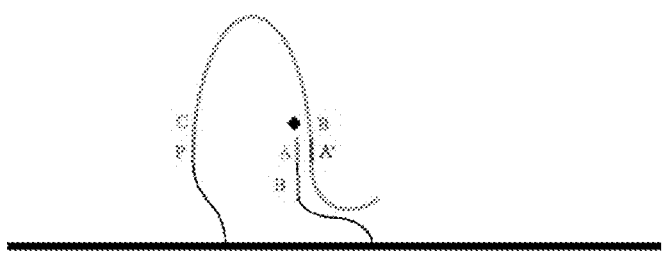

4. Polymerase will make full length copy including universal primer sequence P'.

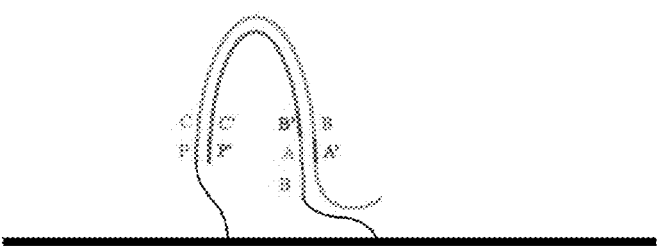

Figure 7A

**Genomic Sequencing.
Generating clusters v5.7, B.**

5. Denature strands. B' sequences
   hybridize to B sequences.

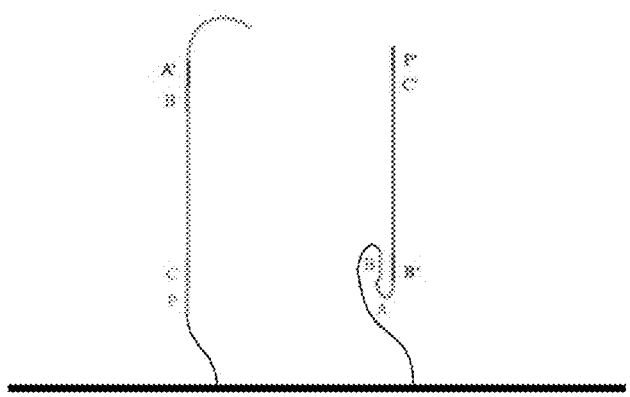

6. Sequence A' will hybridize to a new
   primer A on the surface.
   Strand-displacing polymerase ♦ will
   bind to 3' end of primer A and start
   extending. Meanwhile, sequence P'C'
   will hybridize to a new primer PC on
   surface. Polymerase ♦ will bind to 3'
   end of primer PC and start
   extending.

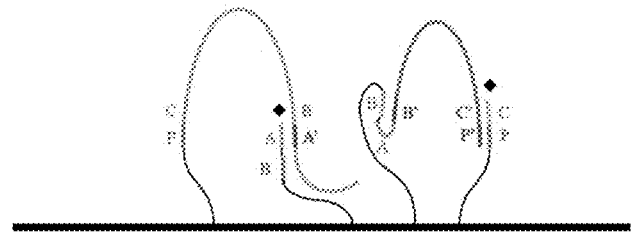

7. The first polymerase will continue to
   extend, making a full length copy
   ending in sequence C'P'. The second
   polymerase will make full length
   copy, displacing, and finally copying
   sequence B.

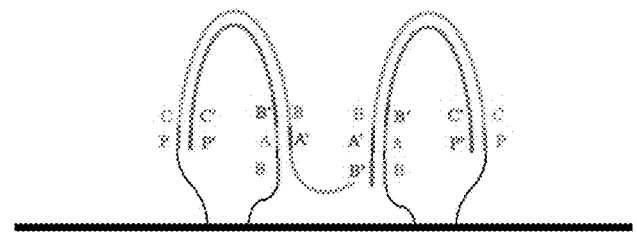

Figure 7B

Genomic Sequencing.
Generating clusters v5.7, III.

8. Denature strands. P'C' products containing boths strands will snap back to form full-length hairpins. B' sequences hybridize to B sequences. Polymerases ♦ will bind to the free 3' ends of B' and extend to form full-length hairpined double-stranded DNA. (Partial denaturation or natural separation of DNA strands under given buffer and temperature conditions may be sufficient to initiate strand-displacing extension of free B' sequences, as well as strand-displacing snap back to form full-length hairpins, liberating full-length single-stranded A primer containing target.)

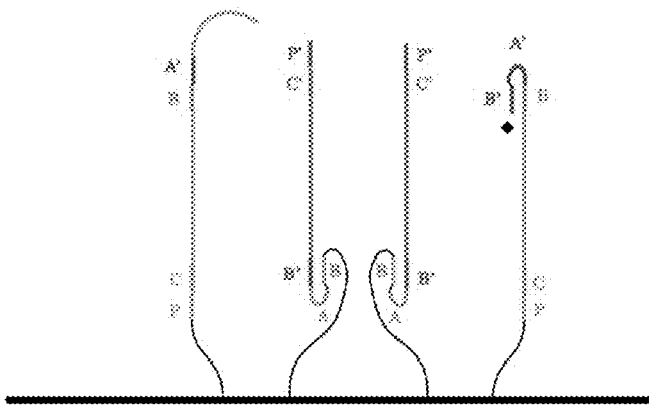

9. Sequences A' will hybridize to new primers A on the surface. Strand-displacing polymerases ♦ will bind to 3' ends of primer A and start extending, displacing the B' sequences, unwinding the hairpins. Meanwhile, sequences P'C' will hybridize to new primers PC on surface. Polymerases ♦ will bind to 3' ends of primer PC and start extending.

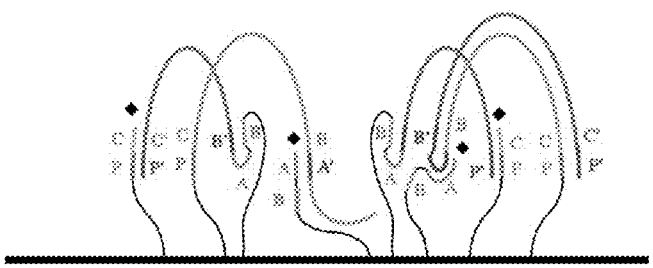

10. The first polymerases will continue to extend, making full length copies ending in sequence P'C' and displacing the full length sequences, which becomes single-stranded. These displaced single strands may snap back to regenerate the full-length hairpins and liberate the newly synthesized A primer strands. The second polymerases will make full length copy, displacing, and finally copying sequence B.

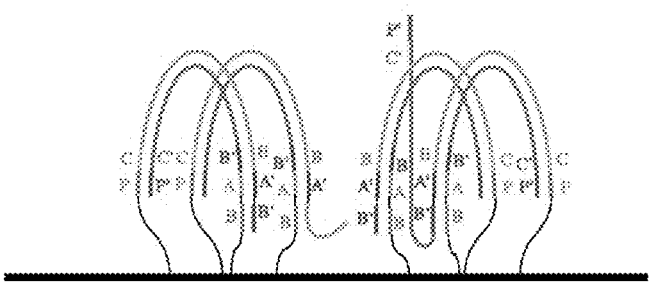

Figure 7C

Genomic Sequencing.
Generating clusters v5.7, IV.

11. Denature strands. P'C' products containing boths strands will snap back to form full-length hairpins. B' sequences hybridize to B sequences. Polymerases ◆ will bind to the free 3' ends of B' and extend to form full-length hairpined double-stranded DNA. (Partial denaturation or natural separation of DNA strands under given buffer and temperature conditions may be sufficient to initiate strand-dispacing extension of free B' sequences, as well as strand-displacing snap back to form full-length hairpins, liberating full-length single-stranded A primer containing target.) Repeat cycles as needed.

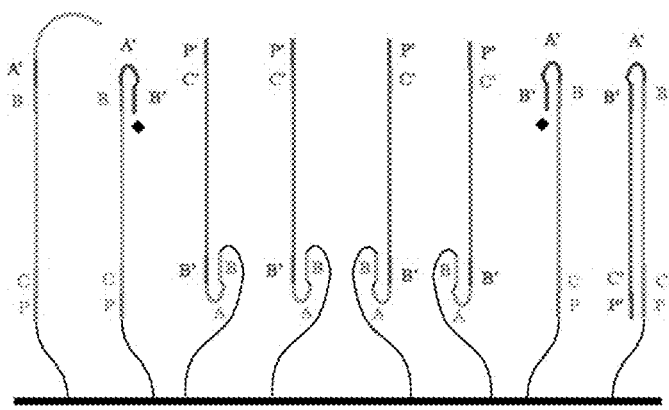

12. After PC primer products are extended to form hairpins, remaining single stranded target sequences are all in the same orientation and suitable for solid-phase sequencing.

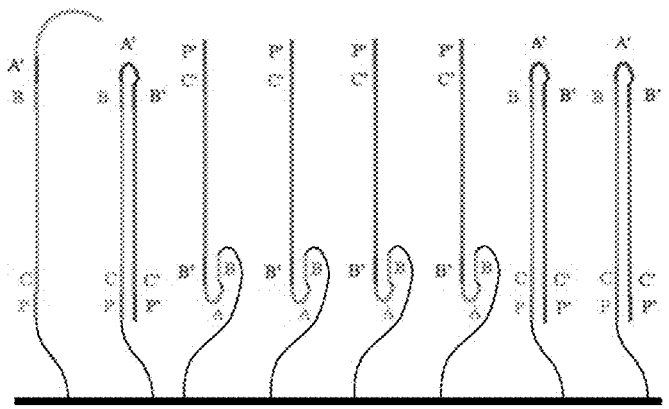

Figure 7D

Genomic Sequencing.
Generating clusters v5.7, V. Example of sequencing by synthesis.

13. Hybridize primer P to amplified strands. Extend a single base with fluorescently labeled (*) nucleotide, which is blocked on the 3' side (.). Image to determine base added at each cluster.

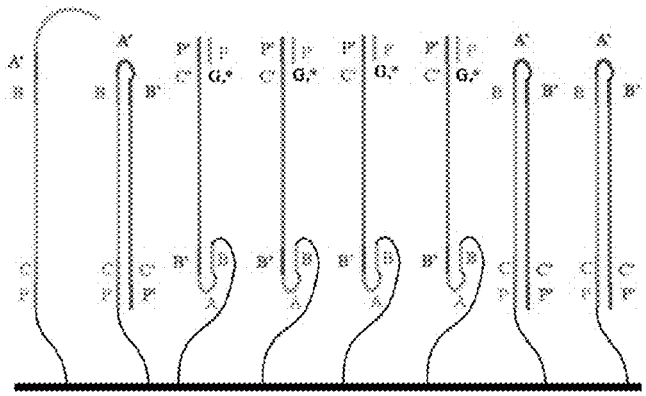

14. Cleave off fluorescent and 3' blocking groups. Extend the next base and image.

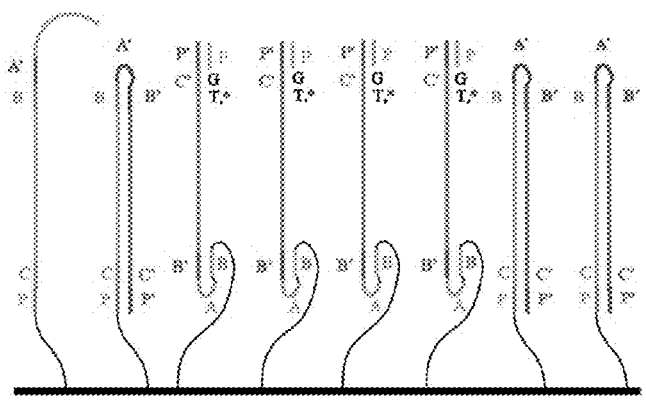

15. Continue the process of base addition, imaging, and cleaving of blocking groups to build a linear sequence at each cluster. If desired, one can avoid reading through the C primer sequence by running the initial approximately 20 reactions without fluorescent reading. Alternatively, the primer may be extended by sequential rounds of adding 3 dNTPs.

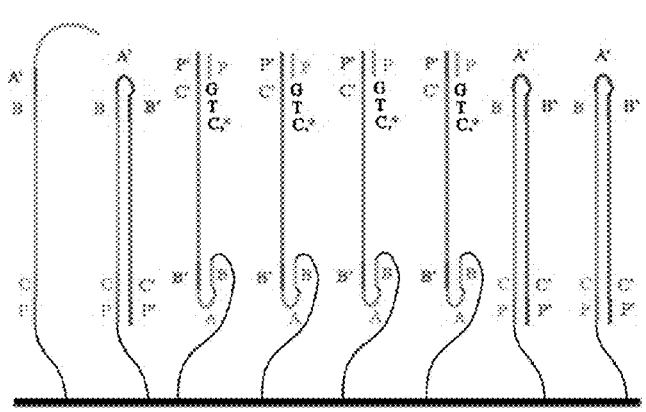

Figure 7E

Genomic Sequencing.
Generating clusters v5.7, VI. Sequencing the opposite strand.

16. Hybridize primer A" to A' regions in hairpinned strands. Primer A" is modified such that it protects the A' region from exonuclease digestion when hybridized to A'. Add Exonuclease I ( to digest single-stranded DNA from the 3' end. Add Exonuclease III ) to digest double-stranded DNA until digestion is blocked by the A" primer.

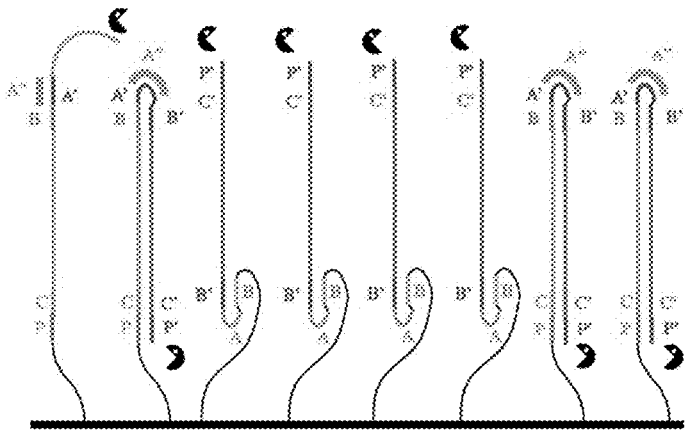

17. Inactivate or wash away enzymes, and denature away A" primer. Remaining single stranded target sequences are all in the same orientation and suitable for solid-phase sequencing.

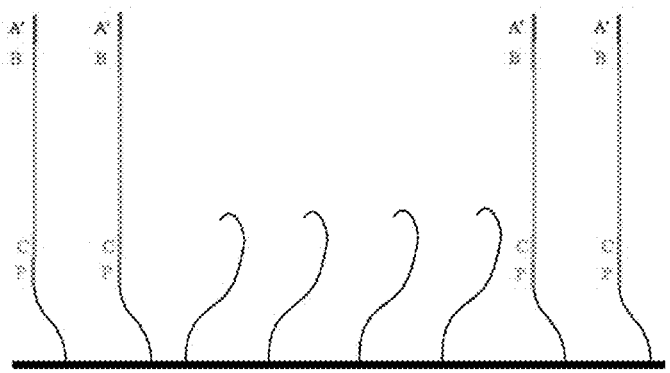

Figure 7F

Genomic Sequencing.
Generating clusters v5.7, VII. Sequencing the opposite strand.

18. Hybridize primer B' to amplified strands. Extend a single base with fluorescently labeled (*) nucleotide, which is blocked on the 3' side ('). Image to determine base added at each cluster. (Note that primer B' may contain all or a portion of primer A sequence on the 5' end.)

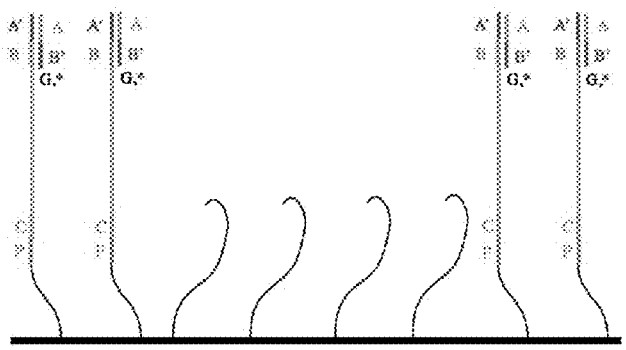

19. Cleave off fluorescent and 3' blocking groups. Extend the next base and image.

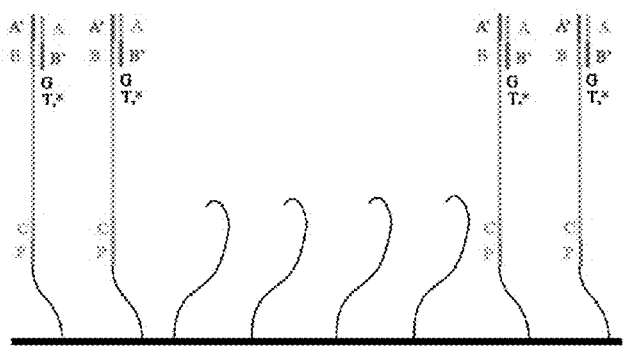

20. Continue the process of base addition, imaging, and cleaving of blocking groups to build a linear sequence at each cluster.

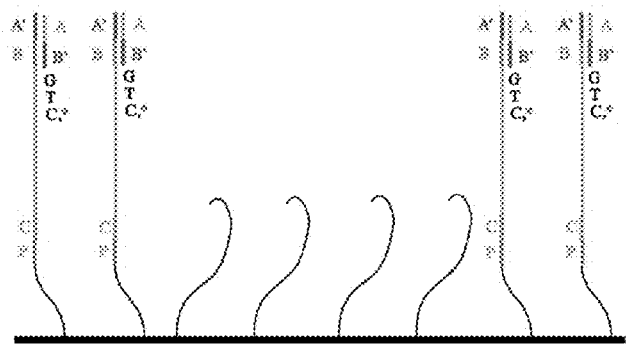

Figure 7G

Genomic Sequencing.
Sequencing of internal regions: v1.0, A.1

1. Single stranded PCR fragment is fixed at one end on the solid surface, amplified on surface. Only one strand is shown.

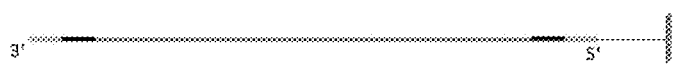

Primer:
pNNNNNSGUA

2. Primers with 5' degenerate nucleotides and one uracil anneal to single strand PCR fragments.

DNA polymerase,
dATP, dCTP, dTTP, ddGTP

3. Primers are extended by DNA polymerase in the presence of dATP, dCTP, dTTP, ddGTP.

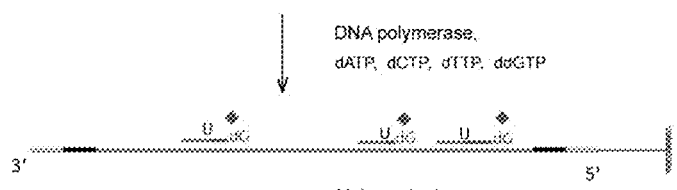

Universal primer,
DNA polymerase,
DNA ligase

4. After wash out the components, univeral primers, DNA polymerase. DNA ligase, and dNTPs are added. The universal primer is extended and ligated to the 5' end of nearst upstream hybridized primer.

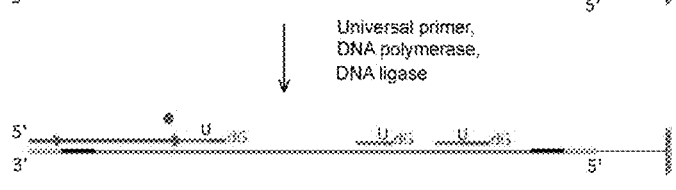

UDG, endoVIII, T4 kinase

5. The degenerate primers are cut at the U site by UDG, endo VIII and T4 kinase

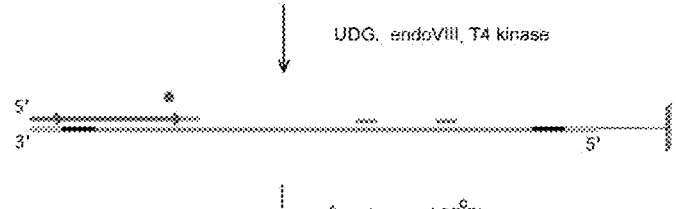

△ (around 65°C)

6. After heating (e.g. 65°C), excess degenerate primers fall off the single strand DNA template.

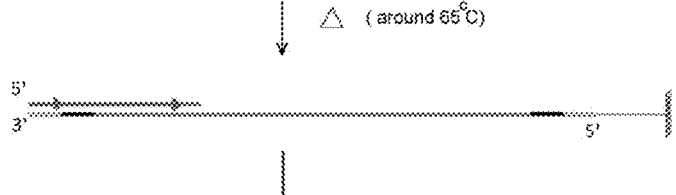

7. Extension products are subjected to solid phase sequencing.

Solid phase sequencing

Figure 8

Genomic Sequencing.
Sequencing of internal regions: Part 1 v1.0, B.1

1. Single stranded PCR fragment is fixed at one end on the solid surface, amplified on surface. Only one strand is shown.

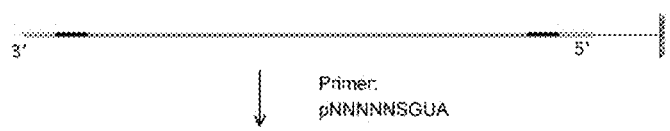

Primer:
pNNNNNSGUA

2. Primers with 5' degenerate nucleotides, one G and one uracil anneal to single strand PCR fragments.

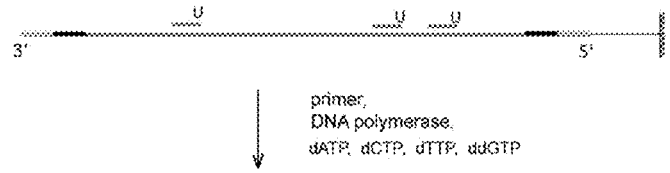

primer,
DNA polymerase,
dATP, dCTP, dTTP, ddGTP

3. Primers are extended by DNA polymerase in the presence of dATP, dCTP, dTTP, ddGTP.

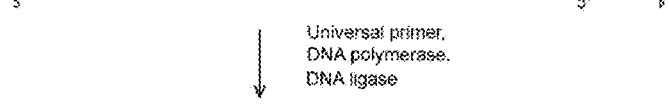

Universal primer,
DNA polymerase,
DNA ligase

4. After wash out the components, universal primers, DNA polymerase, DNA ligase, and dNTPs are added. The universal primer is extended and ligated to the 5' end of nearst upstream hybridized primer.

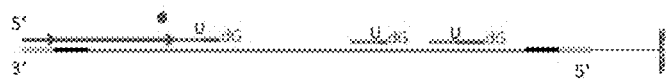

△ ( around 70-75 °C)

5. After heating ( e.g. 70-75 °C), excess degenerate primers annealing to the templates fall off.

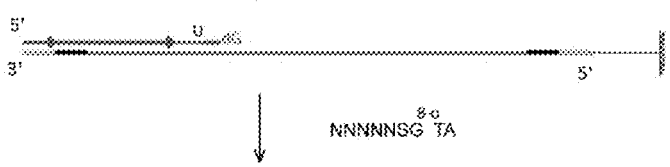

NNNNNSG$^{8-0}$TA

6. A new primer with 5' degenerate nucleotides, an 8 oxoguanine instead of guanine, thymine instead of uracil anneals to a single strand DNA fragment.

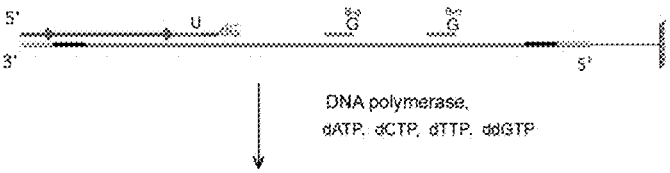

DNA polymerase,
dATP, dCTP, dTTP, ddGTP

7. The degenerate primer is extended with DNA polymerase and dATP,dCTP,dTTP, ddGTP.

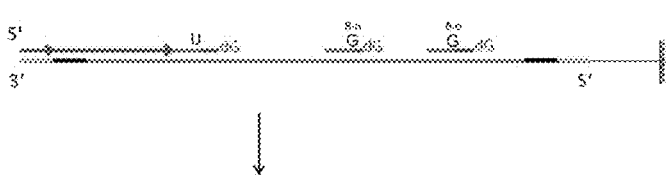

Figure 9A

Genomic Sequencing.
Sequencing of internal regions: Part 2  v1.0,  B.2

8. The degenerate primer is extended with DNA polymerase and dATP,dCTP,dTTP, ddGTP. (From previous page)

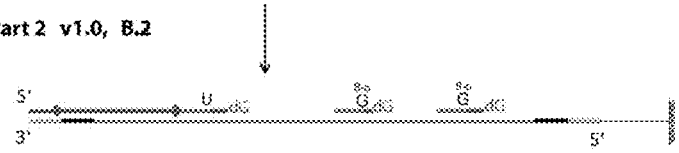

9. UDG, endoVIII and T4 kinase cut the uracil on the primer linked to the universal primer.

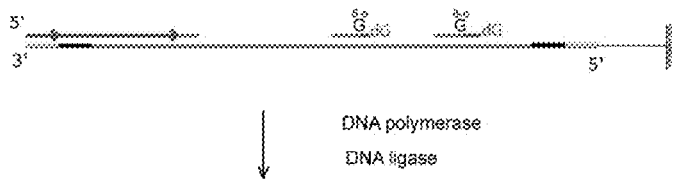

10. The primer is extended with DNA polymerase and ligated to 5' end of the nearst upstream hybridized primer.

11. The degenerate primers are cut at the 8 oxoG site by Fpg. Subsequently T4 kinase removes the 3' phosphate.

12. After heating (e.g. 65 °C), excess degenerate primers fall off the single stranded template.

13. The extention products are subjected to solid phase sequencing.

Solid phase sequencing

Figure 9B

Genomic Sequencing.
Target enrichment v1.0, A.1

1. (Only the target double stranded DNA of interest for enrichment is shown.)

2. Ligation of universal adaptors to each DNA fragment.

3. The double stranded DNA is denatured and rendered into single stranded DNA. Only the top strand is shown.

4. A gene specific primer (upstream) is hybridized to the target single stranded DNA.

5. An downstream gene specific primer with a biotin moiety on the 5' end is ligated to the upstream gene specific primer. A ligation product will only form when the up/down stream primer sequences match perfectly with the DNA template.

6. After low heating (45°C), excess short primers fall off the single stranded DNA. Those primers that are not hybridized are separated (e.g. electrophoresis or spin column) from ligated primers hybridized to the target.

7. Capture the target away from other DNA fragments onto streptavidin immobilized to a solid support, such as paramagnetic beads or a microfabricated fluid chanel. After denaturation, the target single stranded DNA will be released into solution phase.

8. The enriched single stranded DNA will be subjected to either PCR or Sequoia amplification.

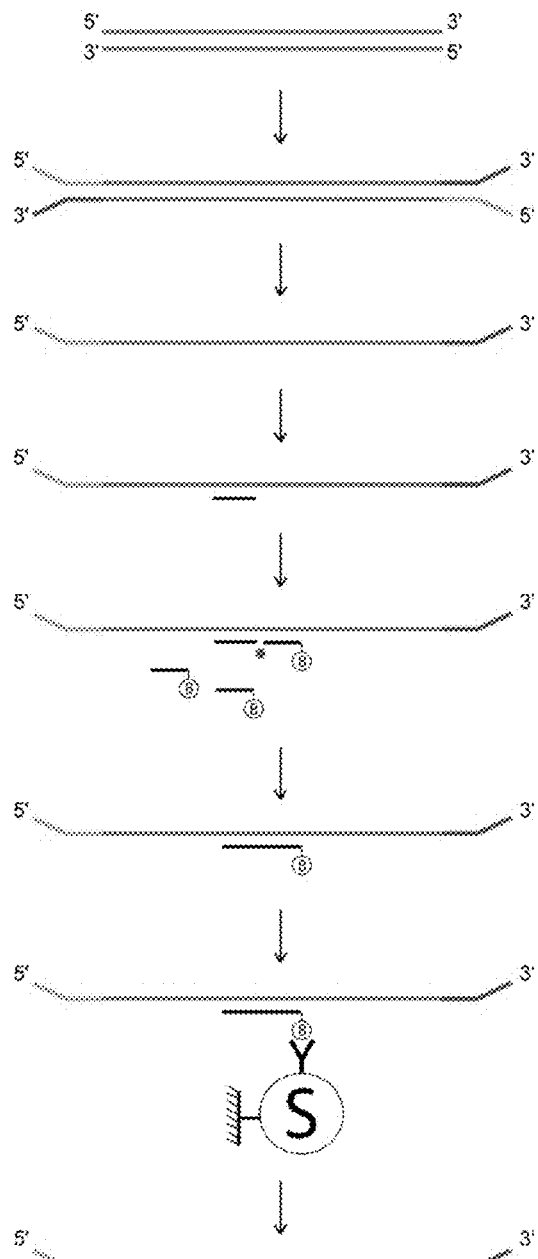

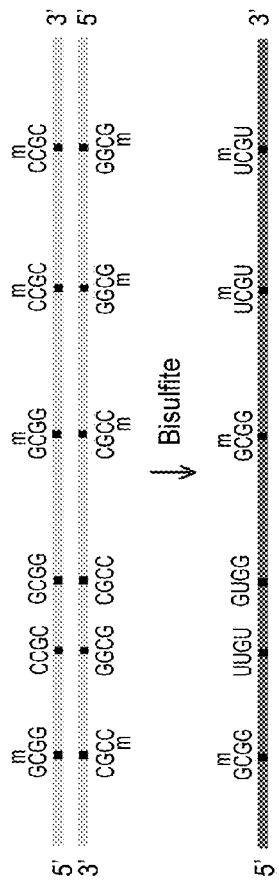
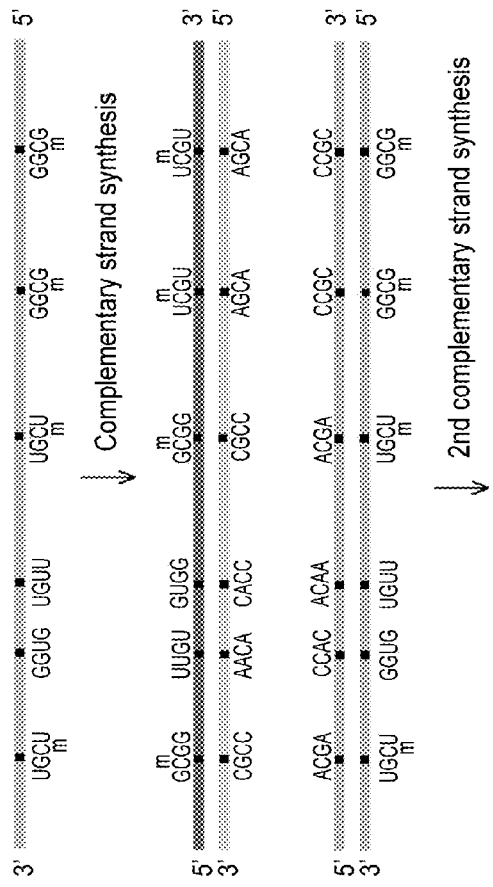

"Methyl-tag" Sequencing

1. Treat DNA with sodium bisulfite to convert unmethylated, but not methylated cytosines into uracils. Only the cytosines present in AciI sites are shown here. Such sites are common in CpG islands, but rare elsewhere in the genome.

2. The resultant strands are not complementary.

3. Synthesize the first complementary strand using 5'-NNNNNNNCG-3' 9-mer primers, E. coli DNA polymerase I, and T4 ligase to seal nicks between adjacent extension products. (Optional: The original bisulfite treated strand may be destroyed using UNG.)

FIG. 11 (Cont.)

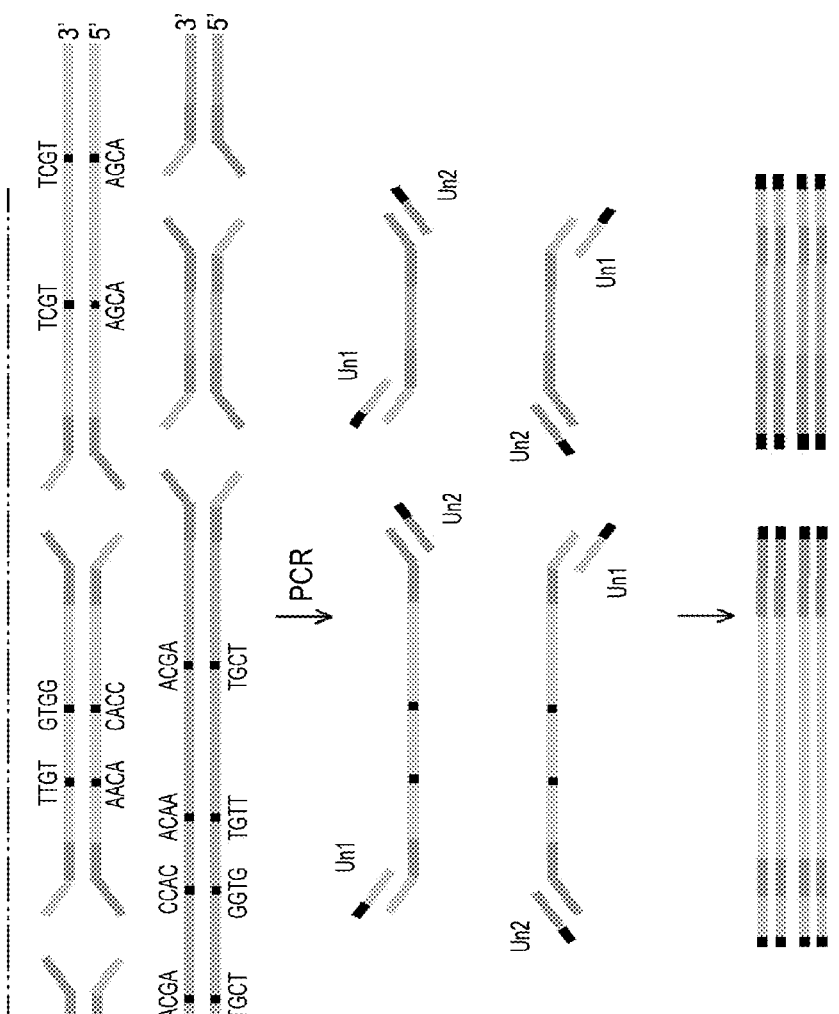

6. Biochemical selection drives the reaction, allowing steps 5 & 6 to be performed simultaneously.

7. Optional: PCR amplify all ligation products using univeral primers and Taq polymerase. Top and bottom strands amplify independently. Primers contain seven identical 5' bases, such that primer dimers and very small fragments form pan-handles and are not amplified.

8. All Ligation or PCR products are subject to solid phase cluster sequencing.

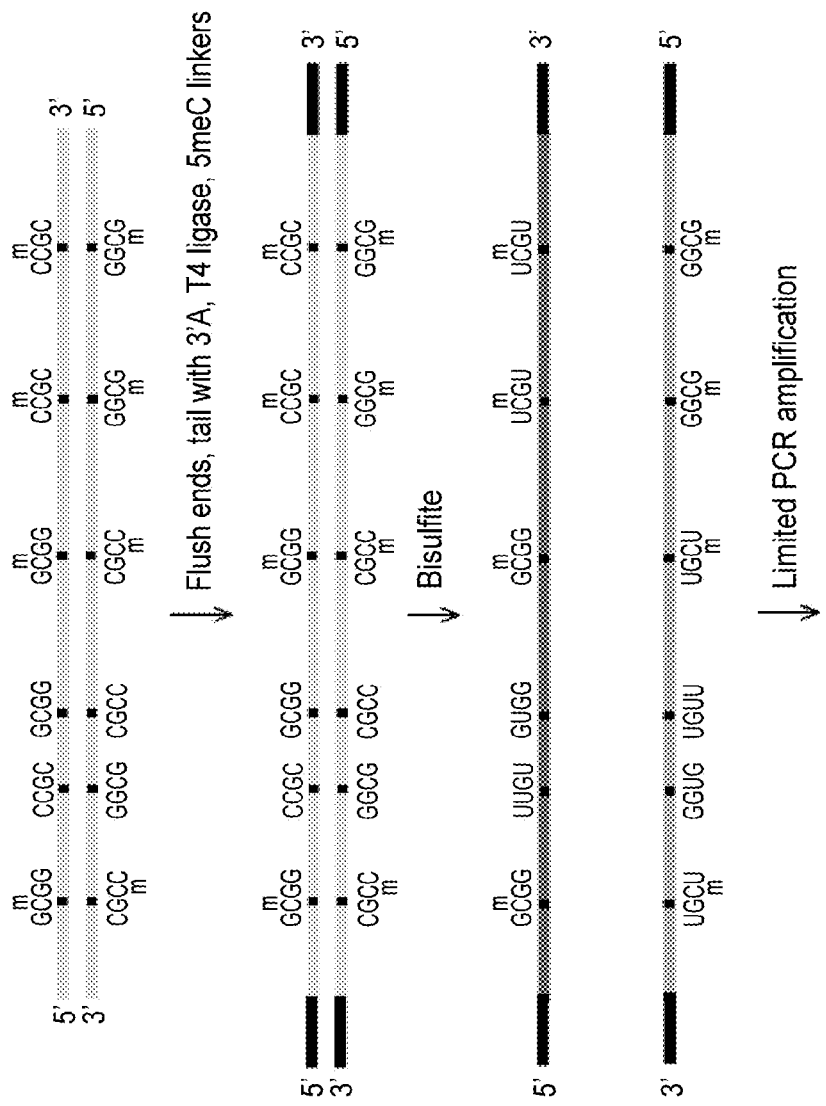

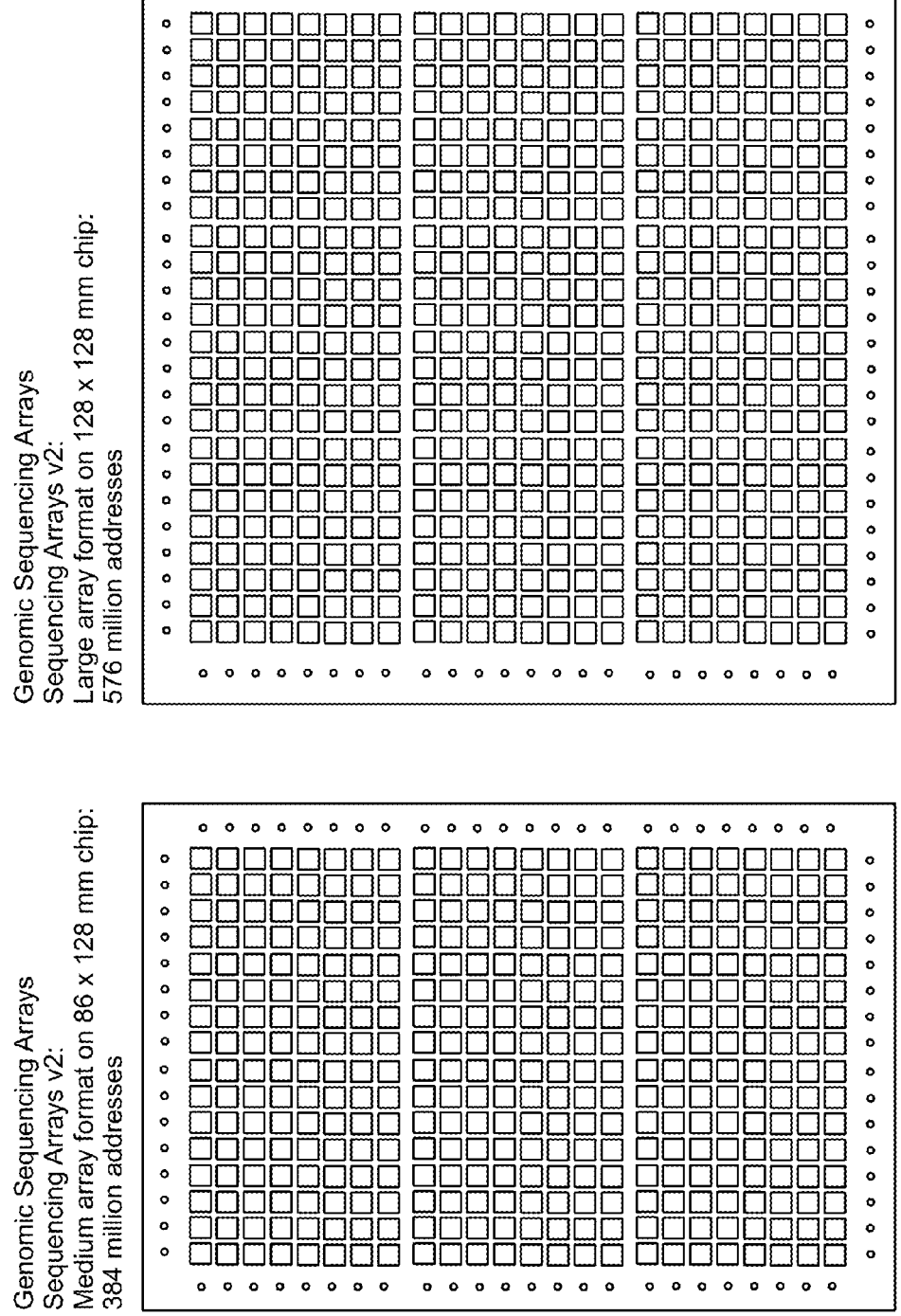

Fluidic Network for Addressing Microwells

COC or PMMA Immobilization Chemistry of Amine-Terminated Oligonucleotides

SU-8 Photoresist
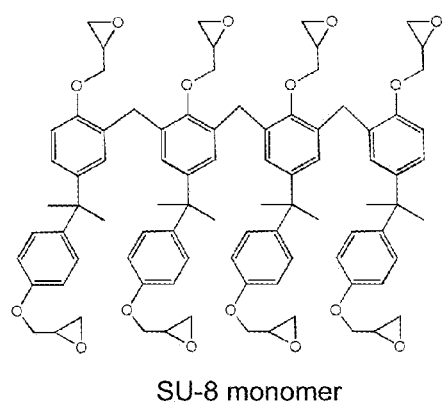
SU-8 monomer
On average, 3.3 epoxy rings remain on each monomer after UV-polymerization reaction.
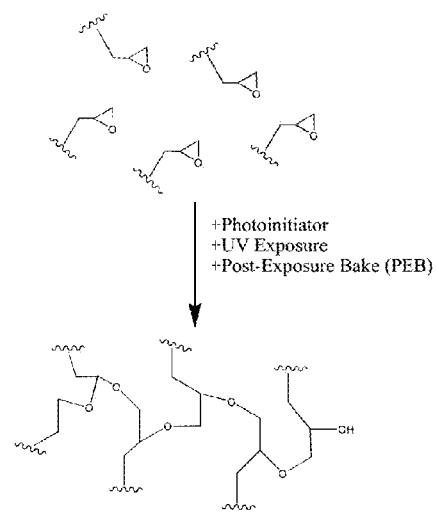
Polymerization of SU-8 upon UV exposure
Figure 23

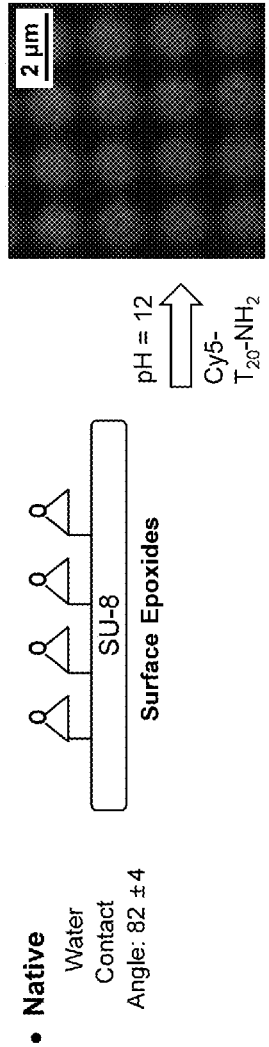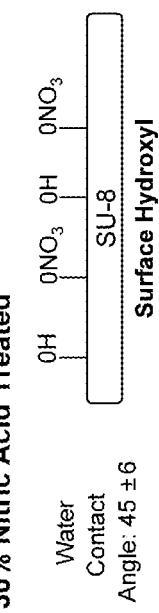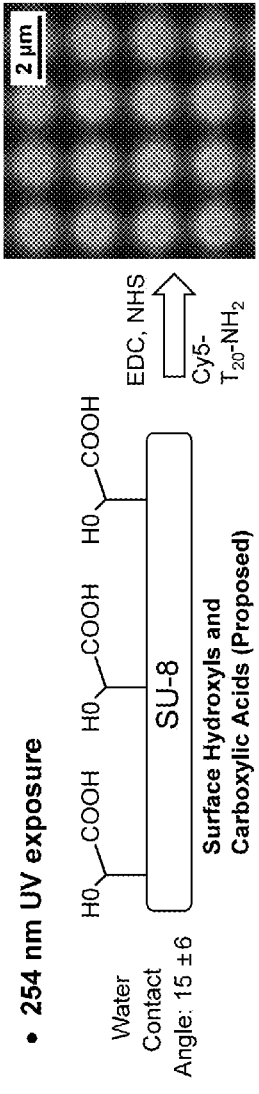

Genomic Sequencing Arrays
Gene-specific Array v9, Step I: Activation

Genomic Sequencing Arrays
Gene-specific Array v9, Step 3: Attachment of zip-code primers.

Genomic Sequencing Arrays
Gene-specific Array v9, Step 4: Addition of composite zip-code complement – Gene-specific Array primer pairs v9.

Genomic Sequencing Arrays
Gene-specific Array v9, Step 4:
Closeup of addition of composite zip-code complement – Gene-specific Array primer pairs v9.

Genomic Sequencing Arrays
Gene-specific Array v9. Step 5: Hybridization and crosslinking of composite zip code complement - Gene-specific Array primer pairs v9.

FIG. 26G

Genomic Sequencing Arrays
Gene-specific Array v9: Example of Gene-specific digital transcriptome.

| Gene A | Gene B | Gene C | Gene D | Gene E | Gene F | Gene G | Gene H |
|--------|--------|--------|--------|--------|--------|--------|--------|
| Gene I | Gene J | Gene K | Gene L | Gene M | Gene N | Gene O | Gene P |
| Gene Q | Gene R | Gene S | Gene T | Gene U | Gene V | Gene W | Gene X |

FIG. 26H

Genomic Sequencing Arrays
Gene-specific Array v9: Example of digital chromosomal copy number analysis.

| Gene A | Gene B | Gene C | Gene D | Gene E | Gene F | Gene G | Gene H |
|--------|--------|--------|--------|--------|--------|--------|--------|
| Gene I | Gene J | Gene K | Gene L | Gene M | Gene N | Gene O | Gene P |
| Gene Q | Gene R | Gene S | Gene T | Gene U | Gene V | Gene W | Gene X |

Genomic Sequencing Arrays
Gene-specific Array v10, Step I: Activation

Genomic Sequencing Arrays
Gene-specific Array v10, Step 3: Attachment of zip-code primers.

Genomic Sequencing Arrays
Gene-specific Array v10, Step 4: Addition of composite zip-code complement - Gene-specific Array primer pairs v10.

Genomic Sequencing Arrays
Gene-specific Array v10, Step 4:
Closeup of addition of composite zip-code complement – Gene-specific Array primer pairs v10.

Genomic Sequencing Arrays
Gene-specific Array v10,Step 5: Hybridization and crosslinking of composite zip code complement - Gene-specific Array primer pairs v10.

FIG. 27G

Genomic Sequencing Arrays
Gene-specific Array v10: Example of Gene-specific mutation analysis.

| Gene A 1-100 | Gene A 101-200 | Gene A 201-300 | Gene A 301-400 | Gene A 100'-1' | Gene A 200'-101' | Gene A 300'-201' | Gene A 400'-301' |
|---|---|---|---|---|---|---|---|
| Gene B 1-100 | Gene B 101-200 | Gene B 201-300 | Gene B 301-400 | Gene B 100'-1' | Gene B 200'-101' | Gene B 300'-201' | Gene B 400'-301' |
| Gene C 1-100 | Gene C 101-200 | Gene C 201-300 | Gene C 301-400 | Gene C 100'-1' | Gene C 200'-101' | Gene C 300'-201' | Gene C 400'-301' |

FIG. 27H

Genomic Sequencing Arrays
Gene-specific Array v10: Example of low level mutation detection.

| Gene A 1-100 | Gene A 101-200 | Gene A 201-300 | Gene A 301-400 | Gene A 100'-1' | Gene A 200'-101' | Gene A 300'-201' | Gene A 400'-301' |
| Gene B 1-100 | Gene B 101-200 | Gene B 201-300 | Gene B 301-400 | Gene B 100'-1' | Gene B 200'-101' | Gene B 300'-201' | Gene B 400'-301' |
| Gene C 1-100 | Gene C 101-200 | Gene C 201-300 | Gene C 301-400 | Gene C 100'-1' | Gene C 200'-101' | Gene C 300'-201' | Gene C 400'-301' |

Genomic Sequencing Arrays
Gene-specific Array v11, Step 1: Activation of first rows.

Genomic Sequencing Arrays
Gene-specific Array v11, Step 2: Addition of Gene-specific Array primer pairs v11.

Genomic Sequencing Arrays
Gene-specific Array v11, Step 3: Covalent attachment at activated regions - Gene-specific Array primer pairs v11.

Genomic Sequencing Arrays
Gene-specific Array v11, Step 4: Activation of next rows.

Genomic Sequencing Arrays
Gene-specific Array v11, Step 5: Addition of next set of Gene-specific Array primer pairs v11.

Genomic Sequencing Arrays
Gene-specific Array v11, Step 7: Activation of next rows.

Genomic Sequencing Arrays
Gene-specific Array v11, Step 8: Addition of Gene-specific Array primer pairs v11.

- Low-dead volume fluidic path
- Chip-to-chip alignment
- $P_{max}$ = 600 psi

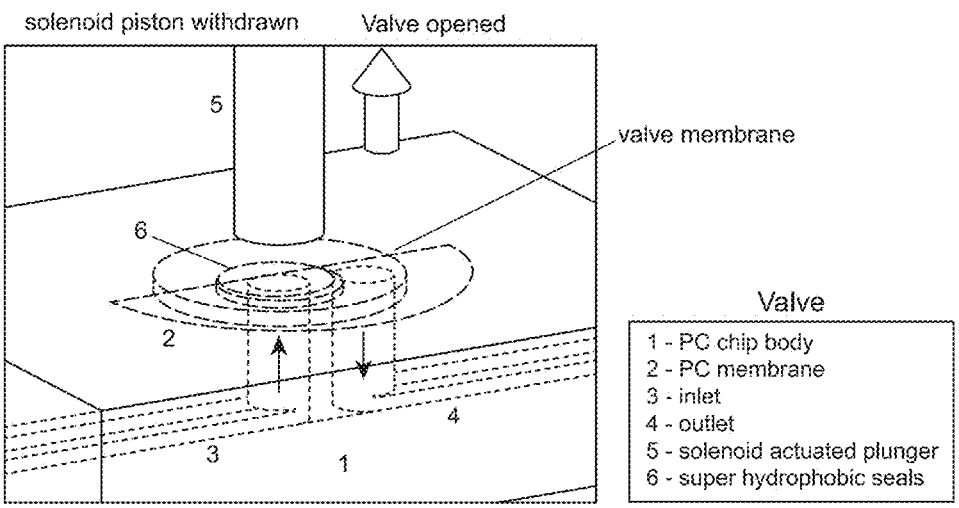
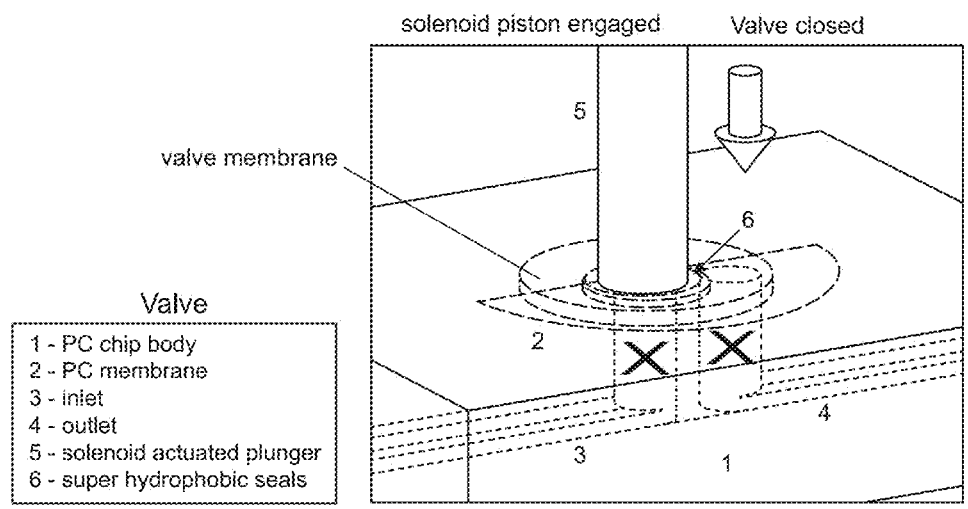

Hashimoto et al., LOC 4 (2004) 638.  ~20 cycles in 1.7 min (500 bp)
Chen et al., Anal. Chem. 77 (2005) 658.  ~20 cycles in 3.9 min (1000 bp)

Adams et al., JACS (2008) 130:8633.

p53 Probe Primers

| Name | Sequences | SEQ ID NO | Note |
|---|---|---|---|
| Cy3-UniA5-comp | 5' Cy3 – GTGAAGCGGTAGTTGGCAGCC – 3' | 31 | |
| Cy3-UniC6-comp | 5' Cy3 – TGGAAGCGGTAGTTGGGTCGA – 3' | 32 | 1 |
| Cy3-p53Ex5-23For | 5' Cy3 – GCACATGACGGAGGTTGTGAGGC– 3' | 33 | 2 |
| Cy3-p53Ex5-23Rev | 5' Cy3 – GCCTCACAACCTCCGTCATGTGC– 3' | 34 | 2 |
| Cy3-p53Ex5-24ForB | 5' Cy3 – TGGAGAGACGACAGGGCTGGTTGC – 3' | 35 | 2 |
| Cy3-p53Ex5-24RevB | 5' Cy3 – GCAACCAGCCCTGTCGTCTCTCCA – 3' | 36 | 2 |
| Cy3-UniA5-NH2 | 5' Cy3 – GGCTGCCAACTACCGCTTCAC-C6-NH2 3' | 37 | 2 |
| Fam-UniA5-comp | 5' Fam – GTGAAGCGGTAGTTGGCAGCC – 3' | 38 | 1 |
| Fam-UniC6-comp | 5' Fam – TGGAAGCGGTAGTTGGGTCGA – 3' | 39 | 1 |
| Cy3 - UniA5 | 5' Cy3 - GGCTGCCAACTACCGCTTCAC 3' | 40 | 3 |
| Cy3 - UniC6 | 5' Cy3 - TCGACCCAACTACCGCTTCCA 3' | 41 | 3 |
| Fam – UniA5 | 5' Fam – GGCTGCCAACTACCGCTTCAC 3' | 42 | 3 |
| Fam – UniC6 | 5' Fam – TCGACCCAACTACCGCTTCCA 3' | 43 | 3 |
| Cy3 - UniA5s | 5' Cy3 - GGCTGCCAACTACCGCTTCsAsC 3' | 44 | 4 |
| Cy3 - UniC6s | 5' Cy3 - TCGACCCAACTACCGCTTCsCsA 3' | 45 | 4 |
| Fam – UniA5s | 5' Fam – GGCTGCCAACTACCGCTTCsAsC 3' | 46 | 4 |
| Fam – UniC6s | 5' Fam – TCGACCCAACTACCGCTTCsCsA 3' | 47 | 4 |
| SeqRevn2.1 | 5' GCAACCAGCCCTGTCGTCTCTCCAGCC -3' | 48 | 5 |
| SeqRevn4.1 | 5' CCTCCCAGAGACCCCAGTTGCAAACCAGAC -3' | 49 | 5 |
| UniA5-BLK | 5' -C18-2'OMeG-2'OMeG-2'OMeC-2'OMeT-GC-2'OMeC-AA-2'OMeC-TAC-2'OMeC-GCT-s-2'OMeT-s-2'OMeC-s-2'OMeA-s-2'OMeC-C3Blk-3' | 50 | 6,7 |
| Fam-T5-cUniA5-T5 | 5' FAM-TTTTT-GTGAAGCGGTAGTTGGCAGCC-TTTTT 3' | 51 | 8 |

Notes
1. Fluorescent probes to hybridize to primers on bead.
2. Fluorescent probe for the p53 amplified sequence.
3. Fluorescent PCR primers to amplify with primers on bead.
4. Fluorescent PCR primers to amplify with primers on bead, with thiophosphate in case with proofreading polymerase.
5. Sequencing Primers.
6. Blocking Primers.
    7. 2'OMe groups are written as "-2'OMeC" for 2'-O-methyl C, for example.
In this oligo, there are 11 bases with 2'-O-methyl groups. The last 4 of them on the 3' end also have thiophosphate linkages to enhance resistance against nucleases. Finally, 3'-Spacer C3 CPG may also act as a blocker of exonuclease activity at the 3'-terminus. A 5' C18 sequence has been added to help block exonuclease activity of the complementary strand.
8. Fluorescently labeled digestion test Primer: Fam-T5-cUniA5-T5.

Figure 45 p53 Solid surface Primers

| Name | Sequence | Notes |
|---|---|---|
| NH2-T15-spacer-UniA5 | 5'-NH2-C6-TTTTTTTTTTTTTTT-C18-GGCTGCCAAC-TACCGCTTCAC-3' (SEQ ID NO:52) | |
| NH2-T14U-spacer-UniC6 | 5'-NH2-C6-TTTTTTTTTTUTTTT-C18-TCGACCCAACTACCGC-TTCCA-3' (SEQ ID NO:53) | |
| B11-spacer-T15-NH2 | 5'-TGAGGGCAGGGCAGTACTGTAGGAAGAGG-C18-TTTTT-TTTTTTTTTT-C6-NH2-3' (SEQ ID NO:54) | |
| B12-spacer-T15-NH2 | 5'-GAGGGCAGGGCGGTACTGTAGGAAGAGG-C18-TTTTT-TTTTTTTTTT-C6-NH2-3' (SEQ ID NO:55) | |
| B13-spacer-T18-NH2 | 5'-GAGGGCAGGGCGGTACTGCGGGAAG-C18-TTTTTTTTT-TTTTTTTTTT-C6-NH2-3' (SEQ ID NO:56) | |
| B14-spacer-T15-NH2 | 5'-GAGGGCAGGGAGGTACTGAGGGAAGAGG-C18-TTTTT-TTTTTTTTTT-C6-NH2-3' (SEQ ID NO:57) | |
| NH2-T20-spacer-UniA5 | 5'-NH2-C6-TTTTTTTTTTTTTTTTTTTT-C18-GGCTGCCAACT-ACCGCTTCAC-3' (SEQ ID NO:58) | |
| NH2-T20-spacer-UniA5s | 5'-NH2-C6-TTTTTTTTTTTTTTTTTTTT-C18-GGCTGCCAACT-ACCGCTTCsAsC-3' (SEQ ID NO:59) | |
| NH2-T19U-spacer-UniC6 | 5'-NH2-C6-TTTTTTTTTTTTTTTUTTTT-C18-TCGACCCAACT-ACCGCTTCCA-3' (SEQ ID NO:60) | |
| NH2-T19U-spacer-UniC6s | 5'-NH2-C6-TTTTTTTTTTTTTTTUTTTT-C18-TCGACCCAACT-ACCGCTTCsCsA-3' (SEQ ID NO:61) | |
| NH2-T25-spacer-UniA5 | 5'-NH2-C6-TTTTTTTTTTTTTTTTTTTTTTTTT-C18-GGCTGC-CAACTACCGCTTCAC-3' (SEQ ID NO:62) | |
| NH2-T24U-spacer-UniC6 | 5'-NH2-C6-TTTTTTTTTTTTTTTTTTTTUTTTT-C18-TCGACC-CAACTACCGCTTCCA-3' (SEQ ID NO:63) | |
| B11-spacer-T20-NH2 | 5'-TGAGGGCAGGGCAGTACTGTAGGAAGAGG-C18-TTTTT-TTTTTTTTTTTTTTT-C6-NH2-3' (SEQ ID NO:64) | |
| B14-spacer-T20-NH2 | 5'- GAGGGCAGGGAGGTACTGAGGGAAGAGG-C18-TTTTT-TTTTTTTTTTTTTTT-C6-NH2-3' (SEQ ID NO:65) | |
| B11-spacer-T25-NH2 | 5'-TGAGGGCAGGGCAGTACTGTAGGAAGAGG-C18-TTTTT-TTTTTTTTTTTTTTTTTTTT-C6-NH2-3' (SEQ ID NO:66) | |

Figure 46

Solid surface Primers (continued)

| Name | Sequence | Notes |
|---|---|---|
| B14-spacer-T25-NH2 | 5'- GAGGGCAGGGAGGTACTGAGGGAAGAGG-C18-TTTTT-TTTTTTTTTTTTTTTTTTTT-C6-NH2 3' (SEQ ID NO:67) | |
| NH2-spacer-T15-B11 | 5'-NH2-C6-TTTTTTTTTTTTTTT-C18-TGAGGGCAGGGCAGT-ACTGTAGGAAGAGGTATC-3' (SEQ ID NO:68) | |
| NH2-spacer-T15-B14 | 5'-NH2-C6-TTTTTTTTTTTTTTT-C18-GAGGGCAGGGAGGT-ACTGAGGGAAGAGGTATC-3' (SEQ ID NO:69) | |
| NH2-spacer-T20-B11 | 5'-NH2-C6-TTTTTTTTTTTTTTTTTTTT-C18-TGAGGGCAGGG-CAGTACTGTAGGAAGAGGTATC-3' (SEQ ID NO:70) | |
| NH2-spacer-T20-B14 | 5'-NH2-C6-TTTTTTTTTTTTTTTTTTTT-C18-GAGGGCAGGG-AGGTACTGAGGGAAGAGGTATC-3' (SEQ ID NO:71) | |
| D1-spacer-T14C-NH2 | 5'- GCCGCCTGAGGTCTGGTTTGCAACTG -C18-TTTTUTTT-TTTTTTT-C6-NH2-3' (SEQ ID NO:72) | |
| D1-spacer-T19C-NH2 (aka D1-spacer-T19U-NH2) | 5'- GCCGCCTGAGGTCTGGTTTGCAACTG -C18-TTTTUTTT-TTTTTTTTTTT-C6-NH2-3' (SEQ ID NO:73) | |
| NH2-spacer-T14C-D1 | 5'-NH2-C6-TTTTTTTTTTUTTTT-C18-GCCGCCTGAGGTCT-GGTTTGCAACTG-Hexanediol-3' (SEQ ID NO:74) | 1 |
| NH2-spacer-T19C-D1 | 5'-NH2-C6-TTTTTTTTTTTTTTTUTTTT-C18-GCCGCCTGAG-GTCTGGTTTGCAACTG-Hexanediol-3' (SEQ ID NO:75) | 1 |
| NH2-T15-PC-spacer-UniC6 | 5'-NH2-C6-TTTTTTTTTTTTTTT-PC-C18-TCGACCCAACTAC-CGCTTCCA-3' (SEQ ID NO:76) | 2 |
| NH2-T20-PC-spacer-UniC6 | 5'-NH2-C6-TTTTTTTTTTTTTTTTTTTT-PC-C18-TCGACCCA-ACTACCGCTTCCA-3' (SEQ ID NO:77) | 2 |
| NH2-T15-spacer-8OdG-UniC6 | 5'-NH2-C6-TTTTTTTTTTTTTTT-C18-TC-8OdG-ACCCAACT-ACC-8OdG-CTTCCA -3' (SEQ ID NO:78) | 3 |
| NH2-T20-spacer-8OdG-UniC6 | 5' -NH2-C6-TTTTTTTTTTTTTTTTTTTT-C18-TC-8OdG-ACCC-AACTACC-8OdG-CTTCCA-3' (SEQ ID NO:79) | 3 |
| NH2-T15-spacer-T5AB-UniC6 | 5'-NH2-C6-TTTTTTTTTTTTTTT--C18-TTTTT-AB-TCGACCC-AACTACCGCTTCCA-3' (SEQ ID NO:80) | 4 |
| D1-PC-spacer-T20-NH2 | 5'-GCCGCCTGAGGTCTGGTTTGCAACTG-PC-C18-TTTTTT-TTTTTTTTTTTTT-C6-NH2 3' (SEQ ID NO:81) | 5,2,6 |

Figure 46 (cont.)

Solid surface Primers (continued)

| Name | Sequence | Notes |
|---|---|---|
| NH2-T20-spacer-UniA5s | 5'-NH2-C6-TTTTTTTTTTTTTTTTTTTT-C18-GGCTGCCAACT-ACCGCTTCsAsC -3' (SEQ ID NO:82) | 5,2,6 |
| NH2-T20-PC-spacer-UniC6s | 5'-NH2-C6-TTTTTTTTTTTTTTTTTTTT-PC-C18-TCGACCCA-ACTACCGCTTCsCsA-3' (SEQ ID NO:83) | 5,2,6 |
| NH2-T20-spacer-UniA5-ab-BK | 5' NH2-C6-TTTTTTTTTTTTTTTTTTTT-C18-GGCTGCCAACT-ACCGCTTCAC-AB- ATTCAACTCTGTC- Hexanediol-3' (SEQ ID NO:84) | 7,8,1 |
| NH2-T20-PC-spacer-UniC6-ab-BK | 5'-NH2-C6-TTTTTTTTTTTTTTTTTTTT-PC-C18-TCGACCCA-ACTACCGCTTCCA-AB-GGCCACTGAC- Hexanediol-3' (SEQ ID NO:85) | 7,8,1 |
| NH2-T20-spacer-UniA5sddC | 5' NH2-C6-TTTTTTTTTTTTTTTTTTTT-C18-GGCTGCCAACT-ACCGCTTCsAsCddC -3' (SEQ ID NO:86) | 9,10 |
| NH2-T20-PC-spacer-UniC6sddC | 5' -NH2-C6-TTTTTTTTTTTTTTTTTTTT-PC-C18-TCGACCCA-ACTACCGCTTCsCsAddC-3' (SEQ ID NO:87) | 9,10 |
| NH2-T20-spacer-UniA5s-Lg primer | 5' -NH2-C6-TTTTTTTTTTTTTTTTTTTT-C18-GGCTGCCAAC-TACCGCTTCAC-TATTCAACTCTGsTsC-3' (SEQ ID NO:88) | 11 |
| NH2-T20-PC-spacer-UniC6s-Lg | 5'-NH2-C6-TTTTTTTTTTTTTTTTTTTT-PC-C18-TCGACCCA-ACTACCGCTTCCA-TGGCCACTGsAsC-3' (SEQ ID NO:89) | 11 |
| NH2-T20-spacer-UniA5-Lg-sddC | 5' -NH2-C6-TTTTTTTTTTTTTTTTTTTT-C18-GGCTGCCAACT-ACCGCTTCAC-TATTCAACTCTGsTsCddC-3' (SEQ ID NO:90) | 12 |
| NH2-T20-PC-spacer-UniC6-Lg-sddC | 5'-NH2-C6-TTTTTTTTTTTTTTTTTTTT-PC-C18-TCGACCCA-ACTACCGCTTCCA-TGGCCACTGsAsCddC-3' (SEQ ID NO:91) | 12 |
| NH2-T20-spacer-UniA5-Lg | 5' NH2-C6-TTTTTTTTTTTTTTTTTTTT-C18-GGCTGCCAAC-TACCGCTTCAC-TATTCAACTCTGTC-3' (SEQ ID NO:92) | 13 |
| NH2-T20-PC-spacer-UniC6-Lg | 5' NH2-C6-TTTTTTTTTTTTTTTTTTTT-PC-C18-TCGACCCA-ACTACCGCTTCCA-TGGCCACTGAC-3' (SEQ ID NO:93) | 13 |
| NH2-T20-spacer-UniA27 | 5' NH2-C6-TTTTTTTTTTTTTTTTTTTT-C18- GGCTGTAGCA-CTGGCAACAAC-3' (SEQ ID NO:94) | 13 |
| NH2-T20-spacer-UniA27-Lg | 5' NH2-C6-TTTTTTTTTTTTTTTTTTTT-C18- GGCTGTAGCA-CTGGCAACAAC-ATTTCAACTCTGTC-3' (SEQ ID NO:95) | 13 |
| NH2-T20-spacer-UniA21-Lg | 5' NH2-C6-TTTTTTTTTTTTTTTTTTTT-C18- CCCTCAAACA-GGTGAATTATTAGCACTTGTAACAACA-3' (SEQ ID NO:96) | 14 |

Figure 46 (cont.)

Solid surface Primers (continued)

| Name | Sequence | Notes |
|---|---|---|
| NH2-T20-spacer-UniA22-Lg | 5' NH2-C6-TTTTTTTTTTTTTTTTTTTT-C18- CCCTCAAACA-GGTGAATTATTAGCCTTTTTTATCTCA-3' (SEQ ID NO:97) | 14 |
| NH2-T20-spacer-UniA23-Lg | 5' NH2-C6-TTTTTTTTTTTTTTTTTTTT-C18- CCCTTTGAGC-AGAGGTTCATTAGCACTTGTAACAACA-3' (SEQ ID NO:98) | 14 |
| NH2-T20-spacer-UniC24-Lg | 5' NH2-C6-TTTTTTTTTTTTTTTTTTTT-C18- CTTGTTGAGC-AGAGGTTCTTTTTTATCTTC-3' (SEQ ID NO:99) | 14 |
| NH2-T20-PC-spacer-UniC24-Lg | 5' NH2-C6-TTTTTTTTTTTTTTTTTTTT-PC-C18- CTTGTTGA-GCAGAGGTTCTTTTTTATCTTC-3' (SEQ ID NO:100) | 14 |
| NH2-T20-spacer-B5-UniA5 | 5' NH2-C6-TTTTTTTTTTTTTTTTTTTT-C18-TGT-CCACAGC-TGCACAGGGCAGGTCTTGTGGCTGCCAACTACCGCTTC-AC-3' (SEQ ID NO:101) | 15 |
| NH2-T20-spacer-B5-UniA5-Lg | 5' NH2-C6-TTTTTTTTTTTTTTTTTTTT-C18-TGT-CCACAGC-TGCACAGGGCAGGTCTTG-T-GGCTGCCAACTACCGCTTC-ACTATTCAACTCTGTC-3' (SEQ ID NO:102) | 15 |
| NH2-T20-spacer-B5-UniA27 | 5' NH2-C6-TTTTTTTTTTTTTTTTTTTT-C18-TGT-CCACAGCT-GCACAGGGCAGGTCTTG-T- GGCTGTAGCACTGGCAACA-AC-3' (SEQ ID NO:103) | 16 |
| NH2-T20-spacer-B5-UniA22 | 5' NH2-C6-TTTTTTTTTTTTTTTTTTTT-C18-TGT-CCACAGCT-GCACAGGGCAGGTCTTG-T- CCCTCAAACAGGTGAATTAT-TAGCCTTTTTTATCTCA -3' (SEQ ID NO:104) | 16 |
| NH2-T20-spacer-B5-UniA23 | 5' NH2-C6-TTTTTTTTTTTTTTTTTTTT-C18-TGT-CCACAGCT-GCACAGGGCAGGTCTTG-T- CCCTTTGAGCAGAGGTTCATT-AGCACTTGTAACAACA-3' (SEQ ID NO:105) | 16 |
| NH2-T20-spacer-B5-UniA5HE | 5' NH2-C6-TTTTTTTTTTTTTTTTTTTT-C18-ACCCACAGCTGC-ACAGGGCAGGTCTTG-T-GGCTGCCAACTACCGCTTCAC-3' (SEQ ID NO:106) | |
| NH2-T20-spacer-B5-UniA22HE | 5' NH2-C6-TTTTTTTTTTTTTTTTTTTT-C18-ACCCACAGCTGC-ACAGGGCAGGTCTTG-T-CCCTCAAACAGGTGAATTATTAG-CCTTTTTTATCTCA -3' (SEQ ID NO:107) | 17 |
| NH2-T20-spacer-B5-UniA23HE | 5' NH2-C6-TTTTTTTTTTTTTTTTTTTT-C18-ACCCACAGCTGC-ACAGGGCAGGTCTTG-T- CCCTTTGAGCAGAGGTTCATTAG-CACTTGTAACAACA -3' (SEQ ID NO:108) | 17 |

Figure 46 (cont.)

Solid surface Primers (continued)

| Name | Sequence | Notes |
|---|---|---|
| NH2-T20-spacer-B4s-UniA5HE | 5' NH2-C6-TTTTTTTTTTTTTTTTTTTT-C18- GGTCTTGGCCA -GTTGGCAAAA -T-GGCTGCCAACTACCGCTTCAC-3' (SEQ ID NO:109) | 17 |
| NH2-T20-spacer-B4s-UniA23HE | 5' NH2-C6-TTTTTTTTTTTTTTTTTTTT-C18- GGTCTTGGCCA -GTTGGCAAAA -T- CCCTTTGAGCAGAGGTTCATTAGCACTT -GTAACAACA -3' (SEQ ID NO:110) | 17 |
| NH2-T20-spacer-B11s-UniA5HE | 5' NH2-C6-TTTTTTTTTTTTTTTTTTTT-C18- GGGCAGGGCAG -TACTGTAGGAA -T-GGCTGCCAACTACCGCTTCAC-3' (SEQ ID NO:111) | 17 |
| NH2-T20-spacer-B11s-UniA23HE | 5' NH2-C6-TTTTTTTTTTTTTTTTTTTT-C18- GGGCAGGGCA -GTACTGTAGGAA -T- CCCTTTGAGCAGAGGTTCATTAGCAC -TTGTAACAACA -3' (SEQ ID NO:112) | 17 |
| NH2-T14dUT5-spacer-UniC6 | 5' NH2-C6-TTTTTTTTTTTTTTdUTTTTT-C18-TCGACCCAACT -ACCGCTTCCA-3' (SEQ ID NO:113) | 18 |
| NH2-T20-spacer-UniC6dU | 5' NH2-C6-TTTTTTTTTTTTTTTTTTTT-C18-TCGACCCAACdU -ACCGCTTCCA-3' (SEQ ID NO:114) | 18 |
| NH2- T14dUT5-spacer-UniC24 | 5' NH2-C6-TTTTTTTTTTTTTTdUTTTTT-C18- CTTGTTGAGC -AGAGGTTCTTTTTTATCTTC-3' (SEQ ID NO:115) | 18 |
| NH2-T20-spacer-UniC24dU | 5' NH2-C6-TTTTTTTTTTTTTTTTTTTT-C18- CTTGTdUGAGC -AGAGGTTCTTTTTTATCTTC-3' (SEQ ID NO:116) | 18 |
| D1-spacer-T14dUT5-NH2 | 5'- GCCGCCTGAGGTCTGGTTTGCAACTG-C18-TTTTTdUTTT -TTTTTTTTTT-C6-NH2 3' (SEQ ID NO:117) | 18,19 |
| NH2-T20-spacer-B0.9s-UniA5HE | 5' NH2-C6-TTTTTTTTTTTTTTTTTTTT-C18- GTACTGTAGGA -AGAGGAAGGAGACA -T-GGCTGCCAACTACCGCTTCAC-3' (SEQ ID NO:118) | 17 |
| NH2-T20-spacer-B11-Lg-UniA5HE | 5' NH2-C6-TTTTTTTTTTTTTTTTTTTT-C18- GGGCAGGGCA -GTACTGTAGGAAGAGG -T-GGCTGCCAACTACCGCTTCAC-3' (SEQ ID NO:119) | 17 |
| NH2-T20-spacer-UniC6dU-2 | 5' NH2-C6-TTTTTTTTTTTTTTTTTTTT-C18-TCGACCCAACTA -CCGCdUTCCA-3' (SEQ ID NO:120) | 20 |
| NH2-T20-spacer-B5-UniA5 | 5' NH2-C6-TTTTTTTTTTTTTTTTTTTT-C18-TGT-CCACAGCT -GCACAGGGCAGGTCTTG-TGGCTGCCAACTACCGCTTCAC-3' (SEQ ID NO:121) | 21 |
| NH2-T20-spacer-B4s-UniA5HE | 5' NH2-C6-TTTTTTTTTTTTTTTTTTTT-C18- GGTCTTGGCCA -GTTGGCAAAA -T-GGCTGCCAACTACCGCTTCAC-3' (SEQ ID NO:122) | 21 |

Figure 46 (cont.)

Solid surface Primers (continued)

| Name | Sequence | Notes |
|---|---|---|
| NH2-T20-spacer-B11s-UniA5HE | 5' NH2-C6-TTTTTTTTTTTTTTTTTTTT-C18- GGGCAGGGCAG-TACTGTAGGAA -T-GGCTGCCAACTACCGCTTCAC-3' (SEQ ID NO:123) | 21 |
| NH2-T20-spacer-UniA23-Lg | 5' NH2-C6-TTTTTTTTTTTTTTTTTTTT-C18-CCCTTTGAGCAGAGGTTCATTAGCACTTGTAACAACA-3' (SEQ ID NO:124) | |
| SeqTemp2.1 | 5' NH2-C6-TTTTTTTTTTTTTTTT-C18- GCAGCTGGAG CTGGA-GAGAC GACAG GGCTGGAGAGACGACAGGGCTGGTTGC -3' (SEQ ID NO:125) | 22 |
| SeqTemp4.1 | 5' NH2-C6-TTTTTTTTTTTTTTTT-C18- TGCCCTATGAGCCGC CTGAGGTCTGGTTTGCAACTGGAGTCTCTGGGA-GG -3' (SEQ ID NO:126) | 22 |

Notes
1. 3' Hexanediol: Hexanediol is a six carbon glycol spacer that is capable of blocking extension by DNA polymerases. This 3' modification is capable of supporting synthesis of longer oligos.
2. PC-C18: Photocleavable spacer phosphoramidite
3. 8OdG: 8-oxo-dG-CE Phosphoramidite
4. AB: Abasic II Phosphoramidite
5. Primers containing thiophosphates to protect the 3' end when using proofreading polymerase. Also D primer with photocleavable linker. Part 2,
6. s: thiophosphate linkage
7. Primers to block the 3' end for release with EndoIV only when binding to target, Part 3.
8. AB:Abasic Phosphoramidite, tetrahydrofuran
9. Primers with ddC to block the 3' end for release with by proofreading polymerase, Part 4
10. Dideoxycytidine (ddC) is a 3' chain terminator that prevents 3' extension by DNA polymerases.
11. Primers with thiophosphate, may bind to array or replication proteins better, Part 5
12. Primers to be made longer with thiophosphate, containing ddC to block 3' end, but released by proofreading polymerase Part 6
13. Long Primers for Array spotting may bind to array or replication proteins better, Part 3
14. Long Primers for Array spotting may bind to array or replication proteins better, Part 4
15. Long Snake Primers for Array spotting may bind to array better, Part 2
16. Long Snake Primers for Array spotting may bind to array better, Part 2
17. Long Snake Primers that allow for the complement to Hairpin and Extend from the 3' end for Array spotting may bind to array better, Part 2
18. "C" Primers for amplification Part 1
19. dU-CE Phosphoramidite: 5'-Dimethoxytrityl-2'-deoxyUridine,3'-[(2-cyanoethyl)-(N,N-diisopropyl)]-phosphoramidite
20. This primer is for synthesis of the opposite strand after treatment with T4 kinase and Taq polymerase (with 5'-3' exonuclease activity)
21. These primers are for making more of the 14G arrays
22. These primers are for printing on the array to serve as controls for the sequencing reaction.

Figure 46 (cont.)

Sequoia Amplification primers: p53 Template

| Name | Sequence | Note |
|---|---|---|
| UniA5 | 5'-GGCTGCCAACTACCGCTTCAC-3' (SEQ ID NO:127) | 7 |
| UniC6 | 5'-TCGACCCAACTACCGCTTCCA-3' (SEQ ID NO:128) | 7 |
| UniA5-A1 | 5'-GGCTGCCAACTACCGCTTCAC-ATGCCCTGACTTTCAACTCT-GTCTC-3' (SEQ ID NO:129) | |
| UniA5-A1.10 | 5'-GGCTGCCAACTACCGCTTCAC-TA-TTCAACTCTGTCTCCTTC-CTCTTCCTAC-3' (SEQ ID NO:130) | |
| UniC6-C1.1 | 5'-TCGACCCAACTACCGCTTCCA-CTCACCTGGAGGGCCACTG-AC-3' (SEQ ID NO:131) | |
| UniC6-C4.1 | 5'-TCGACCCAACTACCGCTTCCA-T-GGCCACTGACAACCACCC-TTAAC-3' (SEQ ID NO:132) | |
| A1-B11 Bridge | 5'-TGTGCCCTGACTTTCAACTCTGTCTC-CTTCCTCTTCCTACAG-TACTGCCCTGCCCTC-3' (SEQ ID NO:133) | |
| A1-B12 Bridge | 5'-TGTGCCCTGACTTTCAACTCTGTCTC-CTTCCTCTTCCTACA-GTACCGCCCTGCCCTC-3' (SEQ ID NO:134) | |
| A1-B13 Bridge | 5'-TGTGCCCTGACTTTCAACTCTGTCTC-CTTCCTCTTCCCGCA-GTACCGCCCTGCCCTC-3' (SEQ ID NO:135) | |
| A1-B14 Bridge | 5'-TGTGCCCTGACTTTCAACTCTGTCTC-CTTCCTCTTCCCTCAG-TACCTCCCTGCCCTC-3' (SEQ ID NO:136) | |
| UniA5-Lg | 5'-GGCTGCCAACTACCGCTTCACTATTCAACTCTGTC-3' (SEQ ID NO:137) | 1 |
| UniC6-Lg | 5'-TCGACCCAACTACCGCTTCCATGGCCACTGAC-3' (SEQ ID NO:138) | 1 |
| UniA21 | 5'-CCCTCAAACAGGTGAATTATTAGCACTTGTAACAACA-3' (SEQ ID NO:139) | 1 |
| UniA22 | 5'-CCCTCAAACAGGTGAATTATTAGCCTTTTTTATCTCA-3' (SEQ ID NO:140) | 1 |
| UniA23 | 5'-CCCTTTGAGCAGAGGTTCATTAGCACTTGTAACAACA-3'(SEQ ID NO:141) | 1 |
| UniA27-LG | 5'-GGCTGTAGCACTGGCAACAACATTTCAACTCTGTC-3' (SEQ ID NO:142) | 1 |
| UniC24 | 5'-CTTGTTGAGCAGAGGTTCTTTTTTATCTTC-3' (SEQ ID NO:143) | 1 |
| UniA5-A1.10 | 5'-GGCTGCCAACTACCGCTTCAC-TA-TTCAACTCTGTCTCCTTC-CTCTTCCTAC-3' (SEQ ID NO:144) | 2 |
| UniA21-A1.10 | 5'-CCCTCAAACAGGTGAATTATTAGCACTTGTAACAACATTTCA-ACTCTGTCTCCTTCCTCTTC-3' (SEQ ID NO:145) | 2 |
| UniA22-A1.10 | 5'-CCCTCAAACAGGTGAATTATTAGCCTTTTTTATCTCATTTCAA-CTCTGTCTCCTTCCTCTTC-3' (SEQ ID NO:146) | 2 |

Figure 47

Sequoia Amplification primers: p53 Template (continued)

| Name | Sequence | Note |
|---|---|---|
| UniA23-A1.10 | 5'-CCCTTTGAGCAGAGGTTCATTAGCACTTGTAACAACATTTCA-ACTCTGTCTCCTTCCTCTTC-3' (SEQ ID NO:147) | 2 |
| UniA27-A1.10 | 5'-GGCTGTAGCACTGGCAACAAC-AT-TTTCAACTCTGTCTCCT-TCCTCTTC-3' (SEQ ID NO:148) | 2 |
| UniC6-C4.1 | 5'-TCGACCCAACTACCGCTTCCA-T-GGCCACTGACAACCACCC-TTAAC-3' (SEQ ID NO:149) | 2 |
| UniC24-C4.1 | 5'- CTTGTTGAGCAGAGGTTCTTTTTTATCTTCATGGCCACTGA-CAACCACCCTTAAC-3' (SEQ ID NO:150) | 2 |
| T5-spacer-B5-UniA5 | 5'-TTTTT-C18-TGTCCACAGCTGCACAGGGCAGGTCTTGTGGC TGCCAACTACCGCTTCAC-3' (SEQ ID NO:151) | 3 |
| T5-spacer-B5-UniA5-Lg | 5'-TTTTT-C18-TGTCCACAGCTGCACAGGGCAGGTCTTGTGG-CTGCCAACTACCGCTTCAC-TATTCAACTCTGTC-3' (SEQ ID NO:152) | 3 |
| T5-spacer-B5-UniA27 | 5'-TTTTT-C18-TGT-CCACAGCTGCACAGGGCAGGTCTTGTG-GCTGTAGCACTGGCAACAAC-3' (SEQ ID NO:153) | 3 |
| T5-spacer-B5-UniA22 | 5' -TTTTT-C18-TGTCCACAGCTGCACAGGGCAGGTCTTGT CC-CTCAAACAGGTGAATTATTAGCCTTTTTTATCTCA-3' (SEQ ID NO:154) | 3 |
| T5-spacer-B5-UniA23 | 5'-TTTTT-C18-TGTCCACAGCTGCACAGGGCAGGTCTTGTCCC-TTTGAGCAGAGGTTCATTAGCACTTGTAACAACA-3' (SEQ ID NO:155) | 3 |
| T5-spacer-B5-UniA22HE | 5'-TTTTT-C18-ACCCACAGCTGCACAGGGCAGGTCTTGTCCCT-CAAACAGGTGAATTATTAGCCTTTTTTATCTCA -3' (SEQ ID NO:156) | 4 |
| T5-spacer-B5-UniA23HE | 5'-TTTTT-C18-ACCCACAGCTGCACAGGGCAGGTCTTGTCCCT-TTGAGCAGAGGTTCATTAGCACTTGTAACAACA -3' (SEQ ID NO:157) | 4 |
| T5-spacer-B5-UniA5HE | 5'-TTTTT-C18-ACCCACAGCTGCACAGGGCAGGTCTTGTGGC-TGCCAACTACCGCTTCAC-3' (SEQ ID NO:158) | 4 |
| UniC6-C2.1 | 5'-TCGACCCAACTACCGCTTCCA-T-GGCCAGACCTAAGAGCA-ATCAGTGAGGAATC-3' (SEQ ID NO:159) | 5 |
| UniC24-C2.1 | 5'-CTTGTTGAGCAGAGGTTCTTTTTTATCTTC-AT-GGCCAGAC-CTAAGAGCAATCAGTGAGGAATC-3' (SEQ ID NO:160) | 5 |
| Primer B11sm | 5'-GAGGGCAGGGCAGTACTGTAGGAA-3' (SEQ ID NO:161) | 6 |
| UniA25 | 5'-TCGACCCAACTACCCGAAGCA-3' (SEQ ID NO:162) | 7 |
| UniC26 | 5'-GGCTGCCAACTACCCGAAGAC-3' (SEQ ID NO:163) | 7 |
| UniA31 | 5'-CTTGCATACAGGTTAATTATTTGAGCAGAGGTTCAC-3' (SEQ ID NO:164) | 7 |

Figure 47 (cont.)

Sequoia Amplification primers: p53 Template (continued)

| Name | Sequence | Note |
|---|---|---|
| UniC32 | 5'-CCCTTTTATCTTCTTGAGCAGAGGTTCACA-3' (SEQ ID NO:165) | 7 |
| UniA33 | 5'-CTTTAACTCGTGAGGTTCTAATCGTTTTTTATCTTC-3' (SEQ ID NO:166) | 7 |
| UniC34 | 5'-GCACTTGTAACAGAGGTTCTAATCGTCAACA-3' (SEQ ID NO:167) | 7 |
| UniA25-A1.10 | 5'-TCGACCCAACTACCCGAAGCA-AT-TTCAACTCTGTCTCCTT-CCTCTTCCTAC-3' (SEQ ID NO:168) | 8 |
| UniA31-A1.10 | 5'-CTTGCATACAGGTTAATTATTTGAGCAGAGGTTCAC-A-TTTC-AACTCTGTCTCCTTCCTCTTC-3' (SEQ ID NO:169) | 8 |
| UniA33-A1.10 | 5'-CTTTAACTCGTGAGGTTCTAATCGTTTTTTATCTTCATTTCAA-CTCTGTCTCCTTCCTCTTC-3' (SEQ ID NO:170) | 8 |
| UniC26-C4.1 | 5'-GGCTGCCAACTACCCGAAGACATAGGCCACTGACAACCA-CCCTTAAC-3' (SEQ ID NO:171) | 8 |
| UniC32-C4.1 | 5'-CCCTTTTATCTTCTTGAGCAGAGGTTCACA-ATA-GGCCACT-GACAACCACCCTTAAC-3' (SEQ ID NO:172) | 8 |
| UniC34-C4.1 | 5'-GCACTTGTAACAGAGGTTCTAATCGTCAACA-ATA-GGCCAC-TGACAACCACCCTTAAC-3' (SEQ ID NO:173) | 8 |
| T5-spacer-B4s-UniA5HE | 5'-TTTTTC18GGTCTTGGCCAGTTGGCAAAATGGCTGCCAAC-TACCGCTTCAC-3' (SEQ ID NO:174) | 9 |
| T5-spacer-B4s-UniA23HE | 5'-TTTTT-C18- GGTCTTGGCCAGTTGGCAAAATCCCTTTGAG-CAGAGGTTCATTAGCACTTGTAACAACA-3' (SEQ ID NO:175) | 9 |
| T5-spacer-B11s-UniA5HE | 5'- TTTTT-C18-GGGCAGGGCAGTACTGTAGGAATGGCTGCC-AACTACCGCTTCAC-3' (SEQ ID NO:176) | 9 |
| T5-spacer-B11s-UniA23HE | 5'-TTTTT-C18-GGGCAGGGCAGTACTGTAGGAATCCCTTTG-AGCAGAGGTTCATTAGCACTTGTAACAACA-3' (SEQ ID NO:177) | 9 |
| T5-spacer-B0.9s-UniA5HE | 5'-TTTTT-C18-GTACTGTAGGAAGAGGAAGGAGACATGGCT-GCCAACTACCGCTTCAC-3' (SEQ ID NO:178) | 9 |
| T5-spacer-B11-Lg-UniA5HE | 5'-TTTTT-C18-GGGCAGGGCAGTACTGTAGGAAGAGGTGGCT-GCCAACTACCGCTTCAC-3' (SEQ ID NO:179) | 9 |
| p53-Ex7-R1 | 5'-GTGGATGGGTAGTAGTATGGAAGAAATC-3' (SEQ ID NO:180) | 10 |
| p53-Ex7-R2 | 5'-AACTGAGTGGGAGCAGTAAGGAGATTC-3' (SEQ ID NO:181) | 10 |
| UniC6-C12.1 | 5'-TCGACCCAACTACCGCTTCCATAAGTGGCTCCTGACCTGG-AGTCTTC-3' (SEQ ID NO:182) | 10 |
| p53-Ex9-R3 | 5'-CGGTGGCTCACGCCTGTAATC-3' (SEQ ID NO:183) | 11 |
| p53-Ex9-R4 | 5'-CACTGTAATCCAGCCTGGGCAAC-3' (SEQ ID NO:184) | 11 |

Figure 47 (cont.)

Sequoia Amplification primers: p53 Template (continued)

| Name | Sequence | Note |
|---|---|---|
| UniC6-C20.1 | 5'-TCGACCCAACTACCGCTTCCAATCAACATGGTGAAATTCTA-TCTCTAC-3' (SEQ ID NO:185) | 11 |
| UniC6-C20.2 | 5' TCGACCCAACTACCGCTTCCATAGGCAGATCACAAGGTCA-GGAGTTC 3' (SEQ ID NO:186) | 11 |
| p53_Ex5_6_F | 5'-TTTGTTTCTTTGCTGCCGTCTTC-3' (SEQ ID NO:187) | |
| p53_Ex5-6_R | 5'-AGGTCAAATAAGCAGCAGGAGAAAG-3' (SEQ ID NO:188) | |

Note

1. LONG Amplification Primers, for just PCR amplifications and in liquid replication Part 1.

2. Amplification conversion Primers, Part 2.

3. LONG Snake Primers, for just PCR amplifications and in liquid isothermal amplification Part 1.

4. Long Snake Primers that allow for the complement to Hairpin and Extend from the 3' end, for just PCR amplifications and in liquid isothermal amplification Part 1.

5. Bridge Primers that allow for smaller amplicon in liquid isothermal amplification Part 1.

6. Potential "Booster" primer, Part 2.

7. Amplification Primers, Part 1.

8. Amplification conversion Primers, Part 2.

9. Long Snake Primers that allow for the complement to Hairpin and Extend from the 3' end, for just PCR amplifications and in liquid isothermal amplification Part 1.

10. These primers are for making 1.2 kb long fragments.

11. These primers are for making 2 kb long fragments.

Figure 47 (cont.)

Optimizing conditions for in liquid "Sequoia" amplification

Primers:

1. UniA5    +  UniC6
2. B5-UniA5 +  UniC6
3. B5-UniA5HE          +  UniC6
4. UniA22   +  UniC24
5. B5-UniA22+  UniC24
6. B5-UniA22HE +  UniC24
7. B5-UniA23+  UniC24
8. B5-UniA23HE +  UniC24

Top picture 1-8   Same primers  0.5 M betaine 9-16  Same primers  1.0 M betaine

Bottom picture 1-8  same primers,   No B11

9-16 same primers,  plus B11.

Solid Phase Amplification on COC substrates
Array Layout (#L2)

1. NH2-T20-spacer-UniA5
2. NH2-T20-PC-spacer-UniC6
3. NH2-T20-spacer-UniA5    +    NH2-T20-PC-spacer-UniC6

4. NH2-T20-spacer-UniA5s
5. NH2-T20-PC-spacer-UniC6s
6. NH2-T20-spacer-UniA5 s    +    NH2-T20-PC-spacer-UniC6s 7. NH2-T20-spacer-UniA5
8. NH2-T19U-spacer-UniC6
9. NH2-T20-spacer-UniA5    +    NH2-T19U-spacer-UniC6

10. NH2-T20-spacer-UniA5
11. NH2-T20-spacer-UniC6dU
12. NH2-T20-spacer-UniA5    +    NH2-T19U-spacer-UniC6

13. NH2-T20-spacer-UniA5s
14. NH2-T19U-spacer-UniC6s
15. NH2-T20-spacer-UniA5 s    +    NH2-T19U-spacer-UniC6s 16. NH2-T20-spacer-UniA5 s + B11-spacer-T20-NH2 + NH2-T19U-spacer-UniC6s
17. NH2-T20-spacer-UniA5s + D1-spacer-T19U-NH2 + NH2-T19U-spacer-UniC6s
18. NH2-T20-spacer-UniA5 s + B11-spacer-T20-NH2
    + D1-spacer-T19U-NH2 + NH2-T19U-spacer-UniC6s 19. Cy3-T20-NH2
20. Cy5-T20-NH2
21. NH2-zip1
22. Cy3-T20-NH2
23. Cy5-T20-NH2
24. NH2-zip1

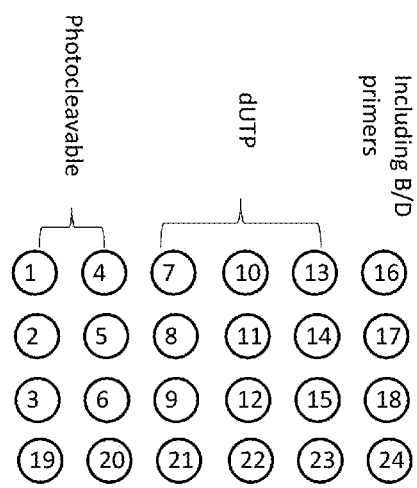

Figure 51

Solid Phase Amplification on COP substrates
Array Layout (#10E)

1. NH2-T20-spacer-UniA23
2. NH2-T20-PC-spacer-UniC24
3. NH2-T20-spacer-UniA23 + NH2-T20-PC-spacer-UniC24
4. NH2-T20-spacer-UniA23 + B11-spacer-T20-NH2 + NH2-T20-PC-spacer-UniC24
5. NH2-T20-spacer-UniA23 + D1-PC-spacer-T20-NH2 + NH2-T20-PC-spacer-UniC24
6. NH2-T20-spacer-UniA23 + B11-spacer-T20-NH2
   + D1-PC-spacer-T20-NH2 + NH2-T20-PC-spacer-UniC24

7. NH2-T20-spacer-B5-UniA23
8. NH2-T20-PC-spacer-UniC24
9. NH2-T20-spacer-B5-UniA23 + NH2-T20-PC-spacer-UniC24
10. NH2-T20-spacer-B5-UniA23 + B11-spacer-T20-NH2 + NH2-T20-PC-spacer-UniC24
11. NH2-T20-spacer-B5-UniA23 + D1-PC-spacer-T20-NH2 + NH2-T20-PC-spacer-UniC24
12. NH2-T20-spacer-B5-UniA23 + B11-spacer-T20-NH2
    + D1-PC-spacer-T20-NH2 + NH2-T20-PC-spacer-UniC24

13. NH2-T20-spacer-B5-UniA23HE
14. NH2-T20-PC-spacer-UniC24
15. NH2-T20-spacer-B5-UniA23HE + NH2-T20-PC-spacer-UniC24
16. NH2-T20-spacer-B5-UniA23HE + B11-spacer-T20-NH2 + NH2-T20-PC-spacer-UniC24
17. NH2-T20-spacer-B5-UniA23HE + D1-PC-spacer-T20-NH2 + NH2-T20-PC-spacer-UniC24
18. NH2-T20-spacer-B5-UniA23HE + B11-spacer-T20-NH2
    + D1-PC-spacer-T20-NH2 + NH2-T20-PC-spacer-UniC24

19. NH2-zip1
20. Cy3-T20-NH2
21. Cy5-T20-NH2
22. NH2-zip1
23. Cy3-T20-NH2
24. Cy5-T20-NH2

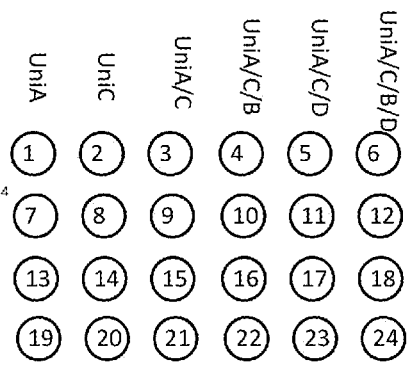

Figure 53

Solid Phase Amplification on COC substrates
Array Layout (#14G)

1. NH2-T20-spacer-UniA5
2. NH2-T20-spacer-UniC6dU
3. NH2-T20-spacer-UniA5    +    NH2-T20-spacer-UniC6dU
4. NH2-T20-spacer-UniA5 + B11-spacer-T20-NH2 + NH2-T20-spacer-UniC6dU
5. NH2-T20-spacer-B5-UniA5    +    NH2-T20-spacer-UniC6dU
6. NH2-T20-spacer-B5-UniA5 + B11-spacer-T20-NH2 + NH2-T20-spacer-UniC6dU 7. NH2-T20-spacer-B5-UniA5HE
8. NH2-T20-spacer-B5-UniA5HE    +    NH2-T20-spacer-UniC6dU
9. NH2-T20-spacer-B5-UniA5HE + B11-spacer-T20-NH2 + NH2-T20-spacer-UniC6dU
10. NH2-T20-spacer-B4s-UniA5HE
11. NH2-T20-spacer-B4s-UniA5HE    +    NH2-T20-spacer-UniC6dU
12. NH2-T20-spacer-B4s-UniA5HE + B11-spacer-T20-NH2 + NH2-T20-spacer-UniC6dU 13. NH2-T20-spacer-B11s-UniA5HE
14. NH2-T20-spacer-B11s-UniA5HE    +    NH2-T20-spacer-UniC6dU
15. NH2-T20-spacer-B11-Lg-UniA5HE
16. NH2-T20-spacer-B11-Lg-UniA5HE    +    NH2-T20-spacer-UniC6dU
17. NH2-T20-spacer-B0.9s-UniA5HE
18. NH2-T20-spacer-B0.9s-UniA5HE    +    NH2-T20-spacer-UniC6dU Spotting concentration: 50 uM
Marker/Control row
Cy3-T20-NH2
Cy5-T20-NH2
NH2-zip1 (50uM, free 3 end)

(Try 1 in 1,000 dilution, no added primers)

1. Uni A5-C6 Template:    UniA5-A1.10    +    UniC6-C4.1

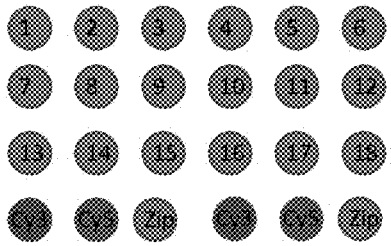
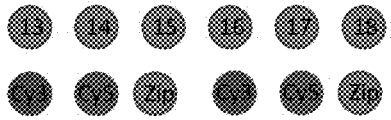

Figure 55A

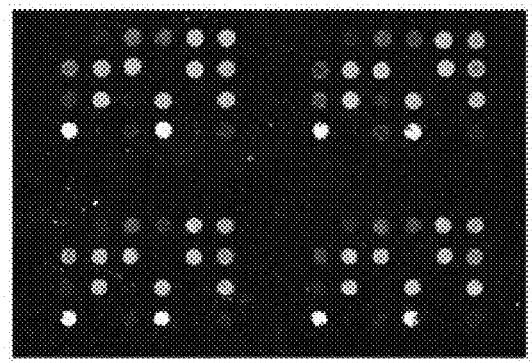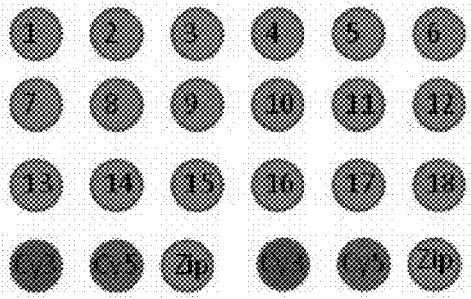
Figure 55B

Solid Phase Amplification on COC substrates
Array Layout (#14G)

1. NH2-T20-spacer-UniA5
2. NH2-T20-spacer-UniC6dU
3. NH2-T20-spacer-UniA5   +   NH2-T20-spacer-UniC6dU
4. NH2-T20-spacer-UniA5 + B11-spacer-T20-NH2 + NH2-T20-spacer-UniC6dU
5. NH2-T20-spacer-B5-UniA5   +   NH2-T20-spacer-UniC6dU
6. NH2-T20-spacer-B5-UniA5 + B11-spacer-T20-NH2 + NH2-T20-spacer-UniC6dU 7. NH2-T20-spacer-B5-UniA5HE
8. NH2-T20-spacer-B5-UniA5HE   +   NH2-T20-spacer-UniC6dU
9. NH2-T20-spacer-B5-UniA5HE + B11-spacer-T20-NH2 + NH2-T20-spacer-UniC6dU
10. NH2-T20-spacer-B4s-UniA5HE
11. NH2-T20-spacer-B4s-UniA5HE   +   NH2-T20-spacer-UniC6dU
12. NH2-T20-spacer-B4s-UniA5HE + B11-spacer-T20-NH2 + NH2-T20-spacer-UniC6dU 13. NH2-T20-spacer-B11s-UniA5HE
14. NH2-T20-spacer-B11s-UniA5HE   +   NH2-T20-spacer-UniC6dU
15. NH2-T20-spacer-B11-Lg-UniA5HE
16. NH2-T20-spacer-B11-Lg-UniA5HE   +   NH2-T20-spacer-UniC6dU
17. NH2-T20-spacer-B0.9s-UniA5HE
18. NH2-T20-spacer-B0.9s-UniA5HE   +   NH2-T20-spacer-UniC6dU Spotting concentration: 50 uM
Marker/Control row
 Cy3-T20-NH2
Cy5-T20-NH2
NH2-zip3 (50uM, free 3 end)

(Try 1 in 1,000 dilution, no added primers)

1. Uni A5-C6 Template:   UniA5-A1.10   +   UniC6-C4.1

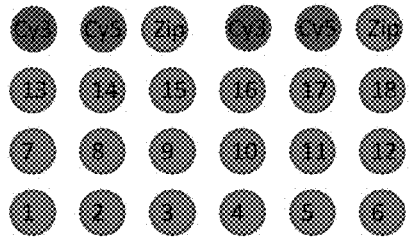

Figure 56

Sequoia Amplification
(0.25M Betaine)

Forward Probe Hybridization

Reverse Probe Hybridization
1/1000 dilution of template; no primer in solution; 3173 exo- polymerase.
PCR /Denature 1 min@~95°C /Forward probe hybridization/ Imaging 1/ USER 15min@~37°C/
/Denature 1 min@~95°C /Reverse probe hybridization/ Imaging 2

Sequoia Amplification
(0.5M Betaine)
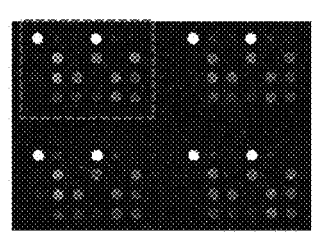
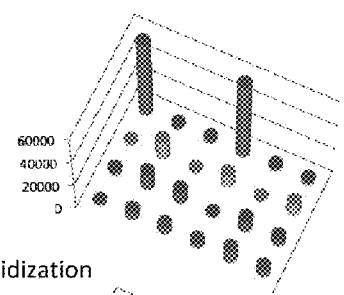
Forward Probe Hybridization
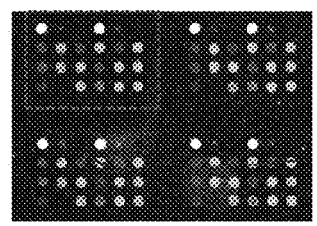
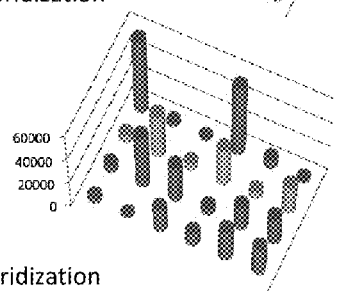
Reverse Probe Hybridization
1/1000 dilution of template; no primer in solution; 3173 exo- polymerase.
PCR /Denature 1 min@~95°C /Forward probe hybridization/ Imaging 1/ USER 15min@~37°C/
/Denature 1 min@~95°C /Reverse probe hybridization/ Imaging 2
Figure 58C

Solid Phase PCR
Different Betaine Concentration

1/1000 dilution of template; no primer in solution; 3173 exo- polymerase.

PCR /Denature 1 min@~95°C /Forward probe hybridization/ Imaging 1(top row) / USER 15min@~37°C/ /Denature 1 min@~95°C /Reverse probe hybridization/ Imaging 2(bottom row)

Fluorescence intensities from each spot of array #14G after USER enzyme cleavage and reverse probe hybridization.

| Spot | PCR primers | 0 M Betaine | 0.25M Betaine | 0.5 M Betaine |
|---|---|---|---|---|
| 1 | NH₂-T20-spacer-UniA5 | 2021 | 638 | 3634 |
| 2 | NH₂-T20-spacer-UniC6dU | 51 | -1182 | 346 |
| 3 | NH₂-T20-spacer-UniA5   +   NH₂-T20-spacer-UniC6dU | 21004 | 16940 | 19312 |
| 4 | NH₂-T20-spacer-UniA5 + B11-spacer-T20-NH₂ + NH₂-T20-spacer-UniC6dU | 8859 | 16871 | 10455 |
| 5 | NH₂-T20-spacer-B5-UniA5   +   NH₂-T20-spacer-UniC6dU | 45900 | 53106 | 25483 |
| 6 | NH₂-T20-spacer-B5-UniA5 + B11-spacer-T20-NH2 + NH₂-T20-spacer-UniC6dU | 24983 | 36305 | 22909 |
| 7 | NH₂-T20-spacer-B5-UniA5HE | 4817 | 11142 | 5847 |
| 8 | NH₂-T20-spacer-B5-UniA5HE   +   NH₂-T20-spacer-UniC6dU | 39003 | 50626 | 42216 |
| 9 | NH₂-T20-spacer-B5-UniA5HE + B11-spacer-T20-NH₂ + NH₂-T20-spacer-UniC6dU | 35831 | 52247 | 29134 |
| 10 | NH₂-T20-spacer-B4s-UniA5HE | 3957 | 6291 | 5493 |
| 11 | NH₂-T20-spacer-B4s-UniA5HE   +   NH₂-T20-spacer-UniC6dU | 30199 | 53340 | 19372 |
| 12 | NH₂-T20-spacer- B4s-UniA5HE + B11-spacer-T20-NH₂ + NH₂-T20-spacer-UniC6dU | 21301 | 41460 | 21833 |
| 13 | NH₂-T20-spacer-B11s-UniA5HE | 3594 | 5369 | 5431 |
| 14 | NH₂-T20-spacer-B11s-UniA5HE   +   NH₂-T20-spacer-UniC6dU | 31666 | 50699 | 33983 |
| 15 | NH₂-T20-spacer-B11-Lg-UniA5HE | 3592 | 6171 | 5471 |
| 16 | NH₂-T20-spacer-B11-Lg-UniA5HE   +   NH₂-T20-spacer-UniC6dU | 45547 | 54360 | 30136 |
| 17 | NH₂-T20-spacer-B0.9s-UniA5HE | 4907 | 5533 | 5682 |
| 18 | NH₂-T20-spacer-B0.9s-UniA5HE   +   NH₂-T20-spacer-UniC6dU | 32824 | 47735 | 22355 |
| 19 | Cy3-T20-NH₂ | 54978 | 54131 | 58254 |
| 20 | Cy5-T20-NH₂ | 771 | 1258 | 2327 |
| 21 | NH₂-zip3 | 440 | -416 | 693 |
| 22 | Cy3-T20-NH₂ | 47521 | 53820 | 55860 |
| 23 | Cy5-T20-NH₂ | 929 | 1751 | 7112 |
| 24 | NH₂-zip3 | 556 | -584 | 980 |

Figure 59B

Solid Phase Amplification on COP substrates
Array Layout (#14G-2)

1. NH2-T20-spacer-UniA5
2. NH2-T20-spacer-UniC6dU
3. NH2-T20-spacer-UniA5    +    NH2-T20-spacer-UniC6dU
4. NH2-T20-spacer-UniA5 + B11-spacer-T20-NH2 + NH2-T20-spacer-UniC6dU
5. NH2-T20-spacer-B5-UniA5    +    NH2-T20-spacer-UniC6dU
6. NH2-T20-spacer-B5-UniA5 + B11-spacer-T20-NH2 + NH2-T20-spacer-UniC6dU 7. NH2-T20-spacer-B5-UniA5HE
8. NH2-T20-spacer-B5-UniA5HE    +    NH2-T20-spacer-UniC6dU
9. NH2-T20-spacer-B5-UniA5HE + B11-spacer-T20-NH2 + NH2-T20-spacer-UniC6dU
10. NH2-T20-spacer-B4s-UniA5HE
11. NH2-T20-spacer-B4s-UniA5HE    +    NH2-T20-spacer-UniC6dU
12. NH2-T20-spacer-B4s-UniA5HE + B11-spacer-T20-NH2 + NH2-T20-spacer-UniC6dU 13. NH2-T20-spacer-B11s-UniA5HE
14. NH2-T20-spacer-B11s-UniA5HE    +    NH2-T20-spacer-UniC6dU
15. NH2-T20-spacer-B11-Lg-UniA5HE
16. NH2-T20-spacer-B11-Lg-UniA5HE    +    NH2-T20-spacer-UniC6dU
17. NH2-T20-spacer-B0.9s-UniA5HE
18. NH2-T20-spacer-B0.9s-UniA5HE    +    NH2-T20-spacer-UniC6dU 19. Cy3-T20-NH2
20. NH2-zip3
21. Temp 4.1
22. Cy3-T20-NH2
23. NH2-zip3
24. Temp 4.1

(1 in 1,000 dilution, no added primers)

1. Uni A5-C6 Template:    UniA5-A1.10    +    UniC6-C4.1

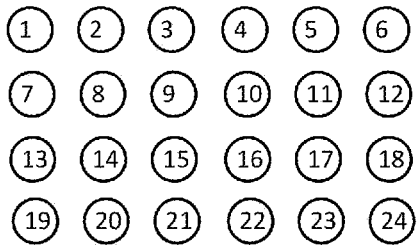

Figure 60

(A) Extension/termination with 5'-Cy3-23R primer, dTTP and Cy5-ddGTP. Left and right panels are fluorescence images collected from Cy3 and Cy5 detection channels, respectively.

(B) Extension/termination with 5'-Cy3-23R primer and Cy5-ddGTP.
Left and right panels are fluorescence images collected from Cy3 and Cy5 channels, respectively.

SEQUENCE LISTING

```
<160> NUMBER OF SEQ ID NOS: 188

<210> SEQ ID NO 1
<211> LENGTH: 9
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(5)
<223> OTHER INFORMATION: N at position 5 is deoxyinosine
<220> FEATURE:
<221> NAME/KEY: misc_feature
<222> LOCATION: (7)..(9)
<223> OTHER INFORMATION: N at positions 7-9 is 5-nitroindole

<400> SEQUENCE: 1 nnanncnnn                                                           9

<210> SEQ ID NO 2
<211> LENGTH: 9
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
```

```
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(5)
<223> OTHER INFORMATION: N at position 5 is deoxyinosine
<220> FEATURE:
<221> NAME/KEY: misc_feature
<222> LOCATION: (7)..(9)
<223> OTHER INFORMATION: N at positions 7-9 is 5-nitroindole

<400> SEQUENCE: 2 nngnncnnn                                                                  9

<210> SEQ ID NO 3
<211> LENGTH: 9
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(5)
<223> OTHER INFORMATION: N at position 5 is deoxyinosine
<220> FEATURE:
<221> NAME/KEY: misc_feature
<222> LOCATION: (7)..(9)
<223> OTHER INFORMATION: N at positions 7-9 is 5-nitroindole

<400> SEQUENCE: 3 nncnncnnn                                                                  9

<210> SEQ ID NO 4
<211> LENGTH: 9
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
```

```
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(5)
<223> OTHER INFORMATION: N at position 5 is deoxyinosine
<220> FEATURE:
<221> NAME/KEY: misc_feature
<222> LOCATION: (7)..(9)
<223> OTHER INFORMATION: N at positions 7-9 is 5-nitroindole

<400> SEQUENCE: 4 nntnncnnn                                                                      9

<210> SEQ ID NO 5
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 5 nnannnnn                                                                       8

<210> SEQ ID NO 6
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
```

```
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 6 nngnnnnn                                                                   8

<210> SEQ ID NO 7
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 7 nncnnnnn                                                                   8

<210> SEQ ID NO 8
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
```

```
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 8 nntnnnnn                                                                          8

<210> SEQ ID NO 9
<211> LENGTH: 7
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(7)
<223> OTHER INFORMATION: N at positions 5-7 is 5-nitroindole

<400> SEQUENCE: 9 nnannnn                                                                           7

<210> SEQ ID NO 10
<211> LENGTH: 7
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(7)
<223> OTHER INFORMATION: N at positions 5-7 is 5-nitroindole
```

```
<400> SEQUENCE: 10 nngnnnn                                                              7

<210> SEQ ID NO 11
<211> LENGTH: 7
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(7)
<223> OTHER INFORMATION: N at positions 5-7 is 5-nitroindole

<400> SEQUENCE: 11 nncnnnn                                                              7

<210> SEQ ID NO 12
<211> LENGTH: 7
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(7)
<223> OTHER INFORMATION: N at positions 5-7 is 5-nitroindole

<400> SEQUENCE: 12 nntnnnn                                                              7

<210> SEQ ID NO 13
<211> LENGTH: 8
<212> TYPE: DNA
<213> ORGANISM: Artificial
<220> FEATURE:
<223> OTHER INFORMATION: Primer
```

```
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is deoxyinosine

<400> SEQUENCE: 13 nnannnnn                                                                 8

<210> SEQ ID NO 14
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is deoxyinosine

<400> SEQUENCE: 14 nngnnnnn                                                                 8

<210> SEQ ID NO 15
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
```

```
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is deoxyinosine

<400> SEQUENCE: 15 nncnnnnn                                                                  8

<210> SEQ ID NO 16
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is deoxyinosine

<400> SEQUENCE: 16 nntnnnnn                                                                  8

<210> SEQ ID NO 17
<211> LENGTH: 7
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
```

```
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(7)
<223> OTHER INFORMATION: N at positions 5-7 is deoxyinosine

<400> SEQUENCE: 17 nnannnn                                                                     7

<210> SEQ ID NO 18
<211> LENGTH: 7
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(7)
<223> OTHER INFORMATION: N at positions 5-7 is deoxyinosine

<400> SEQUENCE: 18 nngnnnn                                                                     7

<210> SEQ ID NO 19
<211> LENGTH: 7
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
```

```
<220> FEATURE:
<221> NAME/KEY: misc_feature
<222> LOCATION: (5)..(7)
<223> OTHER INFORMATION: N at positions 5-7 is deoxyinosine

<400> SEQUENCE: 19 nncnnnn                                                                    7

<210> SEQ ID NO 20
<211> LENGTH: 7
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (5)..(7)
<223> OTHER INFORMATION: N at positions 5-7 is deoxyinosine

<400> SEQUENCE: 20 nntnnnn                                                                    7

<210> SEQ ID NO 21
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 21 nnannnnn                                                                   8
```

```
<210> SEQ ID NO 22
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 22 nngnnnnn                                                              8

<210> SEQ ID NO 23
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 23 nncnnnnn                                                              8

<210> SEQ ID NO 24
<211> LENGTH: 8
<212> TYPE: DNA
<213> ORGANISM: Artificial
```

```
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol disulfide
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (4)..(4)
<223> OTHER INFORMATION: N at position 4 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 24 nntnnnnn                                                                   8

<210> SEQ ID NO 25
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol sulfate
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (3)..(3)
<223> OTHER INFORMATION: N at position 3 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 25 nnnannnn                                                                   8

<210> SEQ ID NO 26
<211> LENGTH: 8
<212> TYPE: DNA
<213> ORGANISM: Artificial
<220> FEATURE:
<223> OTHER INFORMATION: Primer
```

```
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol sulfate
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (3)..(3)
<223> OTHER INFORMATION: N at position 3 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 26 nnngnnnn                                                                8

<210> SEQ ID NO 27
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol sulfate
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (3)..(3)
<223> OTHER INFORMATION: N at position 3 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 27 nnncnnnn                                                                8

<210> SEQ ID NO 28
<211> LENGTH: 8
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is deoxynucleotide base
      containing iodoacetamide or 5-nitropyridylthiol sulfate
```

```
<220> FEATURE:
<221> NAME/KEY: misc_feature
<222> LOCATION: (2)..(2)
<223> OTHER INFORMATION: N at position 2 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (3)..(3)
<223> OTHER INFORMATION: N at position 3 is any deoxynucleotide
<220> FEATURE:
<221> NAME/KEY: misc_feature
<222> LOCATION: (5)..(5)
<223> OTHER INFORMATION: N at position 5 is
      6H,8H-3,4-dihydropyrimido[4,5-C][1,2]oxazin-7-one or
      2-amino-6-methoxyaminopurine
<220> FEATURE:
<221> NAME/KEY: misc_feature
<222> LOCATION: (6)..(8)
<223> OTHER INFORMATION: N at positions 6-8 is 5-nitroindole

<400> SEQUENCE: 28 nnntnnnn                                                                  8

<210> SEQ ID NO 29
<211> LENGTH: 28
<212> TYPE: DNA
<213> ORGANISM: Artificial
<220> FEATURE:
<223> OTHER INFORMATION: Primer

<400> SEQUENCE: 29
cggagtgttg gaggcagtac acgacact                                           28

<210> SEQ ID NO 30
<211> LENGTH: 25
<212> TYPE: DNA
<213> ORGANISM: Artificial
<220> FEATURE:
<223> OTHER INFORMATION: Primer

<400> SEQUENCE: 30
gcctcacaac ctccgtcatg tgctg                                              25

<210> SEQ ID NO 31
<211> LENGTH: 21
<212> TYPE: DNA
<213> ORGANISM: Artificial
<220> FEATURE:
<223> OTHER INFORMATION: Primer

<400> SEQUENCE: 31
gtgaagcggt agttggcagc c                                                  21

<210> SEQ ID NO 32
<211> LENGTH: 21
<212> TYPE: DNA
<213> ORGANISM: Artificial
<220> FEATURE:
<223> OTHER INFORMATION: Primer

<400> SEQUENCE: 32
tggaagcggt agttgggtcg a                                                  21

<210> SEQ ID NO 33
<211> LENGTH: 23
<212> TYPE: DNA
<213> ORGANISM: Artificial
```

-continued

```
<220> FEATURE:
<223> OTHER INFORMATION: Primer

<400> SEQUENCE: 33
gcacatgacg gaggttgtga ggc                                              23

<210> SEQ ID NO 34
<211> LENGTH: 23
<212> TYPE: DNA
<213> ORGANISM: Artificial
<220> FEATURE:
<223> OTHER INFORMATION: Primer

<400> SEQUENCE: 34
gcctcacaac ctccgtcatg tgc                                              23

<210> SEQ ID NO 35
<211> LENGTH: 24
<212> TYPE: DNA
<213> ORGANISM: Artificial
<220> FEATURE:
<223> OTHER INFORMATION: Primer

<400> SEQUENCE: 35
tggagagacg acagggctgg ttgc                                             24

<210> SEQ ID NO 36
<211> LENGTH: 24
<212> TYPE: DNA
<213> ORGANISM: Artificial
<220> FEATURE:
<223> OTHER INFORMATION: Primer

<400> SEQUENCE: 36
gcaaccagcc ctgtcgtctc tcca                                             24

<210> SEQ ID NO 37
<211> LENGTH: 21
<212> TYPE: DNA
<213> ORGANISM: Artificial
<220> FEATURE:
<223> OTHER INFORMATION: Primer

<400> SEQUENCE: 37
ggctgccaac taccgcttca c                                                21

<210> SEQ ID NO 38
<211> LENGTH: 21
<212> TYPE: DNA
<213> ORGANISM: Artificial
<220> FEATURE:
<223> OTHER INFORMATION: Primer

<400> SEQUENCE: 38
gtgaagcggt agttggcagc c                                                21

<210> SEQ ID NO 39
<211> LENGTH: 21
<212> TYPE: DNA
<213> ORGANISM: Artificial
<220> FEATURE:
<223> OTHER INFORMATION: Primer

<400> SEQUENCE: 39
tggaagcggt agttgggtcg a                                                21
```

```
<210> SEQ ID NO 40
<211> LENGTH: 21
<212> TYPE: DNA
<213> ORGANISM: Artificial
<220> FEATURE:
<223> OTHER INFORMATION: Primer

<400> SEQUENCE: 40
ggctgccaac taccgcttca c                                              21

<210> SEQ ID NO 41
<211> LENGTH: 21
<212> TYPE: DNA
<213> ORGANISM: Artificial
<220> FEATURE:
<223> OTHER INFORMATION: Primer

<400> SEQUENCE: 41
tcgacccaac taccgcttcc a                                              21

<210> SEQ ID NO 42
<211> LENGTH: 21
<212> TYPE: DNA
<213> ORGANISM: Artificial
<220> FEATURE:
<223> OTHER INFORMATION: Primer

<400> SEQUENCE: 42
ggctgccaac taccgcttca c                                              21

<210> SEQ ID NO 43
<211> LENGTH: 21
<212> TYPE: DNA
<213> ORGANISM: Artificial
<220> FEATURE:
<223> OTHER INFORMATION: Primer

<400> SEQUENCE: 43
tcgacccaac taccgcttcc a                                              21

<210> SEQ ID NO 44
<211> LENGTH: 21
<212> TYPE: DNA
<213> ORGANISM: Artificial
<220> FEATURE:
<223> OTHER INFORMATION: Primer

<400> SEQUENCE: 44
ggctgccaac taccgcttca c                                              21

<210> SEQ ID NO 45
<211> LENGTH: 21
<212> TYPE: DNA
<213> ORGANISM: Artificial
<220> FEATURE:
<223> OTHER INFORMATION: Primer

<400> SEQUENCE: 45
tcgacccaac taccgcttcc a                                              21

<210> SEQ ID NO 46
<211> LENGTH: 21
<212> TYPE: DNA
<213> ORGANISM: Artificial
<220> FEATURE:
<223> OTHER INFORMATION: Primer
```

<400> SEQUENCE: 46
ggctgccaac taccgcttca c                                              21

<210> SEQ ID NO 47
<211> LENGTH: 21
<212> TYPE: DNA
<213> ORGANISM: Artificial
<220> FEATURE:
<223> OTHER INFORMATION: Primer

<400> SEQUENCE: 47
tcgacccaac taccgcttcc a                                              21

<210> SEQ ID NO 48
<211> LENGTH: 27
<212> TYPE: DNA
<213> ORGANISM: Artificial
<220> FEATURE:
<223> OTHER INFORMATION: Primer

<400> SEQUENCE: 48
gcaaccagcc ctgtcgtctc tccagcc                                        27

<210> SEQ ID NO 49
<211> LENGTH: 30
<212> TYPE: DNA
<213> ORGANISM: Artificial
<220> FEATURE:
<223> OTHER INFORMATION: Primer

<400> SEQUENCE: 49
cctcccagag accccagttg caaaccagac                                     30

<210> SEQ ID NO 50
<211> LENGTH: 21
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (1)..(1)
<223> OTHER INFORMATION: N at position 1 is 2'-O-methylguanosine
<220> FEATURE:
<221> NAME/KEY: misc_feature
<222> LOCATION: (2)..(2)
<223> OTHER INFORMATION: N at position 2 is 2'-O-methylguanosine
<220> FEATURE:
<221> NAME/KEY: misc_feature
<222> LOCATION: (3)..(3)
<223> OTHER INFORMATION: N at position 3 is 2'-O-methylcytidine
<220> FEATURE:
<221> NAME/KEY: misc_feature
<222> LOCATION: (4)..(4)
<223> OTHER INFORMATION: N at position 4 is 2'-O-methylthymidine
<220> FEATURE:
<221> NAME/KEY: misc_feature
<222> LOCATION: (7)..(7)
<223> OTHER INFORMATION: N at position 7 is 2'-O-methylcytidine
<220> FEATURE:
<221> NAME/KEY: misc_feature
<222> LOCATION: (10)..(10)
<223> OTHER INFORMATION: N at position 10 is 2'-O-methylcytidine
<220> FEATURE:
<221> NAME/KEY: misc_feature
<222> LOCATION: (14)..(14)
<223> OTHER INFORMATION: N at position 14 is 2'-O-methylcytidine
<220> FEATURE:
<221> NAME/KEY: misc_feature
<222> LOCATION: (18)..(18)
<223> OTHER INFORMATION: N at position 18 is 2'-O-methylthymidine

```
<220> FEATURE:
<221> NAME/KEY: misc_feature
<222> LOCATION: (19)..(19)
<223> OTHER INFORMATION: N at position 19 is 2'-O-methylcytidine
<220> FEATURE:
<221> NAME/KEY: misc_feature
<222> LOCATION: (20)..(20)
<223> OTHER INFORMATION: N at position 20 is 2'-O-methyladenosine
<220> FEATURE:
<221> NAME/KEY: misc_feature
<222> LOCATION: (21)..(21)
<223> OTHER INFORMATION: N at position 21 is 2'-O-methylcytidine

<400> SEQUENCE: 50
nnnngcnaan tacngctnnn n                                             21

<210> SEQ ID NO 51
<211> LENGTH: 31
<212> TYPE: DNA
<213> ORGANISM: Artificial
<220> FEATURE:
<223> OTHER INFORMATION: Primer

<400> SEQUENCE: 51
tttttgtgaa gcggtagttg gcagcctttt t                                  31

<210> SEQ ID NO 52
<211> LENGTH: 37
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is carbon 18 spacer

<400> SEQUENCE: 52
tttttttttt tttttnggct gccaactacc gcttcac                            37

<210> SEQ ID NO 53
<211> LENGTH: 37
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (11)..(11)
<223> OTHER INFORMATION: N at position 11 is uracil
<220> FEATURE:
<221> NAME/KEY: misc_feature
<222> LOCATION: (16)..(16)
<223> OTHER INFORMATION: N at position 16 is carbon 18 spacer

<400> SEQUENCE: 53
tttttttttt ntttntcga cccaactacc gcttcca                             37

<210> SEQ ID NO 54
<211> LENGTH: 45
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (30)..(30)
<223> OTHER INFORMATION: N at position 30 is carbon 18 spacer
```

<400> SEQUENCE: 54
tgagggcagg gcagtactgt aggaagaggn tttttttttt ttttt    45

<210> SEQ ID NO 55
<211> LENGTH: 44
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (29)..(29)
<223> OTHER INFORMATION: N at position 29 is carbon 18 spacer

<400> SEQUENCE: 55
gagggcaggg cggtactgta ggaagaggnt tttttttttt tttt    44

<210> SEQ ID NO 56
<211> LENGTH: 44
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (26)..(26)
<223> OTHER INFORMATION: N at position 26 is carbon 18 spacer

<400> SEQUENCE: 56
gagggcaggg cggtactgcg ggaagntttt tttttttttt tttt    44

<210> SEQ ID NO 57
<211> LENGTH: 44
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (29)..(29)
<223> OTHER INFORMATION: N at position 29 is carbon 18 spacer

<400> SEQUENCE: 57
gagggcaggg aggtactgag ggaagaggnt tttttttttt tttt    44

<210> SEQ ID NO 58
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 58
tttttttttt tttttttttt nggctgccaa ctaccgcttc ac    42

<210> SEQ ID NO 59
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 59
tttttttttt tttttttttt nggctgccaa ctaccgcttc ac                              42

<210> SEQ ID NO 60
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is Uracil
<220> FEATURE:
<221> NAME/KEY: misc_feature
<222> LOCATION: (21)..(21)
<223> OTHER INFORMATION: N at position 21 is carbon 18 spacer

<400> SEQUENCE: 60
tttttttttt tttttntttt ntcgacccaa ctaccgcttc ca                              42

<210> SEQ ID NO 61
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is Uracil
<220> FEATURE:
<221> NAME/KEY: misc_feature
<222> LOCATION: (21)..(21)
<223> OTHER INFORMATION: N at position 21 is carbon 18 spacer

<400> SEQUENCE: 61
tttttttttt tttttntttt ntcgacccaa ctaccgcttc ca                              42

<210> SEQ ID NO 62
<211> LENGTH: 47
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (26)..(26)
<223> OTHER INFORMATION: N at position 26 is carbon 18 spacer

<400> SEQUENCE: 62
tttttttttt tttttttttt tttttnggct gccaactacc gcttcac                         47

<210> SEQ ID NO 63
<211> LENGTH: 47
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is Uracil
<220> FEATURE:
<221> NAME/KEY: misc_feature
<222> LOCATION: (26)..(26)
<223> OTHER INFORMATION: N at position 26 is carbon 18 spacer

<400> SEQUENCE: 63
tttttttttt tttttttttt nttttntcga cccaactacc gcttcca                         47

```
<210> SEQ ID NO 64
<211> LENGTH: 50
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (30)..(30)
<223> OTHER INFORMATION: N at position 30 is carbon 18 spacer

<400> SEQUENCE: 64
tgagggcagg gcagtactgt aggaagaggn ttttttttt tttttttttt        50

<210> SEQ ID NO 65
<211> LENGTH: 49
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (29)..(29)
<223> OTHER INFORMATION: N at position 29 is carbon 18 spacer

<400> SEQUENCE: 65
gagggcaggg aggtactgag ggaagaggnt tttttttttt ttttttttt        49

<210> SEQ ID NO 66
<211> LENGTH: 55
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (30)..(30)
<223> OTHER INFORMATION: N at position 30 is carbon 18 spacer

<400> SEQUENCE: 66
tgagggcagg gcagtactgt aggaagaggn tttttttttt tttttttttt ttttt  55

<210> SEQ ID NO 67
<211> LENGTH: 54
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (29)..(29)
<223> OTHER INFORMATION: N at position 29 is carbon 18 spacer

<400> SEQUENCE: 67
gagggcaggg aggtactgag ggaagaggnt tttttttttt tttttttttt tttt   54

<210> SEQ ID NO 68
<211> LENGTH: 49
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is carbon 18 spacer

<400> SEQUENCE: 68
tttttttttt tttttntgag ggcagggcag tactgtagga agaggtatc         49
```

```
<210> SEQ ID NO 69
<211> LENGTH: 48
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is carbon 18 spacer

<400> SEQUENCE: 69 ttttttttt tttttngagg gcagggaggt actgagggaa gaggtatc                48

<210> SEQ ID NO 70
<211> LENGTH: 54
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 70
tttttttttt tttttttttt ntgagggcag ggcagtactg taggaagagg tatc        54

<210> SEQ ID NO 71
<211> LENGTH: 53
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 71
tttttttttt tttttttttt ngagggcagg gaggtactga gggaagaggt atc         53

<210> SEQ ID NO 72
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (27)..(27)
<223> OTHER INFORMATION: N at position 27 is carbon 18 spacer
<220> FEATURE:
<221> NAME/KEY: misc_feature
<222> LOCATION: (32)..(32)
<223> OTHER INFORMATION: N at position 32 is Uracil

<400> SEQUENCE: 72
gccgcctgag gtctggtttg caactgnttt tnttttttt tt                      42

<210> SEQ ID NO 73
<211> LENGTH: 46
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (27)..(27)
<223> OTHER INFORMATION: N at position 27 is carbon 18 spacer
```

```
<220> FEATURE:
<221> NAME/KEY: misc_feature
<222> LOCATION: (32)..(32)
<223> OTHER INFORMATION: N at position 32 is Uracil

<400> SEQUENCE: 73
gccgcctgag gtctggtttg caactgnttt tnttttttttt tttttt                46

<210> SEQ ID NO 74
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (11)..(11)
<223> OTHER INFORMATION: N at position 11 is Uracil
<220> FEATURE:
<221> NAME/KEY: misc_feature
<222> LOCATION: (16)..(16)
<223> OTHER INFORMATION: N at position 16 is carbon 18 spacer

<400> SEQUENCE: 74
tttttttttt nttttngccg cctgaggtct ggtttgcaac tg                    42

<210> SEQ ID NO 75
<211> LENGTH: 47
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is Uracil
<220> FEATURE:
<221> NAME/KEY: misc_feature
<222> LOCATION: (21)..(21)
<223> OTHER INFORMATION: N at position 21 is carbon 18 spacer

<400> SEQUENCE: 75
tttttttttt tttttntttt ngccgcctga ggtctggttt gcaactg                47

<210> SEQ ID NO 76
<211> LENGTH: 37
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is photocleavable spacer
      phosphoramidite

<400> SEQUENCE: 76
tttttttttt tttttntcga cccaactacc gcttcca                           37

<210> SEQ ID NO 77
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is photocleavable spacer
      phosphoramidite
```

```
<400> SEQUENCE: 77
tttttttttt tttttttttt ntcgacccaa ctaccgcttc ca                    42

<210> SEQ ID NO 78
<211> LENGTH: 37
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is carbon 18 spacer
<220> FEATURE:
<221> NAME/KEY: misc_feature
<222> LOCATION: (19)..(19)
<223> OTHER INFORMATION: N at position 19 is 8-OXO-dG-CE phosphoramidite
<220> FEATURE:
<221> NAME/KEY: misc_feature
<222> LOCATION: (31)..(31)
<223> OTHER INFORMATION: N at position 31 is 8-OXO-dG-CE phosphoramidite

<400> SEQUENCE: 78
tttttttttt tttttntcna cccaactacc ncttcca                          37

<210> SEQ ID NO 79
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer
<220> FEATURE:
<221> NAME/KEY: misc_feature
<222> LOCATION: (24)..(24)
<223> OTHER INFORMATION: N at position 24 is 8-OXO-dG-CE phosphoramidite
<220> FEATURE:
<221> NAME/KEY: misc_feature
<222> LOCATION: (36)..(36)
<223> OTHER INFORMATION: N at position 36 is 8-OXO-dG-CE phosphoramidite

<400> SEQUENCE: 79
tttttttttt tttttttttt ntcnacccaa ctaccncttc ca                    42

<210> SEQ ID NO 80
<211> LENGTH: 43
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is carbon 18 spacer
<220> FEATURE:
<221> NAME/KEY: misc_feature
<222> LOCATION: (22)..(22)
<223> OTHER INFORMATION: N at position 22 is Abasic II phosphoramidite

<400> SEQUENCE: 80
tttttttttt tttttntttt tntcgaccca actaccgctt cca                   43

<210> SEQ ID NO 81
<211> LENGTH: 46
<212> TYPE: DNA
<213> ORGANISM: Artificial
<220> FEATURE:
<223> OTHER INFORMATION: Primer
```

<220> FEATURE:
<221> NAME/KEY: misc_feature
<222> LOCATION: (27)..(27)
<223> OTHER INFORMATION: N at position 27 is photocleavable spacer
      phosphoramidite

<400> SEQUENCE: 81
gccgcctgag gtctggtttg caactgnttt tttttttttt tttttt                    46

<210> SEQ ID NO 82
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 82
tttttttttt tttttttttt nggctgccaa ctaccgcttc ac                        42

<210> SEQ ID NO 83
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is photocleavable spacer
      phosphoramidite

<400> SEQUENCE: 83
tttttttttt tttttttttt ntcgacccaa ctaccgcttc ca                        42

<210> SEQ ID NO 84
<211> LENGTH: 56
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer
<220> FEATURE:
<221> NAME/KEY: misc_feature
<222> LOCATION: (43)..(43)
<223> OTHER INFORMATION: N at position 43 is Abasic phorphoramidite

<400> SEQUENCE: 84
tttttttttt tttttttttt nggctgccaa ctaccgcttc acnattcaac tctgtc         56

<210> SEQ ID NO 85
<211> LENGTH: 53
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is photocleavable spacer
      phorphoramidite
<220> FEATURE:
<221> NAME/KEY: misc_feature
<222> LOCATION: (43)..(43)
<223> OTHER INFORMATION: N at position 43 is Abasic phorphoramidite

<400> SEQUENCE: 85
tttttttttt tttttttttt ntcgacccaa ctaccgcttc canggccact gac    53

<210> SEQ ID NO 86
<211> LENGTH: 43
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer
<220> FEATURE:
<221> NAME/KEY: misc_feature
<222> LOCATION: (43)..(43)
<223> OTHER INFORMATION: N at position 43 is dideoxycytidine

<400> SEQUENCE: 86
tttttttttt tttttttttt nggctgccaa ctaccgcttc acn    43

<210> SEQ ID NO 87
<211> LENGTH: 43
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is photocleavable spacer
      phosphoramidite
<220> FEATURE:
<221> NAME/KEY: misc_feature
<222> LOCATION: (43)..(43)
<223> OTHER INFORMATION: N at position 43 is dideoxycytidine

<400> SEQUENCE: 87
tttttttttt tttttttttt ntcgacccaa ctaccgcttc can    43

<210> SEQ ID NO 88
<211> LENGTH: 56
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 88
tttttttttt tttttttttt nggctgccaa ctaccgcttc actattcaac tctgtc    56

<210> SEQ ID NO 89
<211> LENGTH: 53
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is photocleavable spacer
      phosphoramidite

<400> SEQUENCE: 89
tttttttttt tttttttttt ntcgacccaa ctaccgcttc catggccact gac    53

<210> SEQ ID NO 90
<211> LENGTH: 57
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer
<220> FEATURE:
<221> NAME/KEY: misc_feature
<222> LOCATION: (57)..(57)
<223> OTHER INFORMATION: N at position 57 is dideoxycytidine

<400> SEQUENCE: 90
tttttttttt tttttttttt nggctgccaa ctaccgcttc actattcaac tctgtcn      57

<210> SEQ ID NO 91
<211> LENGTH: 54
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is photocleavable spacer
    phosphoramidite
<220> FEATURE:
<221> NAME/KEY: misc_feature
<222> LOCATION: (54)..(54)
<223> OTHER INFORMATION: N at position 54 is dideoxycytidine

<400> SEQUENCE: 91
tttttttttt tttttttttt ntcgacccaa ctaccgcttc catggccact gacn         54

<210> SEQ ID NO 92
<211> LENGTH: 56
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 92
tttttttttt tttttttttt nggctgccaa ctaccgcttc actattcaac tctgtc       56

<210> SEQ ID NO 93
<211> LENGTH: 53
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is photocleavable spacer
    phosphoramidite

<400> SEQUENCE: 93
tttttttttt tttttttttt ntcgacccaa ctaccgcttc catggccact gac          53

<210> SEQ ID NO 94
<211> LENGTH: 42
<212> TYPE: DNA
<213> ORGANISM: Artificial

```
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 94
tttttttttt tttttttttt nggctgtagc actggcaaca ac                              42

<210> SEQ ID NO 95
<211> LENGTH: 56
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 95
tttttttttt tttttttttt nggctgtagc actggcaaca acatttcaac tctgtc              56

<210> SEQ ID NO 96
<211> LENGTH: 58
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 96
tttttttttt tttttttttt nccctcaaac aggtgaatta ttagcacttg taacaaca            58

<210> SEQ ID NO 97
<211> LENGTH: 58
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 97
tttttttttt tttttttttt nccctcaaac aggtgaatta ttagccttt ttatctca             58

<210> SEQ ID NO 98
<211> LENGTH: 58
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 98
tttttttttt tttttttttt nccctttgag cagaggttca ttagcacttg taacaaca            58
```

-continued

<210> SEQ ID NO 99
<211> LENGTH: 51
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 99
tttttttttt tttttttttt ncttgttgag cagaggttct tttttatctt c      51

<210> SEQ ID NO 100
<211> LENGTH: 51
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is photocleavable spacer
      phosphoramidite

<400> SEQUENCE: 100
tttttttttt tttttttttt ncttgttgag cagaggttct tttttatctt c      51

<210> SEQ ID NO 101
<211> LENGTH: 71
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 101
tttttttttt tttttttttt ntgtccacag ctgcacaggg caggtcttgt ggctgccaac      60
taccgcttca c      71

<210> SEQ ID NO 102
<211> LENGTH: 85
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 102
tttttttttt tttttttttt ntgtccacag ctgcacaggg caggtcttgt ggctgccaac      60
taccgcttca ctattcaact ctgtc      85

<210> SEQ ID NO 103
<211> LENGTH: 71
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 103
tttttttttt tttttttttt ntgtccacag ctgcacaggg caggtcttgt ggctgtagca    60
ctggcaacaa c    71

<210> SEQ ID NO 104
<211> LENGTH: 87
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 104
tttttttttt tttttttttt ntgtccacag ctgcacaggg caggtcttgt ccctcaaaca    60
ggtgaattat tagccttttt tatctca    87

<210> SEQ ID NO 105
<211> LENGTH: 87
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 105
tttttttttt tttttttttt ntgtccacag ctgcacaggg caggtcttgt ccctttgagc    60
agaggttcat tagcacttgt aacaaca    87

<210> SEQ ID NO 106
<211> LENGTH: 70
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 106
tttttttttt tttttttttt nacccacagc tgcacagggc aggtcttgtg gctgccaact    60
accgcttcac    70

<210> SEQ ID NO 107
<211> LENGTH: 86
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 107
tttttttttt tttttttttt nacccacagc tgcacagggc aggtcttgtc cctcaaacag    60
gtgaattatt agcctttttt atctca    86

```
<210> SEQ ID NO 108
<211> LENGTH: 86
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 108
tttttttttt tttttttttt nacccacagc tgcacagggc aggtcttgtc cctttgagca    60
gaggttcatt agcacttgta acaaca                                        86

<210> SEQ ID NO 109
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 109
tttttttttt tttttttttt nggtcttggc cagttggcaa aatggctgcc aactaccgct    60
tcac                                                                64

<210> SEQ ID NO 110
<211> LENGTH: 80
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 110
tttttttttt tttttttttt nggtcttggc cagttggcaa aatccctttg agcagaggtt    60
cattagcact tgtaacaaca                                               80

<210> SEQ ID NO 111
<211> LENGTH: 65
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 111
tttttttttt tttttttttt ngggcagggc agtactgtag gaatggctgc caactaccgc    60
ttcac                                                               65

<210> SEQ ID NO 112
<211> LENGTH: 81
<212> TYPE: DNA
<213> ORGANISM: Artificial
<220> FEATURE:
<223> OTHER INFORMATION: Primer
```

<220> FEATURE:
<221> NAME/KEY: misc_feature
<222> LOCATION: (21)..(21)
<223> OTHER INFORMATION: N at position 21 is carbon 18 spacer

<400> SEQUENCE: 112
tttttttttt tttttttttt ngggcagggc agtactgtag gaatccctttt gagcagaggt    60 tcattagcac ttgtaacaac a    81

<210> SEQ ID NO 113
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (15)..(15)
<223> OTHER INFORMATION: N at position 15 is Uracil
<220> FEATURE:
<221> NAME/KEY: misc_feature
<222> LOCATION: (21)..(21)
<223> OTHER INFORMATION: N at position 21 is carbon 18 spacer

<400> SEQUENCE: 113
tttttttttt ttttntttttt ntcgacccaa ctaccgcttc ca    42

<210> SEQ ID NO 114
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer
<220> FEATURE:
<221> NAME/KEY: misc_feature
<222> LOCATION: (32)..(32)
<223> OTHER INFORMATION: N at position 32 is Uracil

<400> SEQUENCE: 114
tttttttttt tttttttttt ntcgacccaa cnaccgcttc ca    42

<210> SEQ ID NO 115
<211> LENGTH: 51
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (15)..(15)
<223> OTHER INFORMATION: N at position 15 is Uracil
<220> FEATURE:
<221> NAME/KEY: misc_feature
<222> LOCATION: (21)..(21)
<223> OTHER INFORMATION: N at position 21 is carbon 18 spacer

<400> SEQUENCE: 115
tttttttttt ttttntttttt ncttgttgag cagaggttct ttttatcttc    51

<210> SEQ ID NO 116
<211> LENGTH: 51
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer
<220> FEATURE:
<221> NAME/KEY: misc_feature
<222> LOCATION: (27)..(27)
<223> OTHER INFORMATION: N at position 27 is Uracil

<400> SEQUENCE: 116
tttttttttt tttttttttt ncttgtngag cagaggttct ttttatcttt c         51

<210> SEQ ID NO 117
<211> LENGTH: 46
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (27)..(27)
<223> OTHER INFORMATION: N at position 27 is carbon 18 spacer
<220> FEATURE:
<221> NAME/KEY: misc_feature
<222> LOCATION: (33)..(33)
<223> OTHER INFORMATION: N at position 33 is Uracil

<400> SEQUENCE: 117
gccgcctgag gtctggtttg caactgnttt tnttttttt tttttt               46

<210> SEQ ID NO 118
<211> LENGTH: 68
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 118
tttttttttt tttttttttt ngtactgtag gaagaggaag gagacatggc tgccaactac    60
cgcttcac                                                              68

<210> SEQ ID NO 119
<211> LENGTH: 69
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 119
tttttttttt tttttttttt ngggcagggc agtactgtag gaagaggtgg ctgccaacta    60
ccgcttcac                                                             69

<210> SEQ ID NO 120
<211> LENGTH: 42
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer
<220> FEATURE:
<221> NAME/KEY: misc_feature
<222> LOCATION: (38)..(38)
<223> OTHER INFORMATION: N at position 38 is Uracil

<400> SEQUENCE: 120
tttttttttt tttttttttt ntcgacccaa ctaccgcntc ca                42

<210> SEQ ID NO 121
<211> LENGTH: 71
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 121
tttttttttt tttttttttt ntgtccacag ctgcacaggg caggtcttgt ggctgccaac    60
taccgcttca c                                                        71

<210> SEQ ID NO 122
<211> LENGTH: 64
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 122
tttttttttt tttttttttt nggtcttggc cagttggcaa aatggctgcc aactaccgct    60
tcac                                                                64

<210> SEQ ID NO 123
<211> LENGTH: 65
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 123
tttttttttt tttttttttt ngggcagggc agtactgtag gaatggctgc caactaccgc    60
ttcac                                                               65

<210> SEQ ID NO 124
<211> LENGTH: 58
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: N at position 21 is carbon 18 spacer

<400> SEQUENCE: 124
tttttttttt tttttttttt nccctttgag cagaggttca ttagcacttg taacaaca    58

<210> SEQ ID NO 125
<211> LENGTH: 68
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is carbon 18 spacer

<400> SEQUENCE: 125
tttttttttt tttttngcag ctggagctgg agagacgaca gggctggaga gacgacaggg    60
ctggttgc                                                              68

<210> SEQ ID NO 126
<211> LENGTH: 66
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (16)..(16)
<223> OTHER INFORMATION: N at position 16 is carbon 18 spacer

<400> SEQUENCE: 126
tttttttttt tttttntgcc ctatgagccg cctgaggtct ggtttgcaac tggagtctct    60
gggagg                                                                66

<210> SEQ ID NO 127
<211> LENGTH: 21
<212> TYPE: DNA
<213> ORGANISM: Artificial
<220> FEATURE:
<223> OTHER INFORMATION: Primer

<400> SEQUENCE: 127
ggctgccaac taccgcttca c                                               21

<210> SEQ ID NO 128
<211> LENGTH: 21
<212> TYPE: DNA
<213> ORGANISM: Artificial
<220> FEATURE:
<223> OTHER INFORMATION: Primer

<400> SEQUENCE: 128
tcgacccaac taccgcttcc a                                               21

<210> SEQ ID NO 129
<211> LENGTH: 46
<212> TYPE: DNA
<213> ORGANISM: Artificial
<220> FEATURE:
<223> OTHER INFORMATION: Primer

<400> SEQUENCE: 129
ggctgccaac taccgcttca catgccctga ctttcaactc tgtctc                    46

```
<210> SEQ ID NO 130
<211> LENGTH: 51
<212> TYPE: DNA
<213> ORGANISM: Artificial
<220> FEATURE:
<223> OTHER INFORMATION: Primer

<400> SEQUENCE: 130
ggctgccaac taccgcttca ctattcaact ctgtctcctt cctcttccta c          51

<210> SEQ ID NO 131
<211> LENGTH: 42
<212> TYPE: DNA
<213> ORGANISM: Artificial
<220> FEATURE:
<223> OTHER INFORMATION: Primer

<400> SEQUENCE: 131
tcgacccaac taccgcttcc actcacctgg agggccactg ac                    42

<210> SEQ ID NO 132
<211> LENGTH: 45
<212> TYPE: DNA
<213> ORGANISM: Artificial
<220> FEATURE:
<223> OTHER INFORMATION: Primer

<400> SEQUENCE: 132
tcgacccaac taccgcttcc atggccactg acaaccaccc ttaac                 45

<210> SEQ ID NO 133
<211> LENGTH: 57
<212> TYPE: DNA
<213> ORGANISM: Artificial
<220> FEATURE:
<223> OTHER INFORMATION: Primer

<400> SEQUENCE: 133
tgtgccctga ctttcaactc tgtctccttc ctcttcctac agtactgccc tgccctc    57

<210> SEQ ID NO 134
<211> LENGTH: 57
<212> TYPE: DNA
<213> ORGANISM: Artificial
<220> FEATURE:
<223> OTHER INFORMATION: Primer

<400> SEQUENCE: 134
tgtgccctga ctttcaactc tgtctccttc ctcttcctac agtaccgccc tgccctc    57

<210> SEQ ID NO 135
<211> LENGTH: 57
<212> TYPE: DNA
<213> ORGANISM: Artificial
<220> FEATURE:
<223> OTHER INFORMATION: Primer

<400> SEQUENCE: 135
tgtgccctga ctttcaactc tgtctccttc ctcttcccgc agtaccgccc tgccctc    57

<210> SEQ ID NO 136
<211> LENGTH: 57
<212> TYPE: DNA
<213> ORGANISM: Artificial
<220> FEATURE:
<223> OTHER INFORMATION: Primer
```

```
<400> SEQUENCE: 136
tgtgccctga ctttcaactc tgtctccttc ctcttccctc agtacctccc tgccctc          57

<210> SEQ ID NO 137
<211> LENGTH: 35
<212> TYPE: DNA
<213> ORGANISM: Artificial
<220> FEATURE:
<223> OTHER INFORMATION: Primer

<400> SEQUENCE: 137
ggctgccaac taccgcttca ctattcaact ctgtc                                  35

<210> SEQ ID NO 138
<211> LENGTH: 32
<212> TYPE: DNA
<213> ORGANISM: Artificial
<220> FEATURE:
<223> OTHER INFORMATION: Primer

<400> SEQUENCE: 138
tcgacccaac taccgcttcc atggccactg ac                                     32

<210> SEQ ID NO 139
<211> LENGTH: 37
<212> TYPE: DNA
<213> ORGANISM: Artificial
<220> FEATURE:
<223> OTHER INFORMATION: Primer

<400> SEQUENCE: 139
ccctcaaaca ggtgaattat tagcacttgt aacaaca                                37

<210> SEQ ID NO 140
<211> LENGTH: 37
<212> TYPE: DNA
<213> ORGANISM: Artificial
<220> FEATURE:
<223> OTHER INFORMATION: Primer

<400> SEQUENCE: 140
ccctcaaaca ggtgaattat tagccttttt tatctca                                37

<210> SEQ ID NO 141
<211> LENGTH: 37
<212> TYPE: DNA
<213> ORGANISM: Artificial
<220> FEATURE:
<223> OTHER INFORMATION: Primer

<400> SEQUENCE: 141
ccctttgagc agaggttcat tagcacttgt aacaaca                                37

<210> SEQ ID NO 142
<211> LENGTH: 35
<212> TYPE: DNA
<213> ORGANISM: Artificial
<220> FEATURE:
<223> OTHER INFORMATION: Primer

<400> SEQUENCE: 142
ggctgtagca ctggcaacaa catttcaact ctgtc                                  35
```

```
<210> SEQ ID NO 143
<211> LENGTH: 30
<212> TYPE: DNA
<213> ORGANISM: Artificial
<220> FEATURE:
<223> OTHER INFORMATION: Primer

<400> SEQUENCE: 143
cttgttgagc agaggttctt ttttatcttc                                30

<210> SEQ ID NO 144
<211> LENGTH: 51
<212> TYPE: DNA
<213> ORGANISM: Artificial
<220> FEATURE:
<223> OTHER INFORMATION: Primer

<400> SEQUENCE: 144
ggctgccaac taccgcttca ctattcaact ctgtctcctt cctcttccta c         51

<210> SEQ ID NO 145
<211> LENGTH: 62
<212> TYPE: DNA
<213> ORGANISM: Artificial
<220> FEATURE:
<223> OTHER INFORMATION: Primer

<400> SEQUENCE: 145
ccctcaaaca ggtgaattat tagcacttgt aacaacattt caactctgtc tccttcctct    60
tc                                                                  62

<210> SEQ ID NO 146
<211> LENGTH: 62
<212> TYPE: DNA
<213> ORGANISM: Artificial
<220> FEATURE:
<223> OTHER INFORMATION: Primer

<400> SEQUENCE: 146
ccctcaaaca ggtgaattat tagccttttt tatctcattt caactctgtc tccttcctct    60
tc                                                                  62

<210> SEQ ID NO 147
<211> LENGTH: 62
<212> TYPE: DNA
<213> ORGANISM: Artificial
<220> FEATURE:
<223> OTHER INFORMATION: Primer

<400> SEQUENCE: 147
ccctttgagc agaggttcat tagcacttgt aacaacattt caactctgtc tccttcctct    60
tc                                                                  62

<210> SEQ ID NO 148
<211> LENGTH: 48
<212> TYPE: DNA
<213> ORGANISM: Artificial
<220> FEATURE:
<223> OTHER INFORMATION: Primer

<400> SEQUENCE: 148
ggctgtagca ctggcaacaa cattttcaac tctgtctcct tcctcttc               48
```

```
<210> SEQ ID NO 149
<211> LENGTH: 45
<212> TYPE: DNA
<213> ORGANISM: Artificial
<220> FEATURE:
<223> OTHER INFORMATION: Primer

<400> SEQUENCE: 149
tcgacccaac taccgcttcc atggccactg acaaccaccc ttaac            45

<210> SEQ ID NO 150
<211> LENGTH: 55
<212> TYPE: DNA
<213> ORGANISM: Artificial
<220> FEATURE:
<223> OTHER INFORMATION: Primer

<400> SEQUENCE: 150
cttgttgagc agaggttctt ttttatcttc atggccactg acaaccaccc ttaac      55

<210> SEQ ID NO 151
<211> LENGTH: 56
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 151
tttttntgtc cacagctgca cagggcaggt cttgtggctg ccaactaccg cttcac      56

<210> SEQ ID NO 152
<211> LENGTH: 70
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 152
tttttntgtc cacagctgca cagggcaggt cttgtggctg ccaactaccg cttcactatt    60
caactctgtc                                                         70

<210> SEQ ID NO 153
<211> LENGTH: 56
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 153
tttttntgtc cacagctgca cagggcaggt cttgtggctg tagcactggc aacaac      56

<210> SEQ ID NO 154
<211> LENGTH: 72
<212> TYPE: DNA
<213> ORGANISM: Artificial
```

```
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 154
tttttntgtc cacagctgca cagggcaggt cttgtccctc aaacaggtga attattagcc      60 tttttttatct ca                                                         72

<210> SEQ ID NO 155
<211> LENGTH: 72
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is a, c, g, or t

<400> SEQUENCE: 155
tttttntgtc cacagctgca cagggcaggt cttgtccctt tgagcagagg ttcattagca      60
cttgtaacaa ca                                                          72

<210> SEQ ID NO 156
<211> LENGTH: 71
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 156
tttttnaccc acagctgcac agggcaggtc ttgtccctca aacaggtgaa ttattagcct      60
tttttatctc a                                                           71

<210> SEQ ID NO 157
<211> LENGTH: 71
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 157
tttttnaccc acagctgcac agggcaggtc ttgtcccttt gagcagaggt tcattagcac      60
ttgtaacaac a                                                           71

<210> SEQ ID NO 158
<211> LENGTH: 55
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer
```

```
<400> SEQUENCE: 158
tttttnaccc acagctgcac agggcaggtc ttgtggctgc caactaccgc ttcac      55

<210> SEQ ID NO 159
<211> LENGTH: 53
<212> TYPE: DNA
<213> ORGANISM: Artificial
<220> FEATURE:
<223> OTHER INFORMATION: Primer

<400> SEQUENCE: 159
tcgacccaac taccgcttcc atggccagac ctaagagcaa tcagtgagga atc        53

<210> SEQ ID NO 160
<211> LENGTH: 63
<212> TYPE: DNA
<213> ORGANISM: Artificial
<220> FEATURE:
<223> OTHER INFORMATION: Primer

<400> SEQUENCE: 160
cttgttgagc agaggttctt ttttatcttc atggccagac ctaagagcaa tcagtgagga  60
atc                                                               63

<210> SEQ ID NO 161
<211> LENGTH: 24
<212> TYPE: DNA
<213> ORGANISM: Artificial
<220> FEATURE:
<223> OTHER INFORMATION: Primer

<400> SEQUENCE: 161
gagggcaggg cagtactgta ggaa                                        24

<210> SEQ ID NO 162
<211> LENGTH: 21
<212> TYPE: DNA
<213> ORGANISM: Artificial
<220> FEATURE:
<223> OTHER INFORMATION: Primer

<400> SEQUENCE: 162
tcgacccaac tacccgaagc a                                           21

<210> SEQ ID NO 163
<211> LENGTH: 21
<212> TYPE: DNA
<213> ORGANISM: Artificial
<220> FEATURE:
<223> OTHER INFORMATION: Primer

<400> SEQUENCE: 163
ggctgccaac tacccgaaga c                                           21

<210> SEQ ID NO 164
<211> LENGTH: 36
<212> TYPE: DNA
<213> ORGANISM: Artificial
<220> FEATURE:
<223> OTHER INFORMATION: Primer

<400> SEQUENCE: 164
cttgcataca ggttaattat ttgagcagag gttcac                           36
```

-continued

<210> SEQ ID NO 165
<211> LENGTH: 30
<212> TYPE: DNA
<213> ORGANISM: Artificial
<220> FEATURE:
<223> OTHER INFORMATION: Primer

<400> SEQUENCE: 165 ccctttatc ttcttgagca gaggttcaca                              30

<210> SEQ ID NO 166
<211> LENGTH: 36
<212> TYPE: DNA
<213> ORGANISM: Artificial
<220> FEATURE:
<223> OTHER INFORMATION: Primer

<400> SEQUENCE: 166
ctttaactcg tgaggttcta atcgtttttt atcttc                      36

<210> SEQ ID NO 167
<211> LENGTH: 31
<212> TYPE: DNA
<213> ORGANISM: Artificial
<220> FEATURE:
<223> OTHER INFORMATION: Primer

<400> SEQUENCE: 167
gcacttgtaa cagaggttct aatcgtcaac a                           31

<210> SEQ ID NO 168
<211> LENGTH: 51
<212> TYPE: DNA
<213> ORGANISM: Artificial
<220> FEATURE:
<223> OTHER INFORMATION: Primer

<400> SEQUENCE: 168
tcgacccaac tacccgaagc aatttcaact ctgtctcctt cctcttccta c     51

<210> SEQ ID NO 169
<211> LENGTH: 62
<212> TYPE: DNA
<213> ORGANISM: Artificial
<220> FEATURE:
<223> OTHER INFORMATION: Primer

<400> SEQUENCE: 169
cttgcataca ggttaattat ttgagcagag gttcacattt caactctgtc tccttcctct   60
tc                                                                  62

<210> SEQ ID NO 170
<211> LENGTH: 62
<212> TYPE: DNA
<213> ORGANISM: Artificial
<220> FEATURE:
<223> OTHER INFORMATION: Primer

<400> SEQUENCE: 170
ctttaactcg tgaggttcta atcgtttttt atcttcattt caactctgtc tccttcctct   60
tc                                                                  62

```
<210> SEQ ID NO 171
<211> LENGTH: 47
<212> TYPE: DNA
<213> ORGANISM: Artificial
<220> FEATURE:
<223> OTHER INFORMATION: Primer

<400> SEQUENCE: 171
ggctgccaac tacccgaaga cataggccac tgacaaccac ccttaac          47

<210> SEQ ID NO 172
<211> LENGTH: 56
<212> TYPE: DNA
<213> ORGANISM: Artificial
<220> FEATURE:
<223> OTHER INFORMATION: Primer

<400> SEQUENCE: 172 ccctttatc ttcttgagca gaggttcaca ataggccact gacaaccacc cttaac   56

<210> SEQ ID NO 173
<211> LENGTH: 57
<212> TYPE: DNA
<213> ORGANISM: Artificial
<220> FEATURE:
<223> OTHER INFORMATION: Primer

<400> SEQUENCE: 173
gcacttgtaa cagaggttct aatcgtcaac aataggccac tgacaaccac ccttaac  57

<210> SEQ ID NO 174
<211> LENGTH: 49
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 174
tttttnggtc ttggccagtt ggcaaaatgg ctgccaacta ccgcttcac        49

<210> SEQ ID NO 175
<211> LENGTH: 65
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 175
tttttnggtc ttggccagtt ggcaaaatcc ctttgagcag aggttcatta gcacttgtaa  60
caaca                                                              65

<210> SEQ ID NO 176
<211> LENGTH: 50
<212> TYPE: DNA
<213> ORGANISM: Artificial
<220> FEATURE:
<223> OTHER INFORMATION: Primer
```

```
<220> FEATURE:
<221> NAME/KEY: misc_feature
<222> LOCATION: (6)..(6)
<223> OTHER INFORMATION: N at position 6 is carbon 18 spacer

<400> SEQUENCE: 176
tttttngggc agggcagtac tgtaggaatg gctgccaact accgcttcac          50

<210> SEQ ID NO 177
<211> LENGTH: 66
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 177
tttttngggc agggcagtac tgtaggaatc cctttgagca gaggttcatt agcacttgta    60
acaaca                                                              66

<210> SEQ ID NO 178
<211> LENGTH: 53
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 178
tttttngtac tgtaggaaga ggaaggagac atggctgcca actaccgctt cac         53

<210> SEQ ID NO 179
<211> LENGTH: 54
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: N at position 6 is carbon 18 spacer

<400> SEQUENCE: 179
tttttngggc agggcagtac tgtaggaaga ggtggctgcc aactaccgct tcac        54

<210> SEQ ID NO 180
<211> LENGTH: 28
<212> TYPE: DNA
<213> ORGANISM: Artificial
<220> FEATURE:
<223> OTHER INFORMATION: Primer

<400> SEQUENCE: 180
gtggatgggt agtagtatgg aagaaatc                                     28

<210> SEQ ID NO 181
<211> LENGTH: 27
<212> TYPE: DNA
<213> ORGANISM: Artificial
<220> FEATURE:
<223> OTHER INFORMATION: Primer
```

<400> SEQUENCE: 181
aactgagtgg gagcagtaag gagattc                                27

<210> SEQ ID NO 182
<211> LENGTH: 47
<212> TYPE: DNA
<213> ORGANISM: Artificial
<220> FEATURE:
<223> OTHER INFORMATION: Primer

<400> SEQUENCE: 182
tcgacccaac taccgcttcc ataagtggct cctgacctgg agtcttc          47

<210> SEQ ID NO 183
<211> LENGTH: 21
<212> TYPE: DNA
<213> ORGANISM: Artificial
<220> FEATURE:
<223> OTHER INFORMATION: Primer

<400> SEQUENCE: 183
cggtggctca cgcctgtaat c                                      21

<210> SEQ ID NO 184
<211> LENGTH: 23
<212> TYPE: DNA
<213> ORGANISM: Artificial
<220> FEATURE:
<223> OTHER INFORMATION: Primer

<400> SEQUENCE: 184
cactgtaatc cagcctgggc aac                                    23

<210> SEQ ID NO 185
<211> LENGTH: 48
<212> TYPE: DNA
<213> ORGANISM: Artificial
<220> FEATURE:
<223> OTHER INFORMATION: Primer

<400> SEQUENCE: 185
tcgacccaac taccgcttcc aatcaacatg gtgaaattct atctctac         48

<210> SEQ ID NO 186
<211> LENGTH: 47
<212> TYPE: DNA
<213> ORGANISM: Artificial
<220> FEATURE:
<223> OTHER INFORMATION: Primer

<400> SEQUENCE: 186
tcgacccaac taccgcttcc ataggcagat cacaaggtca ggagttc          47

<210> SEQ ID NO 187
<211> LENGTH: 23
<212> TYPE: DNA
<213> ORGANISM: Artificial
<220> FEATURE:
<223> OTHER INFORMATION: Primer

<400> SEQUENCE: 187
tttgtttctt tgctgccgtc ttc                                    23

```
<210> SEQ ID NO 188
<211> LENGTH: 25
<212> TYPE: DNA
<213> ORGANISM: Artificial
<220> FEATURE:
<223> OTHER INFORMATION: Primer

<400> SEQUENCE: 188
aggtcaaata agcagcagga gaaag                                              25
```

METHODS AND DEVICES FOR DNA SEQUENCING AND MOLECULAR DIAGNOSTICS

This application is a national stage application under 35 U.S.C. §371 from PCT Application No. PCT/US2012/000329, filed Jul. 23, 2012, which claims the benefit of U.S. Provisional Patent Application Ser. No. 61/572,755, filed Jul. 21, 2011 which is hereby incorporated by reference in its entirety.

This invention was made with government support under grant number 1U01AI075470 awarded by the National Institutes of Allergy and Infectious Diseases. The government has certain rights in this invention.

FIELD OF THE INVENTION

The present invention is directed to methods and instrumentation for identifying target nucleotide sequences in a biological sample

BACKGROUND OF THE INVENTION

Cancer care in the U.S. alone costs $171 billion per year. Every year, 1.4 million Americans are diagnosed with cancer, and 565,000 will die from cancer. Worldwide, 12 million individuals get cancer, with a death toll of 7 million per year, almost twice the number from malaria, AIDS, and tuberculosis combined. Current cancer patient treatment falls short because of failures at the diagnostic level. Firstly, individuals with predisposing genetic risk factors are not identified because current technology is not cost effective, and many risk factors still need to be discovered and validated. The molecular signatures of cancers are neither well understood nor rigorously profiled—because current technology is not standardized across platforms. Finally, patients who will not respond to current therapies are not identified, because current technology is not integrated with clinical trials and these profiles have not been properly identified or validated.

The present invention is directed to methods, devices, and instrumentation for nucleic acid amplification and sequencing that is designed to standardize molecular diagnosis and individualize treatment of cancer and other diseases to overcome these and other deficiencies in the art.

SUMMARY OF THE INVENTION

A first aspect of the present invention relates to method for identifying one or more of a plurality of target nucleotide sequences in a sample. This method involves providing a sample potentially containing one or more target nucleotide sequences, and/or complements thereof. Each target nucleotide sequence comprises a first, second, and third target portion, where the second target portion is between the first and third target portions. Also provided is one or more oligonucleotide primer sets. Each primer set is characterized by a first and second oligonucleotide primer. The first oligonucleotide primer of the primer set has a first primer portion complementary to the first target portion and a second primer portion that is the same as the second target portion. The second primer portion of the first oligonucleotide primer is 5' to the first primer portion. The second oligonucleotide primer has a third primer portion that is the same as the third target portion. A polymerase is provided and blended with the sample and the oligonucleotide primer sets to form a polymerase extension reaction mixture. The mixture is subjected to a hybridization and extension treatment. During the hybridization treatment, the first and third primer portions of the first and second oligonucleotide primers, respectively, hybridize to their respective complementary portions of the target nucleotide sequence and/or complement thereof. During the extension treatment, the hybridized oligonucleotide primers extend to form primary primer extension products. The primary primer extension products are denatured from the target nucleotide sequences and complements thereof. The method further involves providing a second polymerase and blending it with the polymerase extension reaction mixture after the hybridization and extension treatments to form a polymerase amplification reaction mixture. The polymerase amplification reaction mixture is subjected to one or more polymerase amplification reaction cycles, each cycle comprising a denaturation, hybridization, and extension treatment. During the denaturation treatment, hybridized nucleic acid sequences are separated, and, during the hybridization treatment, the first and third primer portions of the first and second oligonucleotide primers, respectively, hybridize to their respective complementary portions of the primary primer extension products. During the extension treatment, the hybridized oligonucleotide primers are extended to form first oligonucleotide primer extension products and second oligonucleotide primer extension products. The first and/or second oligonucleotide primer extension products are detected and distinguished to identify the presence of one or more target nucleotide sequences in the sample.

A second aspect of the present invention relates to a method for identifying one or more of a plurality of target nucleotide sequences in a sample. This method involves providing a sample potentially containing one or more target nucleotide sequences, and/or complements thereof. Each target nucleotide sequence comprises a first, second, and third target portion, where the second target portion is between the first and third target portions. Also provided is one or more oligonucleotide primer sets. Each primer set is characterized by a first and second oligonucleotide primer. The first oligonucleotide primer of the primer set has a first primer portion that is the same as the first target portion and a second primer portion that is complementary to the second target portion. The second primer portion of the first oligonucleotide primer is 5' to the first primer portion. The second oligonucleotide primer has a third primer portion that is complementary to the third target portion and a fourth primer-specific portion. The fourth primer-specific portion of the second oligonucleotide primer is 5' to the third primer portion. A polymerase is provided and blended with the sample and the oligonucleotide primer sets to form a polymerase extension reaction mixture. The mixture is subjected to a hybridization and extension treatment. During the hybridization treatment, the first and third primer portions of the first and second oligonucleotide primers, respectively, hybridize to their respective complementary portions of the target nucleotide sequence and/or complement thereof. During the extension treatment, the hybridized oligonucleotide primers extend to form primary primer extension products. The primary primer extension products are denatured from the target nucleotide sequences and complements thereof. The method further involves providing a second polymerase and blending it with the polymerase extension reaction mixture after the hybridization and extension treatments to form a polymerase amplification reaction mixture. The polymerase amplification reaction mixture is subjected to one or more polymerase amplification reaction cycles, each cycle comprising a denaturation, hybridization, and extension treatment. During the denaturation treatment, hybridized nucleic acid sequences are separated, and, during the hybridization treatment, the first and third primer portions of the first and second oligonucleotide primers, respectively, hybridize to their respective complementary portions of the primary primer extension products. During the extension treatment, the hybridized oligonucleotide primers are extended to form first oligonucleotide primer extension products and second oligonucleotide primer extension products. The first and/or second oligonucleotide primer extension products are detected and distinguished to identify the presence of one or more target nucleotide sequences in the sample.

Another aspect of the present invention is directed to a device. This device comprises a solid support having a base surface, a top surface, and a plurality of side surfaces extending between the base and top surfaces. The base surface, top surface, and plurality of side surfaces of the device collectively form a plurality of wells or pillars on the solid support. The device further comprises a plurality of oligonucleotides attached to the side surfaces, but not the base surfaces, of the wells or pillars.

Another aspect of the present invention relates to methods of forming arrays of oligonucleotides on a solid support. The first of these methods involves providing a solid support having a base surface, a top surface, and a plurality of side surfaces extending between the base and top surfaces. The base surface, top surface, and plurality of side surfaces collectively form a plurality of wells or pillars on the solid support. A mask is applied to cover the base surface of the solid support and the masked device is exposed to an activating agent to activate the unmasked surfaces of the solid support, while the masked surfaces of the solid support are non-activated. The mask is removed from the solid support and the exposed solid support is contacted with a plurality of oligonucleotides under conditions effective for the oligonucleotides to attach to the activated surfaces of the solid support, but not the non-activated surfaces of the solid support, thereby forming arrays of oligonucleotides on the solid support.

Another method of forming arrays of oligonucleotides on a solid support of the present invention involves providing a solid support having a planar substrate and a photosensitive layer over a surface of the substrate. The solid support is subjected to a photolithography process under conditions effective to form pillars or wells on the solid support. The solid support is contacted with a plurality of oligonucleotides under conditions effective for the oligonucleotides to attach to portions of the photosensitive layer which are either exposed or left unexposed by the photolithography process but not portions of the photosensitive layer which are left unexposed or exposed, respectively, thereby forming arrays of oligonucleotides on the solid support.

Another aspect of the present invention is directed to a method for identifying one or more of a plurality of target nucleotide sequences in a sample. The first of these methods involves providing a solid support containing primary extension products, where the primary extension products comprise a target nucleotide sequence, or a complement thereof, and a 3' primer binding sequence. Primary primers that are complementary to the primary extension products are provided along with a first DNA polymerase and a mixture of dNTPs, where one or more of the dNTPs contain a modification at its 3' end. The solid support containing the primary extension products, the primary primers, the polymerase, and the dNTPs are blended to form an extension mixture and the mixture is subjected to a hybridization and a polymerase treatment. During the hybridization treatment the primary primers hybridize to complementary primary extension product sequences if present on the solid support. During the polymerase treatment, the hybridized primers extend one or more bases until the polymerase incorporates a modified dNTP. Secondary primers that are complementary to the 3' primer binding sequence of the primary extension products, a second DNA polymerase, and a DNA ligase are provided and blended with the solid support containing the primary extension products and primary primers hybridized thereto to form a polymerase-ligase mixture. The polymerase-ligase mixture is subjected to a hybridization treatment, wherein the secondary primers hybridize to their complementary 3' primer binding sequence of the primary extension products, and a polymerase-ligase treatment, where the hybridized secondary primers extend and ligate to upstream hybridized primary primers to form secondary extension products complementary to a portion of the primary extension products. The method further involves cleaving the primary primers and denaturing the cleaved primers, but not the secondary extension products appended to the primary primers from the primary extension products. The target nucleic acid sequence is identified by sequencing the secondary extension products.

A second method for identifying one or more of a plurality of target nucleotide sequences in a sample involves providing a solid support comprising primary extension products, where the primary extension products comprise a target nucleotide sequence, or a complement thereof, and a 3' primer binding sequence. Primary primers that are complementary to the primary extension products and contain a 3' cleavage site, a first DNA polymerase, and a mixture of dNTPs, where one or more of the dNTPs contain a modification at its 3' end are provided. The solid support containing the primary extension products, the primary primers, the polymerase, and the dNTPs are blended to form a first extension mixture, and the extension mixture is subjected to a hybridization and a polymerase treatment. During the hybridization treatment, the primary primers hybridize to complementary primary extension product sequences if present on the solid support. During the polymerase treatment, the hybridized primers extend one or more bases until the polymerase incorporates a modified dNTP. Secondary primers that are complementary to the 3' primer binding sequences of the primary extension products, a second DNA polymerase, and a DNA ligase are provided and blended with the solid support containing primary extension products and primary primers hybridized thereto, to form a polymerase-ligase mixture. The polymerase-ligase mixture is subjected to a hybridization treatment, wherein the secondary primers hybridize to their complementary 3' primer binding sequence of the primary extension products, and a polymerase-ligase treatment, where the hybridized secondary primers extend and ligate to upstream hybridized primary primers to form secondary extension products complementary to a portion of the primary extension products. Unligated primary primers are denatured from the primary extension products. Tertiary primers that are complementary to the primary extension products and contain a 3' cleavage site that is different than the 3' cleavage site of the primary primers are provided and blended with the solid support containing primary and secondary extension products, the first DNA polymerase, and the dNTPs to form a second extension mixture. The second extension mixture is subject to a hybridization treatment, where the tertiary primers hybridize to complementary primary extension product sequences if present on the solid support, and a polymerase treatment where the hybridized tertiary primers extend one or more bases until the polymerase incorporates a modified dNTP. The primary primer portion of the secondary extension products are cleaved under conditions that liberate a 3' hydroxyl end. The secondary extension products are extended from the liberated 3' hydroxyl end to a hybridized tertiary primer and ligate to the hybridized tertiary primers. The tertiary primers are cleaved under conditions that liberate a 3' hydroxyl end. Cleaved tertiary primers, but not the secondary extension products appended to tertiary primers are denatured from the primary extension products and the target nucleic acid sequence is obtained based on sequencing of the secondary extension products.

Another aspect of the present invention relates to a method for capturing a plurality of target nucleotide sequences. This method involves providing a sample potentially containing one or more target nucleotide sequences or complements thereof and a plurality of oligonucleotide primer sets. Each oligonucleotide primer set is characterized by a first oligonucleotide primer comprising a portion complementary to the target nucleotide sequence, and a second oligonucleotide primer comprising a portion complementary to the target nucleotide sequence and a capture group. A ligase is provided and blended with the sample and the plurality of oligonucleotide primer sets to form a mixture. The mixture is subjected to one or more ligation cycles comprising a denaturation treatment and hybridization treatment. During the hybridization treatment, the oligonucleotide primers hybridize at proximate positions in a base-specific manner to their respective target nucleotide sequences, if present in the sample, and ligate to one another to form a ligated product sequence containing the target-specific portions and the capture group. Unligated second oligonucleotide primers, but not ligated products are denatured from the target nucleotide sequences. The ligated products hybridized to target nucleotide sequences are captured by binding of the capture group to its binding partner.

Another aspect of the present invention relates to methods for enriching target nucleotide sequences prior to characterization of methylation status. In the first of these methods a sample containing one or more target nucleotide sequences that potentially contain methylated CpG sequences is provided. The sample is treated with sodium bisulfite under conditions suitable for converting unmethylated cytosines, but not methylated cytosines in the target nucleotide sequence into uracils. Degenerate oligonucleotide primers, a DNA polymerase, and a DNA ligase are provided and blended with the bisulfite-treated sample to form a polymerase extension reaction mixture. The polymerase extension reaction mixture is subjected to a polymerase extension reaction to form primary extension products. The primary extension products are denatured from the target nucleotide sequences and the polymerase extension reaction is repeated to form secondary extension products. The primary and secondary extension products form double-stranded copies of the bisulfite treated target nucleotide sequence, lacking uracils and methylated cytosines. This method further involves providing a restriction endonuclease having a recognition site that contains at least one CpG dinucleotide, but at least one strand of the recognition sequence does not contain any other cytosine than the CpG dinucleotide. Linker oligonucleotides and a DNA ligase are also provided. The primary and secondary extension products are cleaved at the restriction endonuclease recognition site and the linker oligonucleotides are ligated to the restriction endonuclease cleaved sites. Target nucleotide sequences are enriched prior to characterization of methylation status based on the ligation of linkers to both ends of the cleaved extension products.

A second method of the present invention for enriching target nucleotide sequences prior to characterization of methylation status involves providing a sample containing one or more target nucleotide sequences that potentially contain methylated CpG sequences. Primary linker oligonucleotides and a DNA ligase are also provided and blended with the sample to form a primary linker reaction mixture. The primary linker reaction mixture is subjected to conditions suitable for ligating the linker oligonucleotides to 5' and 3' ends of the target nucleotide sequences. The primary linker reaction mixture is treated with sodium bisulfite under conditions suitable for converting unmethylated, but not methylated cytosines, into uracils. Primary oligonucleotide primers having a sequence complementary to the primary linker oligonucleotides and a polymerase are provided and blended with the bisulfate-treated primary linker reaction mixture to form a polymerase chain reaction mixture. The polymerase chain reaction mixture is subjected to two or more polymerase chain reaction cycles comprising denaturation, hybridization, and extension treatments. During the denaturation treatment, hybridized nucleic acid sequences are separated. During the hybridization treatment, primary oligonucleotide primers hybridize to the linker regions appended to the target nucleotide. During the extension treatment, the hybridized primary oligonucleotide primers extend to form primary extension products. This method further involves providing a restriction endonuclease having a recognition site that contains at least one CpG dinucleotide, but at least one strand of the recognition site does not contain any other cytosine than the CpG dinucleotide. Secondary linker oligonucleotides and a DNA ligase are provided and blended with the polymerase chain reaction mixture after being subjected to one or more polymerase chain reaction cycles to form a secondary linker reaction mixture. The secondary linker reaction mixture is subjected to conditions suitable for cleaving the primary extension products at the restriction endonuclease recognition site to form restriction endonuclease cleaved ends and ligating the secondary linker oligonucleotides to the restriction endonuclease cleaved ends. Target nucleotide sequences are enriched prior to characterization of methylation status based on fragments containing secondary linkers ligated to both ends.

The present invention describes methods, devices, and instrumentation for nucleic acid amplification and sequencing that are designed to standardize molecular diagnostics and individualize treatment of cancer and other diseases. The innovation of the system is a genomic sequencing array, which is based on a new three-dimensional array design combined with a novel solid phase amplification method. The device, which is made of plastic, has the capability to capture and sequence DNA on 576 million to 2.3 billion oligonucleotide addresses, and will be manufactured at a fraction of the cost of traditional chips. The design approach is unique in that pillars or wells add a third-dimension to the array to increase load compared to the standard two-dimensional arrays. In addition, the solid phase amplification technology generates amplicon clusters where the size of the cluster is defined and limited by the size of the pillar or well, avoiding problems with non-optimal cluster density and the formation of overlapping clusters. The amplification method is based on a novel primer design that enables amplification of uniform clusters independent of length, from 200 to 5,000 bases, and can produce 10 to 100-fold cleaner signal-tonoise when implemented in a sequencing-by-synthesis approach. Further, in contrast to current sequencing machines that sequence random fragments, the unique design described herein also allows for sequencing and digital quantification of only those genes required for the validation studies or clinical test used for each patient.

In addition to the genomic sequencing array, the polymer modular microfludic device design of the present invention offers a standardized yet flexible strategy for carrying out the different molecular assays necessary to achieve a robust diagnostic platform. The task-specific module of the fluidic motherboards can be interchanged, thus allowing users to upgrade their machine as new technologies come online, swap different modules in and out to accommodate different molecular assay strategies, and at the same time, provide accessibility to existing fluid handling platforms to allow easy interfacing to the macro-world.

BRIEF DESCRIPTION OF THE DRAWINGS

FIGS. 2A-2E show a schematic depiction of an embodiment of the solid phase nucleic acid amplification and sequencing method of the present invention using the snake primer design. FIG. 2A shows steps 1 through 4 of the method. FIG. 2B shows steps 5 through 7 of the method. FIG. 2C shows steps 8 through 10 of the method. FIG. 2D shows steps 11 and 12 of the method. FIG. 2E shows steps 13 through 15 of the method.

FIGS. 3A-3G show a schematic depiction of an embodiment of the solid phase nucleic acid amplification and sequencing method of the present invention using the snakeHE universal primer design. FIG. 3A shows steps 1 through 4 of the method. FIG. 3B shows steps 5 through 7 of the method. FIG. 3C shows steps 8 through 10 of the method. FIG. 3D shows steps 11 and 12 of the method. FIG. 3E shows steps 13 through 15 of the method. FIG. 3F shows steps 16 through 18 of the method. FIG. 3G shows steps 19 through 21 of the method.

FIGS. 4A-4G show a schematic depiction of an embodiment of the solid phase nucleic acid amplification and sequencing method of the present invention using the snakeHE universal primer design. FIG. 4A shows steps 1 through 4 of the method. FIG. 4B shows steps 5 through 7 of the method. FIG. 4C shows steps 8 through 10 of the method. FIG. 4D shows steps 11 and 12 of the method. FIG. 4E shows steps 13 through 15 of the method. FIG. 4F shows steps 16 through 18 of the method. FIG. 4G shows steps 19 through 21 of the method.

FIGS. 5A-5G show a schematic depiction of an embodiment of the solid phase nucleic acid amplification and sequencing method of the present invention using the snakeHE universal primer design. FIG. 5A shows steps 1 through 4 of the method. FIG. 5B shows steps 5 through 7 of the method. FIG. 5C shows steps 8 through 10 of the method. FIG. 5D shows steps 11 and 12 of the method. FIG. 5E shows steps 13 through 15 of the method. FIG. 5F shows steps 16 and 17 of the method. FIG. 5G shows steps 18 through 20 of the method.

FIGS. 6A-6G show a schematic depiction of an embodiment of the solid phase nucleic acid amplification and sequencing method of the present invention using the snakeHE universal primer design. FIG. 6A shows steps 1 through 4 of the method. FIG. 6B shows steps 5 through 7 of the method. FIG. 6C shows steps 8 through 10 of the method. FIG. 6D shows steps 11 and 12 of the method. FIG. 6E shows steps 13 through 15 of the method. FIG. 6F shows steps 16 through 18 of the method. FIG. 6G shows steps 19 through 21 of the method.

FIGS. 7A-7G show a schematic depiction of an embodiment of the solid phase nucleic acid amplification and sequencing method of the present invention using the snakeHE universal primer design. FIG. 7A shows steps 1 through 4 of the method. FIG. 7B shows steps 5 through 7 of the method. FIG. 7C shows steps 8 through 10 of the method. FIG. 7D shows steps 11 and 12 of the method. FIG. 7E shows steps 13 through 15 of the method. FIG. 7F shows steps 16 and 17 of the method. FIG. 7G shows steps 18 through 20 of the method.

FIG. 8 is a flow diagram showing a method of sequencing internal regions of a target nucleotide sequence using the methods of the present invention.

FIGS. 9A-9B show a flow diagram of a method of sequencing internal regions of a target nucleotide sequence using the methods of the present invention. FIG. 9A shows steps 1 through 7 of the method. FIG. 9B shows steps 8 through 13 of the method.

FIG. 10 is a flow diagram showing a method of target nucleotide sequence enrichment using the methods of the present invention.

FIG. 14 shows a schematic of a medium array format on a 86×128 mm chip containing 384 million oligonucleotide addresses (left) and a large array format on a 128×128 mm chip containing 576 million oligonucleotide addresses (right).

FIG. 15A shows the cylindrical pillars (2 μm diameter and 4.5 μm tall) on the solid support. FIG. 15B is a magnified view of FIG. 15A. FIG. 15C is a photomicrograph showing the array positions, where each position (i.e., each square) contains $1 \times 10^6$ pillars.

FIG. 16A shows a device comprising cylindrical pillars having oligonucleotides attached to the side and top surfaces of the pillars. FIG. 16B is a side view of a device showing pillars having oligonucleotides and pH sensitive reporter dyes immobilized to the side and top surfaces of the pillars. FIG. 16C is a schematic illustration showing oligonucleotide and pH sensitive reporter dye attachment to the pillar surface of the device.

FIG. 23 depicts the SU-8 photoresist surface chemistry.

FIGS. 24A-24C depict methods of SU-8 photoresist surface modification. FIG. 24A shows the native SU-8 surface comprises epoxide rings that are suitable for covalent attachment of oligonucleotides without activation or modification. Amine-terminated oligonucleotides can be added to the native SU-8 surface using alkaline solutions (pH ~12) that hydrolyze surface epoxide groups and form secondary amines with the oligonucleotides carrying a primary amine. FIG. 24B shows SU-8 treated with nitric acid generates surface confined hydroxyl groups that are subsequently reacted with primary amine containing oligonucleotides. FIG. 24C shows SU-8 exposed to UV radiation (254 nm) to generate surface hydroxyls and carboxylic acid groups.

FIG. 26A shows step 1 of the method. FIG. 26B shows step 2 of the method. FIG. 26C shows step 3 of the method. FIG. 26D shows step 4 of the method. FIG. 26E shows a closeup view of step 4 of the method. FIG. 26F shows step 5 of the method. FIG. 26G shows an example of gene expression analysis using the generated array of oligonucleotides. FIG. 26H shows an example of copy number analysis using the generated array of oligonucleotides.

FIG. 27A shows step 1 of the method. FIG. 27B shows step 2 of the method. FIG. 27C shows step 3 of the method. FIG. 27D shows step 4 of the method. FIG. 27E is a closeup view of step 4 of the method. FIG. 27F shows step 5 of the method. FIG. 27G shows an example of gene-specific mutation analysis using the generated array of oligonucleotides. FIG. 27H shows an example of low level mutation detection using the generated array of oligonucleotides.

FIG. 28A shows step 1 of the method. FIG. 28B shows step 2 of the method. FIG. 28C shows step 3 of the method. FIG. 28D shows step 4 of the method. FIG. 28E shows step 5 of the method. FIG. 28F shows step 6 of the method. FIG. 28G shows step 7 of the method. FIG. 28H shows step 8 of the method. FIG. 28I shows step 9 of the method. FIG. 28J shows an array comprising a plurality of different primer sets (e.g., twenty four) represented multiple times across the array.

FIG. 29A is a top-down view of a polymeric modular microfluidic device comprising several functional units or modules that facilitate sample processing and nucleic acid sequencing. Perspective views of the device are shown in FIGS. 29B and 29C. As shown in these Figures, the sequencing module of the device can comprise pillars as shown in FIG. 29B or wells as shown in FIG. 29C.

FIG. 30A shows a three-dimensional rendering of the device and its modular components. FIG. 30B shows a close-up illustration of the solid-phase extraction (SPE) bed filled with an array of high-aspect ratio posts. FIG. 30C is a schematic showing the operation of the device's membrane valve with direct mechanical actuation. FIG. 30D shows the geometry of the continuous flow PCR reactor with dual-depth microchannels for extended residence time and the extension-zone (Den—denaturation, Ext—extension, PA—primer annealing). FIG. 30E is a schematic representation of the detection mode.

FIGS. 32A-32E are schematic depictions of the valving and pumping operations on the fluidic motherboard of the present invention. FIG. 32A shows an open valve where fluid is allowed to pass through the valve when the load (solenoid, 5) is not applied. FIG. 32B shows the valve is closed when the load is applied. FIGS. 32C-32E show the functioning of the pump of the device. As shown in FIG. 32C, the pump is first filled by pipetting solution into the pump chamber with the outlet blocked (3). FIG. 32D shows, following filling, the device is placed in the system and then, a sealing pin (5) is allowed to block the filling port. FIG. 32E shows, to dispense fluid, the solenoid (6) is actuated by allowing fluid to flow through the outlet (3) by opening the super hydrophobic valve (4).

FIG. 34A shows polycarbonate (PC) molded with a microchannel containing micropillars that is used for the purification of a variety of nucleic acids. FIG. 34B is a magnified view of the micropillars in the microchannel. FIG. 34C is a fluorescence microscopic image of UV-photoactivated micropillar surface bound by YOPRO-1 labeled genomic DNA. FIG. 34D is an image of an agarose gel showing PCR amplified gDNA product that was obtained using a polymeric microchannel solid-phase extraction module.

FIG. 35A shows the thermal reactor modules are equipped with a continuous flow (CF) thermal cycling format. FIG. 35B shows a new concept for CF thermal cyclers in which the polymerase extension isothermal zone possesses deeper channel than shallow channels of the renaturation and denaturation zones, which are kinetically much faster. FIG. 35C shows the molding tool that is used to make the CF thermal cycler module of the device. FIG. 35D shows a cross section of the fluidic network comprising the CF thermal cycler with deep and shallow channels. FIG. 35E is a photomicrograph of a CF thermal cycler module of the present invention showing the polymerase extension isothermal zone with deep channels, and renaturation and denaturation zones possessing shallow channels.

FIG. 36A shows grooves between temperature zones to increase the resistance to lateral heat conduction between zones to improve thermal isolation between reaction zones. The graph of FIG. 36B shows the relative intensity of amplification efficiency as a function of reaction time using a device with and without grooves.

FIG. 43A shows the conductometric response generation for 1.0 mL of whole blood seeded with 10 SW620 CTCs (top line) or 0 CTCs (bottom line) processed using the polymeric high-throughput microsampling unit of FIG. 41 at a linear flow velocity of 2.0 mm/s. The selected CTCs were released from the capture surface using 0.25% w/v trypsin in Tris-glycine buffer and transported through the conductivity sensor at 1 μL/min. Conductivity peaks were identified as SW620/HT29 CTCs based on signal-to-noise ratio of 3 associated with the peak in the data trace. The inset represents a magnified view of a section of the data. The conductometrically enumerated cells were subjected to PCR followed by LDR analysis. Also shown are CGE analyses of blood samples after processing using the HTMSU and the electromanipulation unit seeded with HT29-type CTCs (FIG. 43B) or SW620 CTCs (FIG. 43C). Peak (a) represents the primer peak, and peak (b) is the 43 nucleotide LDR product. DNA markers of 20 and 80 nucleotides were co-electrophoresed with the LDR product.

FIG. 45 is a table of the p53 probe primer sequences used in the methods of the present invention.

FIG. 46 is a table of the solid phase p53 primer sequences used in the methods of the present invention.

FIG. 47 is a table of the p53 template amplification primer sequences used in the methods of the present invention.

FIG. 50A is a graph showing the water contact angles following UV or plasma oxidation (the smaller contact angle is indicative of a higher coverage of surface carboxylate groups). FIG. 50B is a scanning fluorescence microscope image of a COC surface exposed to UV light through a photomask and subsequently reacted with amine terminated oligonucleotides (blue squares). FIG. 50C is a graph comparing the fluorescence intensity of non-UV activated areas (background) and UV activated areas of COC that were treated with an amine-terminated oligonucleotide bearing either Cy3, Cy5 or FAM labeling dye. FIG. 50D is a graph comparing the fluorescence intensity of non-UV activated areas (background) and UV activated areas of plasma treated COC surface.

FIG. 51 is a schematic showing the location of oligonucleotide immobilization on array #L2 of the present invention.

FIG. 52A shows a fluorescence image acquired using a ScanArray Express® (Perkin Elmer, Boston, Mass.) microarray scanner after the first hybridization step. FIG. 52B shows a fluorescence image acquired using a ScanArray Express® (Perkin Elmer, Boston, Mass.) microarray scanner after the second hybridization step. FIG. 52C shows a fluorescence image acquired using a ScanArray Express® (Perkin Elmer, Boston, Mass.) microarray scanner after the third hybridization step. FIG. 52D shows a fluorescence image acquired using a ScanArray Express® (Perkin Elmer, Boston, Mass.) microarray scanner after the final hybridization step.

FIG. 53 is a schematic showing the location of oligonucleotide immobilization on array #10E.

FIG. 54A shows a fluorescence image acquired using a ScanArray Express® (Perkin Elmer, Boston, Mass.) microarray scanner after the first hybridization step. FIG. 54B shows a fluorescence image acquired using a ScanArray Express® (Perkin Elmer, Boston, Mass.) microarray scanner after the second hybridization step. FIG. 54C shows a fluorescence image acquired using a ScanArray Express® (Perkin Elmer, Boston, Mass.) microarray scanner after the third hybridization step.

FIGS. 55A-55C show solid phase amplification on cycloolefin copolymer (COC) substrates. FIG. 55A is a schematic of the #14G array layout, showing the location of oligonucleotide immobilization on array. FIG. 55B shows the result of an experiment with hybridization of the forward probe. The intensity of signal is displayed by color (blue, green, yellow, orange, red, white) saturation. FIG. 55C is a comparison of the results on the solid surface using different concentrations of betaine.

FIG. 56 is a schematic of the #14G array layout, showing the location of oligonucleotide immobilization on array. This layout differs from that shown in FIG. 55A by inversion of the array layout.

FIGS. 58A-58C are fluorescence images of the array #14G following forward and reverse probe hybridization after amplification with different concentrations of betaine, i.e., 0M (FIG. 58A), 0.25M (FIG. 58B), and 0.5M (FIG. 58C) used in the reaction mixture.

FIGS. 59A-59B show solid phase PCR using different betaine concentrations in the reaction mixture. FIG. 59A are fluorescence images of array #14G following forward and reverse probe hybridization after amplification with different concentrations of betaine (i.e., 0M, 0.25M, and 0.5M). FIG. 59B is a table of the fluorescence intensities from each spot of array #14G after USER™ enzyme cleavage and reverse probe hybridization.

FIG. 60 is a schematic showing the location of oligonucleotide immobilization on array #14G-2.

FIG. 61A shows fluorescence signals were observed in both the Cy3 channel (from primer) and the Cy5 channel (from extension/termination) when the extension/termination mixture contained both dTTP and Cy5-ddGTP. FIG. 61B shows fluorescence signals were observed in the Cy3 channel (from primer) but were barely seen in the Cy5 channel (from extension/termination) when the extension/termination mixture contained Cy5-ddGTP only (no dTTP).

FIG. 62A shows the SU-8 surface modification scheme using a glycine cross-linker. FIG. 62B show the x-ray photoelectron spectroscopy results of pristine and glycine modified SU-8.

FIG. 64A is a schematic of "click chemistry" on SU-8 surface and FIG. 64B is a fluorescent micrograph image of Cy-3 labeled primer attached to the surface via "click chemistry".

FIG. 68A shows the signal generated with a 10e3 dilution of template, while FIG. 68B shows the signal generated with a 10e4 dilution of template.

FIG. 69A is an epi-fluorescence image of the SU-8 pillar array showing bright spots from pillars containing amplicons that were detected using a probe complementary to a region of the amplicon (23F, 23R). FIG. 69B is a magnified view of one of the pillars. FIG. 69C is an epi-fluorescence image of the array following thermal denaturation at 95° C., showing the loss of the fluorescent probe.

DETAILED DESCRIPTION OF THE INVENTION

Figure 1:
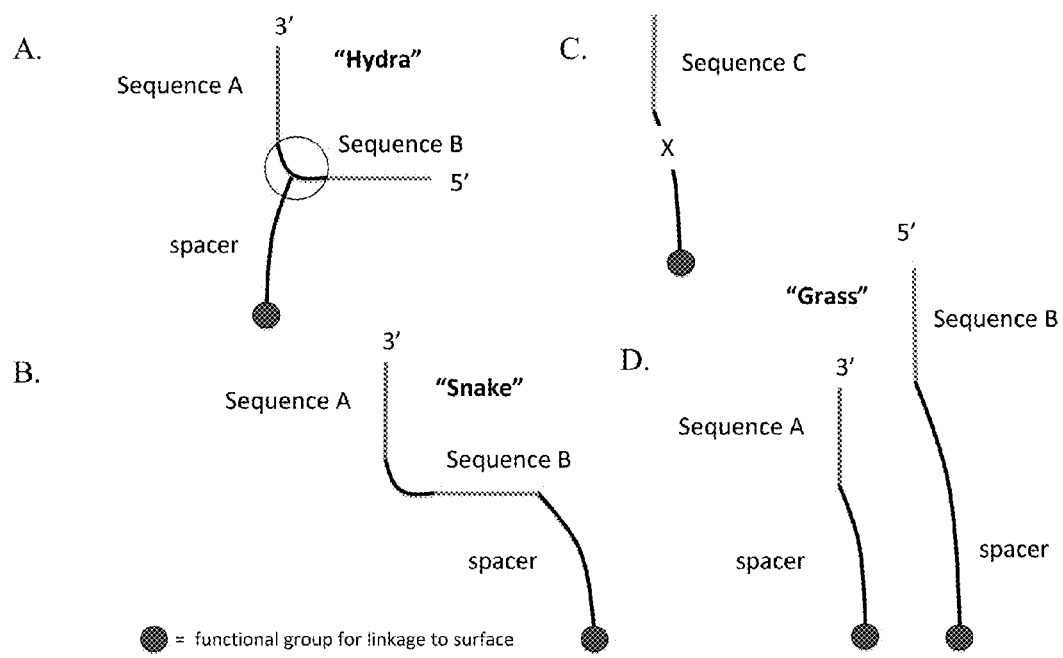
FIGS. 1A-D show first and second oligonucleotide primer designs. The first primer can have a hydra (FIG. 1A), snake (FIG. 1B), or grass (FIG. 1D) configuration. The second primer (FIG. 1C) typically has a grass design. The primers can be used for solution and solid phase amplification methods of the present invention.

The present invention relates generally to the development of a novel nucleic acid amplification technology platform including methods, devices, and instrumentation for the identification of target nucleotide sequences in a sample. Accordingly, a first aspect of the present invention relates to method for identifying one or more of a plurality of target nucleotide sequences in a sample. This method involves providing a sample potentially containing one or more target nucleotide sequences, and/or complements thereof. Each target nucleotide sequence comprises a first, second, and third target portion, where the second target portion is between the first and third target portions. Also provided is one or more oligonucleotide primer sets. Each primer set is characterized by a first and second oligonucleotide primer. The first oligonucleotide primer of the primer set has a first primer portion complementary to the first target portion and a second primer portion that is the same as the second target portion. The second primer portion of the first oligonucleotide primer is 5' to the first primer portion. The second oligonucleotide primer has a third primer portion that is the same as the third target portion. A polymerase is provided and blended with the sample and the oligonucleotide primer sets to form a polymerase extension reaction mixture. The mixture is subjected to a hybridization and extension treatment. During the hybridization treatment, the first and third primer portions of the first and second oligonucleotide primers, respectively, hybridize to their respective complementary portions of the target nucleotide sequence and/or complement thereof. During the extension treatment, the hybridized oligonucleotide primers extend to form primary primer extension products. The primary primer extension products are denatured from the target nucleotide sequences and complements thereof. The method further involves providing a second polymerase and blending it with the polymerase extension reaction mixture after the hybridization and extension treatments to form a polymerase amplification reaction mixture. The polymerase amplification reaction mixture is subjected to one or more polymerase amplification reaction cycles, each cycle comprising a denaturation, hybridization, and extension treatment. During the denaturation treatment, hybridized nucleic acid sequences are separated, and, during the hybridization treatment, the first and third primer portions of the first and second oligonucleotide primers, respectively, hybridize to their respective complementary portions of the primary primer extension products. During the extension treatment, the hybridized oligonucleotide primers are extended to form first oligonucleotide primer extension products and second oligonucleotide primer extension products. The first and/or second oligonucleotide primer extension products are detected and distinguished to identify the presence of one or more target nucleotide sequences in the sample.

In accordance with this aspect of the present invention, the sample provided contains one or more nucleotide sequences, and/or complements thereof, to be identified. The nucleotide sequences can be single stranded or double stranded DNA or cDNA target sequences. The DNA or cDNA sample may be randomly fragmented and treated so as to append one or more of the first, second and/or third target portions, or complements thereof, to the remaining parts of the target sequences or complements thereof. Appending the first, second, and/or third target portions, or complements thereof, to the remaining target nucleotide sequence is achieved using anyone of a variety of enzymatic reactions known in the art. Suitable enzymes include, without limitation, ligases (e.g., *T aquaticus* ligase, *E. coli* ligase, T4 DNA ligase, *Pyrococcus* ligase), polymerases (e.g., Taq polymerase), recombinases, terminal transferases, endonucleases, DNA repair enzymes, and reverse transcriptases.

In certain embodiments of the present invention, the first, second, and/or third portions of the target nucleotide sequences are "universal" primer sequences that are the same for each of the remaining portions of the target nucleotide sequence. In other embodiments of the present invention, the first, second, and/or third portions of the target nucleotide sequences are unique for each of the remaining target portions. In all aspects, the first, second, and third portions of the target nucleotide sequences are complementary to portions of the first or second oligonucleotide primers of a primer set of the present invention.

The remaining target portion of the one or more target nucleotide sequences represents the variable portion of the target nucleotide sequence, i.e., the "gene-specific" portion of the target to be identified. This portion of the target sequence may contain a known, unknown, or partially known nucleotide sequence.

In accordance with this aspect of the present invention, the method steps can be carried out in liquid or solid phase (i.e., solution phase amplification or solid phase amplification). In a preferred embodiment of the present invention, one or both of the first and second oligonucleotide primers of a primer set are attached to a solid support.

FIG. 1 depicts the various primer designs of the present invention. As noted above, the first oligonucleotide primer of a primer set of the present invention has a first primer portion complementary to the first target portion or complement thereof ("Sequence A" in FIG. 1) and a second primer portion that is the same as the second target portion or complement thereof ("Sequence B" in FIG. 1). As shown in FIG. 1, the first oligonucleotide primer can have a "hydra" or "snake" design (FIGS. 1A and 1B, respectively). In either design, the second primer portion of the first oligonucleotide primer is 5' to the first primer portion or complement thereof. In an alternative embodiment of the present invention, the first and second primer portions of the first oligonucleotide primer are split between two separate "grass" primers as shown in FIG. 1 (FIG. 1D). The second oligonucleotide primer of the primer set has a third primer portion ("Sequence C" in FIG. 1C) that is the same as the third target portion. The second oligonucleotide primer is typically a "grass" primer as shown in FIG. 1C. The "X" below the third primer portion of the primer depicted in FIG. 1C indicates the optional presence of a cleavage site.

In accordance with this aspect of the present invention, the oligonucleotide primer sets of the present invention can be in the form of deoxynucleotides, modified deoxyribonucleotides, ribonucleotides, modified ribonucleotides, or nucleotide analogues such as peptide nucleic acid nucleotides (PNA), locked nucleic acid nucleotides (LNA), glycol nucleic acid nucleotides (GNA), and threose nucleic acid nucleotides (TNA).

When amplification is carried out on a solid support, i.e., solid-phase amplification, the solid support can be made from a wide variety of materials. The substrate of the solid support may be biological, nonbiological, organic, inorganic, or a combination of any of these, existing as particles, strands, precipitates, gels, sheets, tubing, spheres, containers, capillaries, pads, slices, films, plates, slides, discs, membranes, etc. In one embodiment of the present invention, the solid support is a plurality of beads, with one or both of the first and second oligonucleotide primers attached thereto. Optionally, the plurality of beads is distributed onto a surface suitable for detecting signal from multiple beads simultaneously. The surface may have any convenient shape, such as a disc, square, circle, etc, and may contain raised or depressed regions for holding the plurality of beads.

In another embodiment of the present invention, the solid support comprises a plurality of three dimensional pillars. A pillar on a solid support, in accordance with the present invention, is any raised structure on the solid support surface having top, bottom, and side surfaces. Pillars can have any geometrical three-dimensional shape, including, without limitation, spherical, cone, cylinder, triangular prism or tetrahedron, cube, rectangular prism, dodecahedron, hexagonal prism, octagonal prism, etc. In this embodiment, one or both of the first and second oligonucleotide primers are attached to the pillar surfaces (i.e., the top and side surfaces of the pillars) but not to surfaces of the solid support between the pillars.

In yet another embodiment of the present invention, the solid support comprises a plurality of wells. A well on a solid support encompasses any depressed region on the solid support having a bottom and side surfaces. Like pillars, the wells of the solid support can have any three-dimensional geometrical configuration. In this embodiment, one or both of the first and second oligonucleotide primers are attached to the side wall surfaces of the wells, but not the bottom surfaces of the well. Methods of making solid supports and suitable devices comprising the solid support containing pillars and wells with oligonucleotide primers attached thereto are described in more detail infra.

The beads, pillars, wells, or other surface structure of the solid support comprise a plurality of the one or both oligonucleotide primers of a primer set. For example, an individual bead, pillar, or well can contain between about $10^2$ (1 hundred) to about $10^9$ (1 billion) oligonucleotides, more preferably between about $10^5$ (100 thousand) to about $10^8$ (100 million) oligonucleotide primers.

In accordance with the method of the present invention, hybridization of a single target nucleotide sequence or complement thereof to one or both of the oligonucleotide primers immobilized on a bead, pillar, or well of the solid support achieves clonal amplification of the target nucleotide sequence. In one embodiment, >0.1% of the beads, pillars, or wells of the solid support contain clonally amplified target nucleotide sequence arising from the hybridization of a single target nucleotide sequence or complement thereof. In another embodiment, >3% of the beads, pillars, or wells of the solid support contain clonally amplified target nucleotide sequence arising from the hybridization of a single target nucleotide sequence or complement thereof. In another embodiment, >30% of the beads, pillars, or wells of the solid support contain clonally amplified target nucleotide sequence arising from the hybridization of a single target nucleotide sequence or complement thereof.

FIGS. 2-5 are schematic illustrations of the various embodiments of the nucleic acid amplification and sequencing technology of this aspect of the present invention. Steps 1-4 of FIG. 2A are common to all embodiments of this method (i.e., step 1-4 of FIGS. 2-5 are the same). In step 1, a sample containing target nucleotide sequences, the complements of the target nucleotide sequence, or both (i.e., double stranded (ds) DNA) are provided. In an embodiment where dsDNA is provided, the sample is exposed to denaturing conditions to denature the target nucleotide sequences from their complement sequences. The target nucleotide sequence and/or their complements thereof are annealed to their complementary portions of immobilized first and second oligonucleotide primers. For simplicity, only hybridization of the antisense strand (i.e., Watson strand or forward strand) to the first oligonucleotide primer is depicted in FIGS. 2-5. However, it should be appreciated that the complement strand, i.e., the reverse strand, sense strand, or Crick strand, can simultaneously hybridize to the second oligonucleotide primer. Primers bound to target nucleotide sequences, or complements thereof, extend using a first polymerase to generate primary primer extension products (FIGS. 2A, 3A, 4A, 5A; step 1). In one embodiment of the present invention, the first polymerase does not possess 5' to 3' or 3' to 5' exonuclease activity or strand displacement activity. Following extension, the original target nucleotide sequences are denatured and washed away (FIGS. 2A, 3A, 4A, 5A; step 2). The liberated ends of the primary extension products will hybridize to their respective complementary portions on non-extended first or second oligonucleotide primers (FIGS. 2A, 3A, 4A, 5A; step 3). Extension of the hybridized primers using a second thermophilic polymerase generates the first and second oligonucleotide primer extension products (FIGS. 2A, 3A, 4A, 5A; step 4). The second polymerase preferably does not have 5' to 3' or 3' to 5' exonuclease activity, but does have strand displacement activity. In reference to FIG. 2B, step 5, the first oligonucleotide primer extension products comprise the first primer portion (A), the second primer portion (B), a third portion (C') that is complementary to the third primer portion, and a fourth portion that is complementary to the second primer portion (B'). The second oligonucleotide primer extension products comprise a first portion (A'), that is complementary to the first primer portion, a second portion (B'), that is complementary to the second primer portion, the third primer portion (C), and a fourth portion (B), that is the same as the second primer portion, wherein the fourth portion is 5' to the second portion.

While carrying out this method of the present invention, it may be necessary to repeat one or more of the above steps. Specifically, to achieve amplification of the plurality of target nucleotide sequences, it may be necessary to provide the second polymerase one or more times and subsequently repeat the blending to form a polymerase chain reaction mixture and subjecting the polymerase chain reaction mixture to one or more polymerase chain reaction cycles.

An important feature of the amplification method of the present invention is that product re-hybridization after an amplification cycle is minimized. The primers are designed such that extension products self-hairpin ("snake" design, hairpin forms between complementary second and fourth portions ("snake")) or hybridize to decoys ("grass" design) to reduce the number of product but not fresh primer bases available for forming hybridization products during the next cycle of amplification. In the "snakeHE" primer design, shown in FIGS. 3-7 and described in more detail below, a looped hairpin is created that extends, via a polymerase reaction, to make a full-length copy of the sense strand onto the complementary strand. While a single-stranded sense strand would be unlikely to rehybridize, a fresh sense "snakeHE" primer would be unhindered in hybridizing to the extended hairpin product. The freshly hybridized "snakeHE" primer extends by a strand-displacing polymerase to make a full-length copy while displacing the previously hair-pinned strand. Thus, amplified product grows like a tree, both in density and circumference. It is limited not by product rehybridization, but by the density of primer loading and polymerase accessibility at the reaction surface.

FIGS. 2A-2E show amplification of a target nucleotide sequence using the basic snake primer design. In this scheme, the second oligonucleotide primer extension products hairpin by hybridization between the second (B') and fourth portions (B), but the hairpin cannot extend due to one or more mismatches at its 3' end (see step 5, FIG. 2B). As depicted in steps 6-7 of FIG. 2B, the first portion (A') of the second oligonucleotide primer extension product hybridizes to a first primer portion of a non-extended first oligonucleotide primer on the solid support surface. A polymerase extends the 3' end of the hybridized first oligonucleotide primer bound to A' and immediately displaces the second portion (B') of the second oligonucleotide extension product hairpin to form additional first oligonucleotide primer extension products. At the same time, the third portion (C') of first oligonucleotide primer extension products hybridize to non-extended second oligonucleotide primers on the solid support surface. A polymerase extends the 3' end of the second oligonucleotide primer to form additional second oligonucleotide extension products. Following extension and the formation of additional first and second oligonucleotide extension products, the strands are denatured. The second and fourth portions of the individual extension products hybridize to each other to form a hairpin; however, free 3' ends (e.g., on the second oligonucleotide extension products) have mismatched bases to prevent extension (FIG. 2C, step 8). These steps are repeated (FIG. 2C, steps 9-10) to achieve target amplification.

Following amplification, the second oligonucleotide extension products are cleaved from the solid support (FIG. 2D, step 11). Such cleavage can be achieved using photolysis. Alternatively, the second oligonucleotide primer portion of the second oligonucleotide extension product is designed to contain a nucleotide or nucleotide analog cleavage site, e.g., a uracil or 8-oxoguanine residue, as shown in FIG. 1C. In this embodiment, cleavage of the second oligonucleotide primer extension product is achieved using uracil-DNA glycosylase (UDG) and endonuclease VIII or formamidopyrimidine [fapy]-DNA-glycosylase (FPG). Following cleavage, and denaturation if necessary, single stranded first oligonucleotide primer extension products remain (FIG. 2D, step 12) which can be identified using solid-phase sequencing (FIG. 2E; steps 13-15). Various methods of solid phase sequencing are known in the art and are suitable for use here. Exemplary sequencing methods include, without limitation, fluorescent primer hybridization, molecular beacon, primer extension, Taqman® 5'-3'exonuclease assay, ligase detection reaction, ligase chain reaction, pyrosequencing, fluorescence-based sequencing-by-synthesis, fluorescence-based sequencing-by-ligation, ion-based sequencing-by-synthesis, and ion-based sequencing-by-ligation.

In the embodiments of this aspect of the present invention depicted in FIGS. 3-5, amplification of a target nucleotide sequence and/or complements thereof, is achieved using a snakeHE primer design. Using this approach both the target nucleotide sequence and complements thereof are identified, e.g., by solid phase sequencing.

In each of these embodiments, first and second oligonucleotide extension products are generated in steps 1-4 as described above. However, unlike the embodiment depicted in FIG. 2, the second and fourth portions of the second oligonucleotide extension products are fully complementary. Therefore, when the second oligonucleotide extension products hairpin by hybridization between the second and fourth portions, the hairpin extends from its 3' end to form full-length hair-pinned second oligonucleotide primer extension products (step 5 of FIGS. 3B, 4B, and 5B). The ability of the second oligonucleotide primer extension product to make a full-length hairpin copy of itself prevents that strand from hybridizing to a single-stranded first oligonucleotide primer extension product. Subsequently, this allows the first primer portion (A) of the first oligonucleotide primer to hybridize to complementary sequences on the full-length hair-pinned second oligonucleotide primer extension products (A') (step 6 of FIGS. 3B, 4B, and 5B). Extension using a polymerase having strand displacement activity generates first oligonucleotide primer extension products while displacing part of the full-length hair-pinned second oligonucleotide primer extension product having the same sequence (step 7, FIGS. 3B, 4B, and 5B). As shown in step 7, (FIGS. 3B, 4B, and 5B), extension of the first oligonucleotide primer, makes a full-length copy of the second oligonucleotide primer extension product, displacing the full-length hair-pinned sequence, rendering it single stranded. Upon denaturation, this displaced single strand may snap back to regenerate the full-length hairpin and liberate the newly synthesized first oligonucleotide primer extension product as show in step 8, of FIGS. 3C, 4C, and 5C. At the same time, the third portion (C') of the first oligonucleotide primer extension product hybridizes to a non-extended second oligonucleotide primer on the surface (step 6, FIGS. 3B, 4B, and 5B). A polymerase extends the 3' end of the second oligonucleotide primer to form additional second oligonucleotide primer extension products (step 7 of FIGS. 3B, 4B, and 5B). Upon denaturation, the second and fourth portions of the first and second oligonucleotide primer extension products hybridize to each other (step 8 of FIGS. 3C, 4C, and 5C). Free 3' ends of the second oligonucleotide primer extension products (B') extend via polymerase to form full-length hairpins. These steps are repeated to achieve amplification of the target nucleotide sequence and/or complements thereof (steps 9-10, FIGS. 3C, 4C, and 5C).

Following amplification, the second oligonucleotide primer extension products are cleaved (step 11, FIGS. 3D and 4D) as described supra. The remaining first oligonucleotide primer extension products are denatured to form single stranded extension products suitable for solid phase sequencing (see FIGS. 3D-3E and 4D-4E, steps 12-15).

FIGS. 3F-3G and 4F-4G depict alternative embodiments for sequencing the complement strand. In the embodiment of FIGS. 3F-3G, third oligonucleotide primers are provided that comprise a fifth primer portion (FIG. 3F, step 16). The fifth primer portion of the third oligonucleotide primer is complementary to a fifth portion of the first oligonucleotide primer extension products. The third oligonucleotide primer is attached to the solid support. In addition, fourth oligonucleotide primers are also provided. The fourth oligonucleotide primers each contain a sequence complementary to a region of the first oligonucleotide primer extension product. Hybridization of the third and fourth oligonucleotide primers to the first oligonucleotide primer extension products is shown in FIG. 3F, step 16. A polymerase and a ligase are provided and blended with first oligonucleotide primer extension products, the third oligonucleotide primers, and the fourth oligonucleotide primers, to form an extension-ligation mixture. The hybridized fourth oligonucleotide primers extend to form complements of a portion of the first oligonucleotide primer extension product (step 16, FIG. 3F) and ligate to the fifth primer portion of hybridized third oligonucleotide primers to form ligation extension products (step 17, FIG. 3F). The first oligonucleotide primer extension products, containing a nucleotide or nucleotide analogue suitable for chemical or enzymatic cleavage, are cleaved from the solid support and denatured from their complementary strands (steps 17-18, FIG. 3F). For example, the first oligonucleotide primer extension products may contain an 8-oxoguanine instead of guanine, facilitating cleavage via formamidopyrimidine [fapy]-DNA glycosylase (Fpg). Following cleavage, the remaining single stranded complement strands are all in the same orientation and are suitable for solid phase sequencing (steps 18-21, FIGS. 3F-3G) using any of the various methods known in the art and described herein.

In an alternative embodiment depicted in FIG. 4, the second oligonucleotide primer extension products are cleaved 3' to the third primer portion (e.g., at a uracil residue or other cleavable nucleotide or nucleotide analog base), leaving the third primer portion of the second oligonucleotide primer extension products attached to the solid support with a phosphate on the 3' end (FIG. 4D, step 11). Following sequencing of the first oligonucleotide primer extension products (FIGS. 4D-4E, steps 12-15), a kinase that selectively hydrolyzes 3' phosphate groups, for example, a T4 kinase, is provided to liberate the 3' phosphate group on the cleaved second oligonucleotide primer extension products (FIG. 4F, step 16). In addition, a third polymerase having 5' to 3' exonuclease activity and lacking strand-displacing activity is also provided and blended with the solid support containing the first oligonucleotide primer extension products, the third primer portions of the cleaved second oligonucleotide primer extension products having the phosphate on their 3' ends, and the kinase to form a kinase-polymerase mixture. This mixture is subjected to a hybridization treatment, where the third primer portions of the cleaved second oligonucleotide primer extension products hybridize to complementary regions on the first oligonucleotide primer extension products (FIG. 4F, step 16). The phosphate on the 3' end of each hybridized third primer portion of the cleaved second oligonucleotide primer extension products is excised and extended to form kinase-polymerase extension products (FIG. 4F, step 17). Each of the kinase-polymerase extension products comprise a first portion (A') that is complementary to the first primer portion, the second primer portion (B) and the third oligonucleotide primer portion (C) (FIG. 4F, step 18). The first oligonucleotide primer extension products are cleaved and denatured from the solid support, and the remaining single-stranded complement strands, in the same orientation, are suitable for solid phase sequencing (FIGS. 4F-4G, steps 18-21). In this embodiment, the first oligonucleotide primer extension products are cleaved by the 5' to 3' exonuclease activity of the polymerase as it extends through the first oligonucleotide primer extension product template. When the polymerase reaches the double stranded, hairpinned portion of the first oligonucleotide primer extension product, i.e., the second and fourth portions hybridized to each other, the 5' to 3' exonuclease activity of the polymerase digests the second portion (B), liberating the first oligonucleotide primer extension product from the solid surface. Meanwhile the polymerase continues to extend through the first portion of the first oligonucleotide primer extension product template.

One advantage of the amplification method of the present invention is that it generates asymmetrical products, wherein the forward strand product is single-stranded, while the reverse strand product is a double-stranded hairpin. This presents a fast approach for sequencing both strands. In another embodiment, depicted in FIGS. 5A-5G, first and second oligonucleotide extension products are generated and amplified using the snakeHE primer design as described above (steps 1-11; FIGS. 5A-5D). When amplification is complete, all second oligonucleotide primer extension products extend to form full-length hairpins while the first oligonucleotide primer extension products remain single stranded target sequences suitable for solid-phase sequencing (FIGS. 5D-E, steps 12-15). To sequence the opposite strand (i.e., the second oligonucleotide primer extension product), the first oligonucleotide primer extension products are removed from the solid support. This can be achieved by digesting the first oligonucleotide primer extension products using an exonuclease having 3' to 5' activity on single stranded DNA, e.g., Exonuclease I (FIG. 5F, step 16). In this embodiment, the double stranded portion of the hairpinned second oligonucleotide primer extension products is also digested to form single stranded second oligonucleotide primer extension products that are suitable for solid phase sequencing. To achieve this selective digestion, nucleotide analogue primers are provided that comprise a sequence that is complementary to the first portion of the second oligonucleotide primer extension products (FIG. 5F, step 16). The nucleotide analogue primers may contain, for example, PNA, LNA, GNA, TNA, and/or 2'-o-methyl modified bases. The nucleotide analogue primers hybridize to the first portion of the second oligonucleotide primer extension products to block digestion. An exonuclease enzyme having 3' to 5' activity on double stranded DNA, e.g., Exonuclease III, digests the portion of the hairpinned second oligonucleotide extension product that is 3' to the first portion of the extension product hybridized to the blocking nucleotide analogue primer (FIG. 5F, step 16). Following digestion, the second oligonucleotide primer extension products are single stranded and suitable for solid-phase sequencing using methods known in the art and described herein (FIG. 5F-5G; step 17-20).

Another advantage of the amplification system of the present invention is the ability to design gene-specific primers, print them on the solid surface, and amplify only those genomic regions that are desired for sequencing. Accordingly, a second aspect of the present invention relates to method for identifying one or more of a plurality of target nucleotide sequences in a sample that involves providing a sample potentially containing one or more target nucleotide sequences, and/or complements thereof. As noted above, the target nucleotide sequence can be the Watson/antisense or the Crick/sense strand of double stranded DNA. FIGS. 6 and 7 are schematic illustrations of this aspect of the present invention where the Crick/sense strand is shown as the target strand; however, the Watson/antisense strand can also simultaneously hybridize for extension and amplification. Each target nucleotide sequence comprises a first, second, and third target portion, where the second target portion is between the first and third target portions. Also provided is one or more oligonucleotide primer sets. Each primer set is characterized by a first and second oligonucleotide primer. The first oligonucleotide primer of the primer set has a first primer portion that is the same as the first target portion and a second primer portion that is complementary to the second target portion. The second primer portion of the first oligonucleotide primer is 5' to the first primer portion. The second oligonucleotide primer has a third primer portion that is complementary to the third target portion, and a fourth primer-specific portion. The fourth primer-specific portion of the second oligonucleotide primer is 5' to the third primer portion. A polymerase is provided and blended with the sample and the oligonucleotide primer sets to form a polymerase extension reaction mixture. The mixture is subjected to a hybridization and extension treatment. During the hybridization treatment, the first and third primer portions of the first and second oligonucleotide primers, respectively, hybridize to their respective complementary portions of the target nucleotide sequence and/or complement thereof. During the extension treatment, the hybridized oligonucleotide primers extend to form primary primer extension products. The primary primer extension products are denatured from the target nucleotide sequences and complements thereof. The method further involves providing a second polymerase and blending it with the polymerase extension reaction mixture after the hybridization and extension treatments to form a polymerase amplification reaction mixture. The polymerase amplification reaction mixture is subjected to one or more polymerase amplification reaction cycles, each cycle comprising a denaturation, hybridization, and extension treatment. During the denaturation treatment, hybridized nucleic acid sequences are separated, and, during the hybridization treatment, the first and third primer portions of the first and second oligonucleotide primers, respectively, hybridize to their respective complementary portions of the primary primer extension products. During the extension treatment, the hybridized oligonucleotide primers are extended to form first oligonucleotide primer extension products and second oligonucleotide primer extension products. The first and/or second oligonucleotide primer extension products are detected and distinguished to identify the presence of one or more target nucleotide sequences in the sample.

In accordance with this aspect of the present invention, the amplification steps can be carried out in liquid or solid phase. In a preferred embodiment, the one or more primers of each primer set are attached to a solid support. One or more steps of this amplification method can be repeated as needed, e.g., additional second polymerase may be added during one or more of the polymerase amplification reaction cycles.

In accordance with this aspect of the present invention, the solid support may comprise beads, pillars, or wells as described supra (and in more detail below). Preferably, the beads, pillars, or wells, contain clonally amplified target nucleotide sequence (e.g., >0.1%, >3%, or >30%) arising from hybridization of a single target nucleotide sequence or complement thereof to that bead, pillar, or well as described supra.

FIGS. 6A-6G and 7A-7G illustrate preferred embodiments of this aspect of the present invention. In step 1, single stranded genomic DNA, either the target strand, the complement, or both, hybridize to their complementary regions of the first and second oligonucleotide primers. As depicted in step 1 of FIGS. 6A and 7A, second (B') and third (C') portions of the target strand (i.e., the Crick strand or sense strand) hybridize to complementary second (B) and third (C) primer portions of the first and second oligonucleotide primers, respectively. Hybridization of the target to the second primer portion of the first oligonucleotide primer is not required, but likely to occur. At the same time, complement strands (i.e., the Watson strand or antisense strand) hybridize to the first oligonucleotide primer via complementary first portions A' and A, respectively. The first and/or second oligonucleotide primers, hybridized to a complementary target nucleotide sequence or its complement, are extended via polymerase activity to form primary extension products (steps 1-4, FIGS. 6A and 7A). In the embodiment shown in both FIGS. 6A and 7A, where the target sequence hybridizes to both the first and second oligonucleotide primers (via the second and third portions), a polymerase having either 5' to 3' exonuclease or strand displacement activity is required. In an embodiment where the target stand sequence hybridizes to only the second oligonucleotide primer or wherein only the complement strand sequence is extended via the first oligonucleotide primer, a polymerase with either of those activities is not required.

The primary extension products hybridize to complementary primer portions of the first and second oligonucleotide primers and extend via polymerase activity to generate first and second oligonucleotide primer extension products (FIGS. 6B and 7B, steps 5-7). The first oligonucleotide primer extension products comprise the first (A) and second (B) primer portions, a third portion (C') that is complementary to the third primer portion, a fourth portion (P') that is complementary to the fourth primer-specific portion, and a fifth portion (B') that is complementary to the second portion. The second oligonucleotide primer extension products comprise a first portion (A') that is complementary to the first primer portion, a second portion (B') that is complementary to the second primer portion, the third primer portion (C), the fourth primer-specific portion (P), and fifth portion (B) that is the same as the second primer portion (FIGS. 6C and 7C, step 8).

Similar to the snakeHE primer design method described supra, the first and second oligonucleotide primer extension product contains fully complementary second and fifth portions (B' and B, respectively) which hybridize to each other forming a hairpin. The hairpin of the second oligonucleotide primer extension product is extended via its 3' end by polymerase activity to form a full-length hair-pinned second oligonucleotide primer extension product (step 8, FIGS. 6C and 7C). As shown in steps 9-10 of FIGS. 6C and 7C, the first portion of second oligonucleotide primer extension product and the third and fourth portions of the first oligonucleotide primer extension products hybridize to complementary regions of non-extended first and second oligonucleotide primers, respectively, on the solid support and are extended via polymerase activity to achieve target nucleotide sequence and/or complement sequence amplification.

In the embodiment of this aspect of the present invention depicted in FIG. 6, the second oligonucleotide extension products are cleaved, following amplification, at a cleavage site located between the third and fourth primer portions (FIG. 6D, step 11). Suitable cleavage sites include any nucleotides, nucleotide analogues, or abasic sites that are susceptible to enzymatic or chemical cleavage (e.g., uracil, 8-oxoguanine). After cleavage, the fourth primer-specific portion of the second oligonucleotide primer extension products remain attached to the solid support with a phosphate on the 3' end (FIG. 6D, step 11). The remaining single stranded first oligonucleotide primer extension products are suitable for solid-phase sequencing using any known method as described herein FIGS. 6D-6E, steps 12-15). The fourth portion (P') of the first oligonucleotide extension product can be used as a universal primer to initiate all the sequencing reactions simultaneously with one primer (FIG. 6E, step13). Under such conditions, the initial 20 or so bases read will be for the known C sequence region. If desired, one can avoid reading through the C primer sequence by running the initial approximately 20 reactions without fluorescent tags on the bases. Alternatively, the primer may be extended by adding 3 dNTPs, and 1 dNTP with a reversible terminator for a few sequential rounds.

Following sequencing of the first oligonucleotide primer extension products, a kinase that selectively hydrolyzes 3' phosphate groups, for example, a T4 kinase, is provided to liberate the 3' phosphate group on the cleaved second oligonucleotide primer extension products (FIG. 6F, step 16). In addition, a third polymerase having 5' to 3' exonuclease activity and lacking strand-displacing activity is provided and blended with the solid support containing the first oligonucleotide primer extension products, the fourth primer-specific portions of the cleaved second oligonucleotide primer extension products having the phosphate on their 3' ends, and the kinase to form a kinase-polymerase mixture. This mixture is subjected to a hybridization treatment, where the fourth primer-specific portion of the cleaved second oligonucleotide primer extension products hybridizes to its complementary region on the first oligonucleotide primer extension products. The phosphate on the 3' end of each hybridized fourth primer-specific portion of the cleaved second oligonucleotide primer extension products is excised and extended to form kinase-polymerase extension products (FIG. 6F, step 17). Each of the kinase-polymerase extension products comprise a first portion (A') that is complementary to the first primer portion, the second primer portion (B), the third primer portion (C), and the fourth primer-specific portion. The first oligonucleotide primer extension products are cleaved and denatured from the solid support and the remaining single-stranded complement strands, in the same orientation, are suitable for solid phase sequencing (FIGS. 6F-6G, steps 18-21). In this embodiment, the first oligonucleotide primer extension products are cleaved by the 5' to 3' exonuclease activity of the polymerase as it extends through the double stranded portion of the first oligonucleotide primer extension product template (i.e., the second and fourth portions hybridized to each other).

For sequencing the complement strand, as depicted in FIGS. 6F-6G, steps 18-21 (and FIGS. 7F-7G, steps 18-21), gene-specific B-A sequence primers are used, and thus as many different primers as there are unique B-A sequences will be required. If desired, this may be avoided by designing the B-A primer to also have a universal sequence, i.e., P2-B-A. Given the ability to amplify any sequence by judicious choice and design of the primers, it may also be desirable to design primers to amplify the forward strand on one set of pillars, wells, or beads, and the reverse strand on another set of pillars, wells, or beads. This would allow for sequencing both strands of a given region during the same sequencing by synthesis run.

In the embodiment of the present invention depicted in FIG. 7, both target nucleotide sequence and complements thereof are amplified on a solid support and identified by solid-phase sequencing. Following amplification and denaturation (FIGS. 7A-7D; steps 1-10), second portions of the first and second oligonucleotide primer extension products hybridize to complementary fifth portions of the same product. Hybridization of the second and fifth portions of the second oligonucleotide primer extension product creates a hairpin near the 3' end that extends to form full-length hairpinned second oligonucleotide primer extension products. The first oligonucleotide primer extension products remain single stranded and are suitable for solid-phase sequencing (FIGS. 7D-7E, steps 12-15). To sequence the opposite strand, first oligonucleotide primer extension products are removed from the solid support. This can be achieved by digesting the first oligonucleotide primer extension products using an exonuclease having 3' to 5' activity on single stranded DNA, e.g., Exonuclease I (FIG. 7F, step 16). The double stranded portion of the hairpinned second oligonucleotide primer extension products are also digested to form single stranded second oligonucleotide primer extension products that are suitable for solid phase sequencing. Selective digestion is achieved using nucleotide analogue primers containing a sequence that is complementary to the first portion of the second oligonucleotide primer extension products (FIG. 7F, step 16). The nucleotide analogue primers hybridize to the first portion of the second oligonucleotide primer extension products to block exonuclease digestion. An exonuclease enzyme having 3' to 5' activity on double stranded DNA, e.g., exonuclease III, digests the portion of the hairpinned second oligonucleotide extension product that is 3' to the first portion of the extension product hybridized to the blocking nucleotide analogue primer (FIG. 7F, step 16). Following digestion, the second oligonucleotide primer extension products are single stranded and suitable for solid-phase sequencing (FIGS. 7F-7G, steps 17-20) using methods known in the art and described herein.

The amplification methods of the present invention are compatible with bead-based amplification, amplification on a planar surface, or amplification on the device of the present invention as described infra. An advantage of bead-based amplification using the method of the present invention is that no messy oil micro-droplet amplification is required. It is only necessary for the beads to be spatially separated such that an amplified target sequence does not "jump" from one bead to another. This may be achieved in a number of different ways, including use of two sets of beads with different densities, where only one set has primers, and the second set is used to spatially separate neighboring beads from the first set. The beads containing the amplified target sequence may be separated from the first set and simultaneously inserted into wells of an array using centrifugation.

The present invention represents the development of a simple approach for generating 400 bases or more of sequence information per target for improved signal-to-noise and longer reads. There are several advantages to using the amplification method of the present invention on pillared surfaces or microwells for sequencing-by-synthesis. Firstly, it can achieve 50,000 to 80,000-fold amplification, which significantly improves signal-to-noise allowing for faster read times and more cost-effective CCD instrumentation (when using pillared surfaces) or more microwells per surface area when using ion potential, for more cost-effective microchips. Further, it is predicted that the efficiency of target DNA capture and subsequent amplification in a microfabricated device will be very high, allowing for simpler up-front processing steps and eliminating the need for pre-PCR amplification for sample enrichment. Secondly, higher loading opens the potential for ultra-long reads (as detailed below), for applications such as discovering all splice variant transcripts. This is based on defined degenerate primer extension from the middle of fragments. There is no need to go more than 50 to 100 bases per SBS round, nor any need for paired end reading, as multiple readings from the same fragment (i.e. 4×100 bases=400 bases) will provide substantial and spatially ordered sequence information. This approach is compatible with pyrosequencing, fluorescence-based sequencing-by-synthesis, ion-based sequencing-by-synthesis, and ion-based sequencing-by-ligation.

Another aspect of the present invention is directed to methods for identifying one or more of a plurality of target nucleotide sequences in a sample. The first of these methods involves providing a solid support containing primary extension products, where the primary extension products comprise a target nucleotide sequence, or a complement thereof, and a 3' primer binding sequence. Primary primers that are complementary to the primary extension products are provided along with a first DNA polymerase and a mixture of dNTPs, where one or more of the dNTPs contain a modification at its 3' end. The solid support containing the primary extension products, the primary primers, the polymerase, and the dNTPs are blended to form an extension mixture and the mixture is subjected to a hybridization and a polymerase treatment. During the hybridization treatment the primary primers hybridize to complementary primary extension product sequences if present on the solid support. During the polymerase treatment, the hybridized primers extend one or more bases until the polymerase incorporates a modified dNTP. Secondary primers that are complementary to the 3' primer binding sequence of the primary extension products, a second DNA polymerase, and a DNA ligase are provided and blended with the solid support containing the primary extension products and primary primers hybridized thereto to form a polymerase-ligase mixture. The polymerase-ligase mixture is subjected to a hybridization treatment, wherein the secondary primers hybridize to their complementary 3' primer binding sequence of the primary extension products, and a polymerase-ligase treatment, where the hybridized secondary primers extend and ligate to upstream hybridized primary primers to form secondary extension products complementary to a portion of the primary extension products. The method further involves cleaving the primary primers and denaturing the cleaved primers, but not the secondary extension products appended to the primary primers from the primary extension products. The target nucleic acid sequence is identified by sequencing the secondary extension products This method and the related method described below are particularly suitable for achieving ultra-long sequencing reads of the target nucleotide sequence, which is desirable for application such as discovering all splice variant transcripts. This aspect of the present invention is depicted in FIG. 8. In step 1, a single stranded target nucleotide sequence, e.g., a PCR fragment or primary extension product, is fixed at one end of a solid support surface. The target nucleotide sequence preferably contains a primer binding sequence on its 3' end and can optionally be amplified. Primary primers comprising a nucleotide sequence complementary to the target nucleotide sequence and a nucleotide, nucleotide analog, or abasic site at or near its 3' end that is suitable for chemical or enzymatic cleavage are hybridized to the single stranded immobilized target strand (FIG. 8, step 2). Suitable nucleotides that are subject to cleavage include pyrimidines and pyrimidine derivatives (e.g., uracil) which are cleaved by glycosylases such as uracil-DNA glycosylase (UDG) and Endonuclease VIII. Suitable nucleotide analogues that are subject to cleavage include, 8-oxoguanine which is cleaved by Fpg. In one embodiment of this aspect of the present invention, the primary primers also contain 5' degenerate or modified nucleotides.

The hybridized primary primers are extended by a DNA polymerase in the presence of a mixture of dNTPs, including one or more dNTPS containing a modification at it 3' end. Preferably, the modification is a chain terminating modification and DNA polymerase extension continues until the chain terminating dNTP is incorporated. (FIG. 8, step 3). Suitable 3' modified chain terminating dNTPs include, without limitation, dideoxynucleotides, 3'blocked reversible terminators, e.g., 3'-O-modified nucleotides such as 3'-O-allyl-2'-deoxyribonucleoside triphosphates and 3'-O-azidomethyl-dNTPs, and 3' unblocked reversible terminators, e.g., Lightning Terminator™ and Virtual Terminator™. Preferably, the DNA polymerase lacks 3' to 5' exonuclease activity. Following extension and one or more optional washes to remove the polymerase and dNTPs, secondary "universal" primers that are complementary to the 3' primer binding site of the target nucleotide sequence are provided along with a DNA polymerase, DNA ligase and dNTPs (FIG. 8, step 4). Preferably, this DNA polymerase lacks both strand displacement activity and 5' to 3' exonuclease activity. The universal primers hybridize to the target nucleotide sequence and extend to the 5' end of the nearest upstream hybridized primary primers. The DNA ligase ligates the 3' end of the extended universal primer to the 5' end of the primary primer, forming secondary extension products. As shown in FIG. 8, step 5, the primary primers containing degenerate nucleotides are cleaved at their cleavable nucleotide base (e.g. uracil) using a suitable enzyme (e.g., UDG and Endo VIII) and a kinase (e.g., T4 kinase) to liberate a 3' hydroxyl end suitable for subsequent polymerase or ligation reaction. The excess degenerate primary primers (i.e., those primers that are not ligated to the extended secondary primer) are denatured from the target nucleotide sequence leaving only the secondary extension product (i.e., the extended secondary primer ligated to an upstream primary primer) hybridized to the target nucleotide sequence (FIG. 8, step 6). The target nucleotide sequence is then detected, e.g., sequenced, by extension of the secondary extension product using primer extension pyrosequencing, fluorescence-based sequencing-by-synthesis, fluorescence-based sequencing-by-ligation, ion-based sequencing-by-synthesis, or ion based sequencing-by-ligation (FIG. 8, step 7).

A second method for identifying one or more of a plurality of target nucleotide sequences in a sample involves providing a solid support comprising primary extension products, where the primary extension products comprise a target nucleotide sequence, or a complement thereof, and a 3' primer binding sequence. Primary primers that are complementary to the primary extension products and contain a 3' cleavage site, a first DNA polymerase, and a mixture of dNTPs, where one or more of the dNTPs contain a modification at its 3' end are provided. The solid support containing the primary extension products, the primary primers, the polymerase, and the dNTPs are blended to form a first extension mixture, and the extension mixture is subjected to a hybridization and a polymerase treatment. During the hybridization treatment, the primary primers hybridize to complementary primary extension product sequences if present on the solid support. During the polymerase treatment, the hybridized primers extend one or more bases until the polymerase incorporates a modified dNTP. Secondary primers that are complementary to the 3' primer binding sequences of the primary extension products, a second DNA polymerase, and a DNA ligase are provided and blended with the solid support containing primary extension products and primary primers hybridized thereto, to form a polymerase-ligase mixture. The polymerase-ligase mixture is subjected to a hybridization treatment, where the secondary primers hybridize to their complementary 3' primer binding sequence of the primary extension products, and a polymerase-ligase treatment, wherein the hybridized secondary primers extend and ligate to upstream hybridized primary primers to form secondary extension products complementary to a portion of the primary extension products. The unligated primary primers are denatured from the primary extension products. Tertiary primers that are complementary to the primary extension products and contain a 3' cleavage site that is different than the 3' cleavage site of the primary primers are provided and blended with the solid support containing primary and secondary extension products, the first polymerase, and the dNTPs to form a second extension mixture. The second extension mixture is subject to a hybridization treatment, where the tertiary primers hybridize to complementary primary extension product sequences if present on the solid support, and a polymerase treatment where the hybridized tertiary primers extend one or more bases until the polymerase incorporates a modified dNTP. The primary primer portion of the secondary extension products are cleaved under conditions that liberate a 3' hydroxyl end. The secondary extension products are extended from the liberated 3' hydroxyl end to a hybridized tertiary primer and ligated to the hybridized tertiary primers. The tertiary primers are cleaved under conditions that liberate a 3' hydroxyl end. Cleaved tertiary primers, but not the secondary extension products appended to tertiary primers are denatured from the primary extension products and the target nucleic acid sequence is obtained based on sequencing of the secondary extension products.

This aspect of the present invention is depicted in FIGS. 9A-9B. Steps 1-4 of this method as shown in FIG. 9A are the same as steps 1-4 in FIG. 8. After the generation of secondary extension products, formed by extension and ligation of the secondary "universal" primer to the 5' end of the nearest upstream hybridized primary primer, excess primary primers are heat denatured (e.g., 70-75° C.) from the target (i.e., template) sequence (FIG. 9A, step 5). Once removed, tertiary primers having a 3' cleavable nucleotide are hybridized to the target sequence (FIG. 9A, step 6). In accordance with this embodiment of the present invention, the 3' cleavable nucleotide in the tertiary primer is different than the 3' cleavable nucleotide of the primary primer. For example, the primary primers may contain a uracil at or near the 3' end, while the tertiary primers contain an 8-oxoguanine at or near the 3' end or vice versa. The tertiary primers may optionally have degenerate or modified nucleotides at the 5' end. Following hybridization to the target sequence, the tertiary primers are extended via a DNA polymerase (FIG. 9, step 7 and step 8) in the presence of a mixture of dNTPs which includes one or more modified dNTPs, preferably a chain terminating modification. Extension of the tertiary primers continues until the polymerase incorporates a modified dNTP that terminates chain elongation (i.e., a chain terminating nucleotide such as a dideoxynucleotide, 3' blocked reversible terminator nucleotide, or a 3'unblocked reversible terminator nucleotide).

The modified 3'nucleotide of the secondary extension product is cleaved using a suitable enzyme. For example, as shown in FIG. 9B, step 9, the secondary extension product contains a uracil at its 3' end which is cleaved using UDG and endo VIII. T4 kinase is subsequently provided to liberate the 3' hydroxyl end of the second extension product rendering it suitable for subsequent polymerase or ligase reaction. The secondary extension product is extended and ligated to the 5' end of the nearest upstream hybridized tertiary primer (FIG. 9B, step 10). In a preferred embodiment of this aspect of the present invention, extension of the secondary extension product is carried out using a DNA polymerase that lacks both strand displacement activity and 5' to 3' exonuclease activity.

In one embodiment of this aspect of the present invention, the non-ligated tertiary primers are cleaved at their 3' cleavable nucleotide using the appropriate enzyme or chemical and treated with a kinase to remove the 3' phosphate group. As shown in FIG. 9, step 11, non-ligated degenerate tertiary primers containing an 8-oxoguanine are cleaved using Fpg. Alternatively, or in conjunction with this cleavage, the remaining unligated tertiary primers are heat denatured from the target nucleotide sequence (FIG. 9B, step 12). The extended secondary extension product is then suitable for solid phase sequencing using any of the methods described supra.

As described supra, solid-phase sequencing of primer extension products of the present invention can be carried out using sequencing chemistries and detection methods known to those of skill in the art (see e.g., Metzker et al., "Sequencing Technologies—The Next Generation," *Nature Rev.* 11:31-46 (2010) and Voelkerding et al., "Next Generation Sequencing for Clinical Diagnostics-Principles and Application to Targeted Resequencing for Hypertrophic Cardiomyopathy," *J. Mol. Diagn.* 12: 539-551 (2010), which are hereby incorporated by reference in their entirety). For example, solid-phase sequencing can be carried out using cyclic reversible terminators in a sequence-by-synthesis process (Illumina, Inc.). This method involves using a mixture of four fluorescently labeled reversible nucleotide dye terminators. A DNA polymerase bound to a primed extension product adds or incorporates the appropriate fluorescent nucleotide dye terminator that is complementary to the extension product template. DNA synthesis is terminated following incorporation of the terminator nucleotide and the remaining unincorporated nucleotides are washed away. Imaging is performed to determine the identity of the incorporated nucleotide, and the fluor and termination moieties of the terminator are subsequently cleaved and washed away. Successive cycles of dye terminator mixture and DNA polymerase introduction, incorporation, and cleavage yield chain elongation.

The dye terminator used in this process can be a 3' blocked terminator, e.g., 3'-O-modified nucleotides such as 3'-O-allyl-2'-deoxyribonucleoside triphosphates (Ju et al., "Four-color DNA Sequencing by Synthesis Using Cleavable Fluorescent Nucleotide Reversible Terminators," *Proc. Nat'l. Acad. Sci. USA* 103:19635-19640 (2006), which is hereby incorporated by reference in its entirety) and 3'-O-azidomethyl-dNTPs (Bentley et al., "Accurate Whole Human Genome Sequencing Using Reversible Terminator Chemistry," *Nature* 456:53-59 (2008), which is hereby incorporated by reference in its entirety). Alternatively the terminator can be a 3' unblocked terminator e.g., Lightning Terminators™ (LaserGen, Inc.) (see Gardner et al., "Rapid Incorporation Kinetics and Improved Fidelity of a Novel Class of 3'OH Unblocked Reversible Terminators," *Nucleic Acids Research doi:*10.1093/nar/gks330 (May 2012) and Litosh et al., "Improved Nucleotide Selectivity and Termination of 3'-OH Unblocked Reversible Terminators by Molecular Tuning of 2-nitrobenzyl Alkylated HOMedU Triphosphates," *Nucleic Acids Research* 39(6):e39 (2011), which are hereby incorporated by reference in their entirety) and Virtual Terminator™ (Helicos BioSciences) (Bowers et al., "Virtual Terminator Nucleotides for Next-Generation DNA Sequencing," *Nat. Methods* 6:593-595 (2003), which is hereby incorporated by reference in its entirety).

As noted above use of dye terminators for sequencing by synthesis is carried out using four bases, each differentially labeled. The use of four reporter labels, one for each base, requires obtaining four separate images at each position on the array after each nucleotide addition to call the incorporated base. For this reason, detection is a time limiting factor in current sequencing procedures. Accordingly, another aspect of the present invention relates to an improved means for detecting the incorporation of labeled nucleotides during the sequence-by-synthesis process to reduce the detection time by 50%. In accordance with this aspect of the invention, the four different nucleotide bases are read using only two different dyes with two different colors. The use of two colors that are spectrally separated so there is no overlap, e.g., fluorescent labels F1 having an emission maximum at 605-610 nm and F2 having an emission maximum at 820-825 nm, allows for the use of mixtures of the two dyes to call the four different bases. For example, all adenine 3'blocked or 3'unblocked bases are labeled with F1, 75% of the cytosine 3'blocked or 3'unblocked bases are labeled with F1 while 25% of the cytosine bases are labeled with F2, 75% of the 3'blocked or 3'unblocked guanine bases are labeled with F2 while 25% of the guanine bases are labeled with F1, and all 3'blocked or 3'unblocked thymine bases are labeled with F2. In this scenario, following the incorporation of a nucleotide, the signal intensities of F1 and F2 are obtained and compared to determine what nucleotide base was incorporated. For example if only F1 signal is detected at a position following nucleotide incorporation, an adenine base was incorporated. If the F1 signal intensity detected is greater than the F2 signal intensity detected, a cytosine was incorporated. If the F2 signal intensity detected is greater than the F1 signal intensity detected, then a guanine base was incorporated, and if only an F2 signal is detected, a thymine base was incorporated. Because only two images are obtained, the use of two reporter labels instead of four reduces the time required to obtain images of all sequencing reads by 50%. One of skill in the art readily appreciates that the example provided above is not meant to be limiting, i.e., labeling of the four bases with two different dyes can be carried out in a variety of ways so as to achieve differential signal intensities upon base incorporation. As the read length increases, there will inevitably be some phasing issues, so a refined calling of the bases would allow for some noise in interpreting the signal, as shown below.

A=F1 signal>>>F2 signal
C=F1 signal>F2 signal
G=F2 signal>F1 signal
T=F2 signal>>>F1 signal Suitable fluorescent reporter labels that do not spectrally overlap and can be used in accordance with this aspect of the invention are well known in the art, e.g., fluorescent dyes can be selected from those having emission maximums ranging from 515-520 nm (e.g., FAM™), 550-555 nm (e.g., JOE™), 580-585 nm (e.g., TAMRA™), 605-610 nm (e.g., ROX™), 665-670 nm (e.g., Cy5™), 690-695 nm (e.g., Cy5.5™), 710-715 nm (e.g., IRDye700™), 785-790 nm (e.g., IRDye40™), to 820-825 nm (e.g., IRDye41™ and IRDye800™). Alternatively, chromophores with different wavelength absorption dyes can be utilized. Chromophores can be appended to dNTPs in a fashion similar to fluorescent dyes typically used in sequencing-by-synthesis approaches. Instead of measuring the fluorescence color elicited following a polymerase incorporation event, the maximum absorption change at one of two or more colors can be measured to decipher the identity of the dNTP that was incorporated.

Another sequence-by-synthesis process that is suitable for use in the present invention is pyrosequencing (e.g., Roche 454). Pyrosequencing is a non-electrophoretic, bioluminescence method that measures the release of inorganic pyrophosphate (PPi) upon the incorporation of a nucleotide base (Ronaghi et al., "A Sequencing Method Based on Real-Time Pyrophosphate," *Science* 281:363-365 (1998) and Ronaghi et al., "Real-Time DNA Sequencing Using Detection of Pyrophosphate Release," *Anal. Biochem.* 242: 84-89 (1996), which are hereby incorporated by reference in their entirety). In this method, a DNA polymerase bound to the primed extension product adds or incorporates the appropriate natural nucleotide base that is complementary to the extension product template. Upon nucleotide incorporation, PPi is released and detected. In one embodiment of the invention, PPi detection occurs via luciferase-mediated light generation, where the luminescent bursts are optically captured with a high-sensitivity CCD camera. The luminescence intensity is directly proportional to the number of nucleotides incorporated. In another embodiment of the invention, a binuclear Zn(II) complex in combination with boronic acid is used to detect PPi release. In this scheme, a binuclear Zn(II) complex becomes fluorescent upon binding PPi or a nucleoside triphosphate, but the signal for triphosphate is quenched when it simultaneously binds an aromatic boronic acid (Lee et al., "A Highly Selective and Sensitive Fluorescence Sensing System for Distinction between Diphosphate and Nucleoside Triphosphates," *J. Org. Chem.* 76:417-423 (2011), which is hereby incorporated by reference in its entirety). In accordance with this embodiment of the present invention, primer extension for sequencing utilizes ribonucleoside triphosphates with an RNA polymerase, such as T7 RNA polymerase. Once a nucleoside is incorporated into the nascent strand, it releases the pyrophosphate, which is captured by the binuclear Zn(II) complex tethered to a pillar or well surface of the solid support as described herein. The PPi—binuclear—Zn(II) complex generates a fluorescent signal on the pillar that is detected. Addition of an aromatic boronic acid in solution, quenches signal emanating from an accidentally captured ribonucleoside triphosphate.

Another sequence-by-synthesis process suitable for use in the present invention involves DNA polymerase mediated single nucleotide base addition and detection of $H^+$ release. In one embodiment, $H^+$ release is detected by an electrode sensor that is beneath an ion selective base membrane of a device of the invention comprising a plurality of wells (see e.g., FIG. 18) (Rothberg et al., "An Integrated Semiconductor Device Enabling Non-Optical Genome Sequencing," *Nature* 475:348-352 (2011), which is hereby incorporated by reference in its entirety). In an alternative embodiment, $H^+$ release can be detected by a pH sensitive dye tethered to a pillar or well surface of the solid support as describe herein. In accordance with this embodiment of the present invention, natural nucleotides are added (one at a time) at a concentration sufficiently high enough that polymerase extends those primers with the correct base to completion releasing $H^+$, which is captured by the pillar tethered dye. After reading the fluorescent (absorbance) signal at the pillars or wells due to $H^+$ capture by the dye, both nucleotides and $H^+$ are removed in a wash step that regenerates the pillars in preparation for the next nucleotide addition.

For the pH colorimetric monitoring of polymerase modulated nucleotide incorporation events, ratiometric measurements are made to provide high quality reads. In this embodiment, absorbance is measured at a wavelength that occurs at the chromophore's isobestic point, where the extinction is independent of pH. This can be done during the washing steps and after equilibrium (pH) has been established with the enzyme buffer. Following this measurement, the detection wavelength is switched where the chromophore responds maximally to the solution pH. The recorded response is thus taken as, $Abs_{pH}/Abs_{iso}$, where $Abs_{pH}$ is the absorbance measured at the wavelength sensitive to pH changes and $Abs_{iso}$ is the absorbance value measured at the isobestic point. This will correct for variations in the pillar-to-pillar load of the pH-sensitive chromophore There are a number of different dyes that can be used that change their spectral characteristics (ground state absorption spectrum) as a result of changes in the pH. Some of these include nortricarbocyanine dyes, norindosquarocyanine dyes and

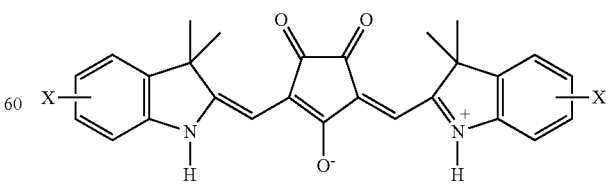

norindocrococyanine dyes as described by Puyol et al., "Characterization of New Norcyanine Dyes and Their Application as pH Chromoionophores in Optical Sensors,"

*Dyes and Pigments* 73(3):383-389 (2007) ("Puyol"), which is hereby incorporated by reference in its entirety. An exemplary synthetic norindocrococyanine dye as described in Puyol is shown below:

These dyes are preferred due to their adjustable pKa (changed by adding electron withdrawing or donating groups into the heteroaromatic groups of these dyes; see Table 1 below), the near-IR absorption bands they produce (does not generate absorbance interferences induced by the polymer pillar), their large extinction coefficients, and the large changes in their extinction induced by subtle pH changes. For example, these dyes show extinction coefficients on the order of 200,000 $cm^{-1}$ $M^{-1}$, with these extinctions dropping to near 0 around the pKa of the chromophore.

TABLE 1

Absorbance maxima, molar extinction coefficients, and pKa values for analogues of norindocrococyanine dye (shown above)

| Dye | X (Abs. Max) | Extinction | pKa |
|---|---|---|---|
| A | H (759 nm) | 1.5 x 10⁵ | 9.7 |
| B | 4,5[benz]- (800 nm) | 7.1 x 10⁴ | 8.6 |
| C | 5-N2O (793 nm) | 1.5 x 10⁵ | 6.5 |
| D | 5-C4H9 (775 nm) | 1.7 x 10⁵ | 9.1 |

Other suitable pH sensitive dyes that can be tethered to pillars of a device of the present invention to detect $H^+$ release during sequencing include the normal acid/base indicator dyes, such as phenolphthalein, bromothymol blue, cresol red, and phenol red to mention a few. Other dyes, such as zinc phthalocyanines, may be tuned to be exquisitely sensitive to pH changes, with either absorbance or fluorescence readout (Topal et al., "Tuning pH Sensitivities of Zinc Phthalocyanines in Ionic Liquid Modified Matrices," *Sensors and Actuators B—Chemical* 156(1):236-244 (2011), which is hereby incorporated by reference in its entirety). In a preferred embodiment of the present invention, the dyes are tuned to have a pKa near the optimal pH for nucleotide addition by the polymerase (i.e., a pKa of around pH 7.5 to 8.5). In addition, many of these acid/base-indicator sensing dyes can be appended with a functional group so as to allow covalently tethering the dye to a solid surface, such as the epoxide groups of the SU-8 pillars. Thus, mixed monolayers of the acid/base indicating dye with the DNA primers used for the target nucleic acid sequence amplification as described herein can be attached to the SU-8 pillars using simple modification chemistries.

A benefit of this strategy is that simple optical hardware can be used to measure the relevant signals (spectral changes induced in the chromophore by pH changes), such as a digital camera's CMOS chip and a light emitting diode. In this regard, no scanning is required if using multiple CMOS chips spanning the area covered by the pillar arrays. In these cases, the signal can be read in near real-time with the major bottleneck in terms of time, being the rate of the reaction (nucleotide incorporation) and the chromophore responding structurally and electronically to the solution pH change. Another advantage is that since the signal (absorbance) is measured under a low light flux, no photobleaching will occur. Coupled to the fact that the pH changes induced by the dye in the sensing chromophore are reversible, the system can be used for monitoring many incorporation events. As stated above, no modifications need to be imposed on the nucleotides because the sensing chromophore is attached to the pillar. Finally, the off-chip positioning of the readout hardware negates the need for placing the fluidics and sequencing platform on an electrode sensing surface, as required for other platforms detecting $H^+$ release, which will significantly reduce the cost of the sequencing chip.

In another embodiment of the present invention, solid-phase sequencing is carried out using a DNA ligase. Methods known in the art involve the utilization of fluorescently labeled oligonucleotide probes that typically contain one or two specific interrogation nucleotides and degenerate and/or universal nucleotide bases. The labeled probe hybridizes to its complementary sequence adjacent to the primed DNA template, and DNA ligase joins the labeled probe to the primer. Non-ligated probes are washed away and fluorescence imaging is used to determine the identity of the ligated probe. Sequencing by ligation of the extension products of the present invention can be carried out using LifeTechnologies' SOLiD platform (Valouev et al., "A High-Resolution, Nucleosome Position Map of *C. elegans* Reveals a Lack of Universal Sequence-Dictated Positioning," *Genome Res.* 18:1051-1063 (2008), which is hereby incorporated by reference in its entirety).

Another aspect of the present invention relates to a new method for sequencing a plurality of target nucleotide sequences. Current sequencing approaches utilizing fluorescence detection require an enzyme to polymerize or ligate a non-natural base analogue or oligonucleotide to the growing primer extension product at very high efficiency so the reaction goes to completion and all extensions are kept in phase. At the same time, the enzyme needs to retain sufficient fidelity to discriminate addition of the correct base that is being interrogated. The method of the present invention separates the process of adding one base at a time (phasing) from the process of reading the sequence. This method of the present invention involves providing primary extension products, where the primary extension products comprise a target nucleotide sequence, or a complement thereof, and a 3' primer binding sequence. Primary primers that are complementary to the 3' primer binding sequence on the primary extension products are provided along with a first DNA polymerase and a mixture of dNTPs, where the dNTPs contain a modification at the 3' end. In accordance with this aspect of the present invention, the 3' modification comprises a 3'-phophorothioate, i.e., the dNTPs are chain terminators. The primary extension products, the primary primers, the polymerase, and the dNTPs are blended to form an extension mixture and the mixture is subjected to a hybridization and a polymerase treatment. During the hybridization treatment the primary primers hybridize to complementary primary extension product sequences if present. During the polymerase treatment, the polymerase incorporates a dNTP having the 3'phosphorothioate, thus terminating the primer chain with the single-base addition. Suitable polymerases are those polymerases lacking 3'-to-5'exonuclease activity, e.g., Klenow fragment and Taq polymerase.

In the next step, a chemical ligation oligonucleotide probe set is provided. This probe set comprises at least four fluorescently labeled degenerate oligonucleotide probes that preferentially hybridize to the template strand directly adjacent to the 3'-phosphorothioate, allowing for a chemical ligation. The degenerate oligonucleotide probes are preferably about 7 or 8 nucleotides in length and comprise a 5' modification that is suitable for reacting with the 3'-phosphorothioate of the extended primer. The oligonucleotide probes also comprise a reporter label, generally on the 3' end, such as a fluorescent or chromophore group. The reporter group corresponds to one or two bases at a defined position in an oligonucleotide probe ("discrimination bases"), which allows for the determination of the complementary one or two bases in the primary extension product (i.e., the template being sequenced). Exemplary oligonucleotide probes in accordance with this aspect of the invention are shown in Table 2 below. As shown in these exemplary probe sequences, the discrimination nucleotides are not the 5' end nucleotides of the probe, but rather these discrimination nucleotides are located 1-4, preferably 2-3, nucleotide positions downstream of the 5' end. Although these probes are shown with a different reporter label for each different base; two different reporter labels can be used to call the four bases following the method described supra.

TABLE 2

Exemplary Chemical Ligation Probes

| | Chemical Oligonucleotide Ligation Probe Sequence | Fold degeneracy |
|---|---|---|
| 1 | 5'CLG-N-(dP/dK)-dA-(dP/dK)-(dI,dC)-d5nI-d5nI-d5nI-F1 (SEQ ID NO: 1)<br>5'CLG-N-(dP/dK)-dG-(dP/dK)-(dI,dC)-d5nI-d5nI-d5nI-F2 (SEQ ID NO: 2)<br>5'CLG-N-(dP/dK)-dC-(dP/dK)-(dI,dC)-d5nI-d5nI-d5nI-F3 (SEQ ID NO: 3)<br>5'CLG-N-(dP/dK)-dT-(dP/dK)-(dI,dC)-d5nI-d5nI-d5nI-F4 (SEQ ID NO: 4) | 128 |
| 3 | 5'CLG-N--(dP/dK)-dA-dN-(dP/dK)-d5nI-d5nI-d5nI-F1 (SEQ ID NO: 5)<br>5'CLG-N--(dP/dK)-dG-dN-(dP/dK)-d5nI-d5nI-d5nI-F2 (SEQ ID NO: 6)<br>5'CLG-N--(dP/dK)-dC-dN-(dP/dK)-d5nI-d5nI-d5nI-F3 (SEQ ID NO: 7)<br>5'CLG-N--(dP/dK)-dT-dN-(dP/dK)-d5nI-d5nI-d5nI-F4 (SEQ ID NO: 8) | 256 |
| 4 | 5'CLG-N--(dP/dK)-dA-(dP/dK)-d5nI-d5bI-d5nI-F1 (SEQ ID NO: 9)<br>5'CLG-N--(dP/dK)-dG-(dP/dK)-d5nI-d5nI-d5nI-F2 (SEQ ID NO: 10)<br>5'CLG-N--(dP/dK)-dC-(dP/dK)-d5nI-d5nI-d5nI-F3 (SEQ ID NO: 11)<br>5'CLG-N--(dP/dK)-dT-(dP/dK)-d5nI-d5nI-d5nI-F4 (SEQ ID NO: 12) | 64 |
| 5 | 5'CLG-N--(dP/dK)-dA-dN-(dP/dK)-dI-dI-dI-F1 (SEQ ID NO: 13)<br>5'CLG-N--(dP/dK)-dG-dN-(dP/dK)-dI-dI-dI-F2 (SEQ ID NO: 14)<br>5'CLG-N--(dP/dK)-dC-dN-(dP/dK)-dI-dI-dI-F3 (SEQ ID NO: 15)<br>5'CLG-N--(dP/dK)-dT-dN-(dP/dK)-dI-dI-dI-F4 (SEQ ID NO: 16) | 256 |
| 6 | 5'CLG-N--(dP/dK)-dA-(dP/dK)-dI-dI-dI-F1 (SEQ ID NO: 17)<br>5'CLG-N--(dP/dK)-dG-(dP/dK)-dI-dI-dI-F2 (SEQ ID NO: 18)<br>5'CLG-N--(dP/dK)-dC-(dP/dK)-dI-dI-dI-F3 (SEQ ID NO: 19)<br>5'CLG-N--(dP/dK)-dT-(dP/dK)-dI-dI-dI-F4 (SEQ ID NO: 20) | 64 |

Legend:
5'CLG = 5'chemical linking group = 5' deoxynucleotide base containing
(i) I—CH2—C═O—NH-deoxy- (iodoacetamide to the 5' CH2 group); or
(ii) NPyS—S—CH2-deoxy- (5-nitropyridylthiol disulfide to the 5' CH2 group)
dI = deoxyinosine
d5nI = 5-nitroindole
dP = pyrimidine derivative "P" (6H,8H-3,4-dihydropyrimido[4,5-c][1,2]oxazin-7-one) which form both amino and imino tautomers, and therefore base pairs with both A and G.
dK = purine derivative "K" (2-amino-9-(2-deoxy-beta-ribofuranosyl)-6-methoxyaminopurine, also called 2-amino-6-methoxyaminopurine), which form both amino and imino tautomers, and therefore base pairs with both C and T.
dP/dK = P/K mix to be equivalent to an N (A/C/G/T mix), all deoxynucleotides
F1-F4 = fluorescent dyes The chemical ligations probes are designed to have sufficient length to hybridize to template DNA in a sequence-specific manner, but not so long that the number of degenerate bases requires too high a concentration of oligonucleotides. The oligonucleotide probe may comprise universal bases, i.e. bases that can pair to more than one natural base to reduce the complexity of degenerate oligonucleotides. In addition, a 5-nitroindole may be incorporated on the non-ligating end of the degenerate oligonucleotide to provide additional stacking interactions (Loakes et al., "5-Nitroindole as an Universal Base Analog," *Nucleic Acids Res.* 22(20):4039-4043 (1994), which is hereby incorporated by reference in its entirety). Alternatively, deoxyinosine, which also provides stacking interactions, may be incorporated on the non-ligating end of the oligonucleotide probes. In one embodiment, the oligonucleotide probe comprises a combination of deoxyinosine, which forms some hydrogen bond interactions to C, T, or A, and deoxycytosine, which base pairs with G, to provide two bases that can pair with all four nucleotides. Alternatively, modified bases designated "P" (6H,8H-3,4-dihydropyrimido[4,5-c][1,2]oxazin-7-one) and "K" (2-amino-9-(2-deoxy-beta-ribofuranosyl)-6-methoxyaminopurine, also called 2-amino-6-methoxyaminopurine, may be used as degenerate bases. A mix of these two nucleotide analogs will be equivalent to a mix of all four natural bases. The pyrimidine derivative P base pairs with either A or G, while the purine derivative K base pairs with either C or T. This dual base-pairing is enabled by the ability of P and K to form both amino and imino tautomers (Lin et al., "Synthesis of Oligodeoxyribonucleotides Containing Degenerate Bases and Their Uses as Primers in the Polymerase Chain Reaction," *Nucleic Acid Res.* 20(19): 5149-52 (1992), Brown et al., "Synthesis and Duplex Stability of Oligonucleotides Containing Adenine Guanine Analogs," *Carbohydrate Res.* 216:129-139 (1991), and Lin et al., "Oligonucleotides Containing Degenerate Bases. Synthesis and Uses," *Meth. Mol. Biol.* 26:187-206 (1994), which are hereby incorporated by reference in their entirety).

The 5' end of incoming chemical ligation oligonucleotide probe contain a leaving group, such as iodoacetamide (I—CH2-C═O—NH-deoxy-) or 5-nitropyridylthiol disulfide (NPyS-S-CH2-deoxy-). This allows for easy displacement of the leaving group by the nucleophilic thiol on the 3'-phosphorothioate of the primer extension strand to form a chemically ligated product (Abe et al., "Rapid DNA Chemical Ligation for Amplification of RNA and DNA Signal," *Bioconjugate Chem.* 19(1):327-333 (2008), Gryaznov et al., "Enhancement of Selectivity in Recognition of Nucleic-Acids via Chemical Autoligation," *Nucleic Acids Res.* 22(12): 2366-2369 (1994), and Metelev et al., "The Synthesis and Properties of Oligodeoxyribonucleotides with Single Mono- and Diphosphoryldithio Internucleotide Links," *Russian J. Bioorganic Chem.* 29(1):50-55 (2003), which are hereby incorporated by reference in their entirety). A sulfur on the 3' phosphate of the extended primer acts as the nucleophile, with either iodine or 5-thio-2-nitrobenzoic acid on the end as the leaving group.

This chemical ligation reaction will be preferentially performed at a temperature between 16° C. and 22° C., although it may be higher or lower. The optimal conditions achieve a balance between obtaining the appropriate specificity for the chemical ligation step and obtaining sufficient product to get signal with both AT rich and GC rich sequences on the template strand.

In some cases, secondary structure of the template strand, such as a hairpin, may interfere with hybridization of the incoming degenerate oligonucleotide and thus some positions may give very weak signal. Secondary structure in the template may be dampened or eliminated by including formamide, or other agents, such as T4 gene 32 protein or thermostable single-stranded binding proteins (commercially available from New England Biolabs, Ipswich, Mass.).

In one embodiment of this aspect of the present invention, a mutant ligase, i.e., a ligase that does not have ligation activity, is included in the chemical ligation reaction mixture to accelerate the chemical ligation reaction, as well as improve specificity and yield on templates that may form secondary structures. A mutant ligase will help orient the degenerate chemical ligation oligonucleotide on the template strand in preparation for formation of the covalent bond to the primer extension product. Mutating the active site lysine residue (so it cannot form the enzyme-AMP structure) will eliminate biological activity of the ligase enzyme.

After detection of fluorescent signal, the ligation product is cleaved using either silver nitrate and/or aqueous iodine to generate a 3' phosphate, replacing the 3'phosphorothioate of the dNTP incorporated into the extended primer (Mag et al., Synthesis and Selective Cleavage of an Oligodeoxynucleotide Containing a Bridged Internucleotide 5'Phosphorothioate Linkage," *Nucleic Acids Res.* 19(7): 1437-1441(1991), which is hereby incorporated by reference in its entirety). The reaction conditions will also convert the 3'-phosphorothioate to a 3'-phosphate even if a ligation event did not occur. This is an important distinction from the standard sequencing by ligation approach, where high yields are required.

In the next step, the 3' phosphate is cleaved from the primer extension product to generate a free 3'OH end using a phosphatase. Suitable phosphatases include, for example, DNA 3'-phosphatase (TPP1) from *Saccharomyces cerevisiae* (Vance et al., "Uncoupling of 3'-Phosphatase and 5'-Kinase Functions in Budding Yeast—Characterization of *Saccharomyces cerevisiae* DNA 3'-Phosphatase (TPP1)," *J. Biol. Chem.* 276(18):15073-15081 (2001), which is hereby incorporated by reference in its entirety), and T4 polynucleotide kinase/3'-phosphatase (Habraken et al., "Further Purification and Characterization of the DNA 3'Phosphatase from Rat-Liver Chromatin Which is Also a Polynucleotide 5'Hydroxyl Kinase," *European J. Biochem.* 171(1-2): 59-66 (1988), which is hereby incorporated by reference in its entirety. The free 3'OH end is a substrate for the next round of sequencing that begins by incorporating the next dNTP containing a 3'phosphorothioate using a polymerase. Synthesis of nucleotides and oligonucleotides containing a 3' phosphorothioate have been described (see e.g., Alefelder et al., "Incorporation of Terminal Phosphorothioates into Oligonucleotides," *Nucleic Acids Res.* 26(21): 4983-4988 (1998), which is hereby incorporated by reference in its entirety).

As noted above, it is possible to use chemical ligation probes encoding two discriminatory nucleotide positions to achieve base calling at two positions in the extension products simultaneously. In accordance with this embodiment of the present invention, oligonucleotide probes of both Group 1 and Group 2 shown in Table 3 below are used in a mixture, e.g., a mixture comprising a concentration of Group 1 probes that is about 2-fold higher than the concentration of Group 2 probes.

TABLE 3

Exemplary Chemical Ligation Probes
Encoding Two Nucleotide Positions

| Chemical Oligonucleotide Ligation Probe Sequence | Fold degeneracy |
|---|---|
| 1 5'CLG-N--(dP/dK)-dA-dN-(dP/dK)-d5nI-d5nI-d5nI-F1 (SEQ ID NO: 21)<br>5'CLG-N--(dP/dK)-dG-dN-(dP/dK)-d5nI-d5nI-d5nI-F2 (SEQ ID NO: 22)<br>5'CLG-N--(dP/dK)-dC-dN-(dP/dK)-d5nI-d5nI-d5nI-F3 (SEQ ID NO: 23)<br>5'CLG-N--(dP/dK)-dT-dN-(dP/dK)-d5nI-d5nI-d5nI-F4 (SEQ ID NO: 24) | 256 |

TABLE 3-continued

Exemplary Chemical Ligation Probes
Encoding Two Nucleotide Positions

| Chemical Oligonucleotide Ligation Probe Sequence | Fold degeneracy |
|---|---|
| 2 5'CLG-N--(dP/dK)-dN-dA-(dP/dK)-d5nI-d5nI-d5nI-F1 (SEQ ID NO: 25)<br>5'CLG-N--(dP/dK)-dN-dG-(dP/dK)-d5nI-d5nI-d5nI-F2 (SEQ ID NO: 26)<br>5'CLG-N--(dP/dK)-dN-dC-(dP/dK)-d5nI-d5nI-d5nI-F3 (SEQ ID NO: 27)<br>5'CLG-N--(dP/dK)-dN-dT-(dP/dK)-d5nI-d5nI-d5nI-F4 (SEQ ID NO: 28) | 256 |

Legend:
5'CLG = 5'chemical linking group = 5' deoxynucleotide base containing
(i) I—CH2—C=O—NH-deoxy- (iodoacetamide to the 5' CH2 group); or
(ii) NPyS—S—CH2-deoxy- (5-nitropyridylthiol disulfide to the 5' CH2 group)
dI = deoxyinosine
d5nI = 5-nitroindole
dP = pyrimidine derivative "P" (6H,8H-3,4-dihydropyrimido[4,5-c][2,2]oxazin-7-one) which form both amino and imino tautomers, and therefore base pairs with both A and G.

The chemical ligation reaction is carried out as described above using the mixture of chemical ligation probes. The two bases are determined by comparing signal intensities of the detected reporter label with each read. For example, using the probes depicted in Table 3 above in a mixture where the concentration of Group 1 probes is 2-fold higher than the concentration of Group 2 probes, the following base calls correlate to signal intensity:

AA=F1 signal>>other signal
AG=F1 signal>F2 signal>>other signal
AC=F1 signal>F3 signal>>other signal
AT=F1 signal>F4 signal>>other signal
GA=F2 signal>F1 signal>>other signal
GG=F2 signal>>other signal
GC=F2 signal>F3 signal>>other signal
GT=F2 signal>F4 signal>>other signal
CA=F3 signal>F1 signal>>other signal
CG=F3 signal>F2 signal>>other signal
CC=F3 signal>>other signal
CT=F3 signal>F4 signal>>other signal
TA=F4 signal>F1 signal>>other signal
TG=F4 signal>F2 signal>>other signal
TC=F4 signal>F3 signal>>other signal
TT=F4 signal>>other signal The advantage of the sequencing approach described above over other approaches is that only polymerase incorporation of the initial 3'-phosphorothioate needs to go to completion. The subsequent chemical ligation step does not need to be efficient, as long as its removal and subsequent dephosphorylation of the 3' end goes to completion. Since the ligation is a chemical step, it can be very rapid for fast cycling times. It can also be performed using limiting oligonucleotide probe concentrations at a temperature that maximizes accuracy of hybridization at the discriminating base(s), as opposed to trying to compromise between fidelity and yield.

Another aspect of the present invention relates to a method for capturing a plurality of target nucleotide sequences. This method involves providing a sample potentially containing one or more target nucleotide sequences and complements thereof and a plurality of oligonucleotide primer sets. Each oligonucleotide primer set is characterized by a first oligonucleotide primer comprising a portion complementary to the target nucleotide sequence, and a second oligonucleotide primer comprising a portion complementary to the target nucleotide sequence and a capture group. A ligase is provided and blended with the sample and the plurality of oligonucleotide primer sets to form a mixture. The mixture is subjected to one or more ligation cycles comprising a denaturation treatment and hybridization treatment. During the hybridization treatment, the oligonucleotide primers hybridize at proximate positions in a base-specific manner to their respective target nucleotide sequences, if present in the sample, and ligate to one another to form a ligated product sequence containing the target-specific portions and the capture group. Unligated second oligonucleotide primers, but not ligated products are denatured from the target nucleotide sequences. The ligated products hybridized to target nucleotide sequences are captured by binding of the capture group to its binding partner. The enriched single stranded DNA can optionally be denatured from the ligated product and/or subject to an amplification reaction of the present invention or other nucleic acid identification reaction.

This aspect of the present invention is particularly suitable for target sequence enrichment prior to sequencing or any other subsequent analysis. Accordingly, the target sample can contain a single stranded or double stranded DNA or cDNA target nucleotide sequence. As shown in the FIG. 10 (step 2), which depicts an embodiment of this aspect of the present invention, universal adaptor or primer binding sequences can be appended to the 5' and/or 3' ends of the target nucleotide sequences or complements thereof using methods and enzymes well known in the art (e.g., ligation, polymerase based extension, recombination, transferase reaction, endonuclease reaction, DNA repair reactions, and reverse transcription).

When carrying out this method of the present invention, it may be desirable to denature the target nucleotide sequence from its complement prior to adding the oligonucleotide primers (FIG. 10, step 3). Subsequently, one or more upstream target sequence specific primers and downstream target sequence specific primers are hybridized to the single-stranded target sequence. One of the primers, contains a capture moiety on its 5'end (downstream primer) or 3' end (upstream primer). The upstream and downstream primers are designed to hybridize to nearby regions of the target sequence, preferably adjacent regions of the target nucleotide sequence. In one embodiment of the present invention, the upstream and downstream primers hybridize to adjacent positions on the target nucleotide sequence and, in the presence of a ligase, ligate to form a ligation product when both primers hybridize to the target nucleotide sequence without mismatch (FIG. 10, step 5). Suitable ligases include, without limitation, thermostable ligases, such as, for example *Thermus aquaticus* ligase, *Thermus thermophilus* ligase, 9° N DNA ligase, Taq DNA ligase, *E. coli* ligase, T4 ligase, and *Pyrococcus* ligase.

In an alternative embodiment of the present invention, the upstream and downstream primers hybridize to nearby, but not juxtaposed positions of the target nucleotide sequence. In this embodiment, a polymerase extends the downstream primer to the upstream primer and a ligase ligates the two primers to form a ligation product. In either embodiment, the ligation product, hybridized to the target nucleotide sequence, contains the capture group. Excess non-ligated hybridized and non-hybridized primers are removed from the sample by denaturation and separation (e.g., electrophoresis or spin column separation) (FIG. 10, step 6). The target nucleotide sequence is then captured by exposing the sample to the capture moiety binding partner. For example, as shown in FIG. 10, step 7, a suitable capture moiety is biotin and a suitable binding partner is streptavidin. Alternative capture and binding partners that can be used in accordance with this method of the present invention include, without limitation, maltose and maltose binding protein, chitin and chitin binding protein, amylase and MBP, glutathione transferase and glutathione-S-transferase, histag and NTA matrix, integrin and integrin binding peptides. In a preferred embodiment of the present invention, the binding partner is immobilized on a solid support, for example, and without limitation, paramagnetic beads or a microfabricated fluid channel. Using this approach, the target nucleotide sequences can be separated from other DNA fragments in the sample. If desired, captured target sequences can be denatured from the hybridized ligation product, releasing it into the solution phase (FIG. 10, steps 7 and 8). The enriched target sequence is then suitable for subsequent amplification, sequencing, or other analyses.

In an alternative embodiment of the present invention, oligonucleotides complementary to the target nucleotide sequences desired for enrichment are synthesized with a linking group such that they are suitable for attachment to pillars or another high aspect ratio surface on a solid support. Means of attaching such linking groups (e.g., amino group on oligonucleotide to carboxylic acid on the surface, or biotin on the oligonucleotide to streptavidin on the surface) are well understood by those skilled in the art. The attachment of multiple capture oligonucleotides to the surface may be random, i.e., more than one different oligonucleotide is on a given pillar. A further refinement would include using two sets of oligonucleotides, one set for the + strand, the other set for the − strand, that are spatially separated when attached to the solid support, such that they do not accidentally hybridize to each other during the hybridization step. The sample DNA (preferably already containing universal adaptor or primer binding sequences appended to the 5' and/or 3' ends of the target nucleotide sequences) is denatured and hybridized to the oligonucleotides on the solid support under conditions suitable to allow for sequence-specific capture of target nucleotide sequences. Such conditions include flowing the solution containing the target nucleotide sequences over the solid surface containing pillars or other high aspect ratio surface under optimized temperature and buffer conditions to maximize target nucleotide sequence capture by sequence-specific hybridization. The enriched single stranded DNA can optionally be denatured from the complementary sequences on the solid support and/or subject to an amplification reaction of the present invention or other nucleic acid identification reaction.

Another aspect of the present invention relates to methods for enriching target nucleotide sequences prior to characterization of methylation status. In the first of these methods, a sample containing one or more target nucleotide sequences that potentially contain methylated CpG sequences is provided. The sample is treated with sodium bisulfite under conditions suitable for converting unmethylated cytosines, but not methylated cytosines in the target nucleotide sequence into uracils. Degenerate oligonucleotide primers, a DNA polymerase, and a DNA ligase are provided and blended with the bisulfite-treated sample to form a polymerase extension reaction mixture. The polymerase extension reaction mixture is subjected to a polymerase extension reaction to form primary extension products. The primary extension products are denatured from the target nucleotide sequences and the polymerase extension reaction is repeated to form secondary extension products. The primary and secondary extension products form double-stranded copies of the bisulfite treated target nucleotide sequence lacking uracils and methylated cytosines. This method further involves providing a restriction endonuclease having a recognition site that contains at least one CpG dinucleotide, but at least one strand of the recognition sequence does not contain any other cytosine than the CpG dinucleotide. Linker oligonucleotides and a DNA ligase are also provided. The primary and secondary extension products are cleaved at the restriction endonuclease recognition site and the linker oligonucleotides are ligated to the restriction endonuclease cleaved sites. Target nucleotide sequences are enriched prior to characterization of methylation status based on said ligation of linkers to both ends of the cleaved extension products. The enriched target nucleotide sequences are subsequently subject to solid phase amplification and sequencing for methylation characterization as described supra.

Figure 11:
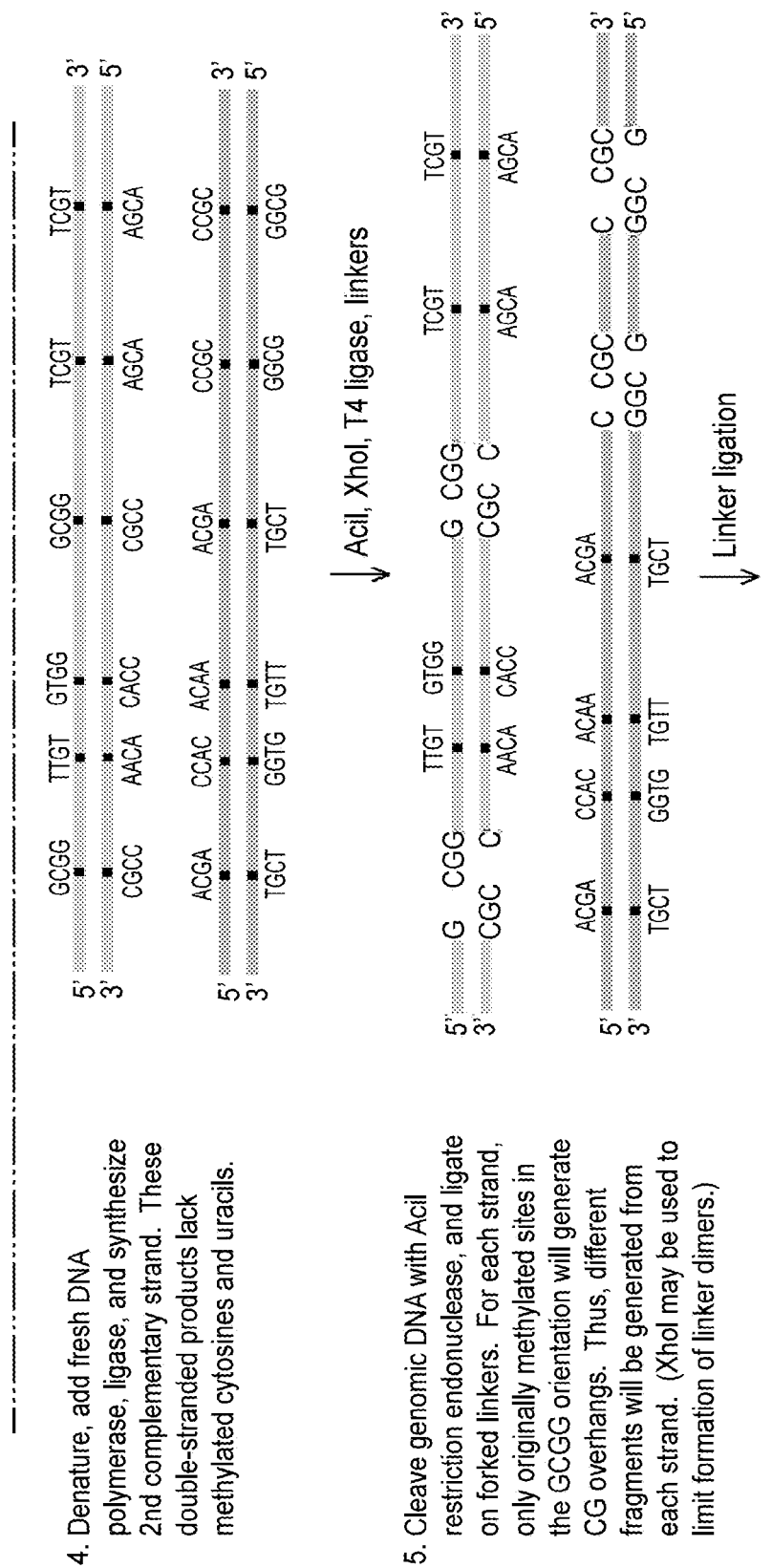
FIG. 11 is a flow diagram showing a method of enriching target nucleotide sequences prior to characterization of methylation status using the methods of the present invention.

FIG. 11 depicts the general steps of this aspect of the present invention. As shown in FIG. 11, step 1, the sample contains one or more double-stranded target DNA sequences that are potentially methylated at one or more CpG nucleotides. In the example of FIG. 11, a single double-stranded DNA target is shown. In addition, while only the cytosines in AciI restriction endonuclease recognition sites are show in the target sequence of FIG. 11, other methylated and/or unmethylated cytosines will exist in the target nucleotide sequence. AciI sites are common in CpG islands and rare elsewhere in the genome.

The initial step of this method of the present invention is the preparation of sodium bisulfite modified genomic DNAs. In a preferred embodiment, genomic DNA is incubated with bisulfite and hydroquinone solution for 15-20 hours, more preferably 16 hours, in a DNA thermal cycler (Perkin Elmer Cetus). Suitable cycling conditions involve incubating at 50° C. for 20 minutes, incubating at 85° C. for 15 seconds, and repeating this cycle 45 times. In another embodiment of this process, diethylenetriamine can be used instead of hydroquinone as a catalyst for sodium bisulfite modification. The bisulfite treatment of the target sequence is catalyzed by diethylenetriamine, and the bisulfite solution is pre-equilibrated with argon gas to eliminate the dissolving oxygen before adding the catalyst. The reaction mixture is then incubated under cycling conditions to periodically dissociate both strands of genomic DNA to maximize the bisulfite modification efficiency. Suitable cycling conditions involve incubating at 50° C. for 20 minutes, incubating at 85° C. for 15 seconds, and repeating this cycle 45 times.

The bisulfite treated DNA can be desalted with Wizard DNA clean-up kit (Promega, Madison, Wis.) or, alternatively, it can be desalted using MICROCON centrifugal filter devices (Millipore, Bedford, Mass.). This eliminates bisulfite and fragmented small pieces of nucleic acid molecules while concentrating the treated sample. The desalted DNA is ethanol precipitated, and the DNA pellet is resuspended in deionized H$_2$O or proper buffer until PCR amplification.

As shown in step 2 of FIG. 11, the double-stranded DNA target sequence is no longer complementary following bisulfite treatment. In step 3 of the process shown in FIG. 11, complementary strand synthesis (both first and second strand) is initiated using degenerate oligonucleotide primers and a DNA polymerase, such as *E. coli* DNA polymerase I. Other suitable polymerases include either a native or recombinant thermostable polymerase from *Thermus aquaticus, Thermus thermophilus, Pyrococcus furious*, or *Thermotoga maritime*. In a preferred embodiment, the degenerate primers are about nine nucleotides in length and contain a CG dinucleotide at or near the 3' end. Hybridization and extension of the degenerate primers along the bisulfite modified DNA template generates extension products that are subsequently joined via ligation using a suitable ligase, such as T4 ligase. When the primer extends across the DNA, the polymerase makes a copy of the uracil containing DNA, incorporating an A opposite T, an A opposite U, a T opposite A, a C opposite G, and a G opposite 5-methyl C as well as residual native C that did not undergo deamination during the bisulfite treatment. Accordingly, the resultant complementary strands lack methylated cytosines and uracils.

The sample is denatured and fresh polymerase, ligase, and primer (if necessary) are added to synthesize the second strand (FIG. 11, step 4). This process can be repeated one or more times to generate a sufficient quantity of double stranded copies of the bisulfite treated target sequence. The original bisulfite treated strand may optionally be destroyed using UNG.

As shown in step 5 of this process as depicted in FIG. 11, the double-stranded copies of the bisulfite treated target sequence are subject to restriction endonuclease digestion. It may be preferable, but not required, to inactivate the polymerase prior to the restriction endonuclease digestion. The restriction endonuclease digestion is preferably carried out using the AciI restriction endonuclease enzyme recognizing GCGG or CCGC sites. However, restriction endonuclease enzymes cleaving at CGCG, ACGT or TCGA sites can also be used. For each strand, only originally methylated sites in the GCGG orientation will generate CG overhangs (i.e., sticky ends) upon cleavage with AciI. The DNA ligase, linker oligonucleotides, and XhoI can be added to the restriction endonuclease reaction, with biochemical selection driving the reaction simultaneously. XhoI limits the formation of linker dimers, and DNA ligase ligates linkers to the AciI cleaved ends of the target sequence (FIG. 11, step 6). DNA fragments containing linker oligonucleotides on both the 5' and 3' end can optionally be amplified, e.g., using PCR (FIG. 11, step 7). In accordance with this embodiment, the linker oligonucleotides preferably contain universal primer binding sequences to facilitate amplification and subsequent capture or separation for downstream methylation or sequencing analysis (FIG. 11, step 8).

A second method of the present invention for enriching target nucleotide sequences prior to characterization of methylation involves providing a sample containing one or more target nucleotide sequences that potentially contain methylated CpG sequences. Primary linker oligonucleotides and a DNA ligase are also provided and blended with the sample to form a primary linker reaction mixture. The primary linker reaction mixture is subjected to conditions suitable for ligating the linker oligonucleotides to 5' and 3' ends of the target nucleotide sequences. The primary linker reaction mixture is treated with sodium bisulfite under conditions suitable for converting unmethylated, but not methylated cytosines, into uracils. Primary oligonucleotide primers having a sequence complementary to the primary linker oligonucleotides, and a polymerase are provided and blended with the bisulfite-treated primary linker reaction mixture to form a polymerase chain reaction mixture. The polymerase chain reaction mixture is subjected to two or more polymerase chain reaction cycles comprising denaturation, hybridization, and extension treatments. During the denaturation treatment, hybridized nucleic acid sequences are separated. During the hybridization treatment, primary oligonucleotide primers hybridize to the linker regions appended to the target nucleotide. During the extension treatment, the hybridized primary oligonucleotide primers extend to form primary extension products. This method further involves providing a restriction endonuclease having a recognition site that contains at least one CpG dinucleotide, but at least one strand of the recognition site does not contain any other cytosine than the CpG dinucleotide. Secondary linker oligonucleotides and a DNA ligase are provided and blended with the polymerase chain reaction mixture after being subjected to one or more polymerase chain reaction cycles, to form a secondary linker reaction mixture. The secondary linker reaction mixture is subjected to conditions suitable for cleaving the primary extension products at the restriction endonuclease recognition site to form restriction endonuclease cleaved ends and ligating the secondary linker oligonucleotides to the restriction endonuclease cleaved ends. Target nucleotide sequences are enriched prior to characterization of methylation status based on fragments containing secondary linkers ligated to both ends.

Figure 12:
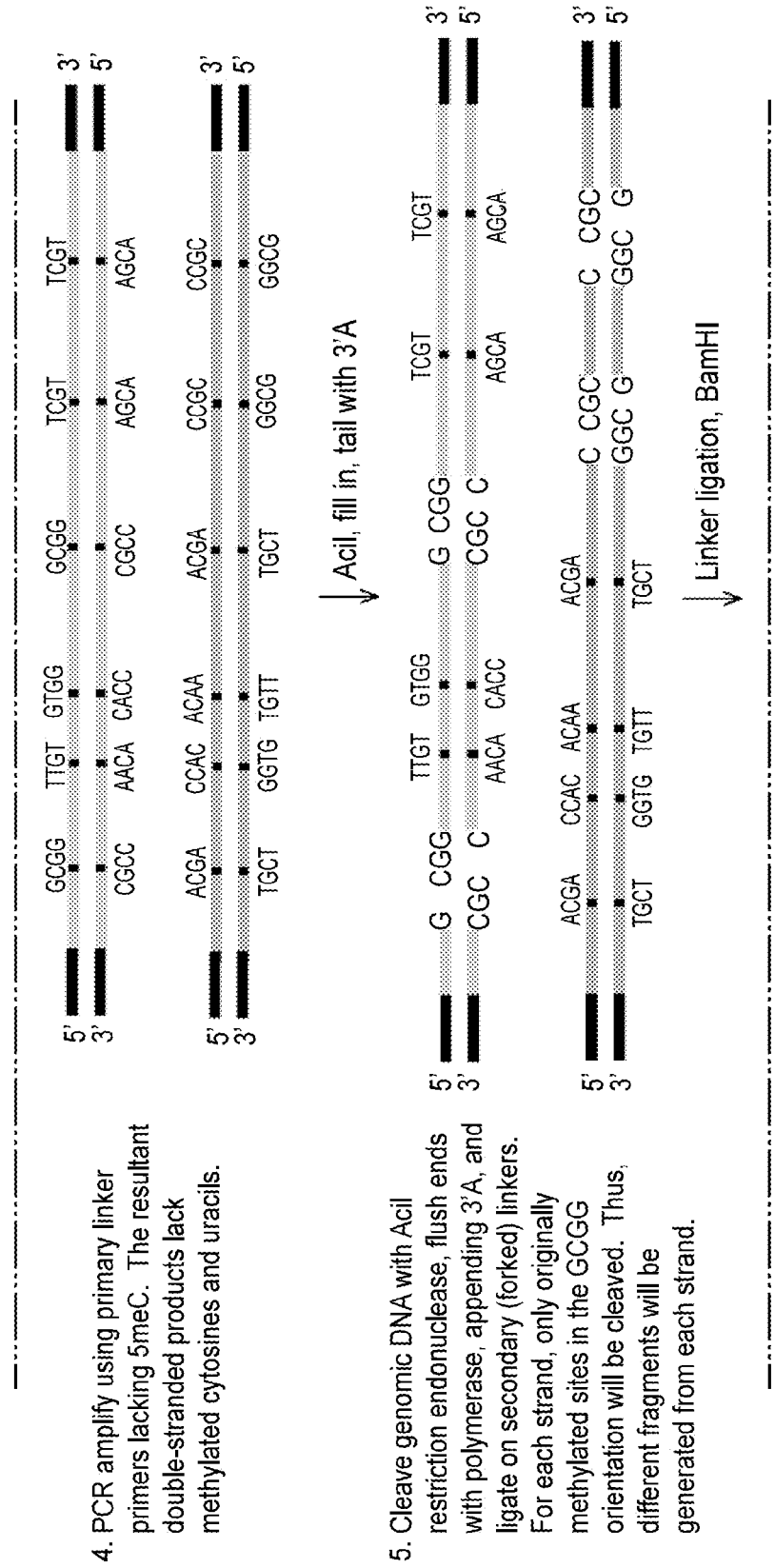
FIG. 12 is a flow diagram depicting a method of enriching target nucleotide sequences prior to characterization of methylation status using the methods of the present invention.
Figure 12:
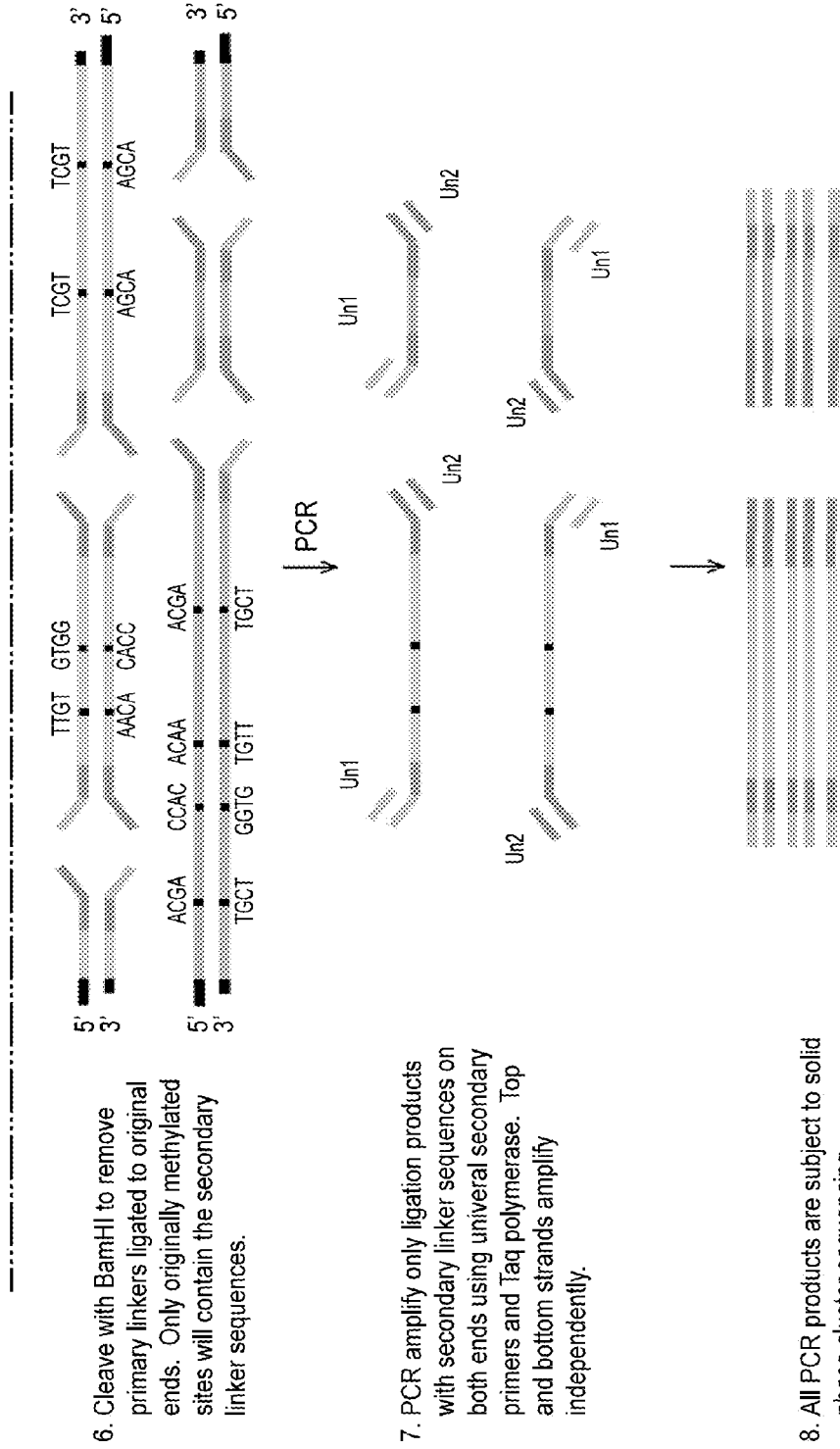
Figure 13:
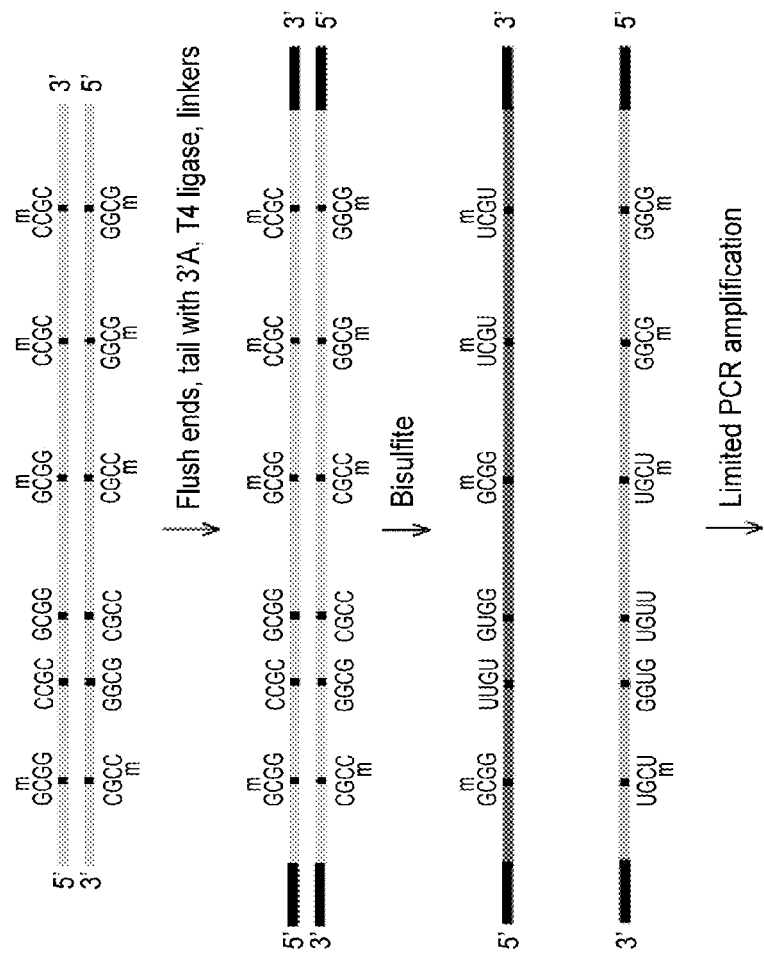
FIG. 13 is a flow diagram showing a method of enriching target nucleotide sequences prior to characterization of methylation status using the methods of the present invention.
Figure 13:
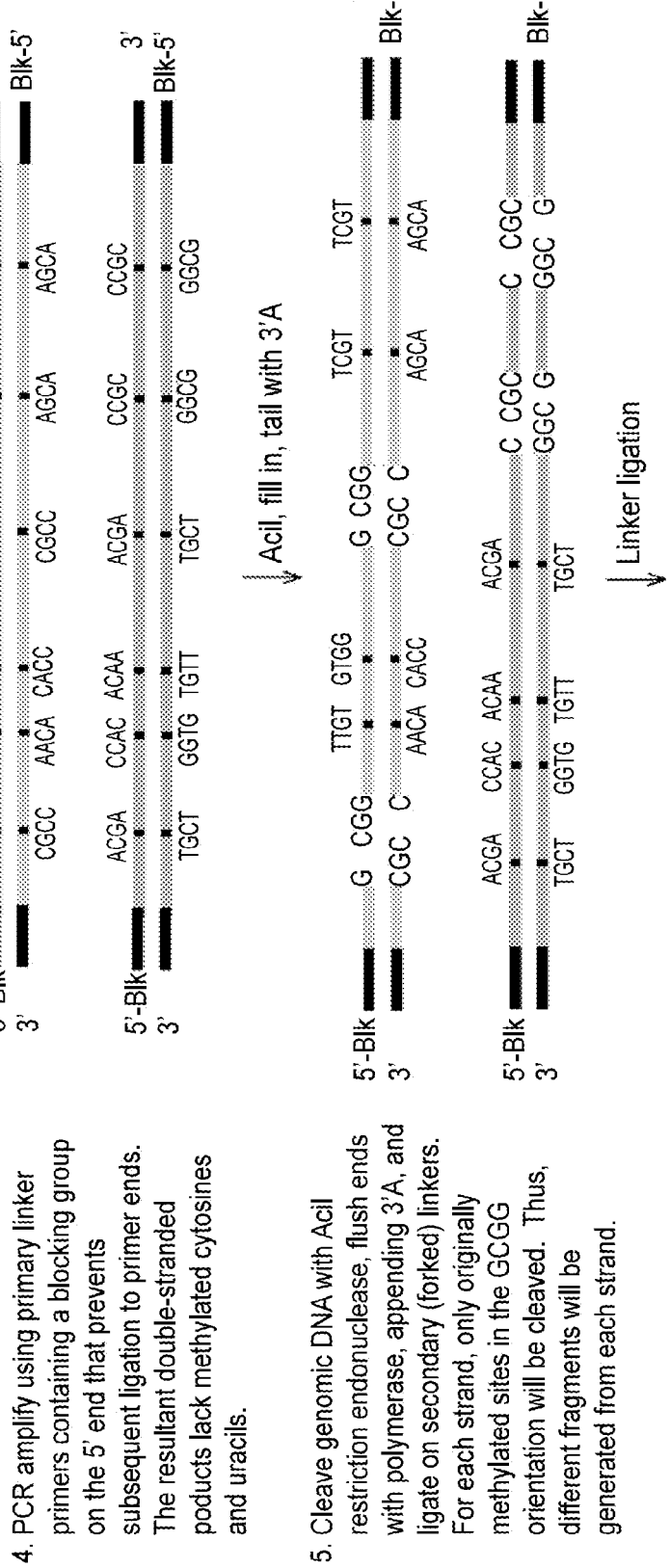
Figure 13:
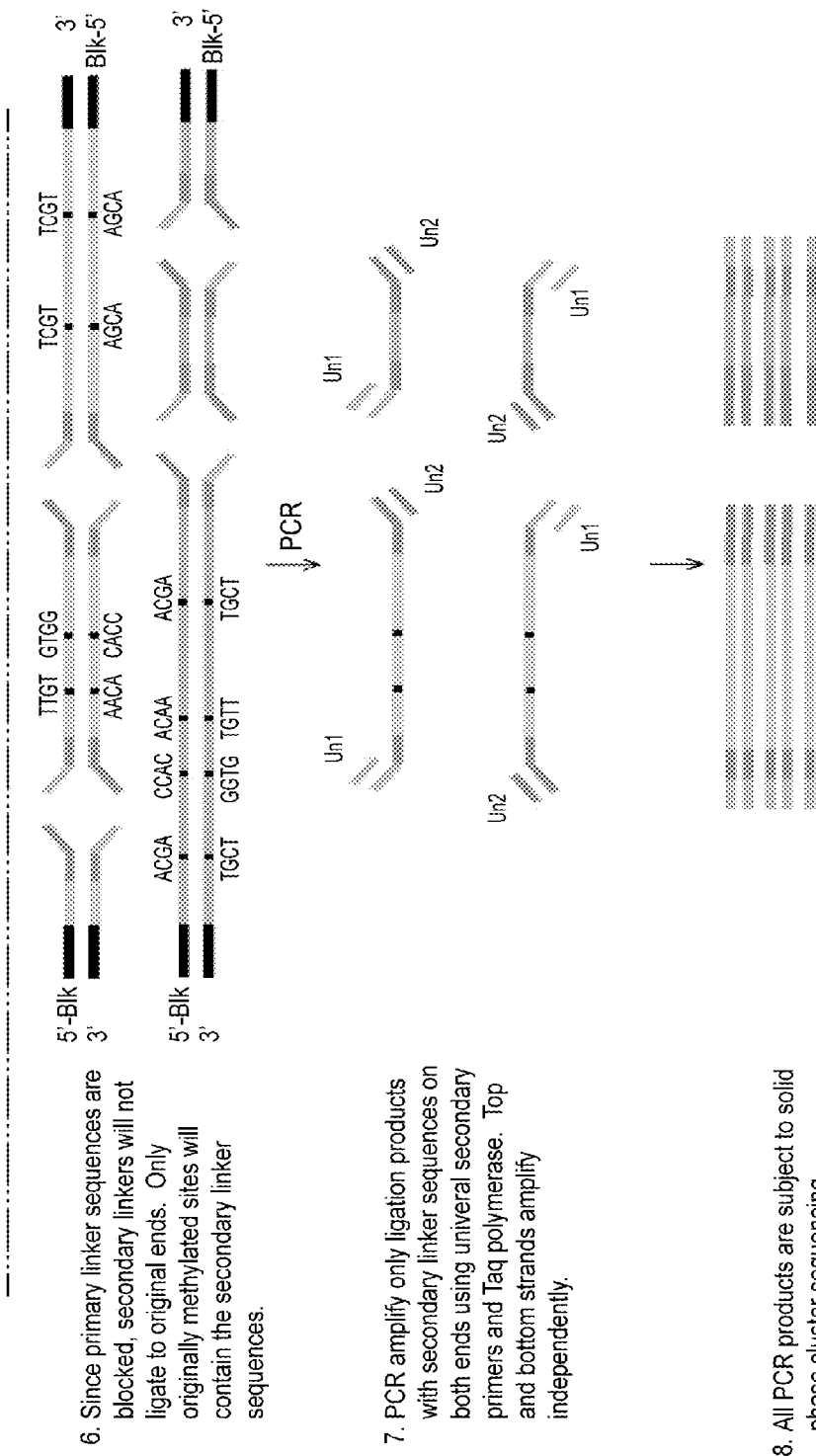

As depicted in embodiments of this aspect of the invention shown in FIGS. 12 and 13, the target genomic DNA sequence is preferable sheared and the ends are flushed using a polymerase that appends 3'adenine nucleotide bases prior to ligating the primary oligonucleotide linkers to the target sequence. In the embodiment shown in FIG. 12 (step 1), the linker oligonucleotides optionally contain a methylated cytosine residue and a restriction endonuclease site. The methylated cytosine in the linker oligonucleotide sequence will be retained during bisulfite treatment, preserving the original linker nucleotide sequence and therefore, the restriction endonuclease recognition site therein.

Following bisulfite treatment of the methylated target sequences as described above (FIGS. 12 and 13, steps 2 and 3), the resultant stands are PCR amplified using linker specific primers. As before, the double-stranded PCR products lack methylated cytosines and uracil. The amplified products are cleaved using AciI or other appropriate restriction endonuclease as described above. Following digestion, the sticky ends created by AciI cleavage are flushed using a polymerase to append 3' adenines, rendering the cleaved ends suitable for the attachment of secondary linker oligonucleotides. FIGS. 12 and 13 illustrate alternative processes to avoid linker ligation to the original ends of the target strand. In the embodiment of FIG. 12, where the primary linkers contain a methylated cytosine and a restriction endonuclease recognition sequence, the sample is treated with a second restriction endonuclease, in this case BamHI, which corresponds to the restriction endonuclease recognition site in the primary linker sequence. Restriction endonuclease digestion cleaves the primary linker oligonucleotides from the original ends leaving stick ends to which the secondary linkers will not append. In the alternative embodiment shown in FIG. 13, PCR amplification of the bisulfite modified target sequences is carried out using primary linker primers that contain a blocking group or modifier on their 5' or 3' ends that prevent subsequent linker ligation (FIG. 13, step 4). Suitable blocking or modifying groups include, without limitation, a DMS(O)MT-group, a MMT-group, TEG (hydrophilic triethylene glycol ethylamine derivative), Dithiol phophoramidite (DTPA), TOSYL modifiers, photocleavable biotin phosphoramidite modifiers, and fluorescent modifiers. Using either of these embodiments, only the originally methylated sites will contain the secondary linker sequences on both 5' and 3' ends (FIGS. 12 and 13, step 6). The secondary linker sequences contain universal primer binding sequences, and subsequent PCR amplification of the products containing only the secondary linkers sequences is achieved using universal secondary primers (FIGS. 12 and 13, step 7).

Another aspect of the present invention is directed to a device. This device comprises a solid support having a base surface, a top surface, and a plurality of side surfaces extending between the base and top surfaces. The base surface, top surface, and plurality of side surfaces of the device collectively form a plurality of wells or pillars on the solid support. The device further comprises a plurality of oligonucleotides attached to the side surfaces, but not the base surface, of the wells or pillars.

In contrast to traditional array devices, which are made from silicon or glass, the solid support of the device of the present invention comprises a polymer. Polymeric material is a suitable solid support surface because of its excellent optical properties and very low background fluorescence. In addition, polymers can be shaped with micro-scale and nano-scale three-dimensional structures using low-cost and established molding techniques, such as hot embossing or injection molding. This will allow for the production of structured supports in high quantities at low-cost, appropriate for commercialization. Suitable polymeric materials include, without limitation, poly(methyl methacrylate), polycarbonates, epoxy-based resins, copolymers, polysulfones, elastomers, and polymeric organosilicons.

The device of the present invention can be any size format for assimilation into existing sequencing and array instrument systems. Preferable formats include, without limitation, 86 mm (w)×43 mm (1), 86 mm×128 mm (standard 8×12 microtiter plate), or 128 mm×128 mm formats.

In a preferred embodiment of the present invention, the solid support of the device contains a plurality of patterned array positions as shown in FIG. 14, with each array position comprising a plurality of pillars or wells (each square of FIG. 14 represents a patterned array position comprising a plurality of pillars or wells).

Figures 15A, 15B, 15C:
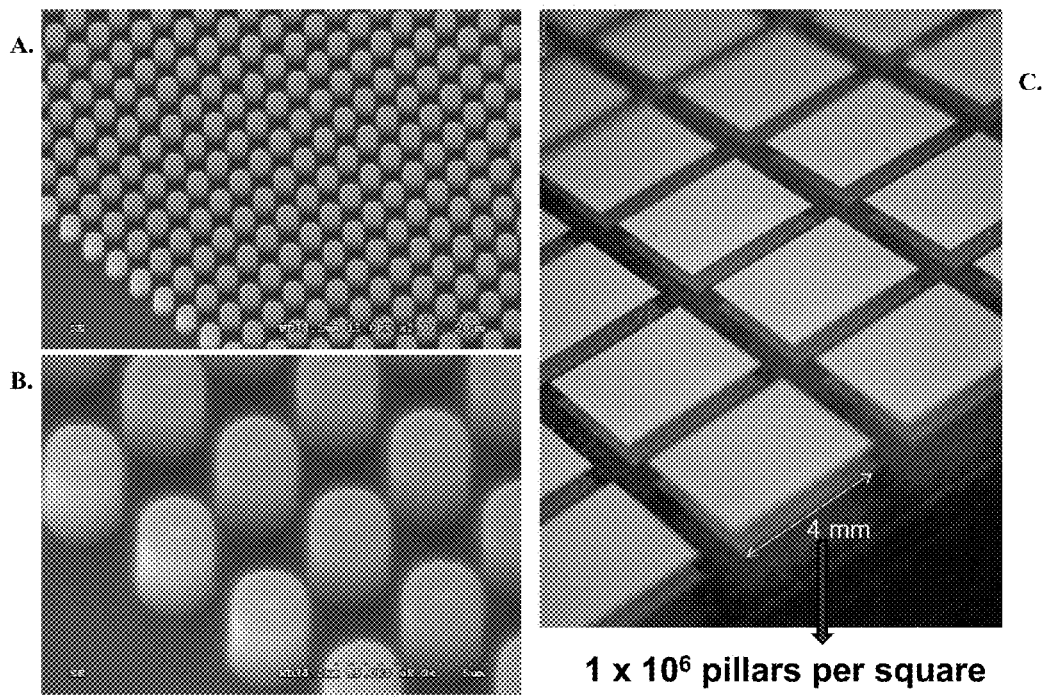
FIGS. 15A-15C show a device of the present invention comprising cylindrical pillars.

The device of the present invention is three-dimensional with the base surface, top surface, and plurality of side surfaces collectively forming a plurality of pillars or wells. The three-dimensional design of the device of the present invention allows for increased nucleic acid loading compared to traditional two-dimensional devices. The pillars and wells of the device can be any geometrical three-dimensional shape, including, without limitation, spherical, cone, cylinder, triangular prism or tetrahedron, cube, rectangular prism, dodecahedron, hexagonal prism, octagonal prism, etc. In one embodiment of the present invention, the device consists of an array (4×4 mm) of pillars in 128 squares as shown in FIGS. 15A-15C. FIG. 15A is a photomicrograph showing cylindrical pillars, each 2 μm in diameter and 4.5 μm tall, on the base surface of the device. FIG. 15B is a magnified view of FIG. 15A. FIG. 15C shows some of the 128 squares (i.e., 4×4 mm patterned array positions) on an array, with each of the 128 square array positions containing about $1\times10^6$ pillars per square.

In some embodiments of the invention, it may be desirable to increase the surface area of the pillar. This can be achieved by using rectangular pillars instead of cylindrical pillars. The geometric shape of the pillars is determined by the mask pattern used to cross-link the polymer during pillar fabrication. For example, a 1 μm diameter cylindrical pillar that is 10 μm in height, has a surface area of $3.14\times10^{-7}$ cm$^2$. In contrast, the surface area of a rectangular (square) pillar having these same dimensions is $4.0\times10^{-7}$ cm$^2$. This represents a 21% increase in surface area. In addition, the pillar rows can be offset to provide better interaction of solution-borne reagents with those covalently anchored to the pillar surface. Increased surface area on the pillars is particularly preferred in embodiments of the invention where pH sensitive dyes are tethered to the pillars for detecting H+ release after nucleotide incorporation during sequencing.

Figure 16A:
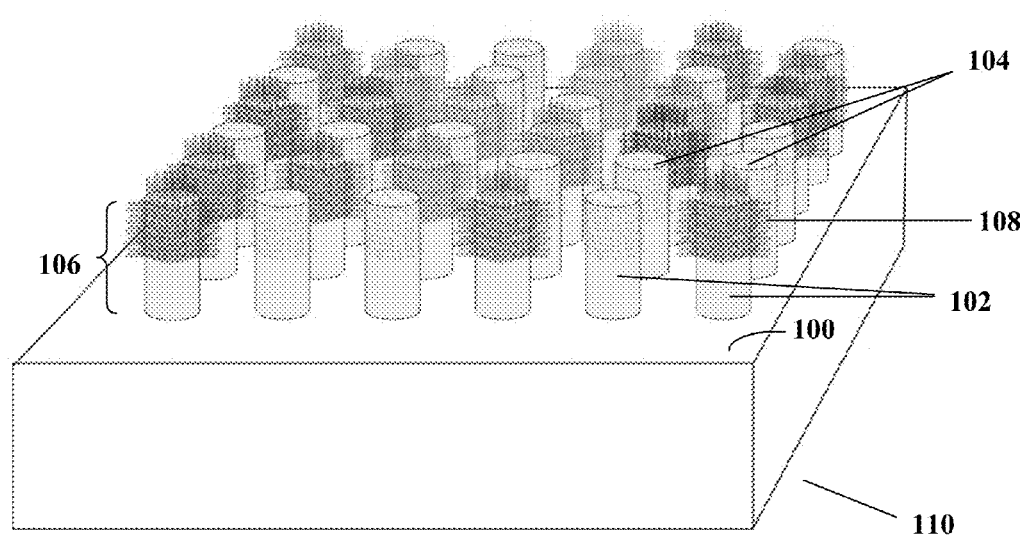
FIGS. 16A-16C show the three-dimensional architecture of a device of the present invention.
Figure 16B:
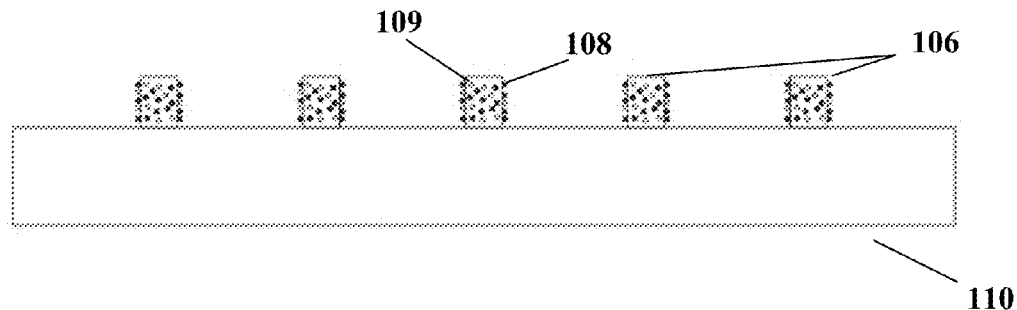
Figure 16C:
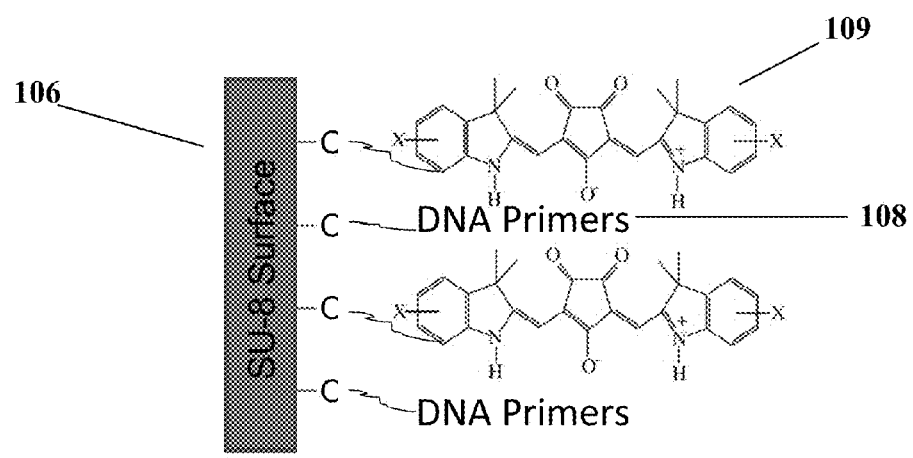

Pillar structures of a device of the present invention are shown in more detail in the schematics of FIGS. 16A-16C. FIG. 16A shows a segment of solid support 110 comprising base surface 100, top surface 104, and plurality of side surfaces 102 that collectively form a plurality of pillars 106 on the solid support surface. Pillars 106 have a height of about 1 µm to about 20 µm. More preferably, pillar height is about 2.5 µm to about 5 µm. Pillar width is about 1 µm to about 5 µm. Depending of the size format of the device, the device may contain anywhere from between about 1 million to about 5 billion pillars on the base surface of the solid support with an edge-to-edge spacing of about 0.5-3 µm. The device may also contain less than 1 million pillars, but preferably at least 100,000 pillars. These pillars can possess aspect ratios (aspect ratio=structure height/structure width) up to 20 that can easily be produced via hot embossing or injection molding.

Pillars 106 on the device further comprise a plurality of oligonucleotides 108 attached to side surfaces 102 and top surfaces 104, but not base surface 100 of a solid support 110 as depicted in FIG. 16A. An advantage of the three dimensional structure of the pillars is the increased DNA loading capacity compared to a two dimensional surface. For example, if the desired surface density of DNA probe is 41 pmol/cm$^2$ DNA, the three dimensional pillar structure will comprise $8.5 \times 10^6$ DNA molecules while a two-dimensional surface will only contain $7.7 \times 10^5$ DNA molecules. In accordance with this aspect of the present invention, any given pillar of the device can contain between about $10^2$ (1 hundred) to about $10^9$ (1 billion) oligonucleotides, more preferably between about $10^5$ (100 thousand) to about $10^8$ (100 million) oligonucleotides.

The pillars of the device may further comprise pH sensitive dyes or reporters 109 for detecting H+ release during sequencing-by-synthesis processes as described supra (FIG. 16B-16C). In one embodiment of the invention, the pillars 106 are solid-supports with low porosity. Accordingly, the sequencing primers 108 and pH sensing reporters 109 are anchored to the surface only (FIG. 16C). While this limits the total load to each pillar, the advantage of this approach is that the fluid dynamics are highly favorable, allowing rapid exchange of solution reagents to the pillar array, where sequencing is occurring.

In accordance with this embodiment of the present invention and as described herein, SU-8 photoresist is a preferred non-porous surface material for pillar construction. By way of example only, a dye surface density on a SU-8 pillar of $10^{-10}$ moles/cm$^2$ can be achieved on a pillar (1 µm×10 µm) having a surface area of $3.14 \times 10^{-7}$ cm$^2$ containing a mixed monolayer of oligonucleotide probes and pH dyes on it. To achieve this end, the dye and DNA oligonucleotide pillar loads are each $3.14 \times 10^{-17}$ moles (31.4 amol), respectively. The resulting dye concentration on the pillar surface is 4.0 mM and the change in absorbance per base addition per pillar at this concentration is 0.4 AU.

In another embodiment of the present invention, the polymer pillars are made porous using a variety of techniques, such as plasma treatment of the polymer support. Approaches for loading pH sensitive dyes into porous nanostructures have been reported by Kim et al., "Dye-Loaded Porous Nanocapsules Immobilized in a Permeable Polyvinyl Alcohol Matrix: A Versatile Optical Sensor Platform," *Analytical Chem.* 84(6):2695-2701 (2012), which is hereby incorporated by reference in its entirety. Making the polymer porous dramatically increases the load of the sequencing primers and reporters used to monitor pH changes or other reporter, such as a fluorescent reporter attached to the nucleotide.

Figure 17:
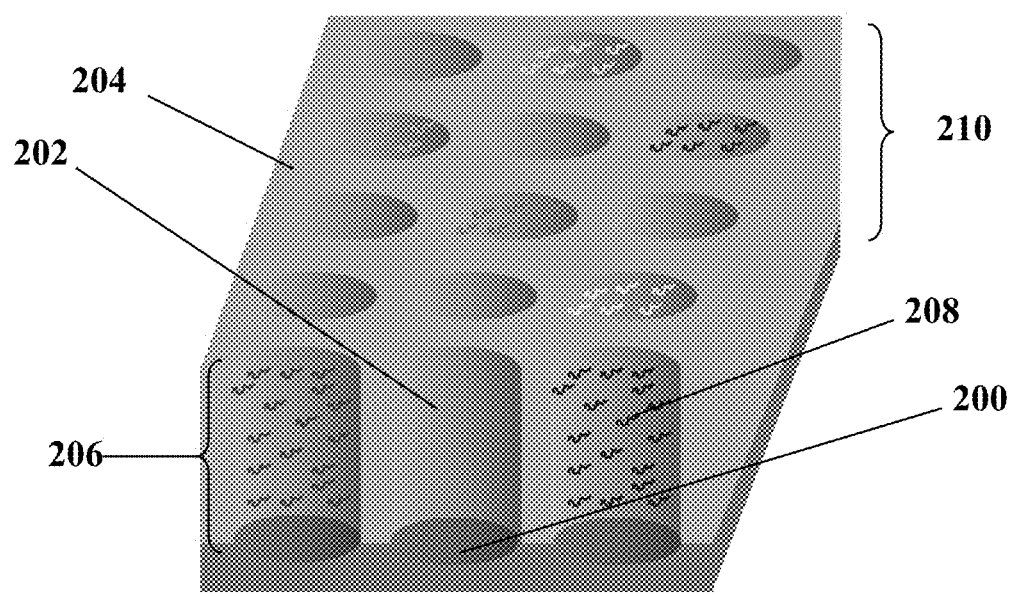
FIG. 17 is a schematic of the three-dimensional architecture of a device of the present invention comprising wells having oligonucleotides attached to the side surfaces, but not the base surfaces of the wells.

A device of the present invention comprising a plurality of wells is shown in the schematic of FIG. 17. FIG. 17 shows a segment of solid support 210 comprising base surface 200, top surface 204, and plurality of side surfaces 202 that collectively form a plurality of wells 206. Wells of the device 206 have a depth of about 1 µm to about 20 More preferably, well depth is about 2.5 µm to about 5 Wells of the device have a diameter of about 0.25 µm to about 10 In a preferred embodiment of the present invention, the solid support of the device contains a plurality of patterned array positions with each array position comprising a plurality wells. Depending of the size format of the device, the device may contain anywhere from between about 50 nm and 10 µm wells. These wells can possess aspect ratios (aspect ratio=structure height/structure width) up to 20 that can easily be produced via hot embossing or injection molding. The device may contain anywhere from between about 1 million to about 5 billion wells on the solid support. The device may also contain less than 1 million wells, but preferably at least 100,000 wells.

Wells 206 on the device (FIG. 17), in accordance with this aspect of the present invention, further comprise a plurality of oligonucleotides 208 attached to side surfaces 202, but not base surface 200 of the solid support as depicted in FIG. 17. In a preferred embodiment of the present invention, the oligonucleotides are also not attached to top surface 204 of the device. Any given well of the device may contain between about $10^2$ (1 hundred) to about $10^9$ (1 billion) oligonucleotides, more preferably between about $10^5$ (100 thousand) to about $10^8$ (100 million) oligonucleotides.

In a preferred embodiment of the present invention, each pillar or well of the device contains the same oligonucleotide or set of oligonucleotides (i.e., each well or pillar contains numerous copies of a single primer pair for amplification as described above). In another embodiment of the present invention, a plurality of pillars or wells on the device contain one type or set of oligonucleotides and another plurality of pillars or wells on the device contain a different type or set of oligonucleotides. In accordance with this embodiment the device can contain between about 2 to about 200,000 different oligonucleotides.

In one embodiment of the present invention, the base surface and the top and side surfaces of the solid support are made of the same polymer material. In accordance with this embodiment of the present invention, selected surfaces of the solid support are activated to generate functional groups suitable for oligonucleotide attachment. When the solid surface comprises pillar structures as shown in FIG. 16, only side surfaces 102 and top surfaces 104 of pillars 106 are activated, while base surface 100 remains non-activated. In this embodiment, plurality of oligonucleotides 108 of the device are attached to activated top surfaces 104 and side surfaces 102 of the pillars, and not base surfaces 100 between pillars, which remain non-activated. When the solid surface comprises well structures as shown in FIG. 17, only side surfaces 202 are activated while base surface 200 and preferably top surface 204 of the wells remain non-activated. This select activation limits oligonucleotide attachment to side surfaces 202 of the wells, and prevents oligonucleotide attachment to base 200 or top surfaces 204 of the wells. Methods of achieving selected activation of the solid support surface, e.g., photomasking, are known in the art and are described infra. Suitable functional groups generated upon activation include, without limitation, reactive groups such as silanol, olefin, amino, hydroxyl, maleimides, sulfhydryl, aldehyde, keto, halo, acyl halide, or carboxyl groups. Methods of attaching oligonucleotides to the solid support are well known in the art (e.g., EDC/NHS coupling chemistry) and are described infra.

In an alternative embodiment of the present invention, the base surface of the solid support comprises a first substrate material and the top and side surfaces comprise a second substrate material. The first substrate material, comprising the base surface of the solid support, is any material that is not photosensitive, including, without limitation, glass, an ion selective membrane, quartz, silicon, and borosilicate. In contrast, the second substrate material, comprising the top and side surfaces of the solid support, is a photosensitive material. The photosensitive material can be a negative or positive tone photoresist. An exemplary array device in accordance with this aspect of the present invention comprises polymer pillars (e.g., SU-8) on a glass substrate. In this embodiment, selective activation of the solid support surfaces is not necessarily required to regulate oligonucleotide attachment, because functional groups may pre-exist on the photosensitive substrate surface. Alternatively, the photosensitive layer of the device may be activated or modified to form desired functional groups for oligonucleotide attachment. However, in accordance with this embodiment, photomasking or any other method of selective substrate activation is not required because the non-photosensitive material is not activated. In accordance with this embodiment of the present invention, oligonucleotides attach to the photosensitive material (e.g., polymer material) of the top and side surfaces of the solid support, but not to the base material comprising a different, non-activated material (e.g., glass).

Figure 18:
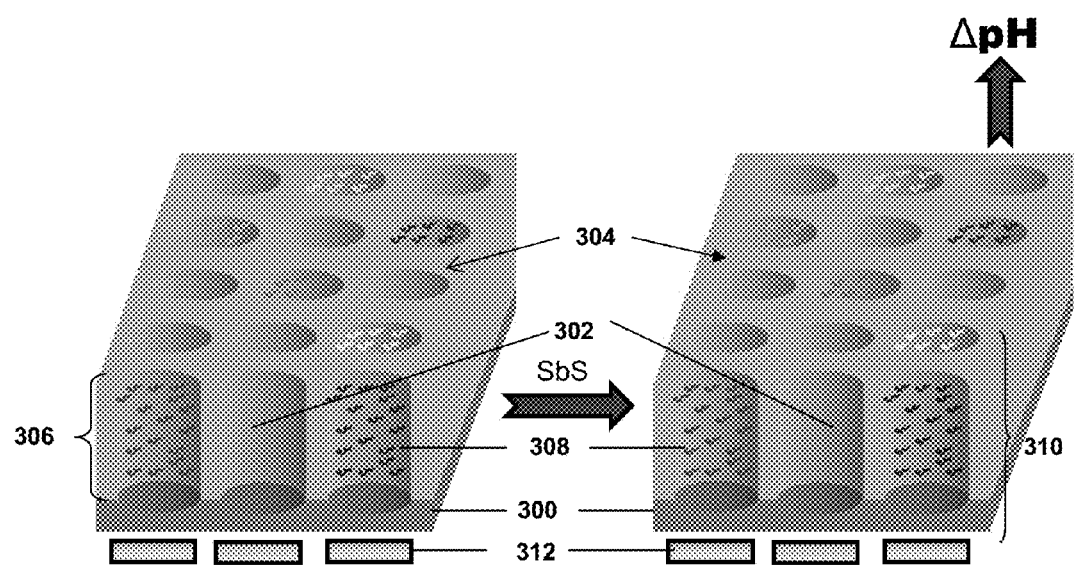
FIG. 18 is a schematic showing a portion of a device of the present invention comprising a plurality of wells with oligonucleotides attached to the side surfaces, but not the base surface of the device. The base surface of the device comprises an ion selective membrane that is positioned above an array of electrodes suitable for detecting electrochemical changes across the ion-selective membrane.

FIG. 18 depicts an exemplary array device of this aspect of the present invention that comprises polymer wells 306 patterned by photolithography on an ion-selective membrane 300. The plurality of oligonucleotides 308 in this embodiment are attached to side surfaces 302 of the wells, but not base surface 300, as described supra. These wells are positioned above an array of electrodes 312 so that the potential across the ion-selective membrane comprising base surface 300 can be measured. Since the surface modification chemistry is specific for the resist used to form the wells, covalently tethered oligonucleotides 308 attach specifically to resist side surface 302 and not the ion membrane of base substrate 300. Although SU-8 is a preferred substrate material in this example, it should be appreciated that other resist materials can also be utilized as the second substrate material.

When performing sequencing-by-synthesis in the wells of the device shown in FIG. 18, $H^+$ ions are released upon incorporation of a dNTP, changing the pH of the solution (Pourmand et al., "Direct Electrical Detection of DNA Synthesis," *Proc. Nat'l. Acad. Sci.* 103(17):6466-70 (2006), which is hereby incorporated by reference in its entirety). The $H^+$ is converted to voltage and detected by electrode sensor 312 that is beneath the ion selective base membrane 300 of the device (Anderson et al., "A System for Multiplexed Direct Electrical Detection of DNA Synthesis," *Sensors & Actuators* 129:79-86 (2008) and Miller et al., "Genetic Diversity and Population Structure of Endangered Marsupial *Sarcophilus harrisii* (Tasmanian Devil)," *Proc. Nat'l. Acad. Sci.* doi/10.1073 (2011), which are hereby incorporated by reference in their entirety). Semiconductor sensing devices and ion chips suitable for multiplex detection of DNA synthesis based on electrical/chemical detection and methods of making the same are known in the art (see U.S. Patent Application Publication No. US2009/0026082 to Rothberg et al. and Rothberg et al., "An Integrated Semiconductor Device Enabling Non-Optical Genome Sequencing," *Nature* 475:348-352 (2011), which are hereby incorporated by reference in their entirety) and are suitable for use in the device of the present invention.

Analogous to a polymerase based reaction, a ligation reaction also releases $H^+$, which can also be measured using a device of the present invention having an ion-permeable membrane and electrode sensors beneath each microwell as shown in FIG. 18. Accordingly, ligation-based methods may be used in this device of the present invention to detect single-nucleotide polymorphisms, mutations, insertions, deletions, DNA rearrangements, splice-site variants, and sequencing.

There are a number of advantages to using the device of the present invention depicted in FIG. 18 that affords electrical detection of DNA synthesis. Firstly, solid phase amplification can be carried out in the well, avoiding the need to carry out emulsion PCR using beads as current electrical detection techniques require. Secondly, detecting dNTP incorporation does not require optical imaging, and consequently does not require fluorescently labeled dyes. Ion based sequencing methods also do not have the same sequence read biases as other methods. For example, ion-based sequencing can read through portions of DNA with skewed base ratios (e.g., high ratio of AT bases) more accurately than other existing sequencing technologies. This label-free, electronic detection of DNA synthesis greatly simplifies and accelerates the sequence-by-synthesis method, rendering it more useful for diagnostic applications.

Figure 19:
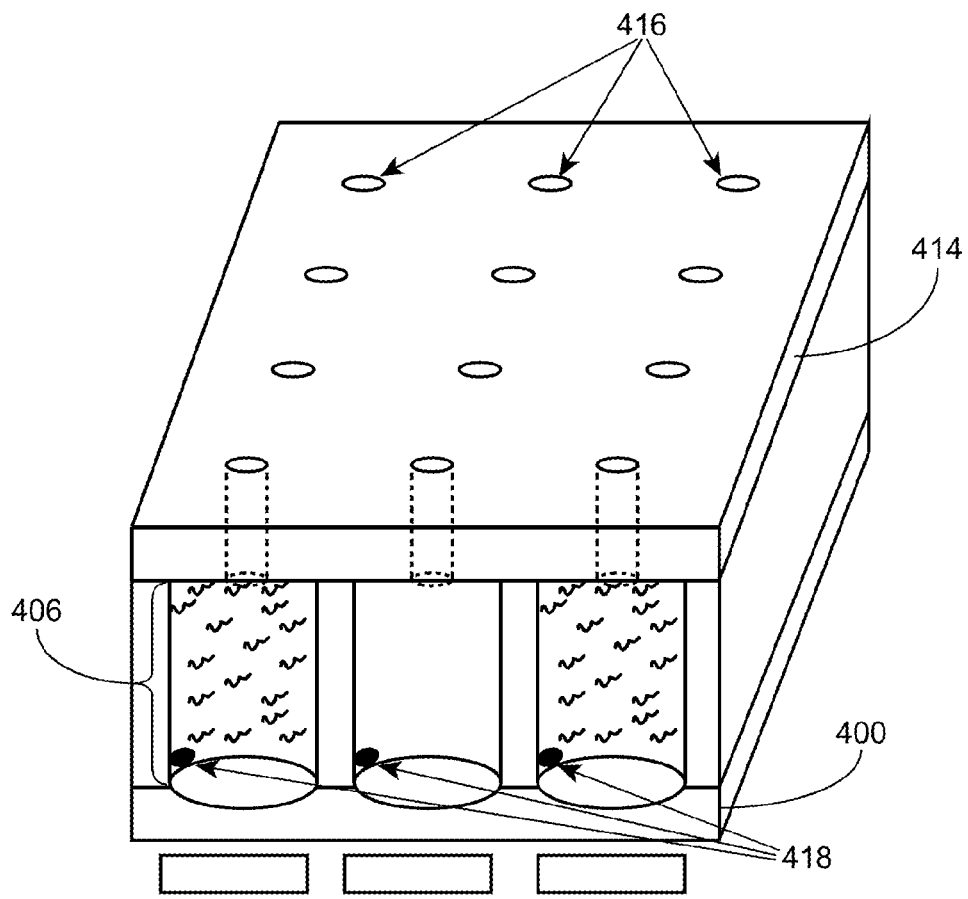
FIG. 19 is a schematic showing a fluidic network for addressing microwells of a device of the present invention.

Array devices comprising wells, such as that shown in FIG. 18, can further comprise fluidic networks that consist of a polymer membrane, same as the substrate, that cover each well and provide the ability to individually address each well or series of wells. A diagram of this architecture is shown in FIG. 19, in which a cover plate 414 with patterned through holes 416 is used to allow access to each well 406 by a fluid entering from the top. Through holes 416 are lithographically prepared in the same manner in which the microwells are so that they are aligned properly with respect to the wells. Exit through holes 418 are placed on the side of each well. With proper placement of the exit through hole and the entrance through hole on the top of each well, dead or unswept volumes are minimized, and well washing and filling times are reduced. This architecture provides the added advantage of allowing for division of the array, such that multiple samples, i.e., 8, 24, 96 or more samples can be sequenced simultaneously.

The array devices depicted in FIGS. 18 and 19 have the added advantage of being reusable. The immobilized oligonucleotides of the resist portion of the device can be removed using any organic solvent that the resist is soluble in, e.g., chloroform. The ion membrane can be cleaned for reuse using an appropriate solution, such as, for example, a diluted hydrofluoric acid solution) The array of electrodes beneath the ion permeable membrane is an expensive component of the device; however, with the ability to clean the resist and ion selective membrane of the device, the entire device can be reused several times, significantly cutting the cost of ion-based nucleic acid sequencing.

The surfaces of the solid support may also contain a layer of linker molecules that couple the oligonucleotides to the solid support, although it will be understood that the linker molecules are not required elements of the present invention. The linker molecules are preferably of sufficient length to permit polymers in a completed substrate to interact freely with molecules exposed to the substrate. The linker molecules should be 6-50 atoms long to provide sufficient exposure. Suitable linker molecules can be selected based upon their hydrophilic/hydrophobic properties. The linker molecules may be, for example, aryl acetylene, ethylene glycol oligomers containing 2-10 monomer units, diamines, diacids, amino acids, or combinations thereof.

The linker molecules can be attached to the substrate via carbon-carbon bonds using, for example, (poly)tri-fluorochloroethylene surfaces. The linker molecules may optionally be attached in an ordered array, i.e., as parts of the head groups in a polymerized monolayer. In alternative embodiments, the linker molecules are adsorbed to the surface of the substrate.

The device of the present invention can comprise various types of oligonucleotides depending on the application. In one embodiment of the present invention, the oligonucleotides of the device are capture oligonucleotide probes as described in U.S. Pat. Nos. 6,852,487 and 7,455,965 to Barany et al., which are hereby incorporated by reference in their entirety. Accordingly, the present invention also encompasses a method of capturing a plurality of target nucleotide sequence on a solid support. This method involves contacting the device of the present invention with a plurality of target nucleotide sequences under conditions effective for hybridization between the plurality of capture oligonucleotides on the solid support surface and their complementary target nucleotide sequences. Preferably, the target nucleotide sequences are labeled to facilitate the detection of captured target sequences.

In another embodiment of the present invention, the immobilized oligonucleotides constitute one or more primers of one or more primer sets. Following capture of a target nucleotide sequence, the primer is extended via a polymerase enzyme to generate the complement of the target strand. Alternatively, the captured oligonucleotide is amplified via a solid phase amplification reaction and detected, for example, by sequencing. Suitable solid phase amplification methods include the solid phase amplification method of the present invention described supra. In accordance with this embodiment of the present invention, preferably >0.1% of the pillars or wells of the device may contain clonally amplified target nucleotide sequences arising from hybridization of a single target nucleotide sequence to a pillar or well, more preferably, >3% of the pillars or wells of the device contain clonally amplified target nucleotide sequences arising from hybridization of a single target nucleotide sequence to a pillar or well, and most preferably, >30% of the pillars or wells of the device contain clonally amplified target nucleotide sequences arising from hybridization of a single target nucleotide sequence to a pillar or well.

Other suitable methods of solid-phase amplification that can be carried out using the device of the present invention are described in U.S. Pat. No. 6,017,738 to Morris et al., U.S. Pat. No. 7,741,463 to Gormley et al., U.S. Pat. No. 7,754,429 to Rigatti et al., and U.S. Pat. No. 6,355,431 to Chee et al., and U.S. Patent Publication No. 2009/0226975 to Sabot et al., U.S. Patent Publication No. 2001/0036632 to Yu et al., 2008/0108149 to Sundararajan et al., and U.S. Patent Publication No. 2005/0053980 to Gunderson et al., which are hereby incorporated by reference in their entirety. The device of the present invention is also suitable for carrying out other multiplex nucleic acid reactions including, without limitation, single-base or multi-base extension reactions, primer extension assays, solid-phase sequencing, solid phase oligonucleotide ligation assay, pair end reads, RNA sequencing, copy number analysis, ChIP sequencing, and others as described in U.S. Patent Application Publication No. 2010/0015626 to Oliphant et al., which is hereby incorporated by reference in its entirety.

Another aspect of the present invention relates to methods of forming arrays of oligonucleotides on a solid support. The first of these methods involves providing a solid support having a base surface, a top surface, and a plurality of side surfaces extending between the base and top surfaces. The base surface, top surface, and plurality of side surfaces collectively form a plurality of wells or pillars on the solid support. A mask is applied to cover the base surface of the solid support and the masked device is exposed to an activating agent to activate the unmasked surfaces of the solid support, while the masked surfaces of the solid support are non-activated. The mask is removed from the solid support and the exposed solid support is contacted with a plurality of oligonucleotides under conditions effective for the oligonucleotides to attach to the activated surfaces of the solid support, but not to the non-activated surfaces of the solid support, thereby forming arrays of oligonucleotides on the solid support.

In accordance with this aspect of the present invention, the solid support preferably comprises a polymer material. Suitable polymers include, without limitation, poly(methyl methacrylate), polycarbonates, polysulfones, elastomers, and polymeric organosilicones. The solid support having a base surface, top surface and plurality of side surfaces extending between the base and top surfaces is formed from a solid support having a planar surface where the planar surface has been treated to form base, top, and a plurality of side surfaces. In one embodiment, the planar surface is subjected to hot embossing as described in U.S. Patent Application Publication No. 2004/0191703 to Soper et al., which is hereby incorporated by reference in its entirety. This approach is preferred when the solid support comprises a polymeric material. In an alternative embodiment of this aspect of the present invention, the planar surface is subjected to photolithography.

In one embodiment of the present invention, the solid support of the array comprises a plurality of patterned array positions, each array position comprising a plurality of pillars or wells. As described supra, the pillar and well structures can be formed to accommodate any geometrical three-dimensional structure of suitable height, depth, and width as described supra.

Figure 20:
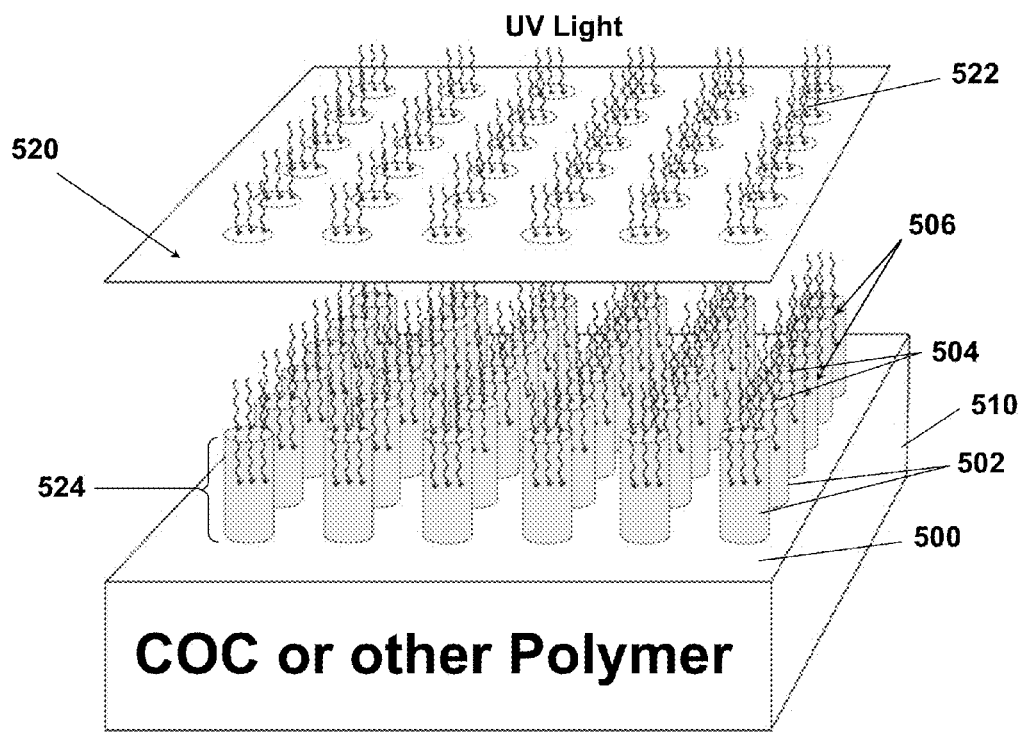
FIG. 20 shows the use of a photomask to achieve selective UV exposure activation of polymer pillars on a device of the present invention.

Methods of modifying surfaces of polymers for the attachment of biological molecules, including oligonucleotides, is described in U.S. Patent Application Publication No. 2004/0191703 to Soper et al., which is hereby incorporated by reference in its entirety. To achieve selective activation and attachment of different oligonucleotides at the different array positions, the plurality of patterned array positions on the solid support are selectively masked and exposed to an activating agent, e.g., UV light, as shown in the embodiment of the present inventions depicted in FIG. 20. The solid support 510 has base surface 500, top surfaces 504, and plurality of side surfaces 502 extending between base surface 500 and top surfaces 504 which collectively form plurality of pillars 506. A mask 520 is applied to cover base surface 500 and the masked device is exposed to activating agent 522 to activate unmasked surfaces 524 of the solid support, while masked surfaces 500 of the solid support are non-activated. Mask 520 is removed from solid support 510 and the exposed solid support is contacted with a plurality of oligonucleotides under conditions effective for the oligonucleotides to attach to activated surfaces 524 of the solid support, but not to the non-activated surfaces 500 of the solid support, thereby forming arrays of oligonucleotides on the solid support.

In one embodiment of this aspect of the present invention, the activating agent is actinic light. Preferably, exposure to actinic light is carried out in an oxidizing atmosphere. In many applications, ordinary air is suitable, although it is also possible to use an atmosphere with a higher or lower concentration of oxygen (or other oxidizing agent) to modify the patterning if desired. Higher concentrations of oxygen would be expected to facilitate surface oxidation. Other oxidizing agents known in the art may be used in lieu of, or in addition to, oxygen, for example $SO_2$, $NO_2$, or CNBr (see e.g., Kavc et al., "Surface Modification of Polyethylene by Photochemical Introduction of Sulfonic Acid Groups," *Chem. Mater* 0.12:1053-1059 (2000); Meyer et al, "Surface Modification of Polystyrene by Photoinitiated Introduction of Cyano Groups," *Macromol. Rapid Commun.* 20:515-520 (1999), which are hereby incorporated by reference in their entirety). Actinic light exposure activates polymer surfaces, promoting photooxidation and generating carboxyl groups on the exposed surfaces. Suitable surfaces for actinic light activation include, without limitation, acrylate polymers (e.g., PMMA), aromatic polymers (e.g., polystyrene, phenoxy resins), polyamides, polysulfones, and copolymers.

Figure 21:
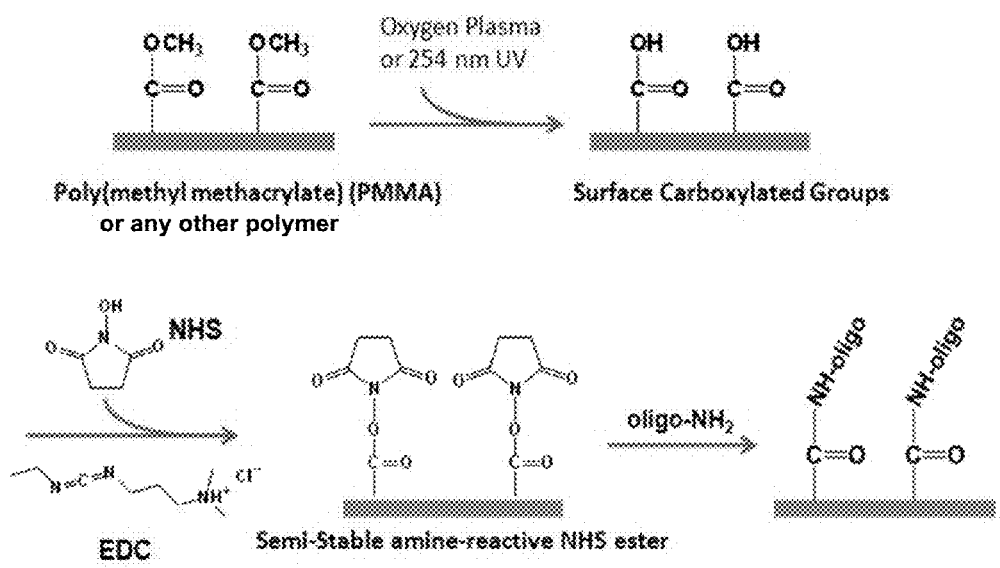
FIG. 21 shows cyclic olefin copolymer (COC) or Poly (methyl methacrylate) (PMMA) immobilization chemistry of amine-terminated oligonucleotides.

Activation of the array surface using actinic light as the activating agent can be achieved via exposure to broadband ultraviolet light, narrow band UV lamps (e.g., 254 nm), or UV lasers at frequencies absorbed by the polymers being used. Alternatively, activation of the array surface can be achieved using an oxygen plasma as the activating agent. The "active sites" may be selectively patterned by exposure through a photomask (FIG. 20), by direct "writing" on the surface with a focused UV source, or by other means for selectively exposing portions of the surface to the activating agent (e.g., actinic light or oxygen plasma), while leaving the remaining portions of the surface substantially unexposed. Cyclic olefin copolymer (COC) is a particularly attractive material for array fabrication in accordance with the methods of the present invention due to its extraordinarily low autofluorescence levels and its ability to generate a high density of functional groups following UV or oxygen plasma exposure Oligonucleotides, preferably, amine-terminated oligonucleotides are attached to the activated areas of the surface using methods well know in the art, e.g., click chemistry using ethyl-3-(3-dimethylaminopropyl) carbodiimide hydrochloride (EDC) as a crosslinker and N-hydroxysuccinimide (NETS) an intermediate ester as shown in FIG. 21. However, other attachment chemistries can be used as well, such as disulfides, maleimides, or siloxanes. When forming an array containing a plurality of pillars, oligonucleotides are attached to activated top and side surfaces of the pillars, but not to the masked surfaces between pillars. When forming an array containing a plurality of wells, oligonucleotides are attached to activated side surfaces of the wells, but not the masked top and bottom surfaces.

Another method of forming arrays of oligonucleotides on a solid support of the present invention involves providing a solid support having a planar substrate and a photosensitive layer over a surface of the substrate. The solid support is subjected to a photolithography process under conditions effective to form pillars or wells on the solid support. The solid support is contacted with a plurality of oligonucleotides under conditions effective for the oligonucleotides to attach to portions of the photosensitive layer which are either exposed or left unexposed by the photolithography process but not portions of the photosensitive layer which are left unexposed or exposed, respectively, thereby forming arrays of oligonucleotides on the solid support.

Figure 22:
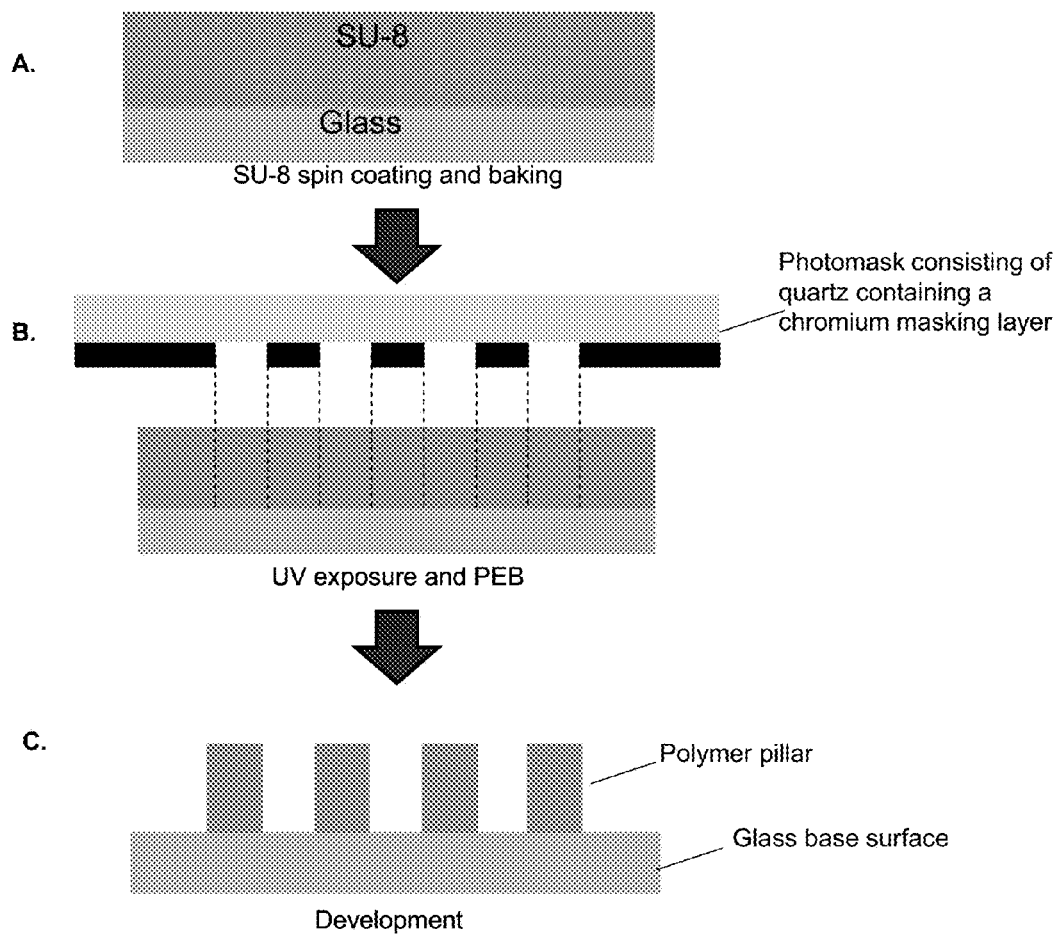
FIG. 22 shows the process of creating micropillars made from a negative tone resist, such as SU-8, on a glass surface. The formation of these pillars on glass creates different surface chemistries that can be specifically elaborated upon, such as the selective attachment of oligonucleotides exclusively on the SU-8 surface.

FIG. 22 depicts a method of forming arrays of oligonucleotides according to this aspect of the invention. As shown in FIG. 22A, the planar substrate of the solid support (e.g., glass) is spin coated with the photosensitive layer (e.g., SU-8) to a desired thickness (can range from 1 µm to 100 µm in thickness). The substrate is subjected to a pre-bake step as shown in FIG. 22A (e.g., 6 minutes at 65° C., 18 minutes at 95° C., and 6 minutes at 65° C.) and then exposed to UV radiation (345 nm) or other light source, through a photomask to generate pillars (FIG. 22B) or wells. The pillars are formed only where the resist film is exposed to the UV radiation due to extensive cross linking, making the material non-soluble in the developing solution while the areas not exposed to UV radiation are removed during the subsequent developing phase of the process. Following exposure to UV radiation, the solid support is subject to a post-exposure baking (PEB) step (e.g., 4 minutes at 65° C., 14 minutes at 95° C., and 4 minutes at 65° C.) and developed for 10 minutes to create pillars that will not release from the glass surface when subjected to heat required for subsequent amplification or other reactions (FIG. 22C). The non-exposed resist is removed using the proper developing solution, leaving the photosensitive pillars in place. The height and width of pillars and wells formed by the photolithographic process on the solid support are the same as those described supra. Suitable photosensitive materials include, without limitation a positive tone resist (e.g., AZ5214, Shipley 1813, AZ6612, AZ1505, etc.) or a negative tone resist (e.g., SU-8, M1001F, M1002F, etc.). Suitable substrate materials include, without limitation, glass, an ion selective membrane, quartz, silicon, and borosilicate.

Various methods of generating functional groups on photosensitive surfaces (i.e., SU-8 or one of its variants) to allow for the covalent attachment of oligonucleotides to the solid support are known in the art. Suitable functional groups include, without limitation, a carboxyl group, a carbonyl group, a hydroxyl group, an amino group, an epoxy group, and a silanol group.

SU-8 is a preferred surface material that comprises epoxide rings suitable for covalent attachment of oligonucleotides without additional activation or modification (FIG. 23; see also Wang et al., "Surface Graft Polymerization of SU-8 for Bio-MEMS Applications," *J. Micromech. Microeng.* 17:1371-1380 (2007), which is hereby incorporated by referenced in its entirety). In one embodiment, amine-terminated oligonucleotides can be added to the SU-8 surface using alkaline solutions (pH ~12) that hydrolyze surface epoxide groups and form secondary amines with the oligonucleotides carrying a primary amine (see FIG. 24A). Alternatively, SU-8 pillars or wells are treated with nitric acid to generate surface confined hydroxyl groups that are subsequently reacted with primary amine containing oligonucleotides (FIG. 24B; Wang et al., "Surface Graft Polymerization of SU-8 for Bio-MEMS Applications," *J. Micromech. Microeng.* 17:1371-1380 (2007), which is hereby incorporated by referenced in its entirety). In yet another embodiment, SU-8 polymer pillars or wells are exposed to UV radiation (254 nm) to generate surface hydroxyls and carboxylic acid groups (FIG. 24C). These approaches do not require a contact optical mask because the solid support substrate comprises a material that does not change its surface chemistry following exposure to the activating agent. Accordingly, the interstitial space is not functionalized and oligonucleotides will not attach to these locations.

Figure 25:
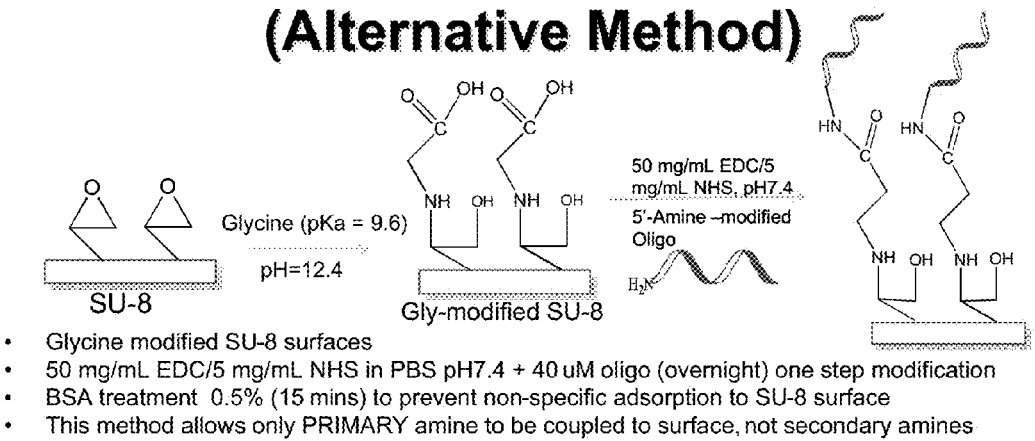
FIG. 25 shows a method of selective SU-8 photoresist surface modification.

Alternative attachment chemistries compatible with epoxy-based resists, such as SU-8, are also suitable for use in the methods of present invention. For example, in one embodiment a cross-linking reagent is used to modify the functional group present on the surface of the support. Suitable crosslinking reagents include, without limitation, glycine, glutaraldehyde, and aminopropyltriethoxysilane (APTES). The chemistry for glycine modification is shown in FIG. 25. Following glycine attachment using high pH conditions to hydrolyze the epoxide rings, standard EDC/NHS coupling chemistry is used to generate an amide linkage between a 5'-primary amine-containing oligonucleotide and the pendant carboxy-end of the amino acid glycine. The primary advantage of this modification strategy is that glycine only contains one amino group. The hydrolytic step employed for attachment of amine groups to epoxides is not selective for primary amines only and thus, can couple secondary amines to the surface. For example, the secondary amine for the nucleotide of thymine can react with the epoxide groups at high pH as well, which may make the oligonucleotide unavailable for subsequent amplification. Thus, the use of the glycine cross linker will provide a higher probability of generating a 5'-end attached to the desired oligonucleotides.

FIGS. 26-28 illustrate three approaches for attaching oligonucleotides to the plurality of patterned array positions on the solid support. In the approach shown in FIGS. 26A-26H, zip-code oligonucleotides are first attached to the activated surfaces to guide oligonucleotides to their desired location on the array. FIG. 26A shows the surface of the solid support, where the squares are the patterned array positions containing a plurality of circles that each represent a cluster of pillars or wells. In step 1, the side and top surfaces of the pillars or side surfaces of the wells are selectively activated. Following activation, zip-code oligonucleotides are added to rows or columns of the array via fluidic channels (FIG. 26B) and immobilized to the pillar or well surface via reaction with the functional group on the activated pillar or well surface. Zip-code oligonucleotides are synthetic oligonucleotides, having unique sequences of between 10-40 nucleotides in length all having similar melting temperatures so as to facilitate hybridization to complementary nucleotide sequences under uniform hybridization conditions. The sequences of the zip-code oligonucleotides differ significantly from each other (i.e., by at least 25% when aligned) and from any known genomic sequence to avoid cross-reactivity to an incorrect target sequence. Methods of making zip-code oligonucleotides are disclosed in U.S. Pat. Nos. 6,852,487 and 7,455,965 to Barany et al., which are hereby incorporated by reference in their entirety.

Figure 26A:
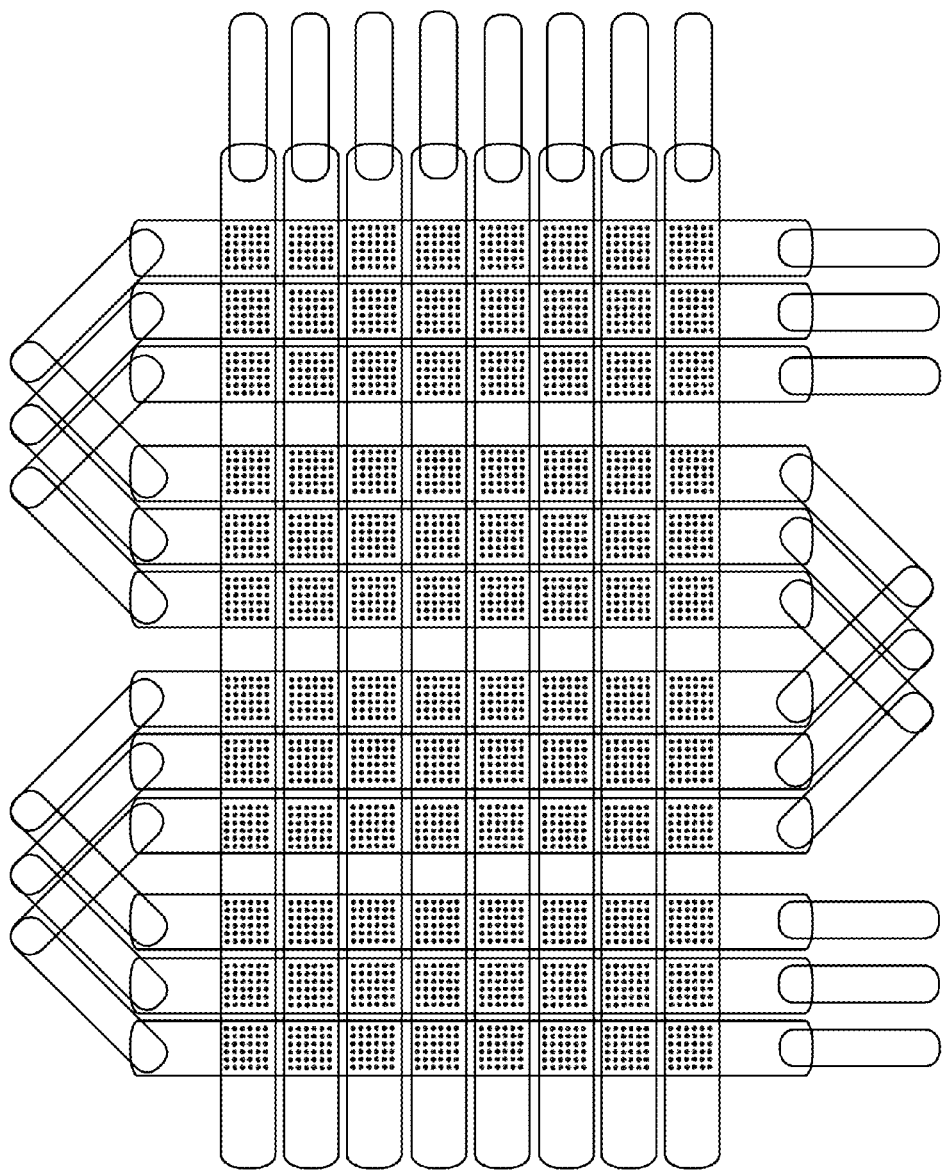
FIGS. 26A-26H are schematic drawings showing a method of UV activation and guided oligonucleotide attachment to a device of the present invention where the resulting array of oligonucleotides is suitable for SNP and copy number analyses.
Figure 26B:
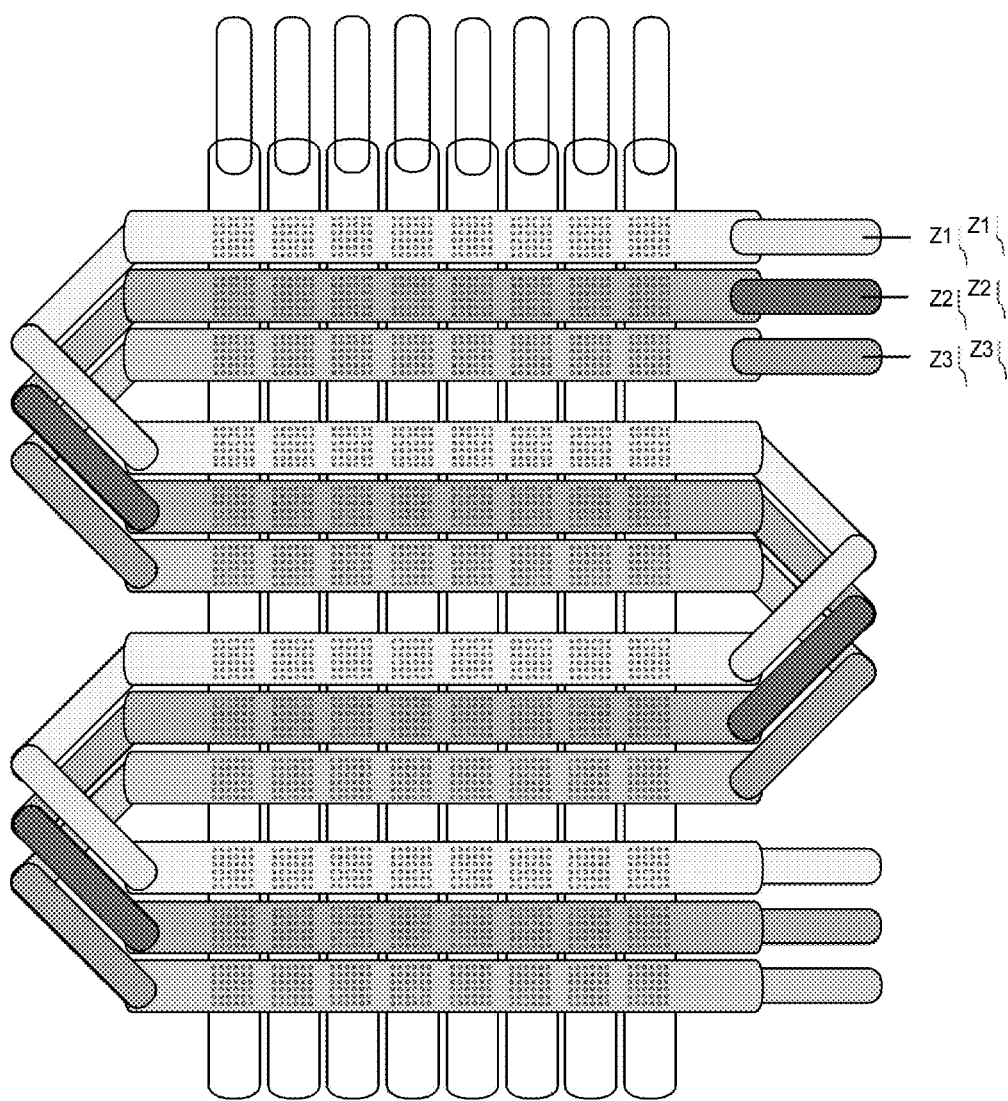
Figure 26C:
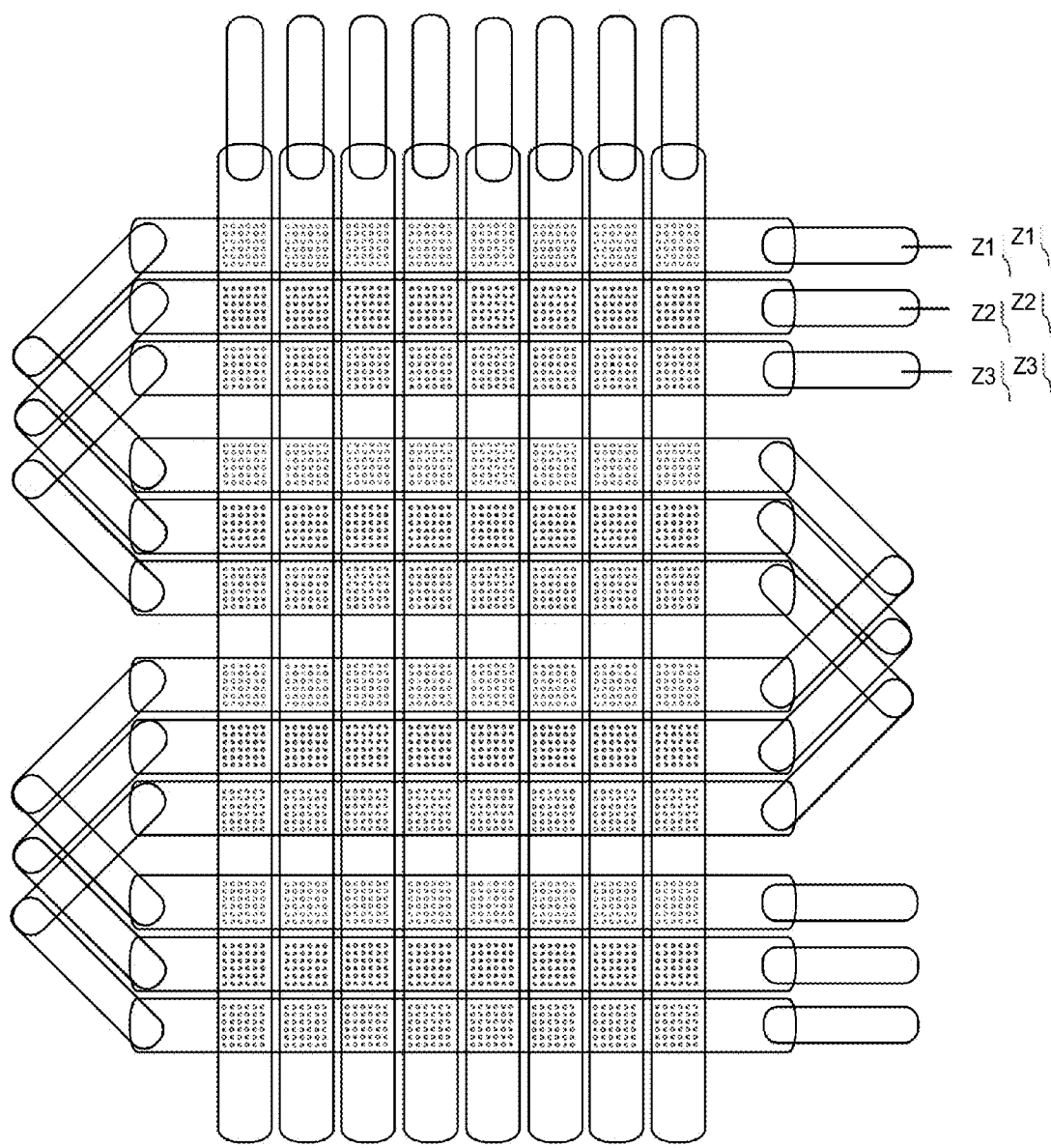
Figure 26D:
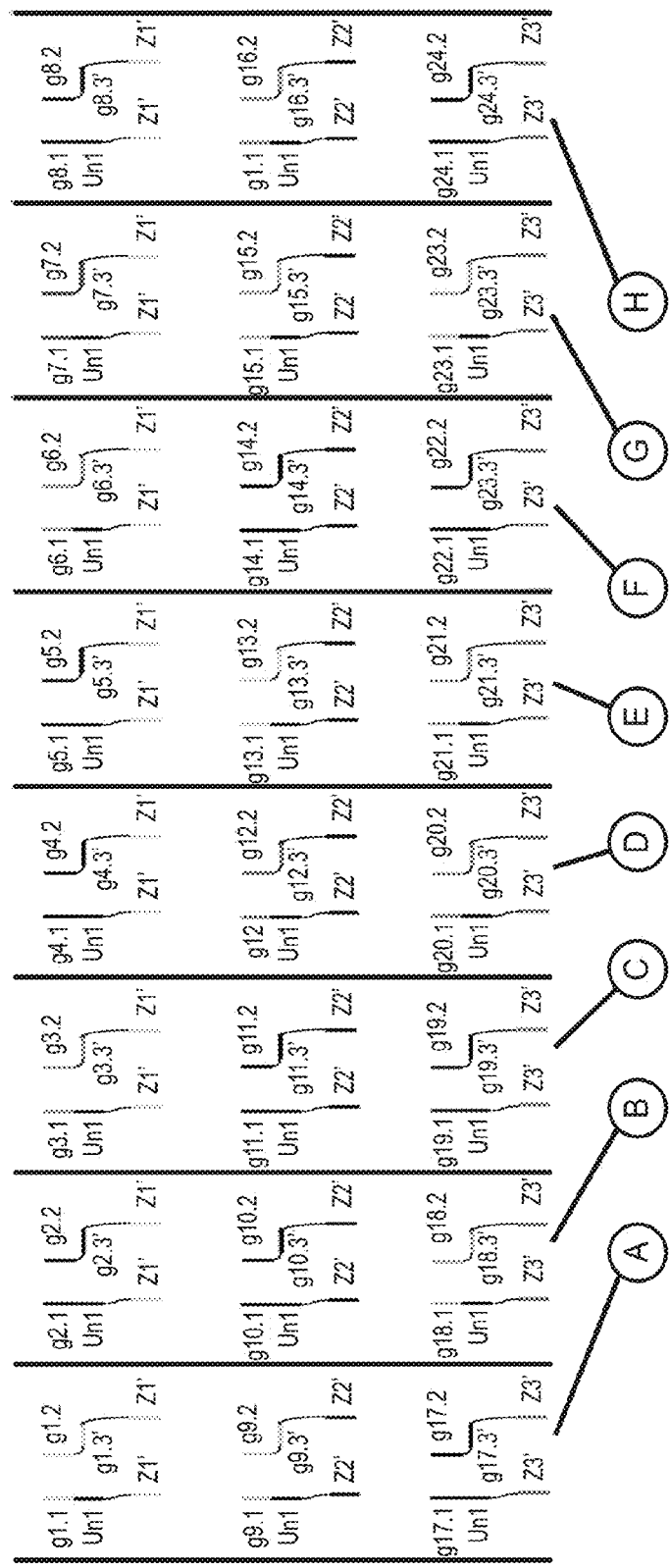
Figure 26D:
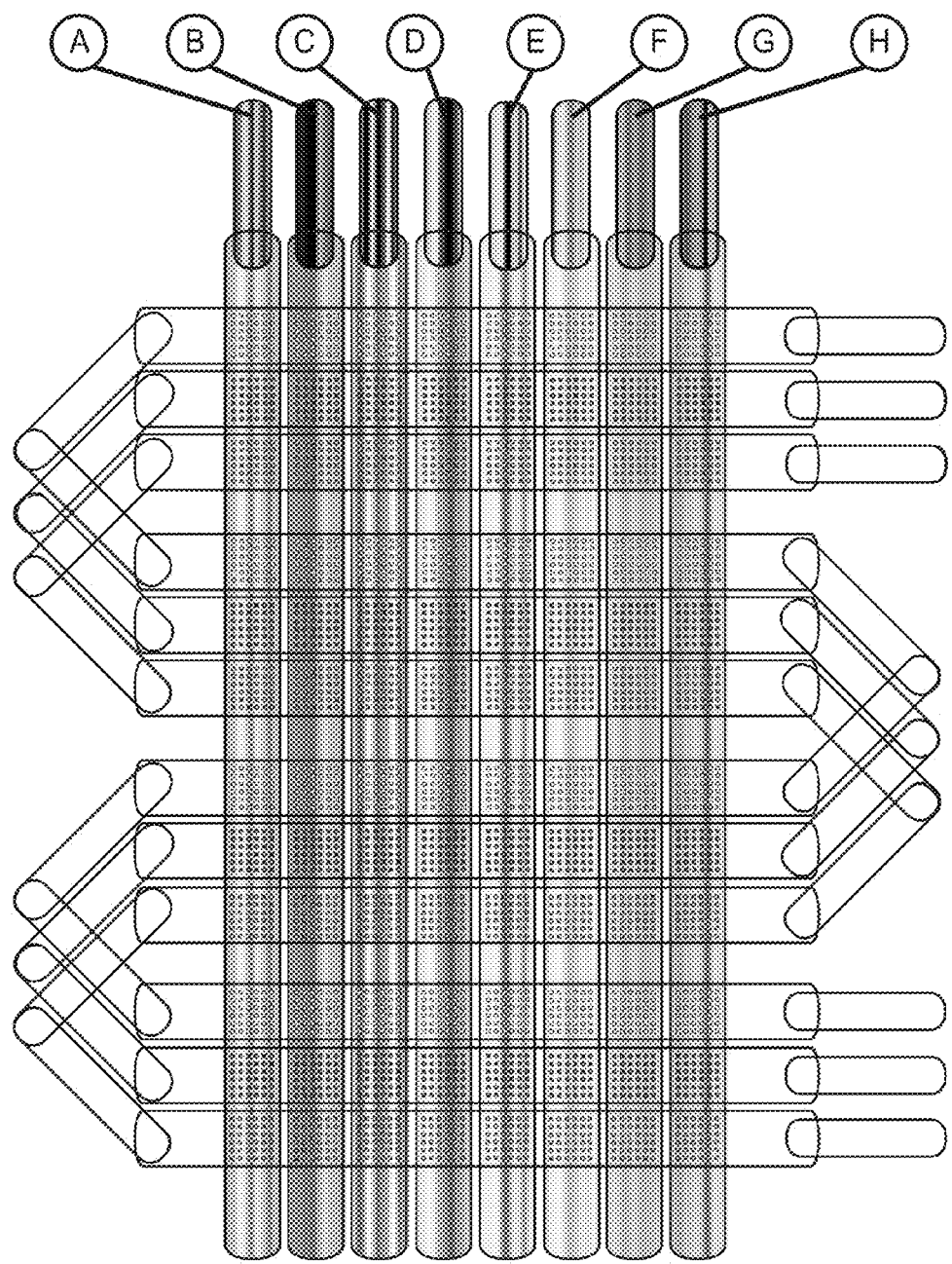
Figure 26E:
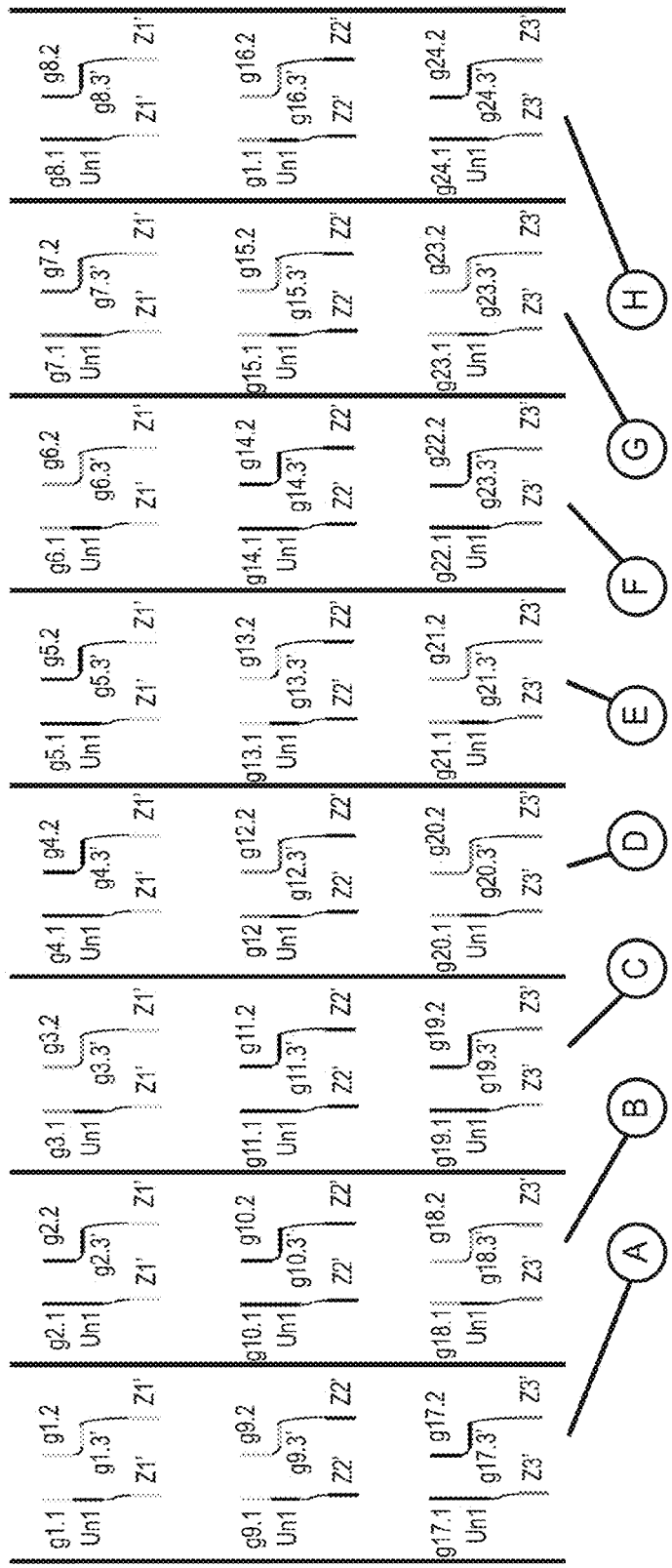
Figure 26E:
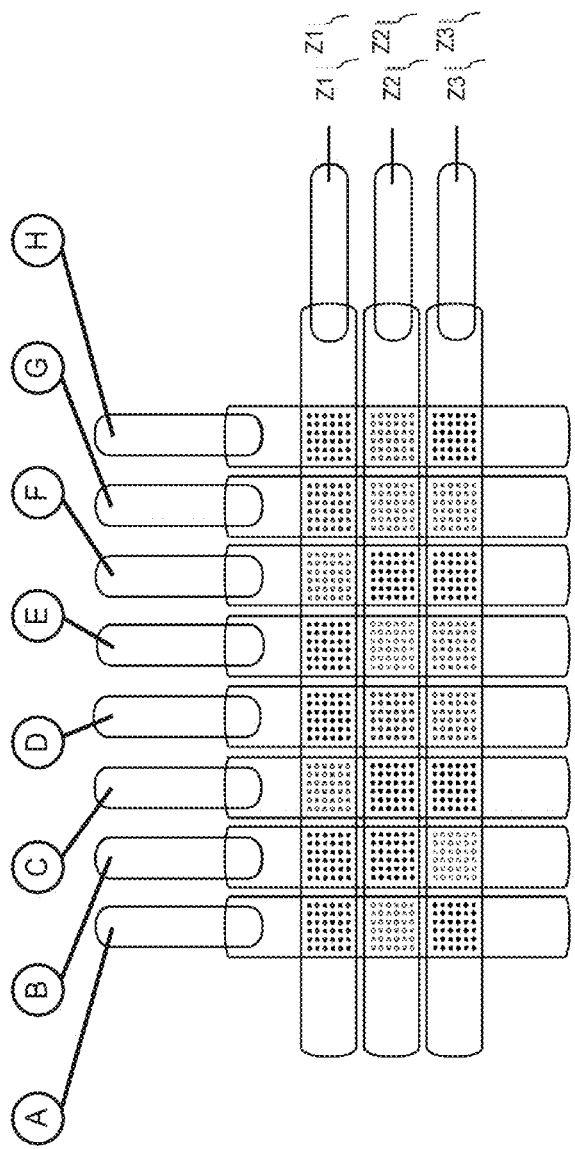
Figure 26F:
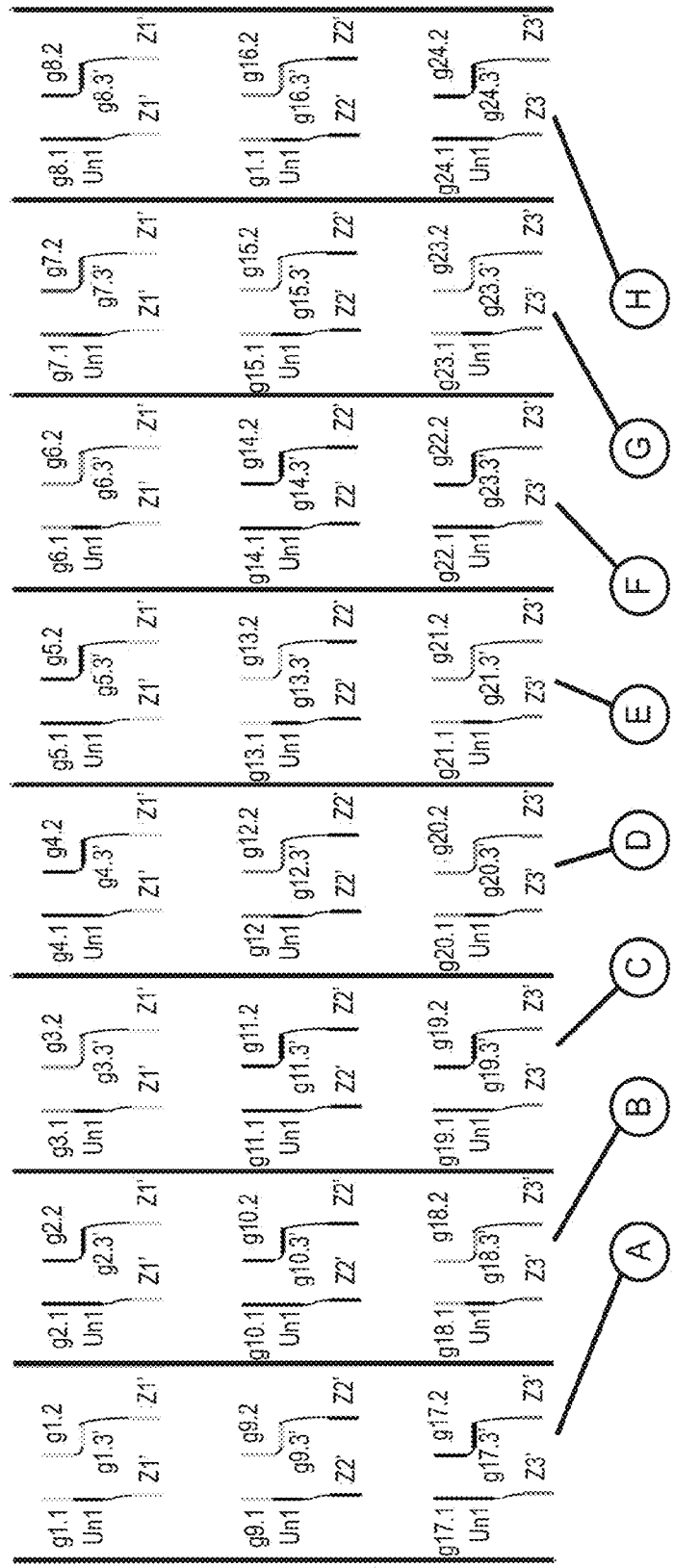
Figure 26F:
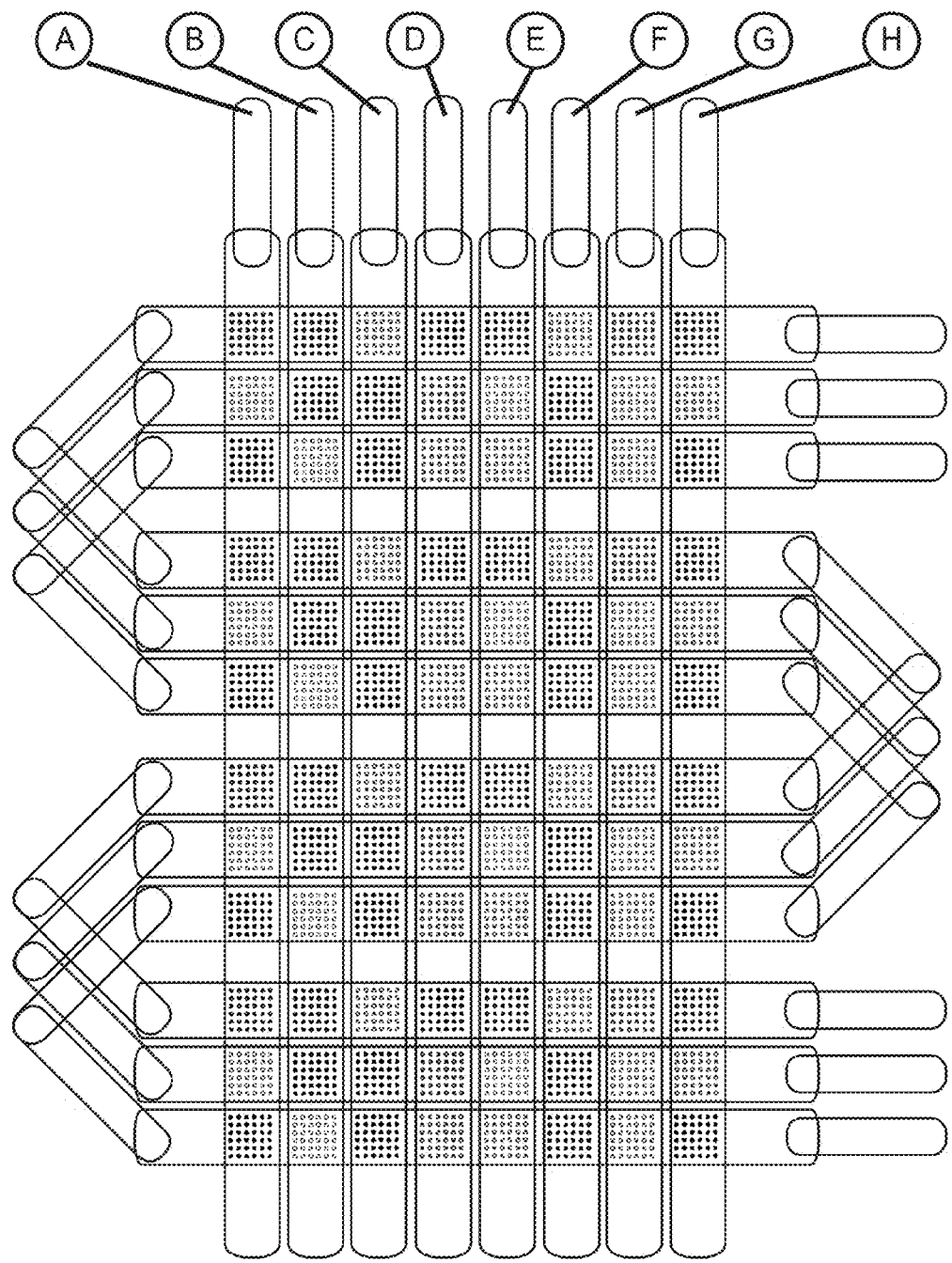
Figure 26G:
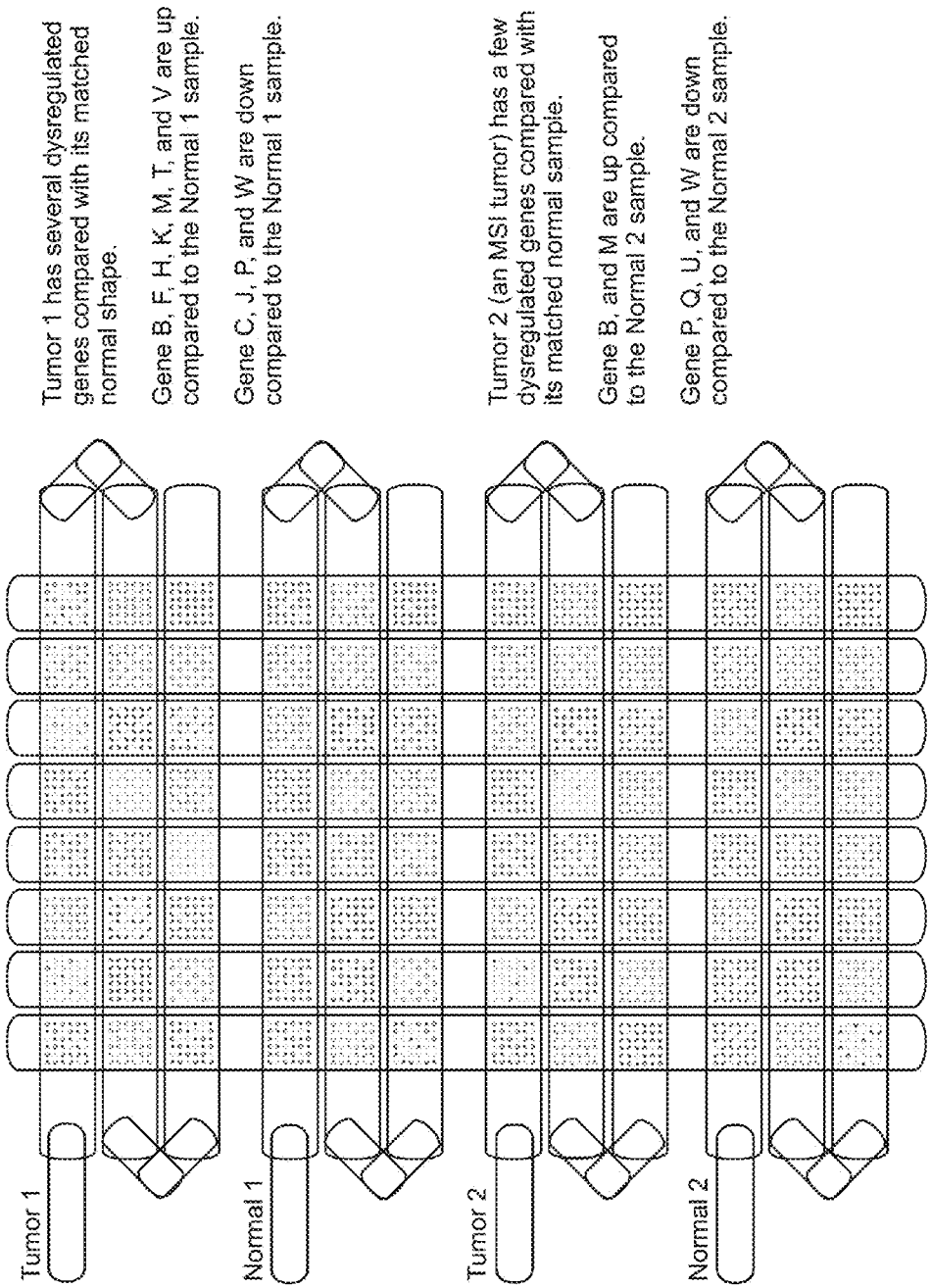
Figure 26H:
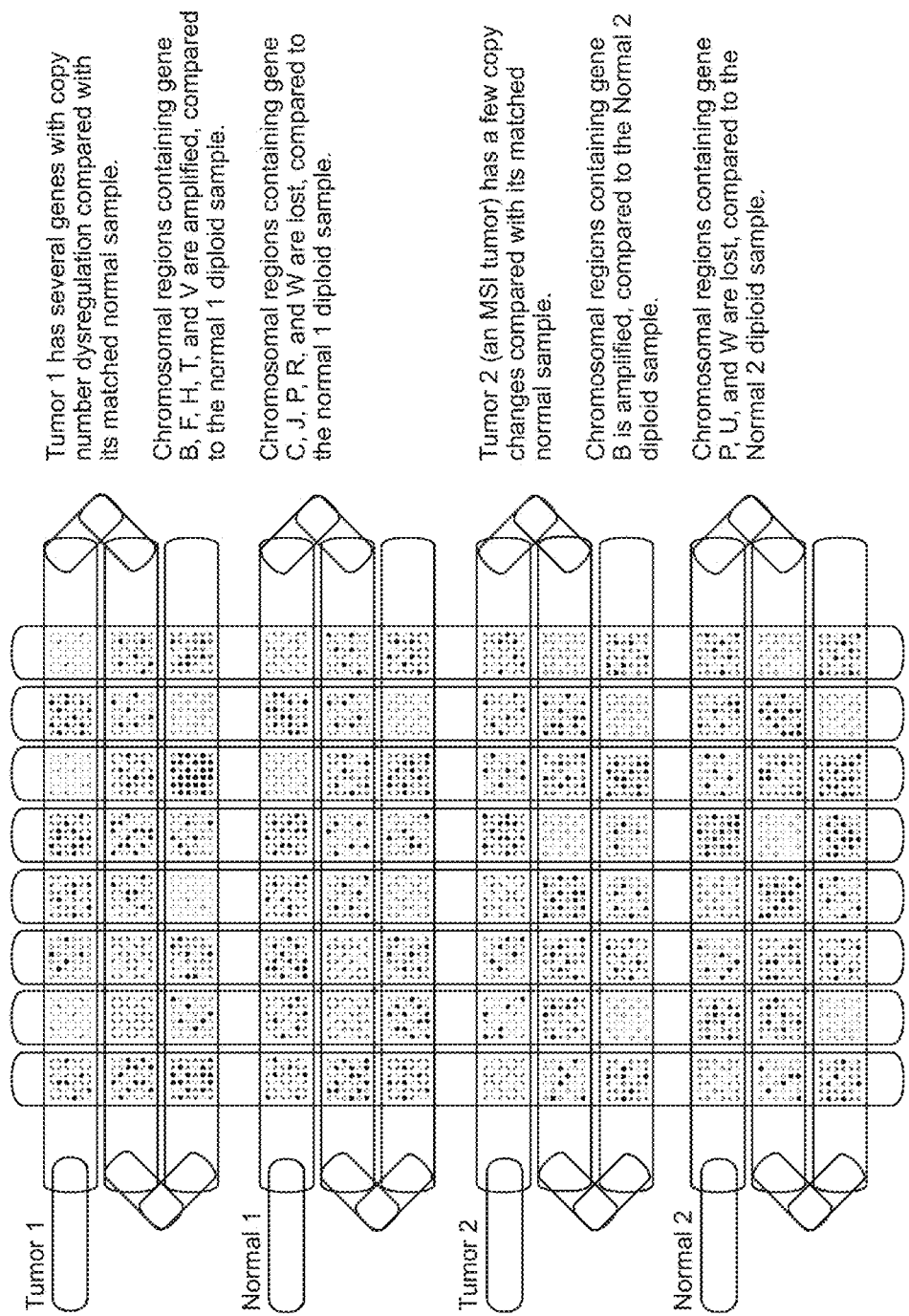

As shown in FIG. 26C, three different zip-code oligonucleotides (i.e., Z1, Z2, and Z3) are attached to the array surface, one zip-code oligonucleotide per row (in this example, each row is repeated four times on the array). Once the zip-code oligonucleotides are attached to the pillars or wells of the solid support, the oligonucleotides of interest, each having a portion of its sequence complementary to a respective zip-code oligonucleotide sequence, are added to the solid support. In FIG. 26D, composite oligonucleotides of interest, in this example gene specific primer sets that also contain a sequence that is complementary to one of the three zip-code oligonucleotides are added to columns of the array. Three different composite oligonucleotide primer sets, each set containing a Z1, Z2, or Z3 complement sequence are added via a fluidic channel to each column of the array (FIG. 26E). The composite oligonucleotides hybridize to their complementary zip-code oligonucleotide sequence and are cross-linked to maintain immobilization (FIG. 26F). Using this approach, a single primer set is attached to each of four or more repeated pillar clusters across the array. As shown in FIG. 26E, twenty-four different primer sets are represented on the array. Since each primer set is represented four times across the array, the expression of twenty-four genes can be assessed in four different samples simultaneously on the array as depicted for the tumor and control samples in FIGS. 26G and 26H. Using this type of an array, gene expression analysis as shown in FIG. 26G or copy number analysis as shown in FIG. 26H can be carried out. Alternatively, an array design as depicted in FIG. 27A-27H, where each oligonucleotide primer set represents different regions of the same gene, is used to obtain sequencing information. Oligonucleotide attachment in this array design is carried out as depicted and described for FIGS. 26A-26H and is shown in FIGS. 27A-27H.

Figure 28A:
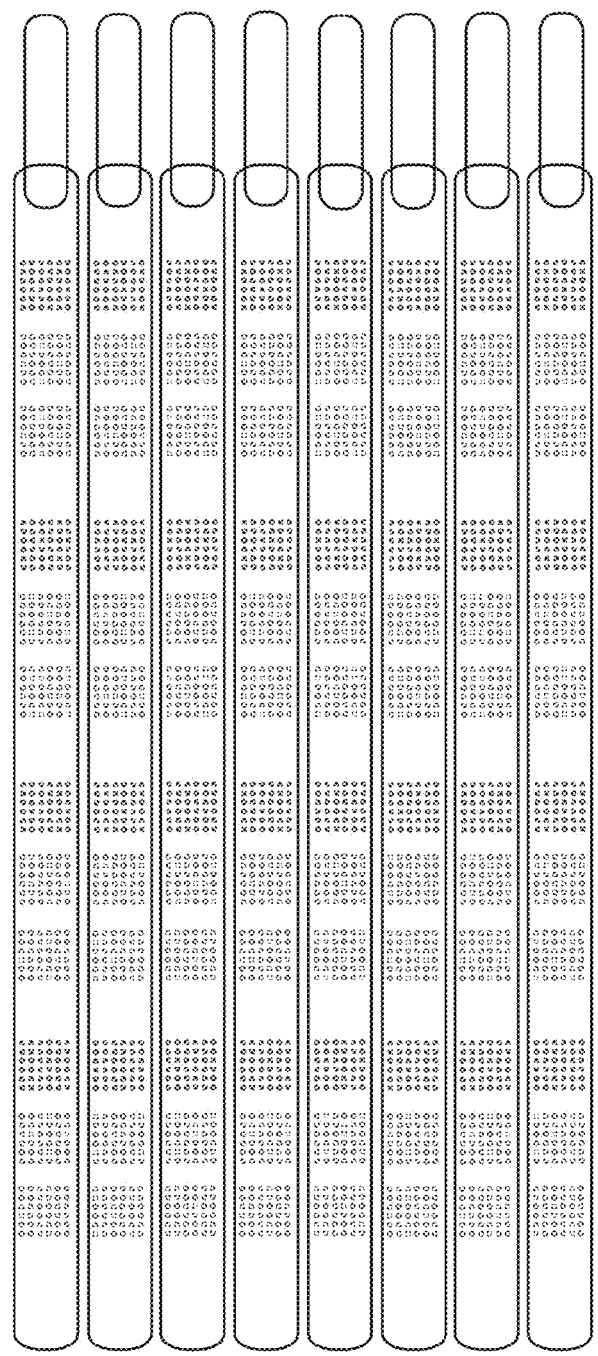
FIGS. 28A-28J are schematic drawings showing a method of UV activation and guided oligonucleotide attachment to a device of the present invention where the resulting array of oligonucleotides is suitable for SNP and copy number analyses.
Figure 28B:
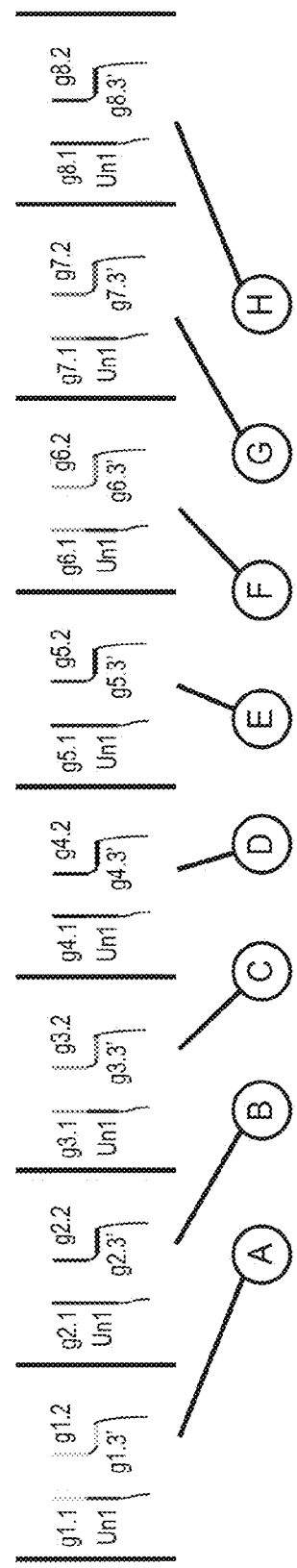
Figure 28B:
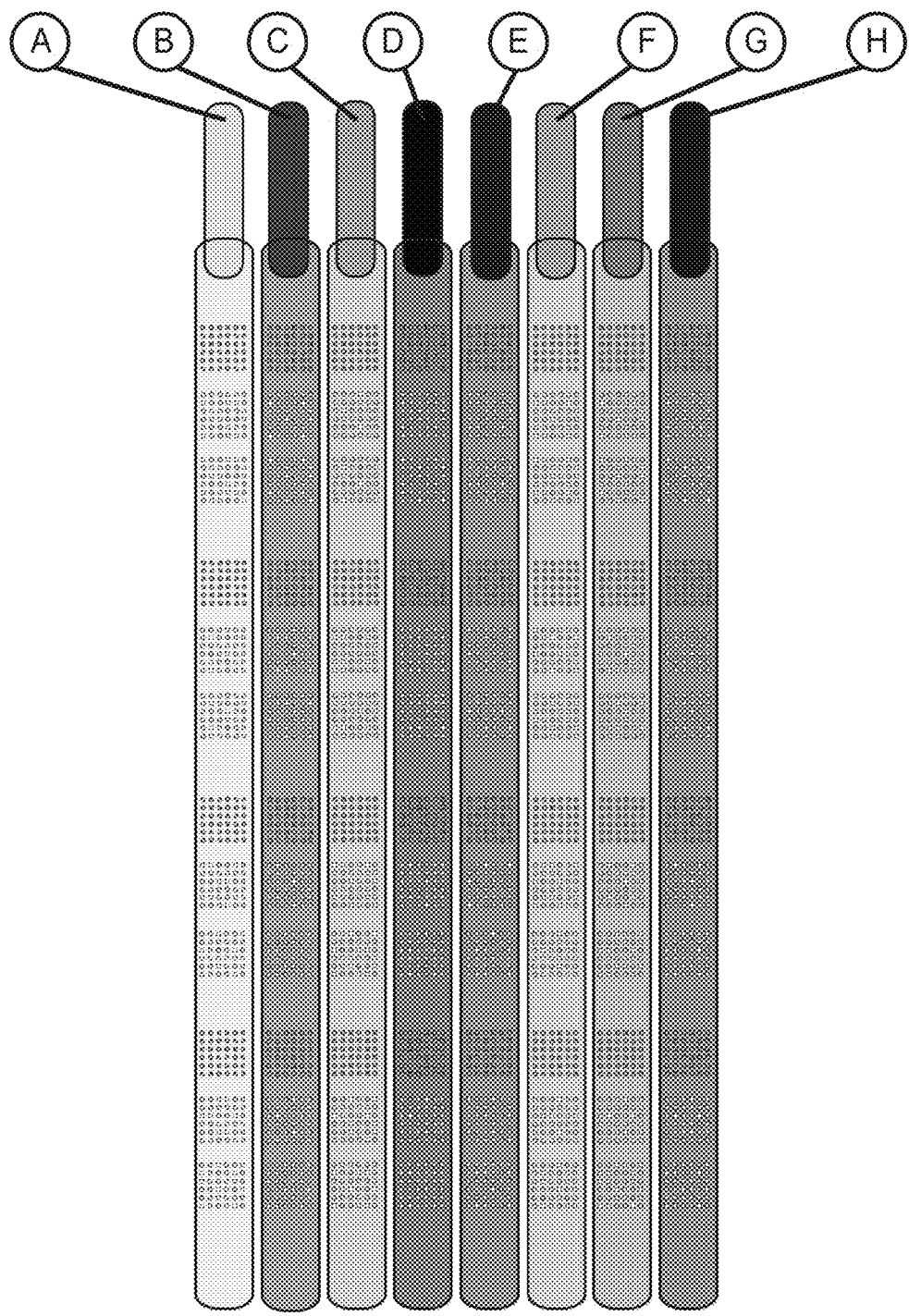
Figure 28C:
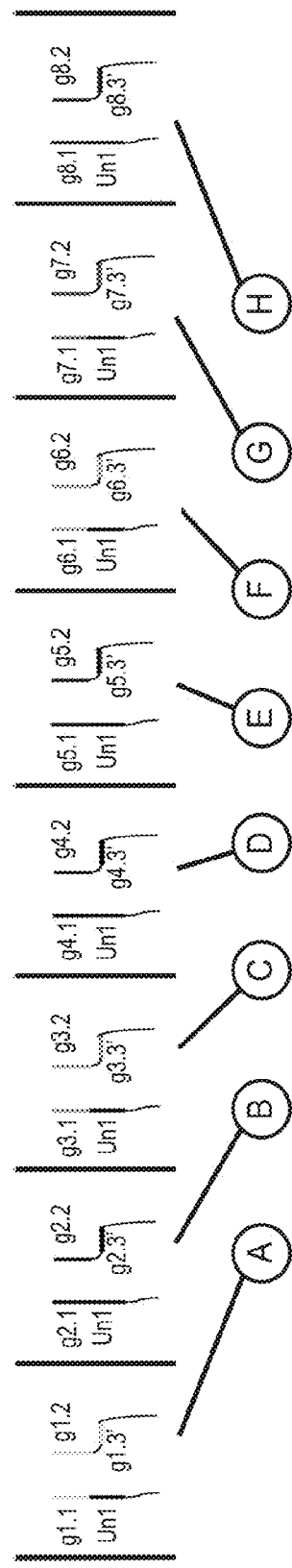
Figure 28C:
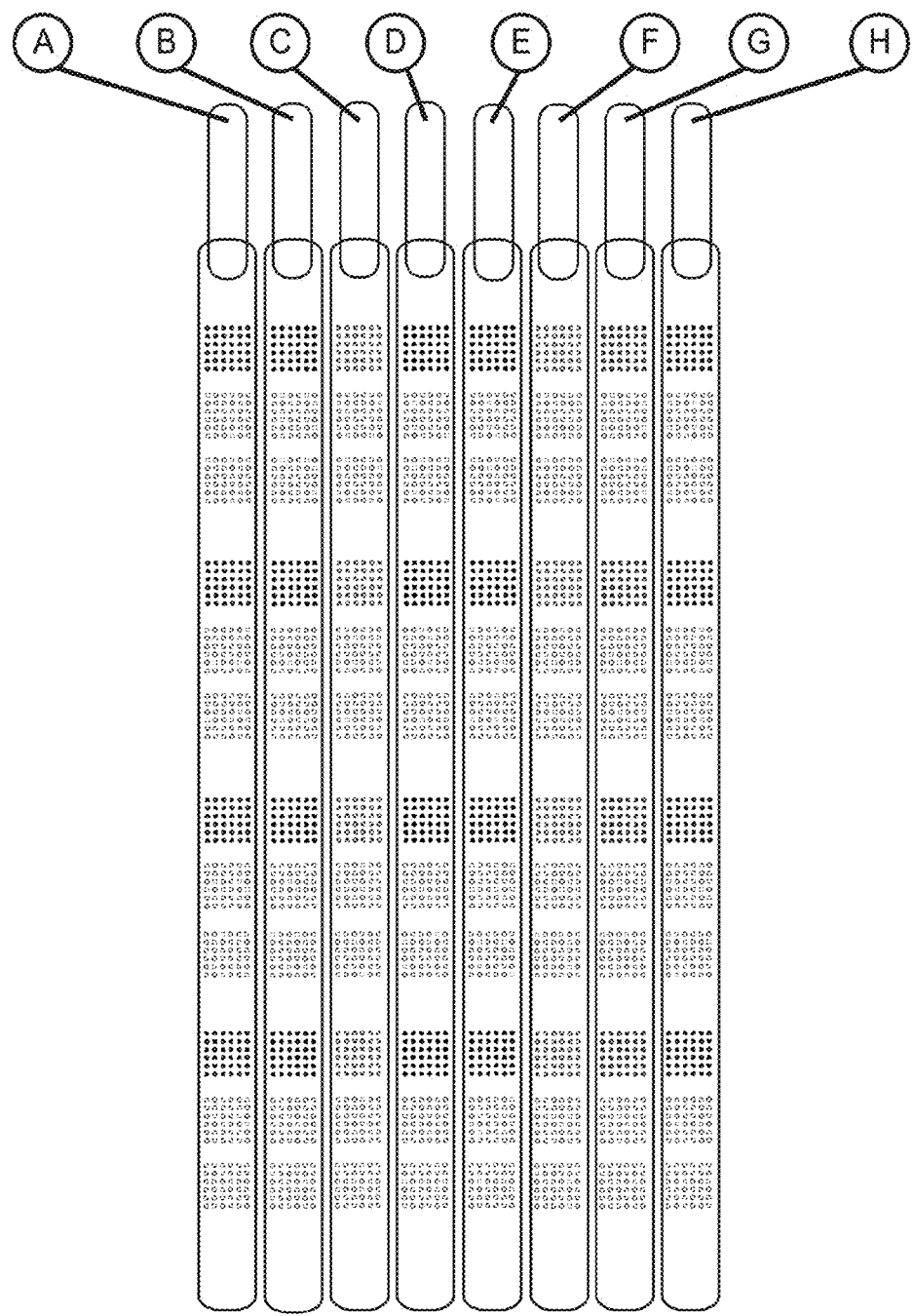
Figure 28D:
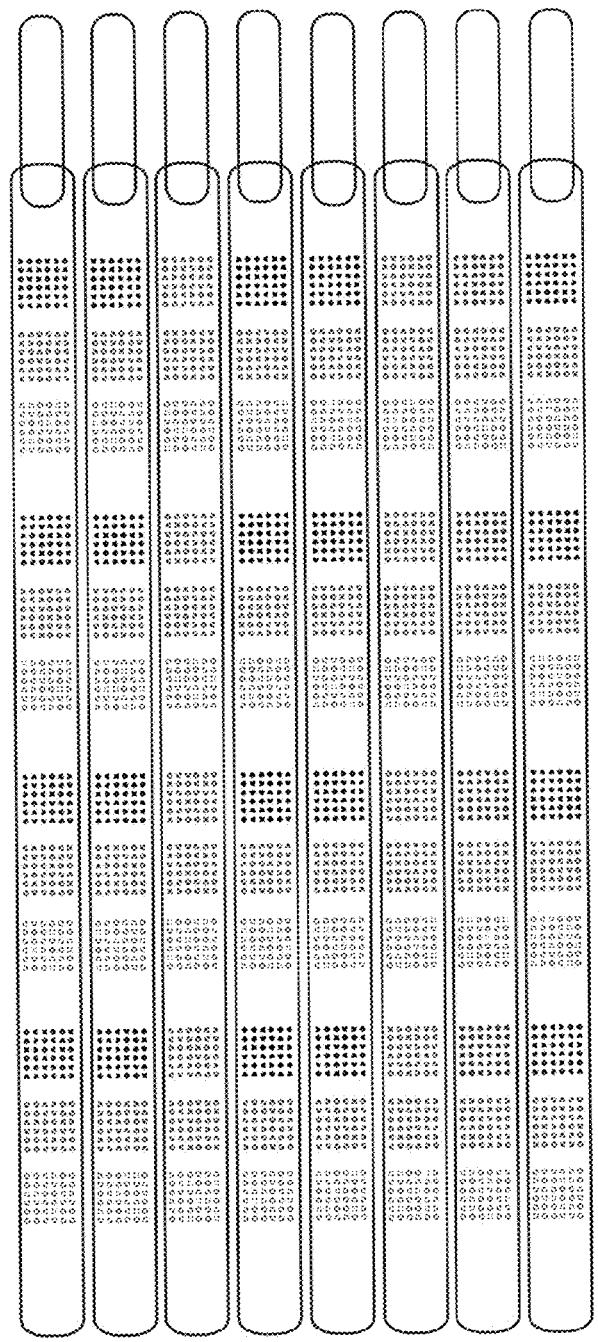
Figure 28E:
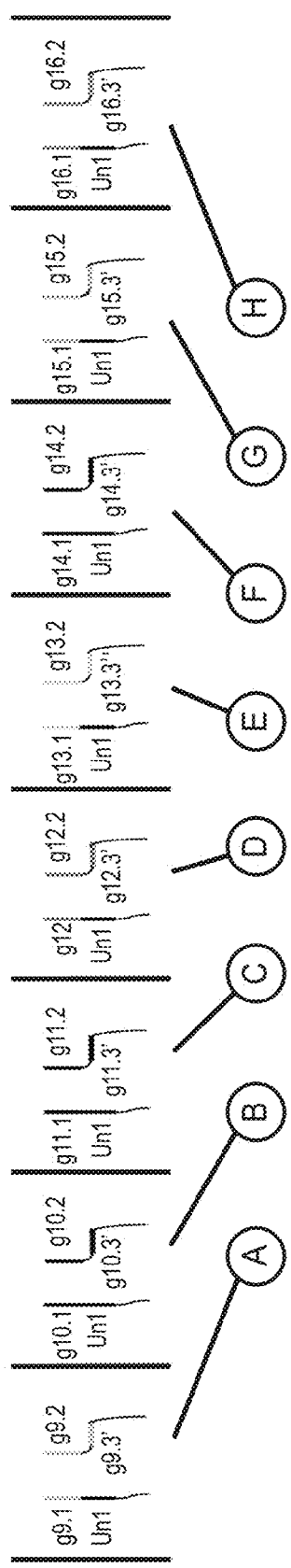
Figure 28E:
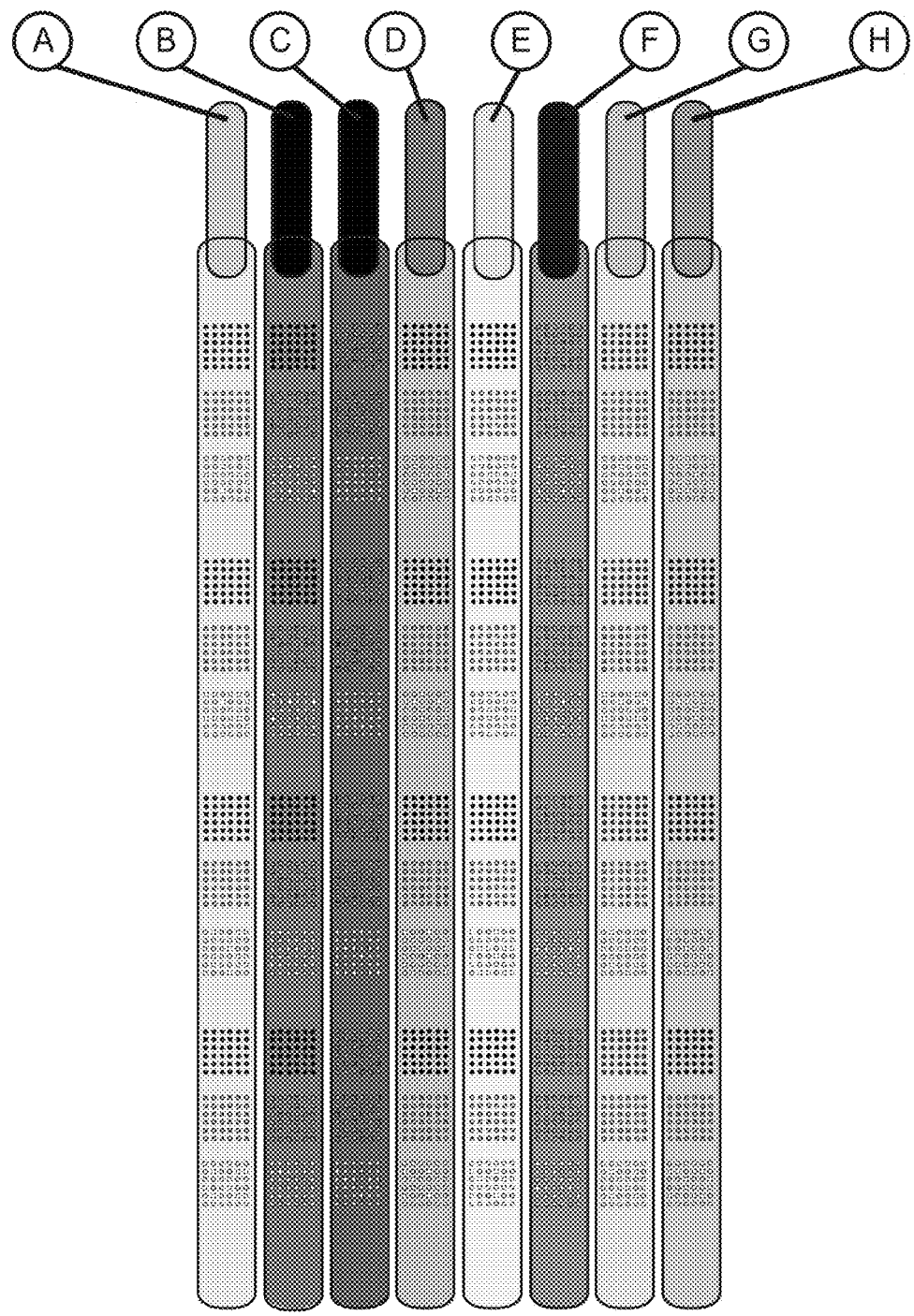
Figure 28F:
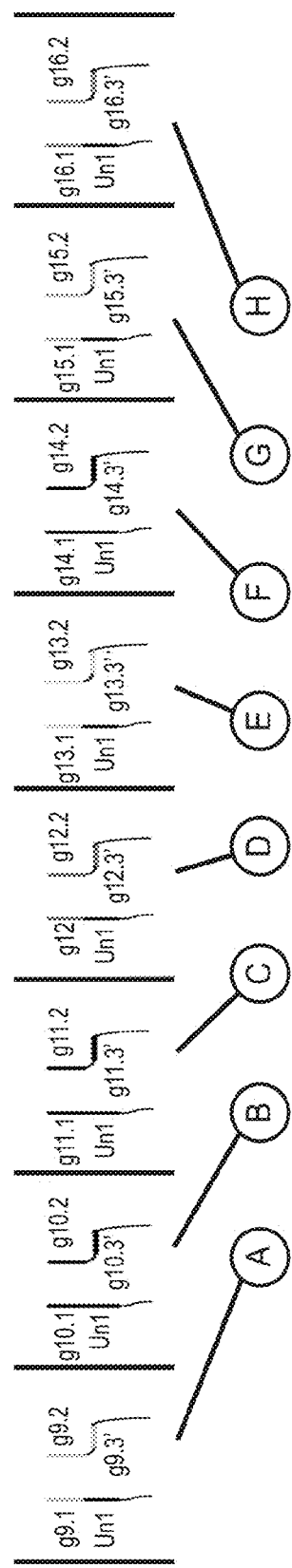
Figure 28F:
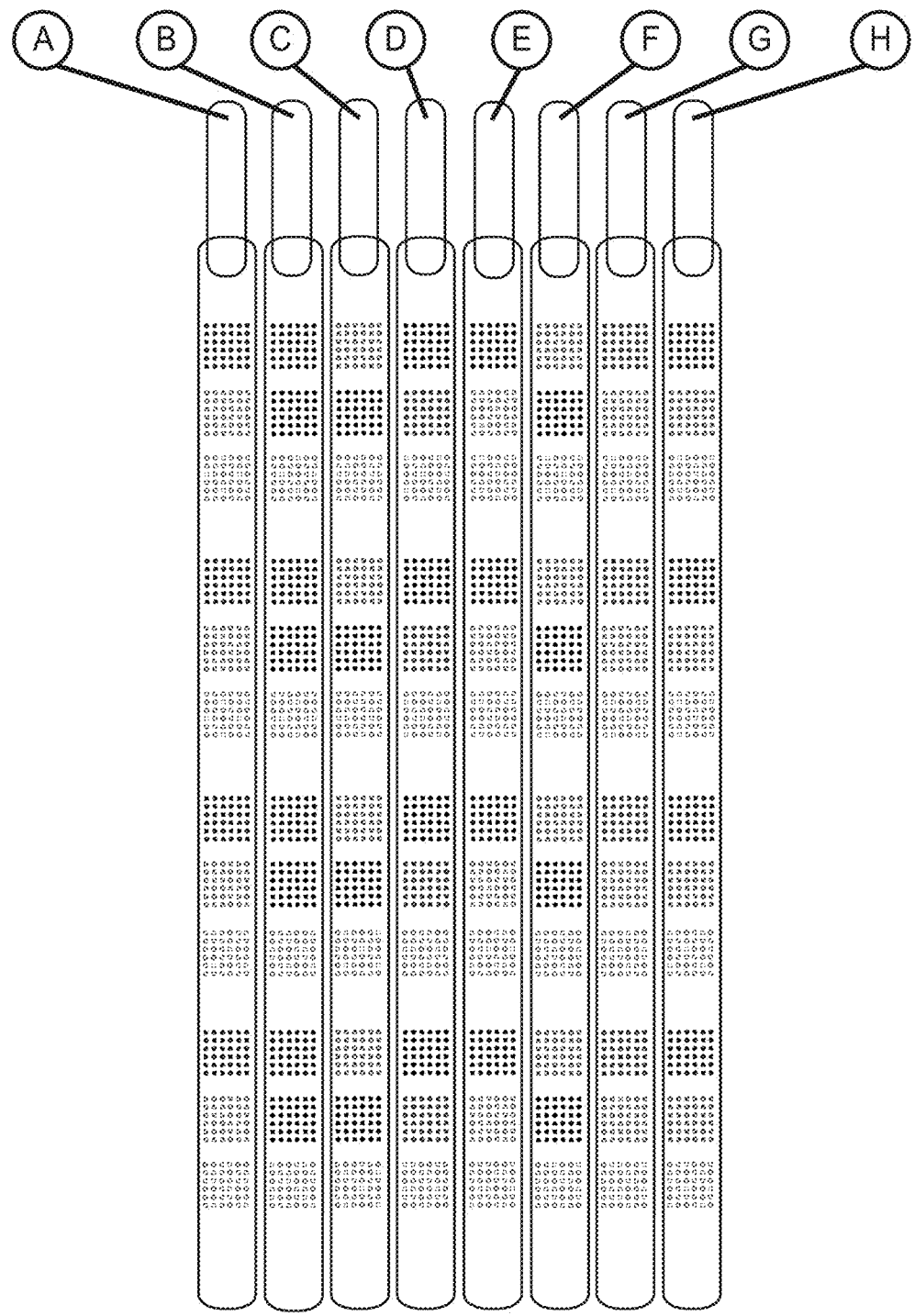
Figure 28G:
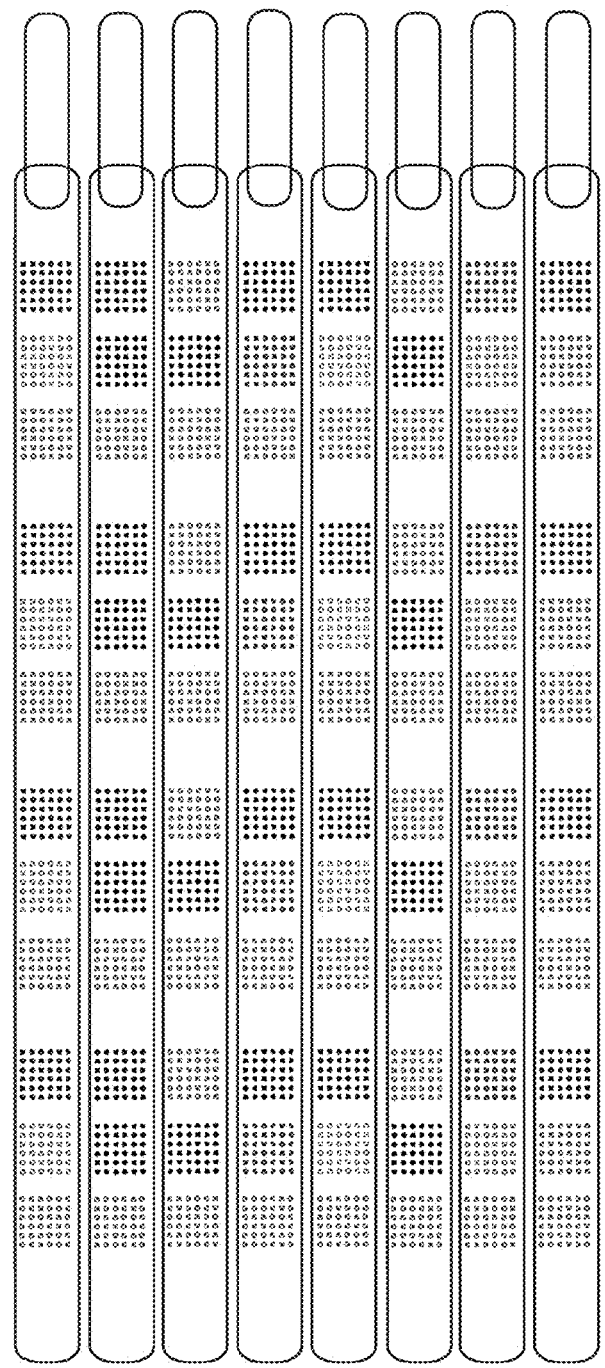
Figure 28H:
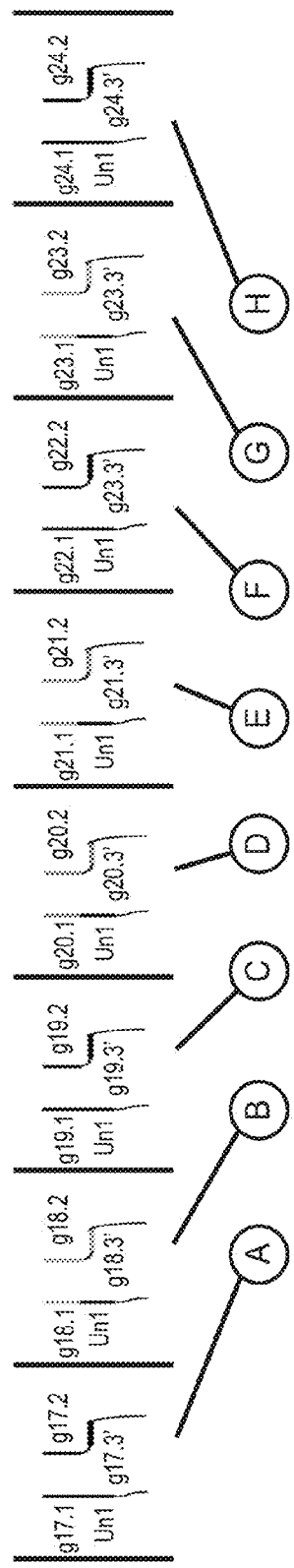
Figure 28H:
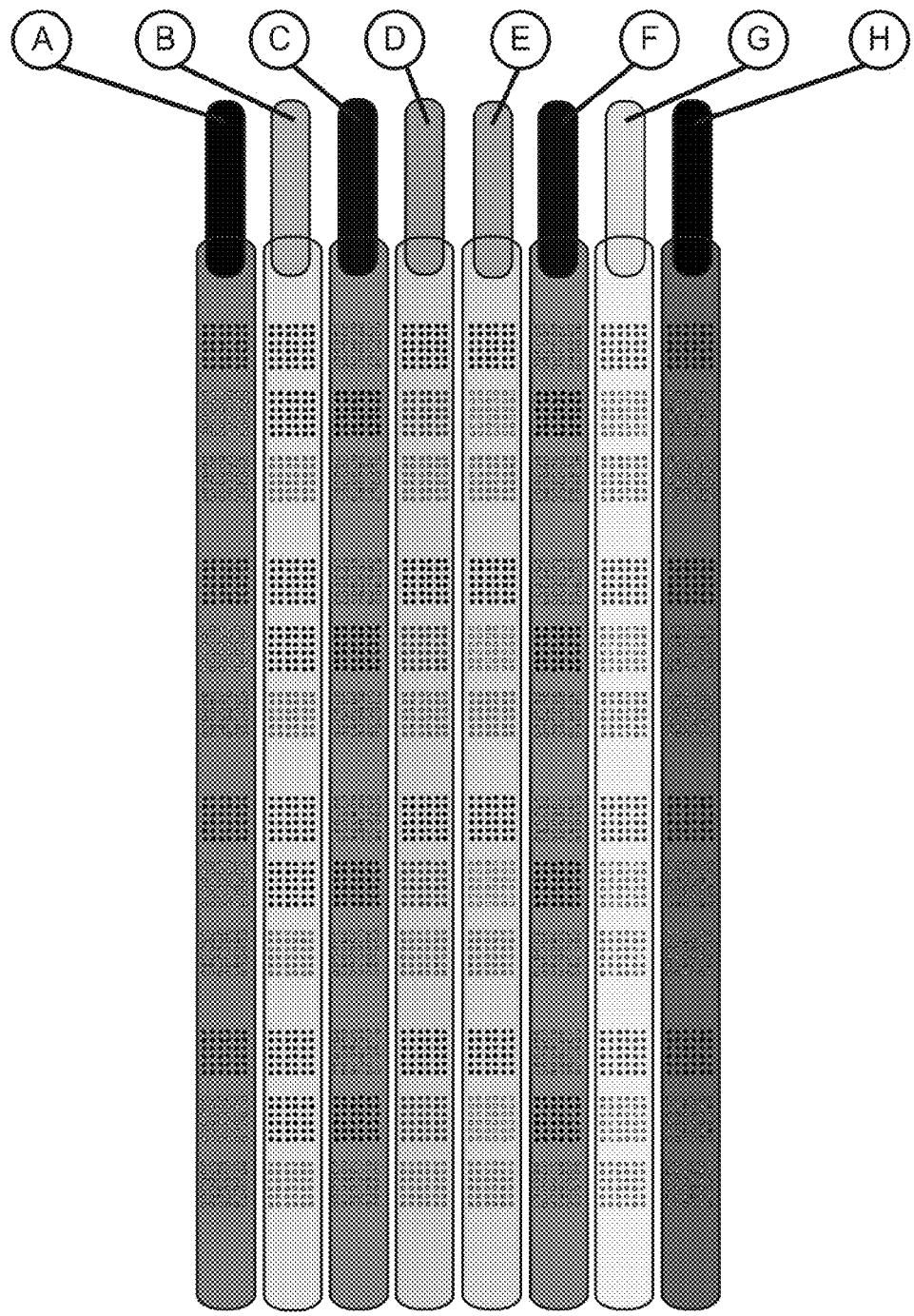
Figure 28I:
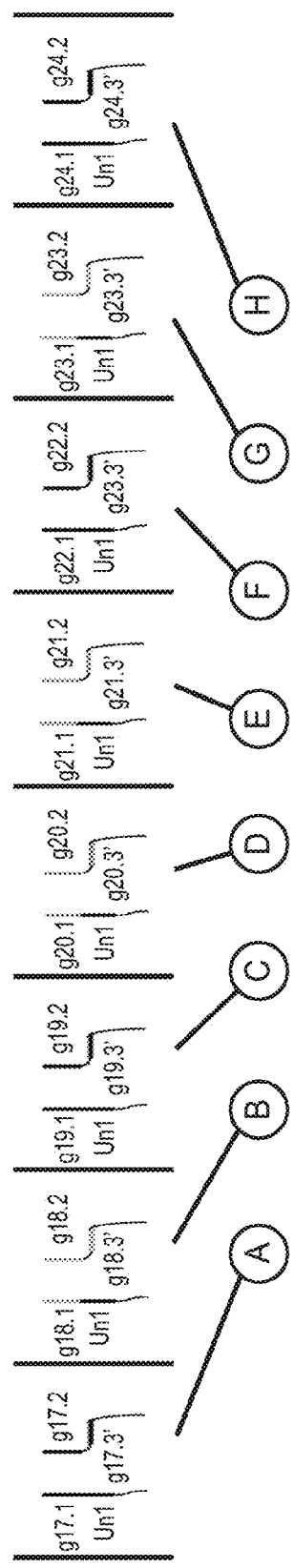
Figure 28I:
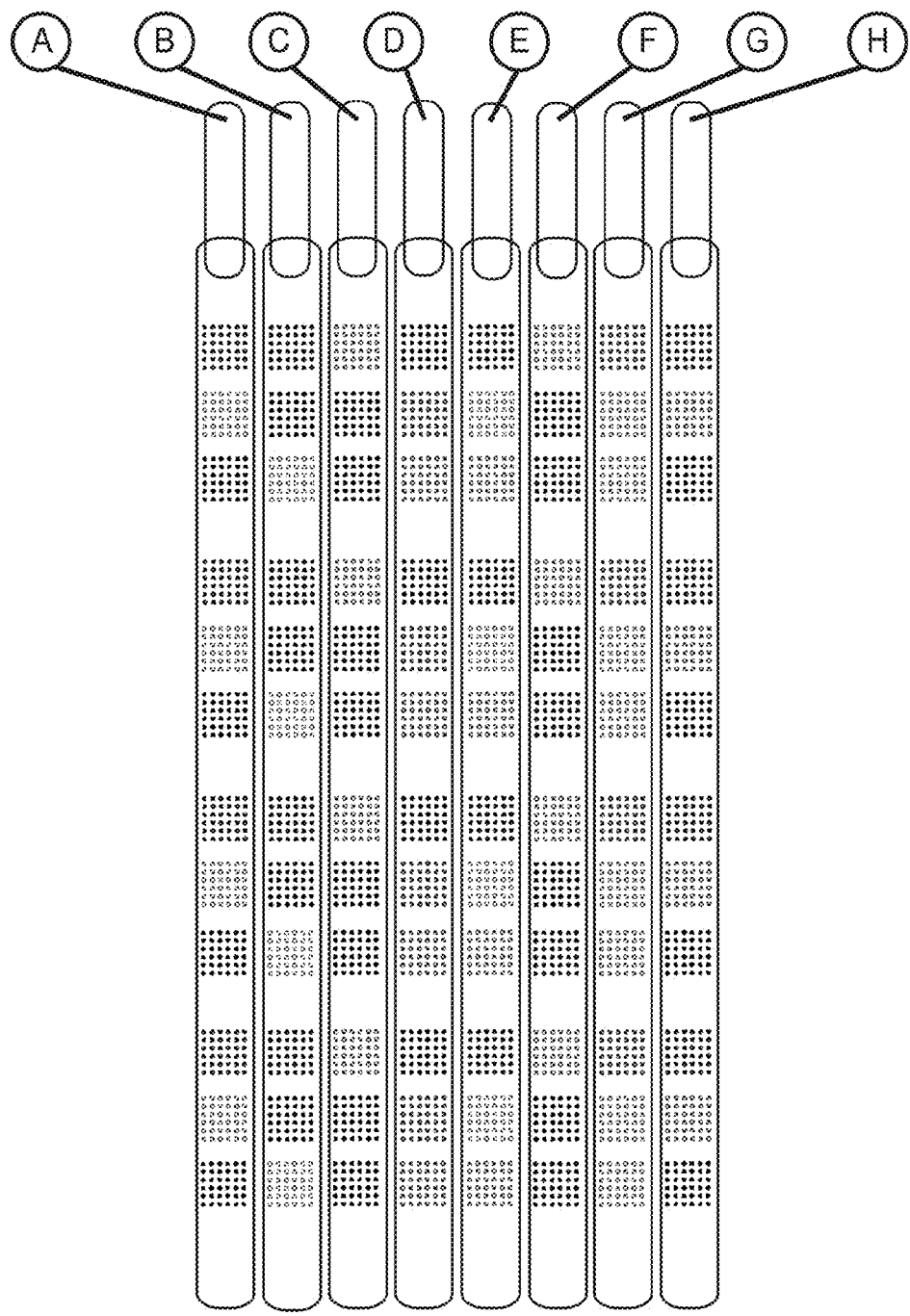
Figure 28J:
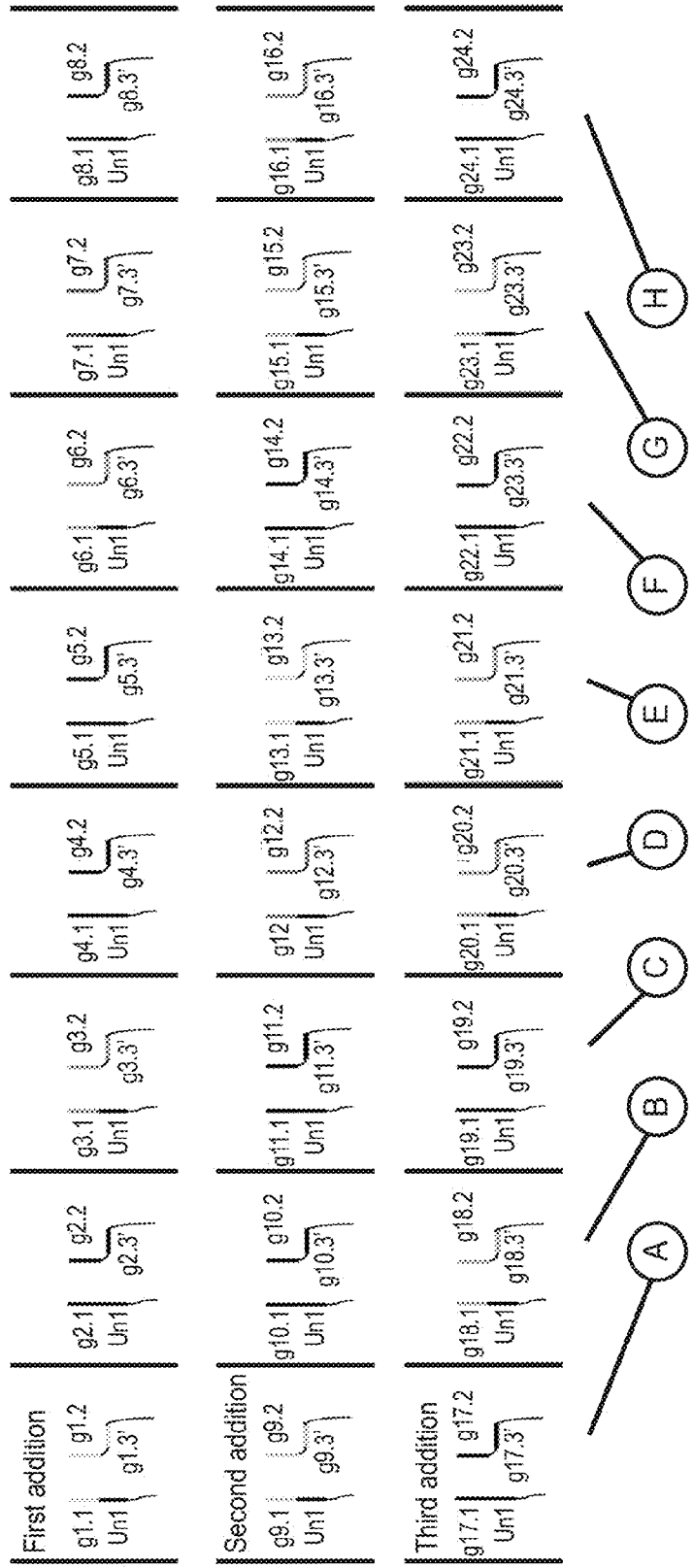
Figure 28J:
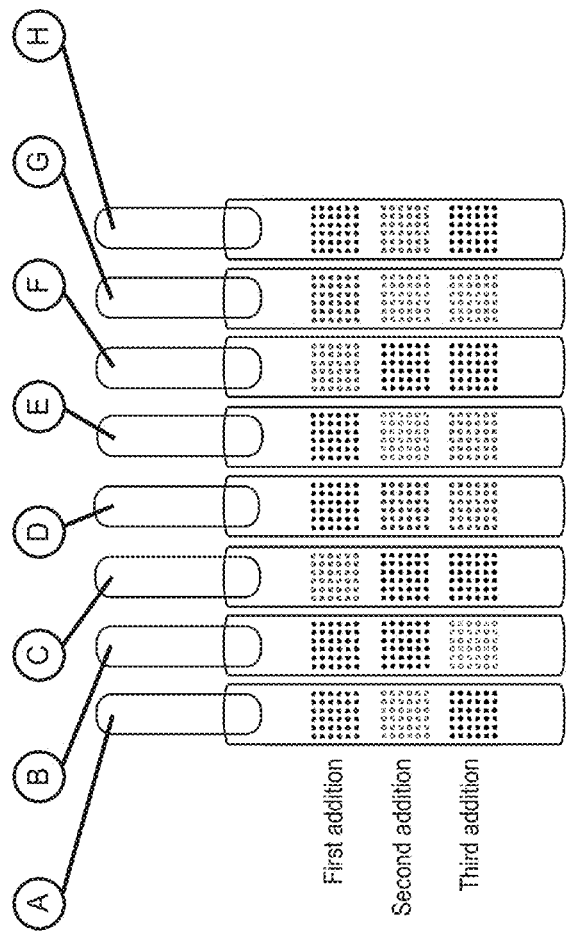

FIGS. 28A-28J depict an alternative approach for attaching oligonucleotides of interest on the pillar or well surfaces of the array. In this embodiment, selective pillar clusters are activated, in this example, by row (FIG. 28A). The desired oligonucleotides (e.g., gene-specific or universal primer sets) are added via fluidic column channels (FIG. 28B) across the array. Using this approach, the oligonucleotides are covalently attached only to the selectively activated rows of pillar or well surfaces (FIG. 28C). Following the addition and attachment of the first set of oligonucleotides, a second set or row of pillar or well clusters are selectively activated (FIG. 28D), and a second set of oligonucleotides are added to each column for covalent attachment to the activated pillars or wells (FIGS. 28E-28F). These steps of selective activation and oligonucleotide attachment are repeated (FIG. 28G-28I) to generate an array comprising a plurality of different primer sets (e.g., twenty four) represented multiple times across the array (FIG. 28J).

Figure 27A:
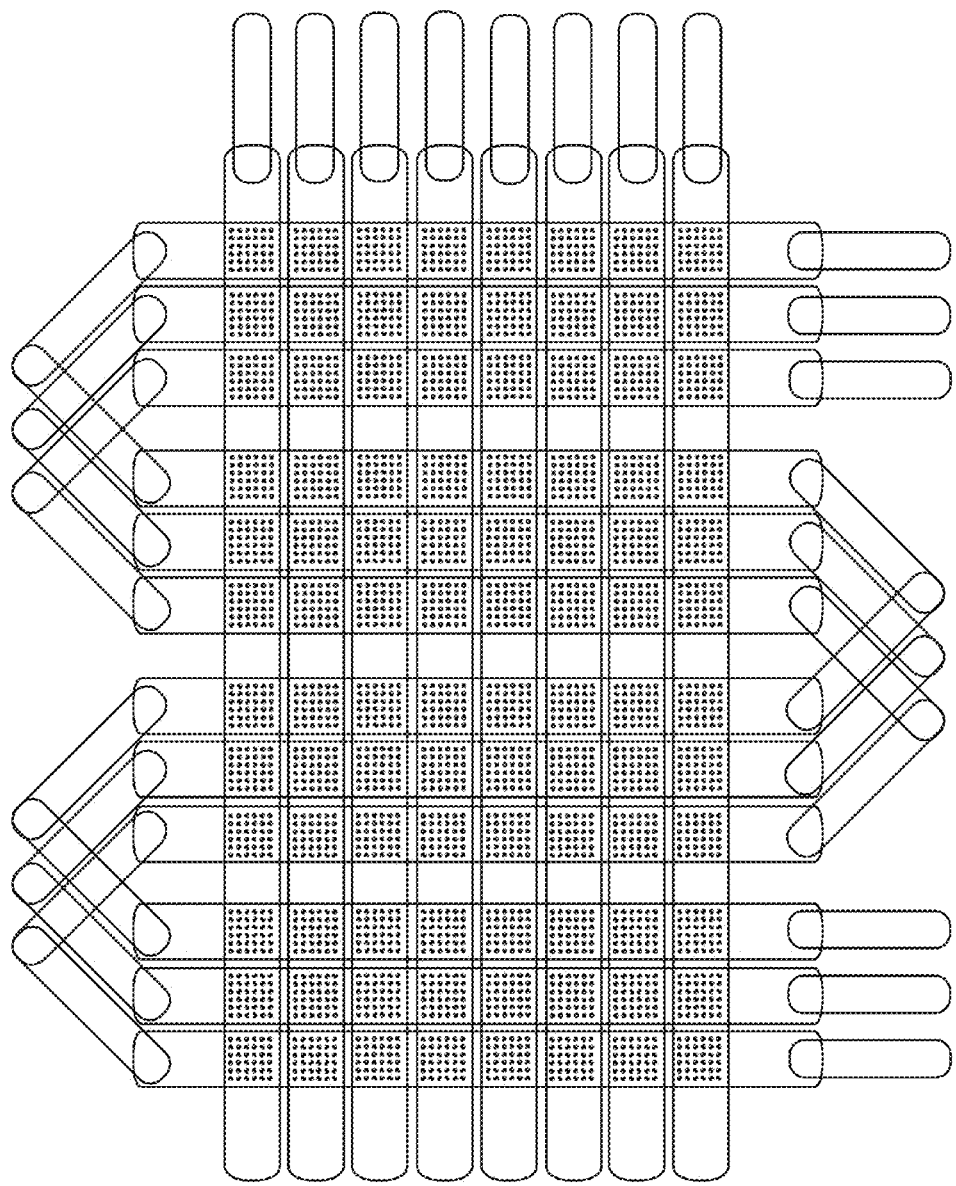
FIGS. 27A-27H are schematic drawings showing a method of UV activation and guided oligonucleotide attachment to a device of the present invention where the resulting array of oligonucleotides is suitable for low level mutation detection.
Figure 27B:
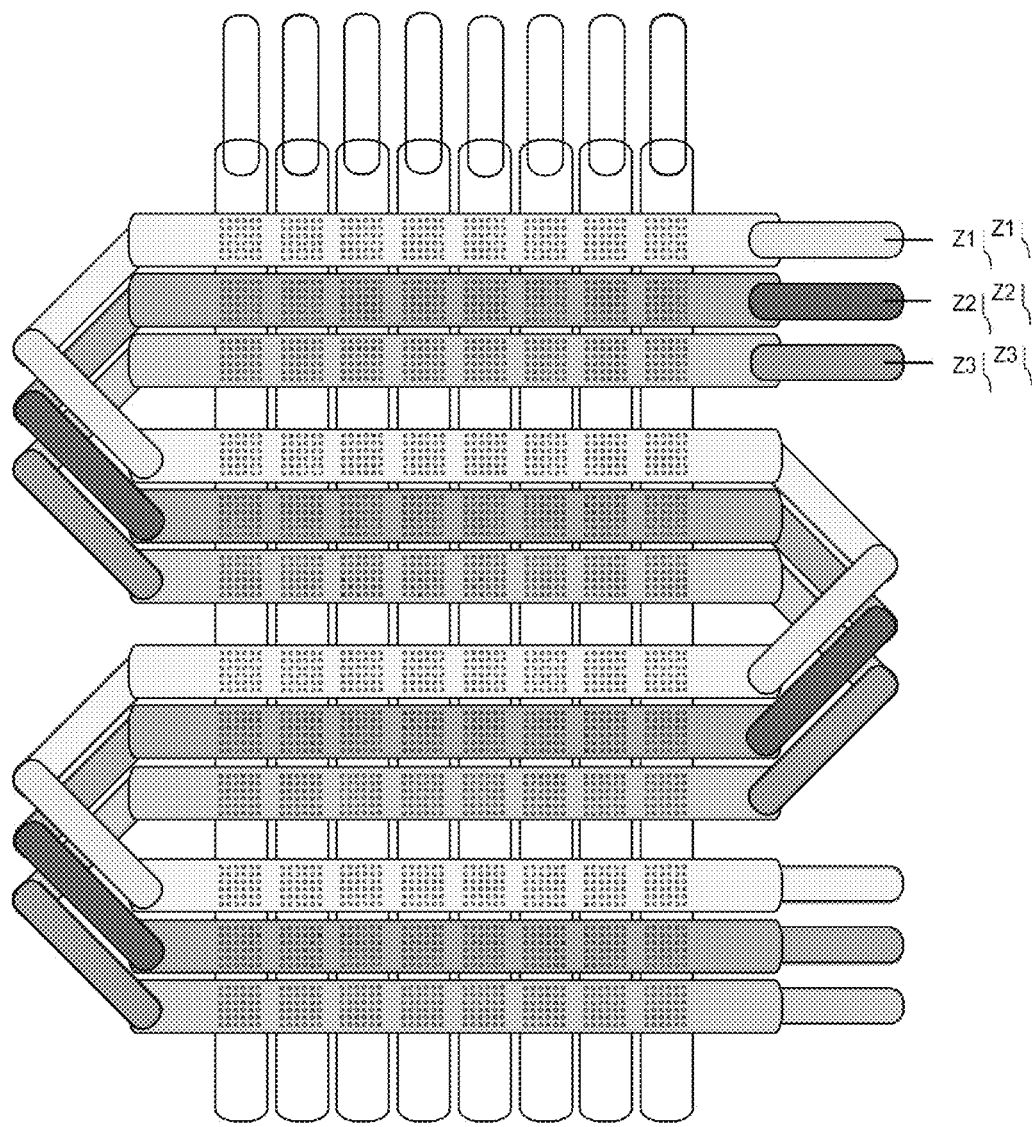
Figure 27C:
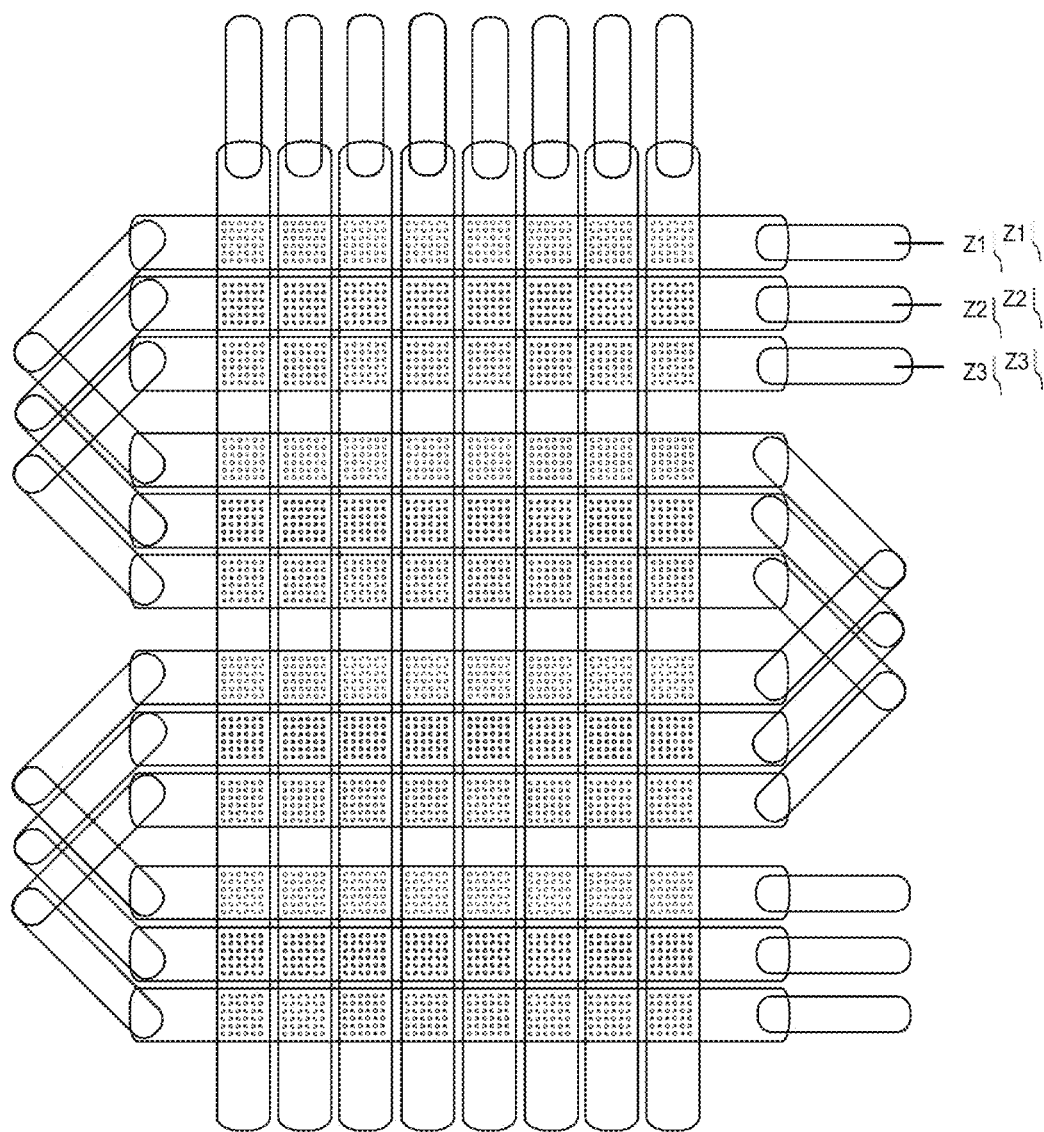
Figure 27D:
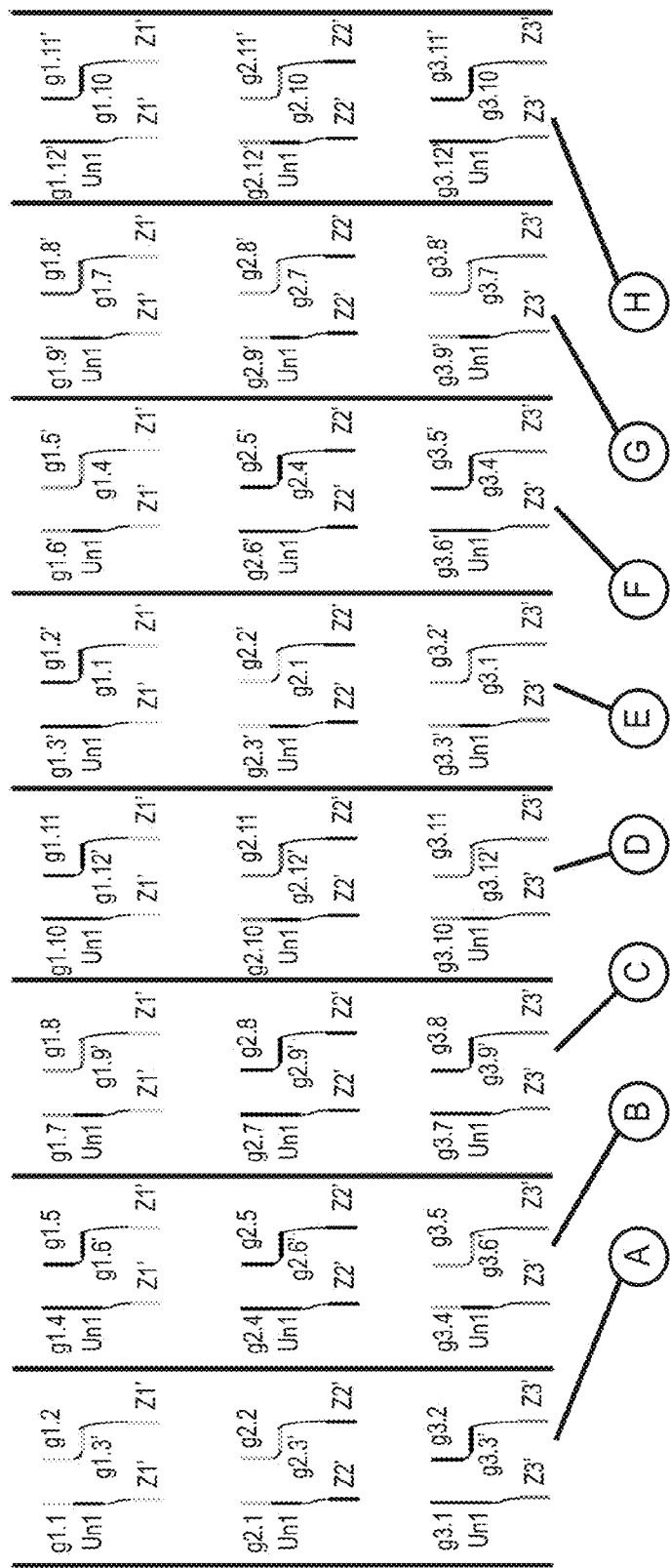
Figure 27D:
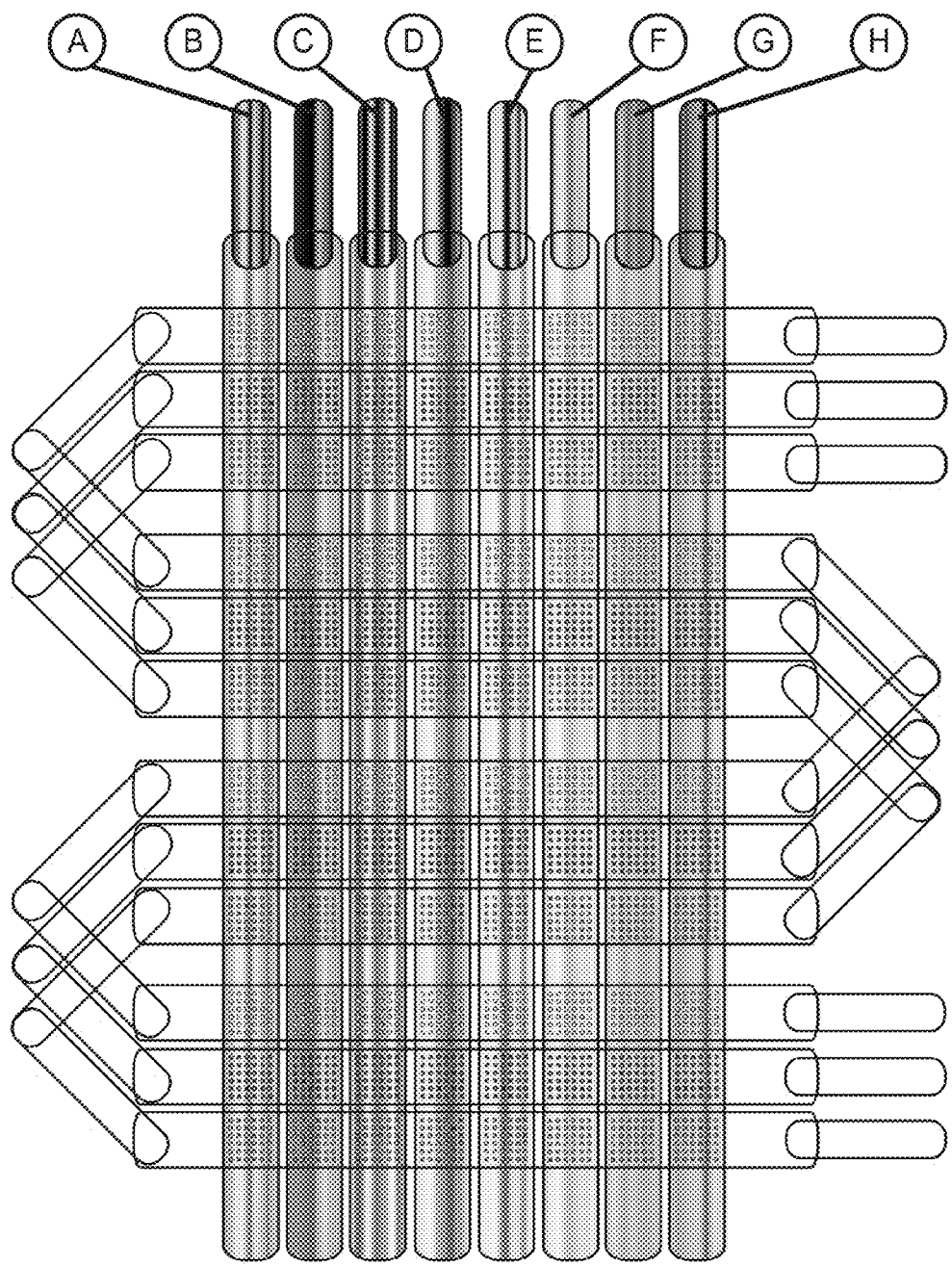
Figure 27E:
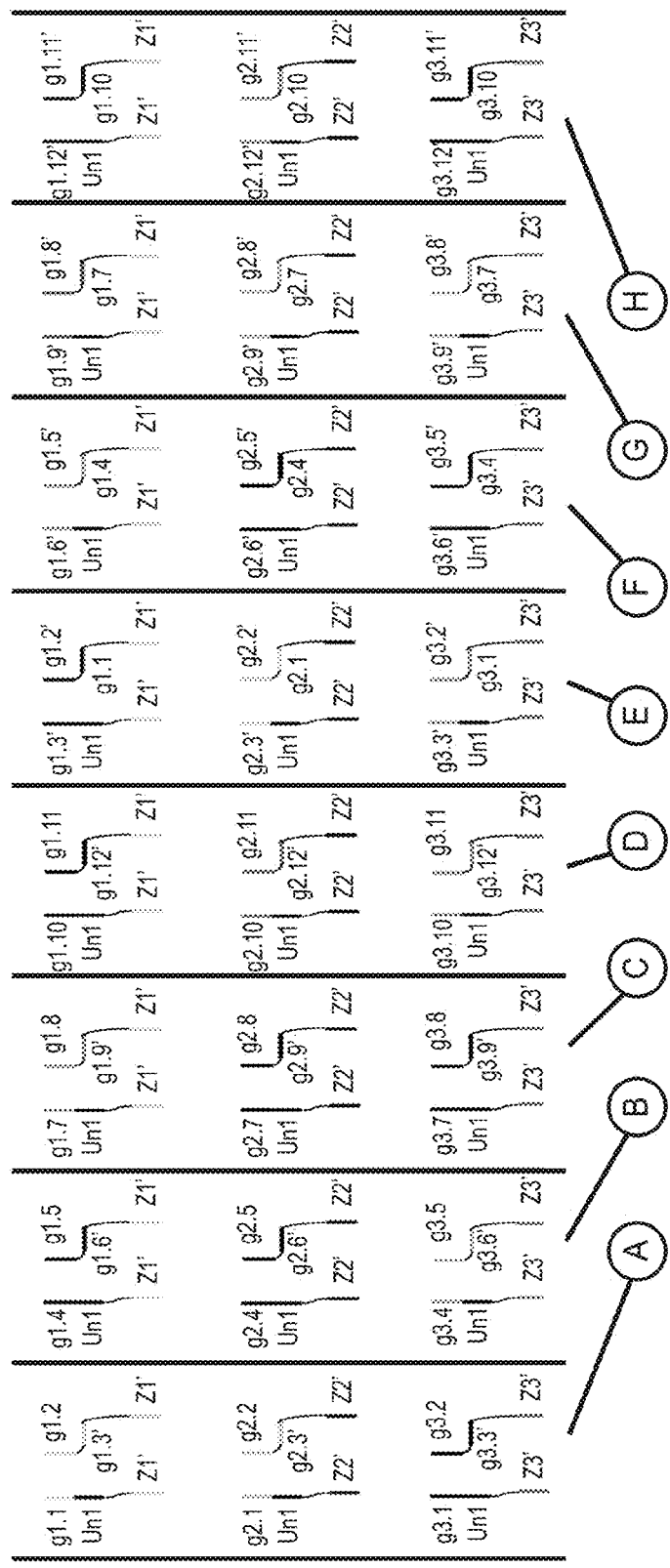
Figure 27E:
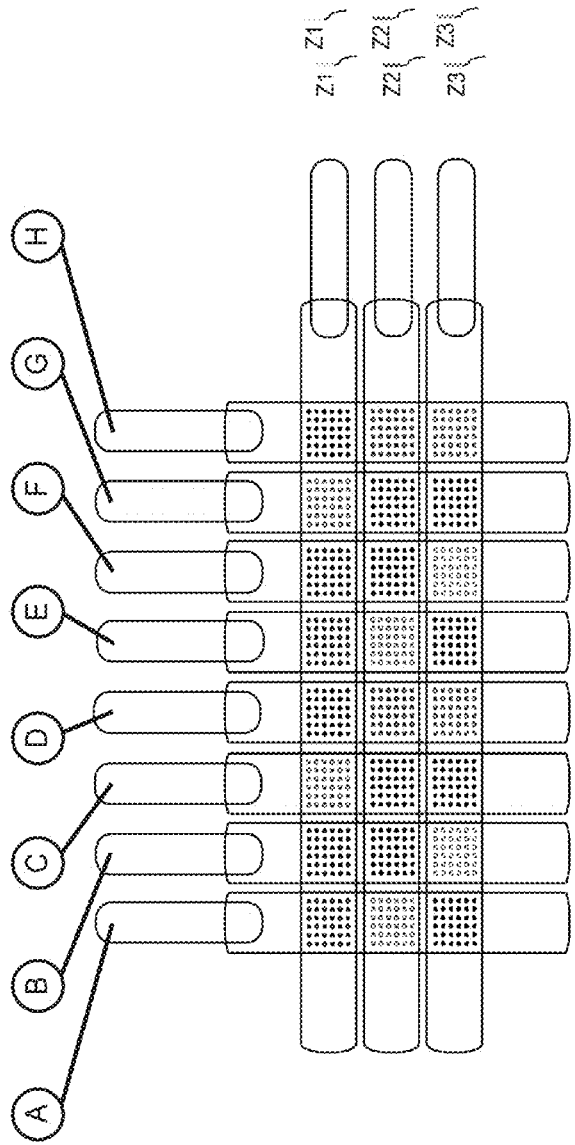
Figure 27F:
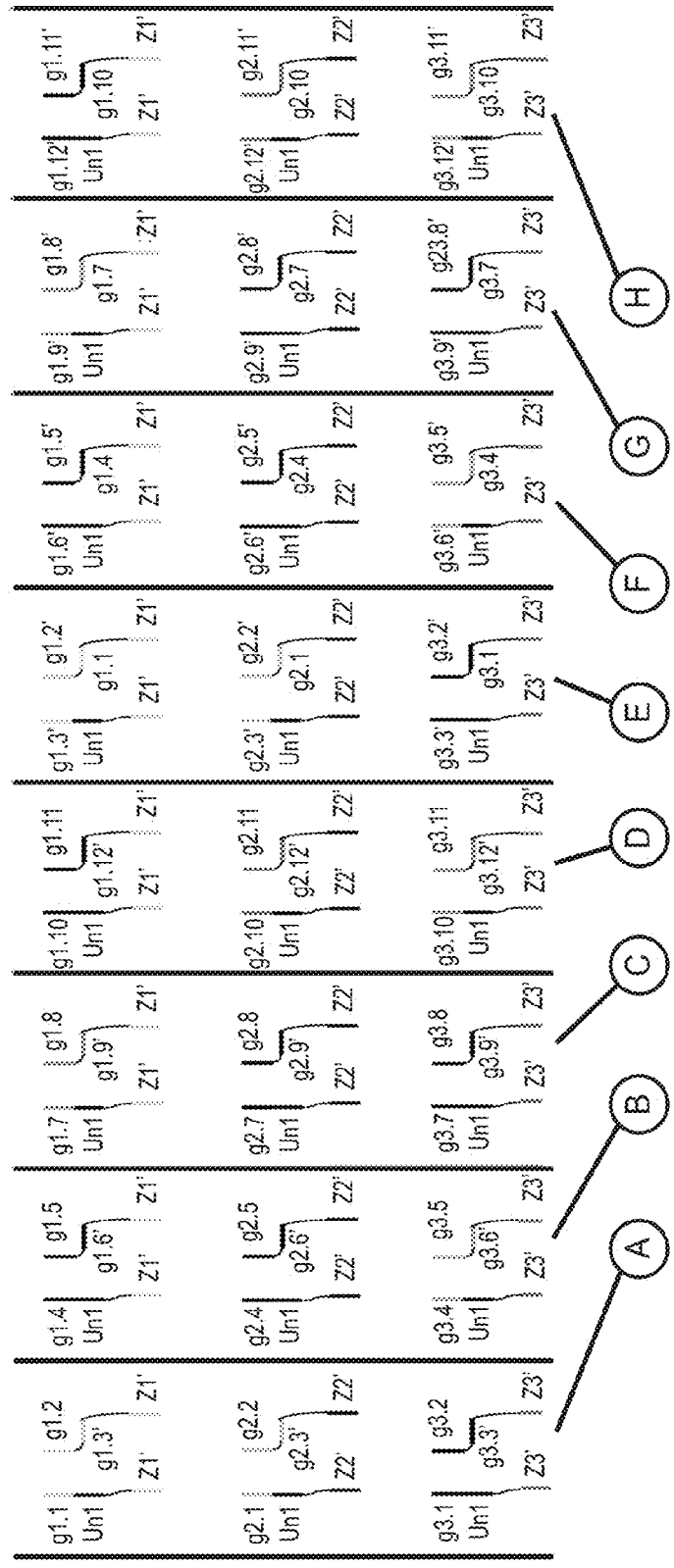
Figure 27F:
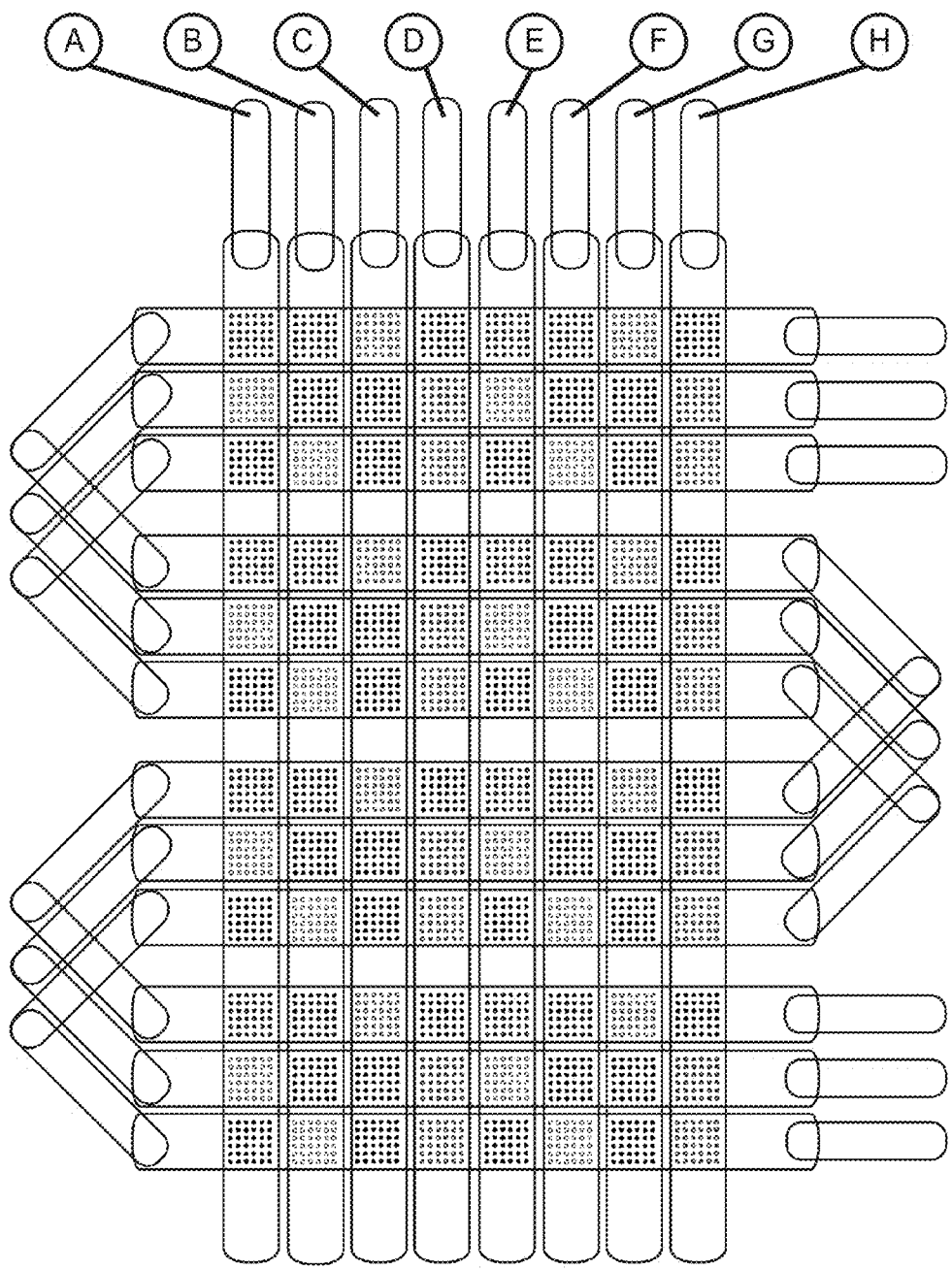
Figure 27G:
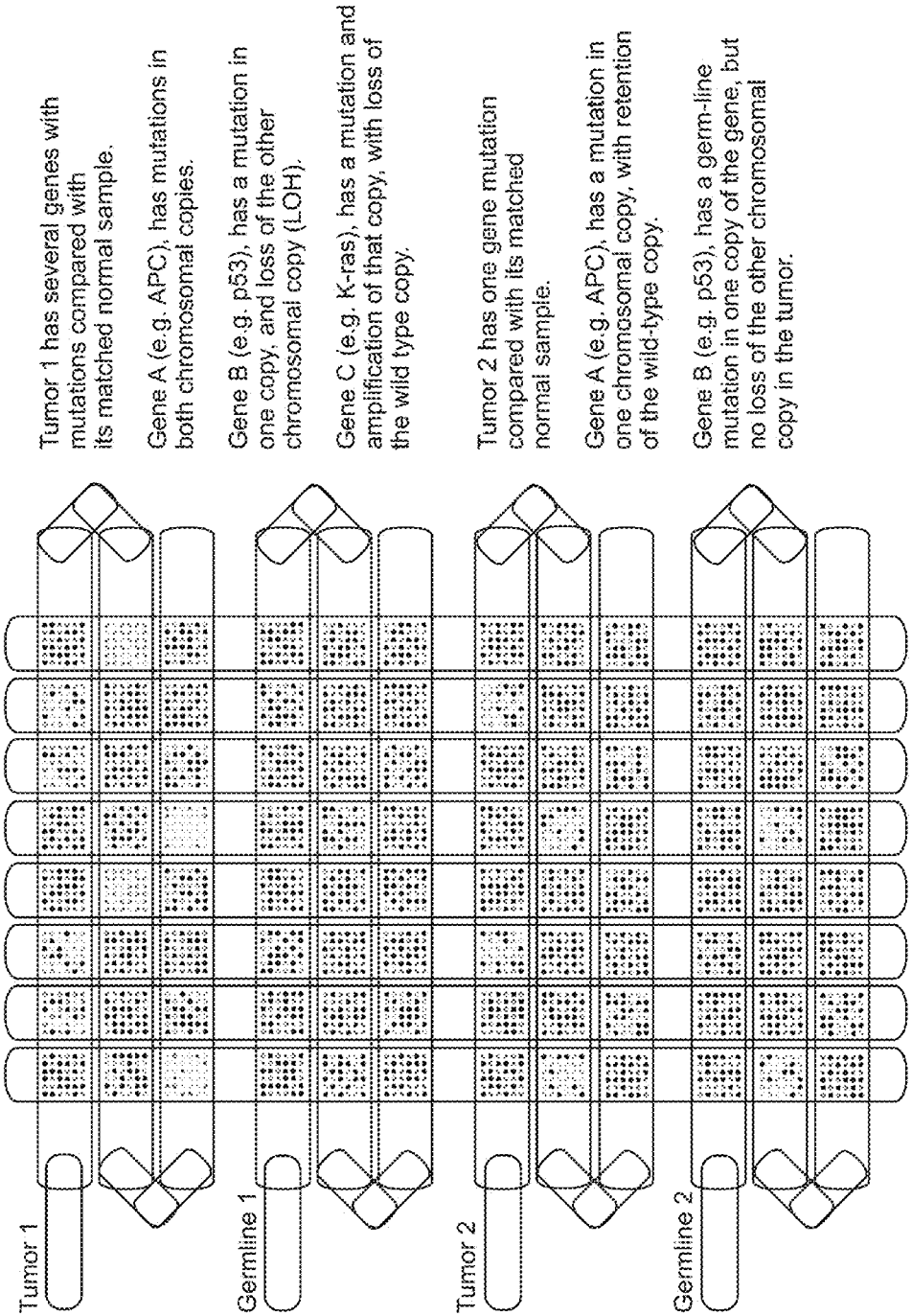
Figure 27H:
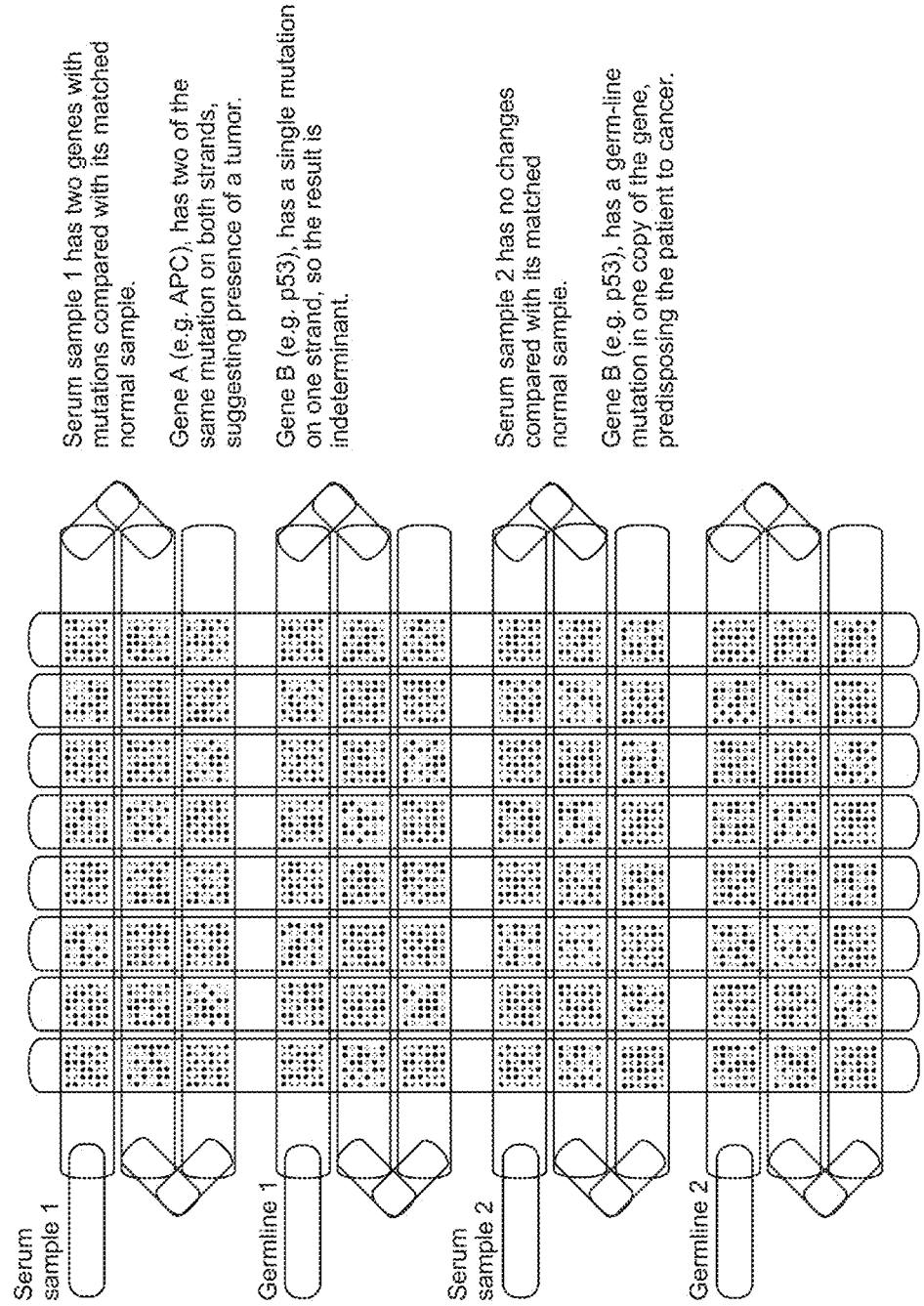

The process of attaching oligonucleotides to a solid using the methods of the present invention is both highly scalable and low cost. The microfabricated array devices of the present invention have the capacity to sequence 400 bases each on DNA captured and cluster amplified at 128 million, 384 million, 576 million, or 2.3 billion addresses respectively, generating up to 200-400 billion bases in a single run, in a single day. A variation of this new format provides for direct capture of gene-specific sequences directly from the genome, allowing for accelerated sequencing that would not be possible using conventional chips. Further, by using gene-specific primers and mini-sequencing, one can determine expression, copy number, and SNP information in short runs of just 10-20 bases, see FIGS. 26G-26H. In a third variation of this process, chips with "super-addresses" are used to identify low level mutations for early detection of cancers (FIGS. 27F-27G). As noted above, this approach is also compatible with use of microwells.

Figure 29A:
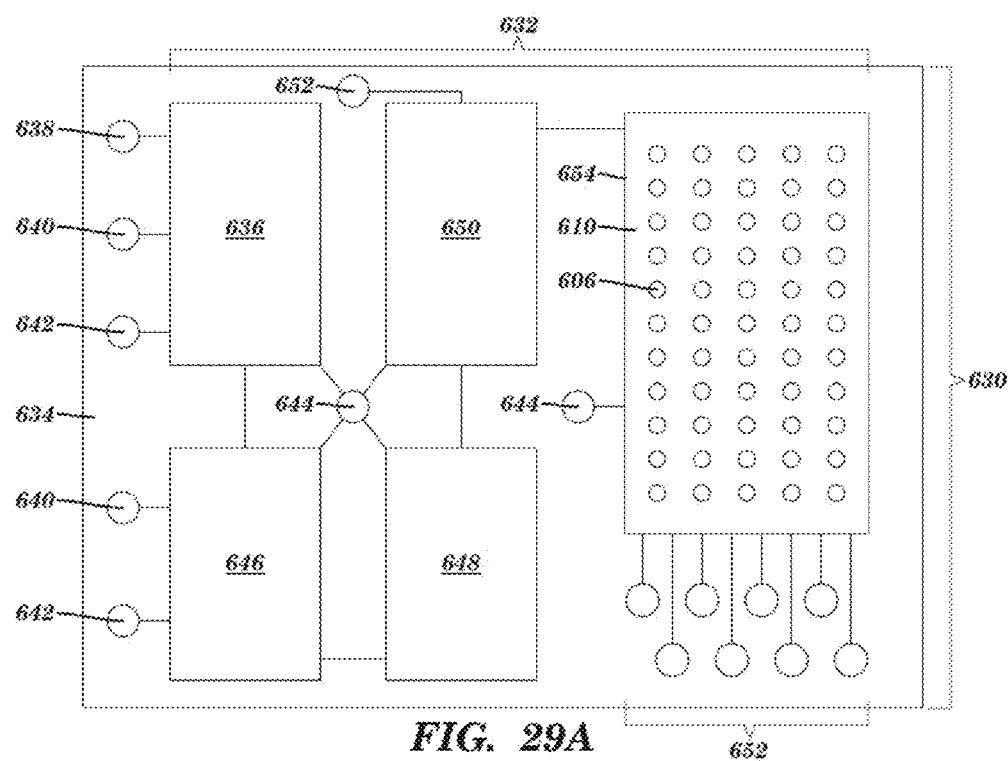
FIGS. 29A-29C are schematic representations of a polymeric modular microfluidic device of the present invention.
Figure 29B:
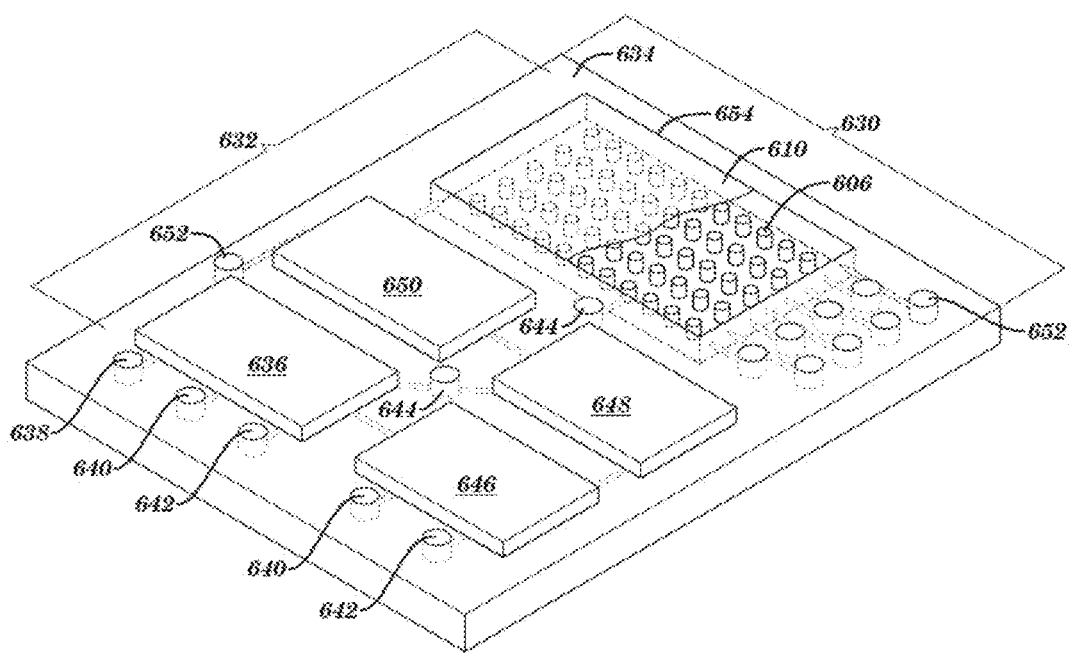
Figure 29C:
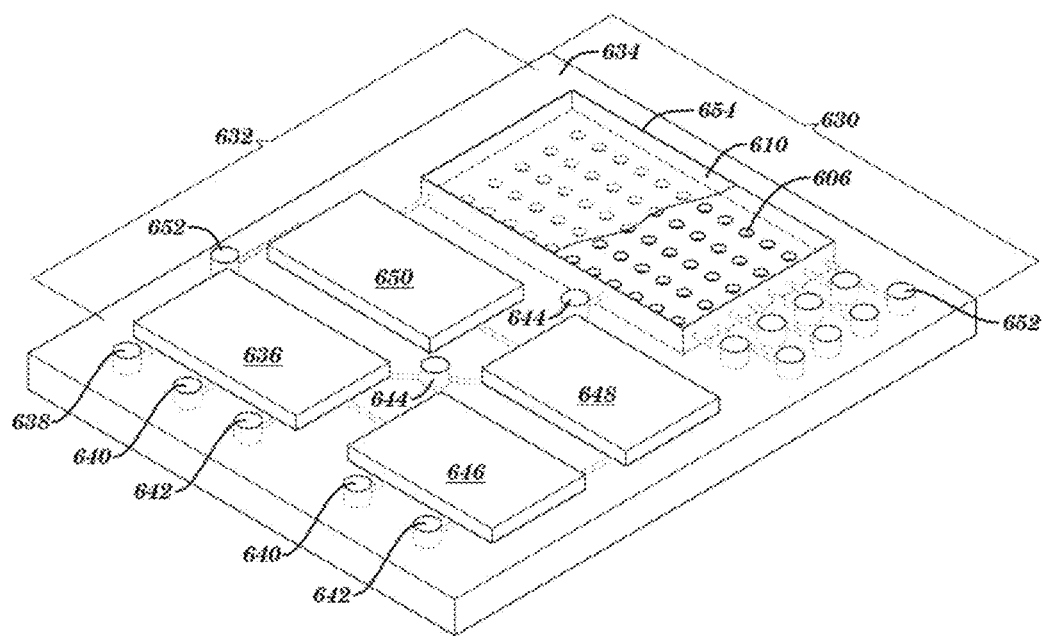

Another aspect of the present invention relates to the design and fabrication of a polymeric modular microfluidic device 630 comprising several functional units or modules 632 that facilitate sample processing and nucleic acid sequencing (FIGS. 29A-29C). A modular approach using a microfluidic device 630 that will accept task-specific modules 632 is similar in format to a computer and the electronic microprocessor (in this case, a fluidic bio-processor). This fluidic bio-processor serves as the heart of the integrated system, which also contains electronic, fluidic and optical support components. These components are poised either on-chip and/or off-chip to keep the bio-processor cost low to allow for one-time use demanded by diagnostic applications and to prevent sample carry-over artifacts. Other advantages of this design approach include; (1) the ability to match the material properties to the processing step(s) situated on the module; (2) integration of new technologies into the instrument as they evolve; (3) simplify the fabrication process for producing integrated systems; and (4) provide flexibility in assembling modules to accommodate different assay strategies.

The microfluidic device 630 has at its core a fluidic motherboard 634 into which one "plugs in" task-specific modules 632 to provide flexibility in the assay that can be employed without requiring the need to re-engineer the device. Fluidic ports connect modules 632 to the microfluidic motherboard 634, providing the fluidic analog of the electronic microprocessor found in every computer. These fluidic ports are described in more detail infra and are depicted if FIG. 31. FIGS. 29A-29C provide schematic representations of an exemplary microfluidic device 630 of the present invention that is built to accommodate different task-specific modules 632 to ultimately achieve DNA sequencing. In this example, module 636 functions to isolate the desired targets from a clinical sample, e.g., circulating tumor cells, cell free DNA, exosomes, etc. This module 636 is fluidically connected to a sample input port 638, which receives the sample, a wash buffer reservoir 640, an elution buffer reservoir 642, and a waste reservoir 644. This module 636 is also fluidically coupled to a second "purification" module 646 that functions to extract and purify genomic DNA, e.g., by solid phase extraction, once the cellular targets are lysed (if required). The purification module 646 is also fluidically coupled to a wash buffer reservoir 640, an elution buffer reservoir 642, the waste reservoir 644, and a third module 648. The third module 648 functions to carry out hydrodynamic shearing of DNA to prepare the appropriate sized fragments for sequencing. This module 648 is fluidically coupled to a fourth module 650 designed to carry out biochemical reactions required for sample library preparation (e.g., adaptor ligation) prior to sequencing. The library preparation module 650 is fluidically coupled to a reagent input reservoir 652, the waste reservoir 644, and the sequencing module 654. The library preparation module may further comprise a thermal modulator component that facilitates thermal modulation or thermal cycling of the samples as necessary to effectuate the appropriate reactions. As described supra, the sequencing module 654 comprises a solid support 610 with a plurality of structures 606 that take the form of pillars 606 as depicted in the perspective of FIG. 29B or wells 606 as depicted in the perspective of FIG. 29C. As described supra, oligonucleotide primers are coupled to these structures 606 to facilitate amplification and sequencing of target nucleic acid molecules in a biological test sample as described supra. In some embodiments of the invention, particularly where the structures 606 comprise pillar structures, pH sensitive dyes may also be coupled to the structures, interspersed with the immobilized oligonucleotides. The sequencing module 654 is coupled to reagent inputs 652 and a waste reservoir 644. The pumping of fluids into/from the appropriate reservoirs and modules can be affected using hydrodynamic flow with valves poised on the fluidic motherboard. While FIGS. 29A-29C depict an exemplary microfluidic device 630 of the present invention, one of skill in the art would readily appreciate that each microdevice will have the ability to program in the appropriate series of molecular processing steps by including different modules to create a family of universal instrument platforms. As new technologies evolve, they will be integrated into universal instrument platforms.

The modules can have a footprint of 86 mm (w)×128 mm (l) with the same configuration as a standard 8×12 microtiter plate that provides simple assimilation into existing fluid handling hardware found in many clinical laboratories and thus the ability to process many samples in parallel. The modules can also be 86 mm×43 mm and represent a "mini-device" that would process fewer samples in parallel. Each module will have a standard input/output configuration to be easily integrated to a "standard" fluidic motherboard. For example, 16 microfluidic input/output ports for reagents/buffers/wash/waste can be employed on the perimeter of both 86 mm sides (4.5 mm spacing), and either 24 or 8 input/output ports for samples/products on the left and right sides, respectively. This standardization of modules will allow for the integration of new technologies directly into the motherboard as they are developed, accelerating the innovation cycle. This approach will obviate the need to generate new instruments to accommodate new technologies.

A significant innovation of this system is the genomic sequencing array module of the present invention described supra. In one embodiment, the sequencing module comprises customized arrays of up to 1536 unique sequence sites allowing for "mini-sequencing" reactions for 10 to 20 bases to identify and quantify mutations, drug resistance elements, multiple exons and genes. Total running time for these arrays is about 90 to 120 minutes. In another embodiment, the system comprises the amplification/genome sequencing of 2.3 billion addresses, to allow for 400 cycles of sequencing-by-synthesis. This system will generate 200 to 400 billion bases of information per run with a total running time of about 1-3 days.

Figures 30A, 30B, 30C, 30D, 30E:
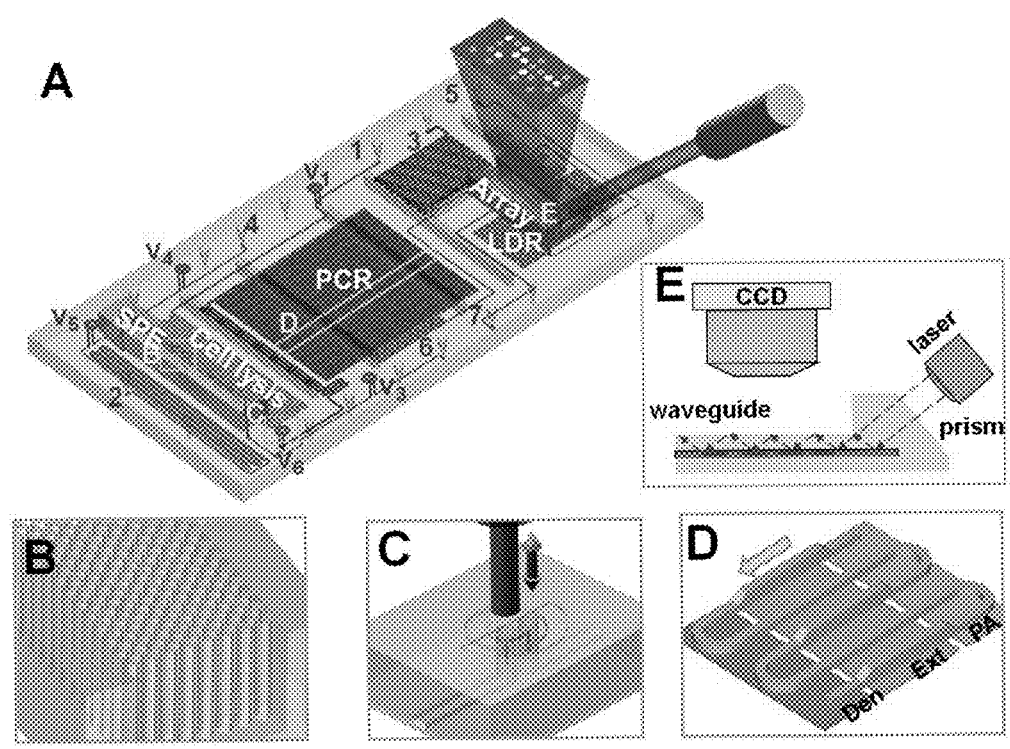
FIGS. 30A-30E are schematic depictions of a polymeric microfluidic device containing an integrated module system, and components thereof, of the present invention.

An integrated system has been designed that can directly process clinical input samples, such as blood, saliva, urine, sputum, etc. and search for sequence variations in DNA. The integrated and module system that has been fabricated is depicted in FIG. 30A. The integrated system contains two modules, one for the solid-phase extraction ("SPE") and purification of DNA secured from sputum or other biological samples and the other module contains a universal array equipped with an embedded waveguide. The fluidic motherboard contains modules that are used for the lysis of cellular material, and thermal reactions required for PCR and a ligase detection reaction (LDR). FIG. 30A is a three-dimensional rendering of the chip and the detection method. The fluidic inlets and outlets of the fluidic motherboard include: 1—sample inlet, 2—PCR mix inlet, 3—LDR mix inlet, 4—ethanol and air inlet, 5—array wash inlet, 6—vacuum connection, 7—waste. V1-V6 are the on-chip membrane valves (note that V2 is positioned next to SPE module on the cell lysis microchannel and is not visible in current view). The insets of FIG. 30A (i.e., B-E) are shown as magnified views in FIGS. 30B-30E respectively. FIG. 30B is a close-up illustration of the solid-phase extraction (SPE) bed showing a DNA capture bed filled with an array of high-aspect ratio posts. FIG. 30C is a schematic showing the operation of the on-chip membrane valve with direct mechanical actuation—electrically actuated solenoid presses on the center of the polymer membrane closing the passage of fluid from the bottom layer through the valve and back to bottom layer. FIG. 30D shows the geometry of the continuous flow PCR reactor with dual-depth microchannels for extended residence time and the extension-zone (Den—denaturation, Ext—extension, PA—primer annealing). FIG. 30E is a schematic representation of the detection mode. Laser excitation is coupled to the waveguide through an integrated prism. Light travelling through the waveguide excites the labeled LDR products hybridized to zip code oligonucleotides spotted at the bottom of the waveguide. Resulting fluorescence signal is imaged with CCD array.

Figure 31A:
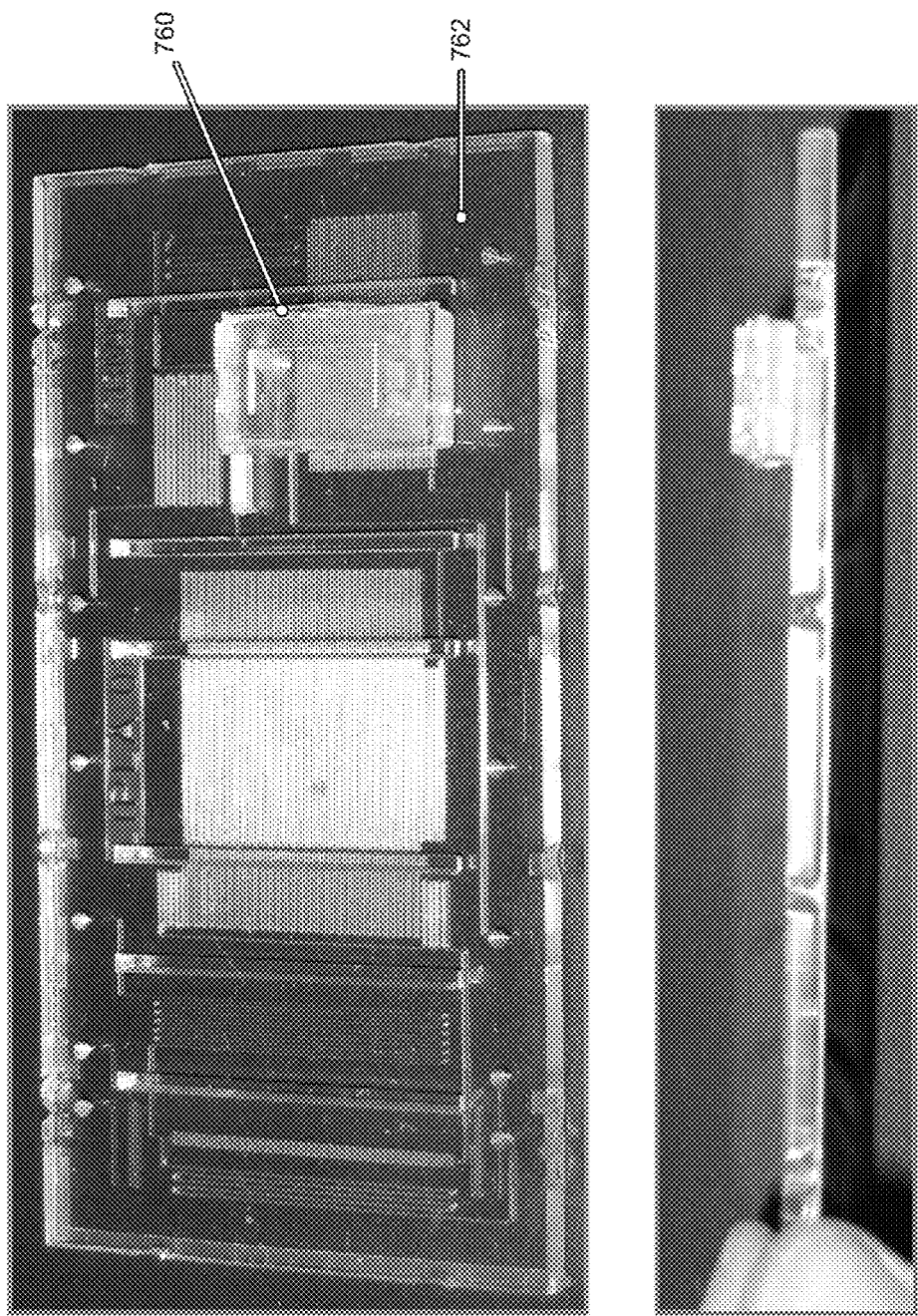
FIG. 31 shows the module-to-motherboard connections of a microfluidic device of the present invention.
Figure 31B:
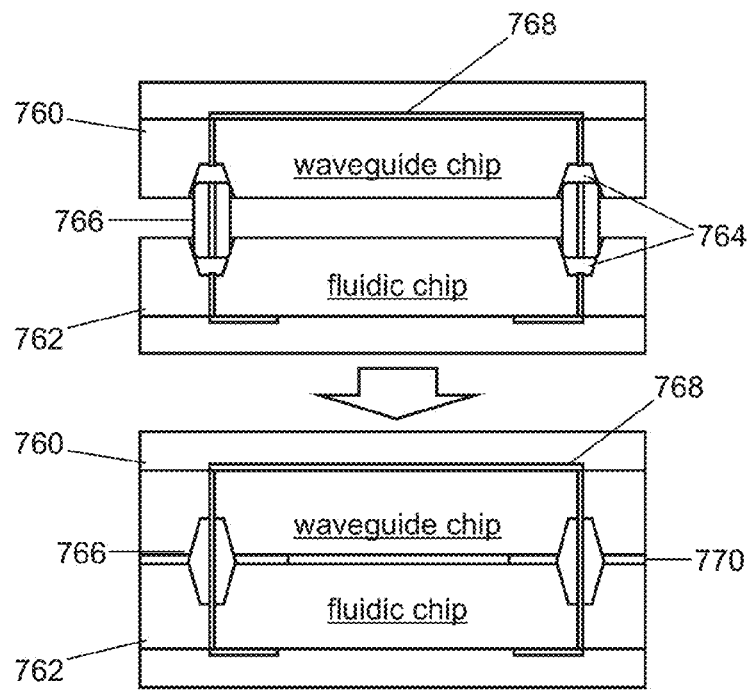
Figure 31C:
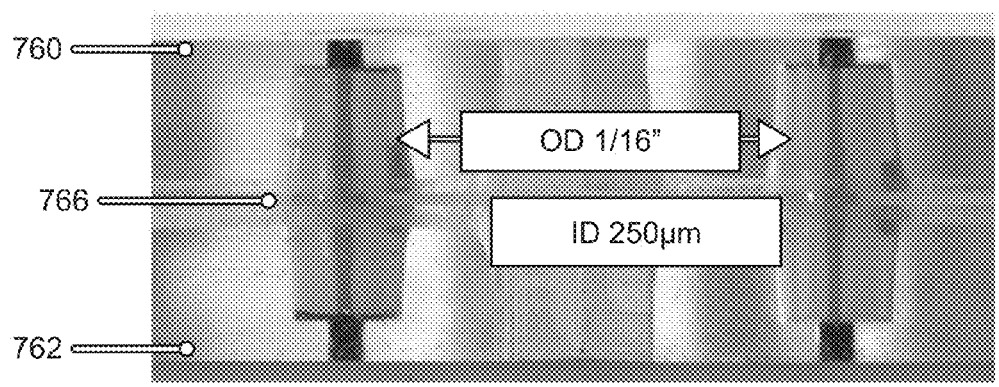

Module-to-motherboard connections are shown in FIGS. 31A-31C. FIG. 31A is a photomicrograph of a motherboard 762 containing various modules, e.g., array module 760. FIG. 31B is a schematic showing the module-to-motherboard connections which were fabricated using laser drilling and consisted of conically-shaped ports 764 with semi-rigid moldable tube 766 into which a piece of plastic tubing 768 was inserted. Once plastic tube 768 is inserted into the ports, a compression force is applied to the module and motherboard and sealed with adhesive 770. The interconnected so formed could withstand pressures to 600 psi and also align the module with the motherboard. FIG. 31C is a photomicrograph of the fabricated module-to-motherboard connection.

Figure 32C:
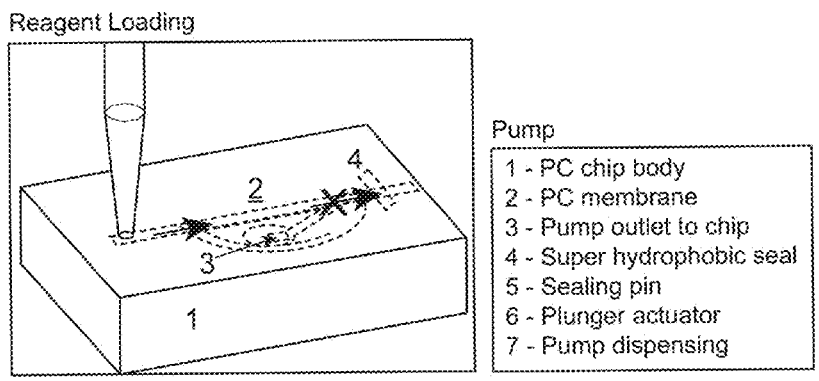
Figure 32D:
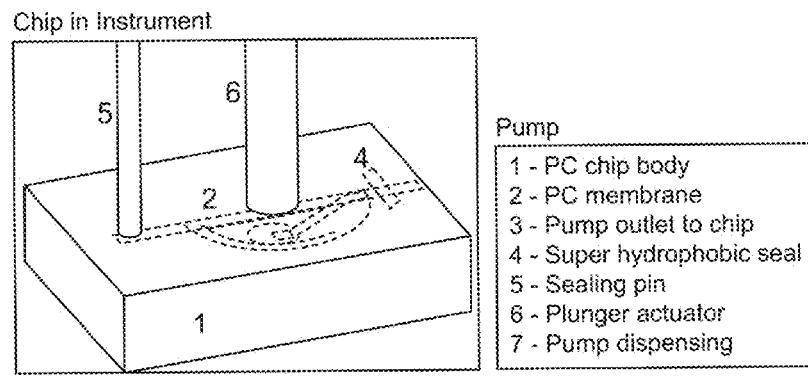
Figure 32E:
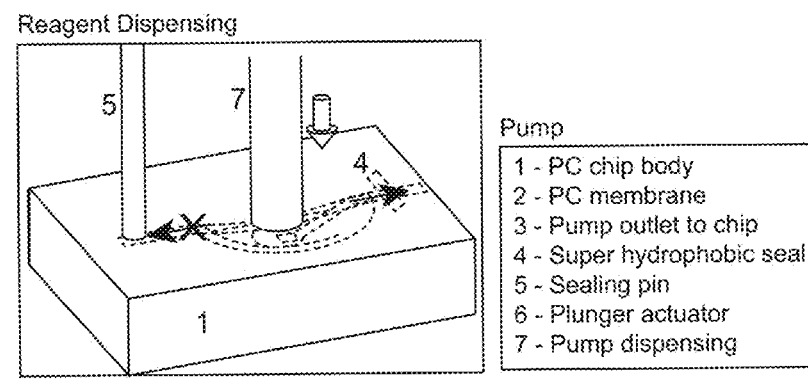

A novel approach for valving and pumping operations on the fluidic motherboard has been developed, which consists of using a thin (200 µm) polycarbonate or other thermoplastic membrane positioned over an in/out fluidic channel making up the valve seat. This valve arrangement (see FIGS. 32-33) is normally open, and application of a load on the membrane will close the valve. The operation of the valve is shown in FIGS. 32A-32B in which the fluidic substrate (1) is enclosed with the PC membrane (2). The substrate is molded with fluidic channels (3, 4) that dump into the valve seat. When the load (solenoid, 5) is not applied (FIG. 32A), fluid is allowed to pass through the valve. When the load is applied (FIG. 32B), the valve is closed. The membrane can be made super hydrophobic (6) to prevent leakage when actuated. When functioning as a pump (see FIGS. 32C-32E), the pump is first filled (FIG. 32C) by pipetting solution into the pump chamber with the outlet blocked (3). Following filling, the chip is placed in the system (FIG. 32D) and then, a sealing pin (5) is allowed to block the filling port. To dispense fluid (FIG. 32E), the solenoid (6) is actuated by allowing fluid to flow through the outlet (3) by opening the super hydrophobic valve (4).

Figure 33:
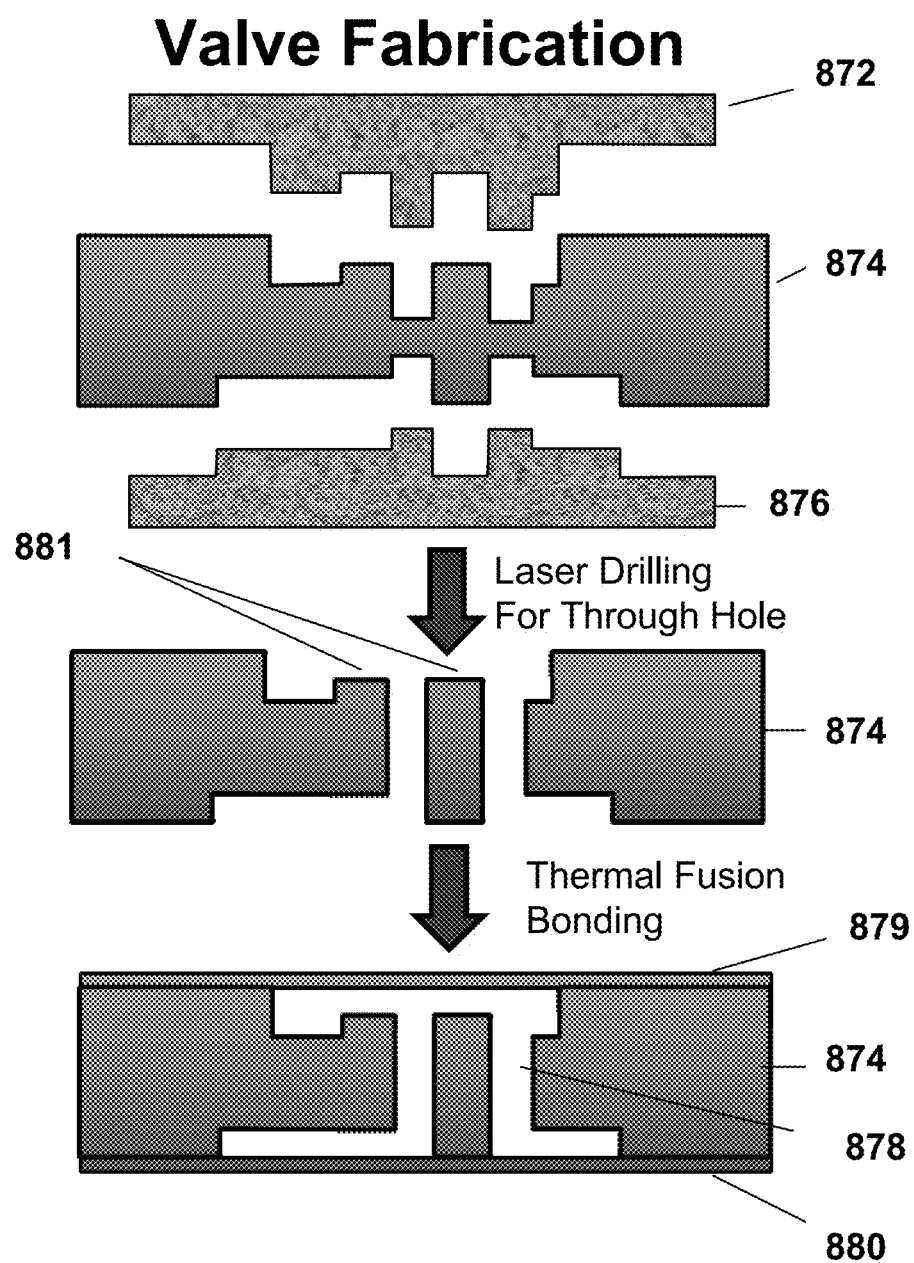
FIG. 33 shows valve fabrication on the microfluidic device of the present invention.
Figure 34A:
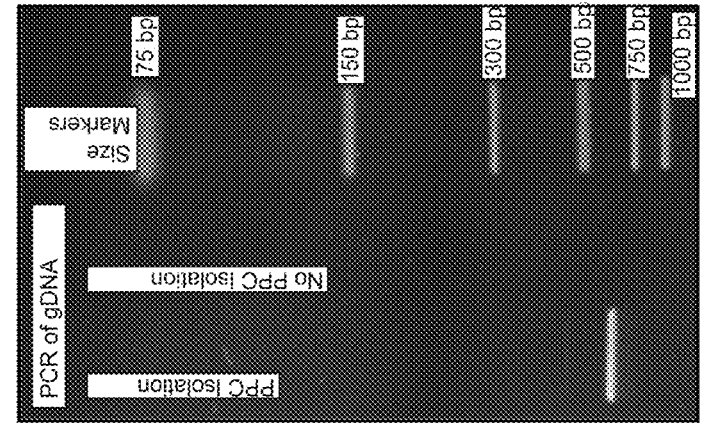
FIGS. 34A-34D show the solid phase extraction (SPE) module on a microfluidic device of the present invention used for the purification of nucleic acids from biological samples.
Figure 34B:
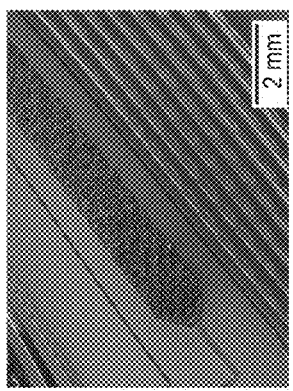
Figure 34C:
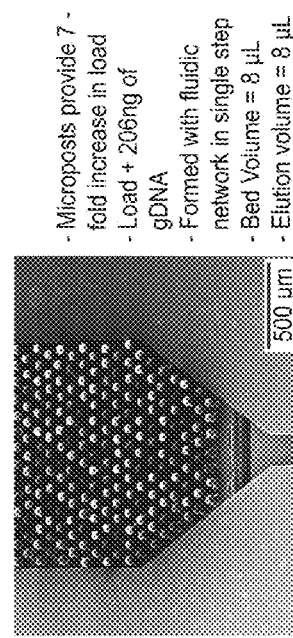
Figure 34D:
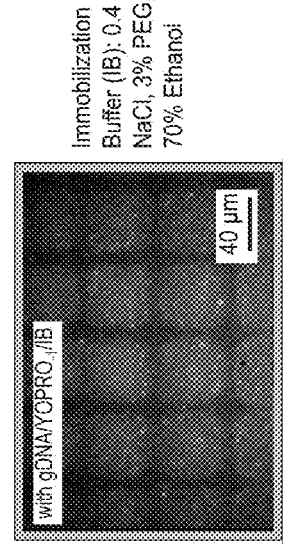

These valves are fabricated as shown in the schematic of FIG. 33. The polymer substrate 874 is shaped by front/back side molding using two different molding tools 872 and 876 in one step to make the fluidic network 878 and valve seat 881, and then thermally sealing cover plate 879 and bottom plate 880, with cover plate 879 functioning also as the valving membrane. Both the cover plate 879 and bottom plate 880 are thermally sealed onto the fluidic network 878. Because the "break point" of the material, in this case polycarbonate, is not exceeded, the material returns to its normal position upon removal of the load (have not exceeded the elasticity regime of the material). These valves can also function as a pump, by further increasing the load on the polymer membrane to dispense a volume of fluid that is dependent on the volume of the reservoir underneath the membrane. The pumping speed depends on the rate of change of load applied to the polymer membrane (see FIG. 32B). Several modules critical to the integrated module have been designed, fabricated, and evaluated for operation as described below.

The solid-phase extraction (SPE) module for the purification of nucleic acids from clinical samples is shown in FIG. 34. FIG. 34A shows polycarbonate (PC) molded with a microchannel containing micropillars that is used for the purification of a variety of nucleic acids, such as cycle sequencing reaction products, PCR products, genomic DNA and total RNA (Xu et al., "Solid-Phase Reversible Immobilization in Microfludic Chips for the Purification of Dye Labeled DNA Sequencing Fragments," *Anal. Chem.* 75(13): 2975-84 (2003) and Witek et al., "Purification and Preconcentration of Genomic DNA from Whole Cell Lysates Using Photoactivated Polycarbonate (PPC) Microfluidic Chips," *Nucleic Acids Res.* 10:e74 (2006), which are hereby incorporated by reference in their entirety). FIG. 34B is a magnified view of the micropillars in the microchannel. To produce the SPE active surface, a UV-photoactivation protocol produces a high density of carboxylic acids on the PC surface that serves as the extraction surface. FIG. 34C is a fluorescence microscopic image of UV-photoactivated micropillar surface bound by YOPRO-1 labeled genomic DNA (Witek et al., "Purification and Preconcentration of Genomic DNA from Whole Cell Lysates Using Photoactivated Polycarbonate (PPC) Microfluidic Chips," *Nucleic Acids Res.* 10:e74 (2006), which is hereby incorporated by reference in its entirety). Bound gDNA (small bright spots) is present predominantly only within those areas that were exposed to the UV radiation with negligible amounts of gDNA found in unexposed, non-activated regions. The advantages of this method include: (1) inexpensive device fabrication through micro-replication into PC; (2) quick and simple bed activation procedure using UV irradiation; (3) scalability of the fabrication process to high volume mass production; (4) versatility—various nucleic acids can be selectively purified by using the proper immobilization buffer and; (5) very high target recoveries with good removal of endogenous proteins. Typical recovery is ~84% of the target material using this extraction bed. FIG. 34D is an image of an agarose gel showing PCR amplified gDNA product that was obtained using a polymeric microchannel solid-phase extraction module (Witek et al., "Purification and Preconcentration of Genomic DNA from Whole Cell Lysates Using Photoactivated Polycarbonate (PPC) Microfluidic Chips," *Nucleic Acids Res.* 10:e74 (2006), which is hereby incorporated by reference in its entirety). The device can also be used for the purification of RNA and different sized DNAs as well.

Figures 35A, 35B, 35C, 35D, 35E:
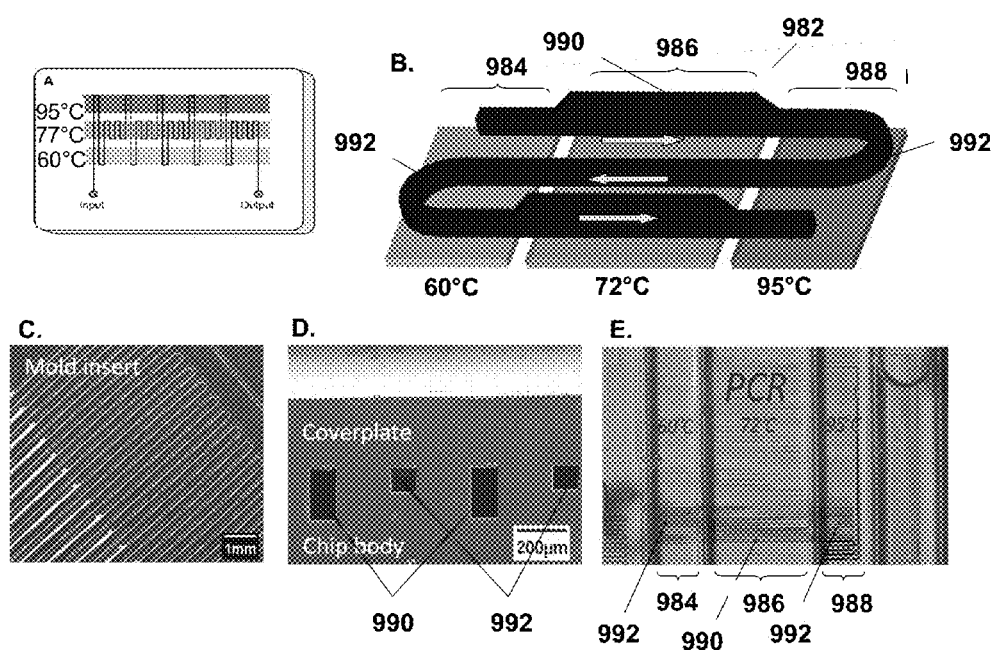
FIGS. 35A-35E show the micro-scale thermal cycling modules operating on a continuous flow process on the fluidic motherboard of the microfluidic device of the present invention.
Figures 36A, 36B:
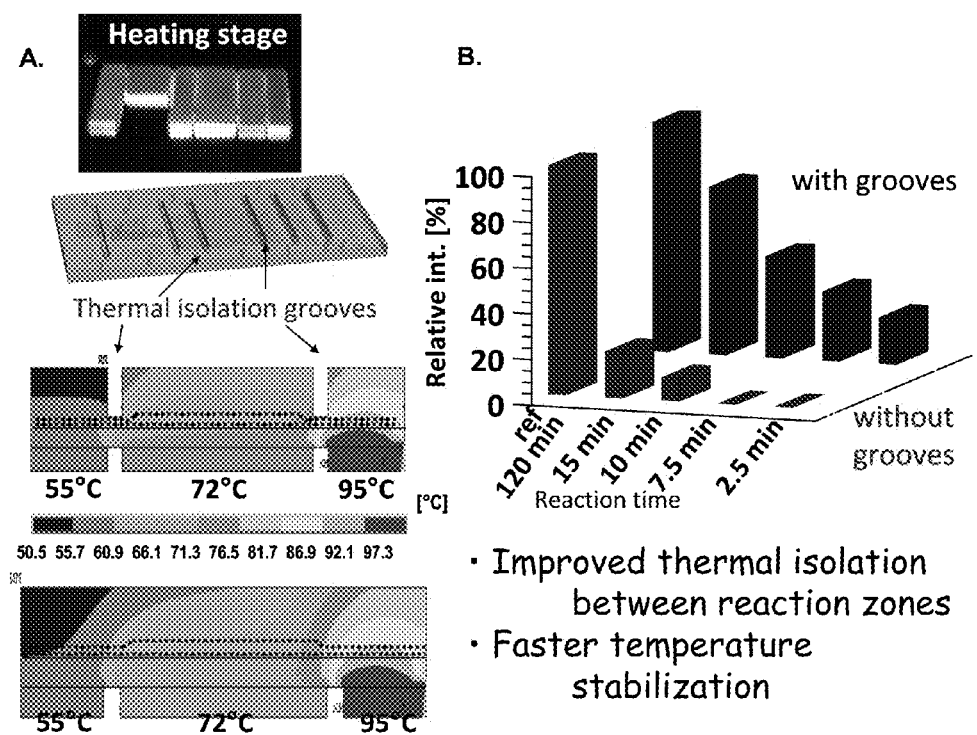
FIGS. 36A-36B show the incorporation of thermal isolation grooves between the reaction zones of the thermal cycling modules of the fluidic motherboard of the present invention.
Figure 37:
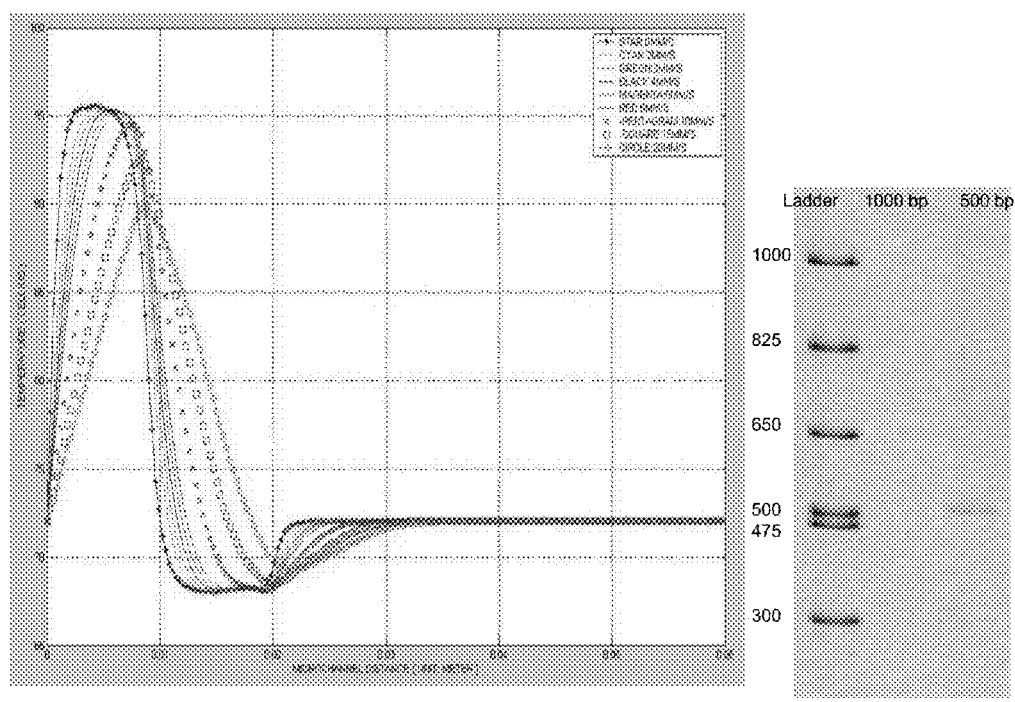
FIG. 37 is data from ANSY simulations showing the effects of different linear flow rates (mm/s) on the temperature distribution of a fluid plug moving into an isothermal zone for a continuous flow thermal cycler. In the present case, the thermal reaction modeled was a PCR with three temperature zones, 95° C., 67° C., and 72° C. Along the x-axis is plotted the distance the plug travels into the isothermal zone. As can be seen, faster linear velocities result in the inability to reach the 95° C. (denaturation) zone. Shown to the right is a gel image of CF-PCR products generated from k-DNA template for both a 1,000 bp and 500 bp product. The absence of a band at 1,000 bp for this 20-cycle PCR is because the linear velocity employed (4 mm/s) has exceeded the kinetic rate of building a 1,000 bp amplicon using Taq polymerase; the band at 500 bp is present because sufficient time has been allotted to build this amplicon (see Hashimoto et al., "Rapid PCR in a Continuous Flow Device," *Lab Chip* 4(6):638-45 (2004) and Chen et al., "Electrokinetically Synchronized Polymerase Chain Reaction Microchip Fabricated in Polycarbonate," *Anal. Chem.* 77(2):658-66 (2005), which are hereby incorporated by reference in their entirety).

Micro-scale thermal cycling modules operating on a continuous flow process are shown in FIGS. 35-37. The generated thermal reactor modules are equipped with a continuous flow (CF) thermal cycling format as shown, for example, in FIG. 35A (Kopp et al., "Chemical Amplification: Continuous-Flow PCR on a Chip," *Science* 280:1046-48 (1998), which is hereby incorporated by reference in its entirety). CF-polymerase chain reactors (CFPCRs) offer unique capabilities for the ultra-fast amplification of target DNA fragments using repeated thermal cycling, typically over three temperature ranges (i.e., 90-95° for denaturation, 50-70° for renaturation, and 70-75° for extension). In this arrangement, isothermal zones are poised along a race-track channel and small packets of fluids are shuttled through these zones to provide thermal cycling. Several modifications have been made to CFPCRs to improve temperature distribution and thermal management of the device, ultimately enhancing amplification efficiencies by significant margins. For example, the schematic of FIG. 35B shows a new concept for continuous flow thermal cyclers 982 in which the polymerase extension isothermal zone 986 possesses deeper channel 990 than shallow channels 992 of the renaturation 984 and denaturation 988 zones, which are kinetically much faster. Deeper channels 990 produce a larger channel cross section and thus, a lower linear velocity producing a longer residence time in this zone without requiring a larger footprint. FIG. 35C shows the molding tool that is used to make the CFPCR device. FIG. 35D shows a cross section of the fluidic network comprising the CFPC device with deeper channels 990 and the shallow channels 992. FIG. 35E is a photomicrograph of a CFPCR module of the present invention showing the polymerase extension isothermal zone 986 with deep channels 990, and renaturation 984 and denaturation 988 zones possessing shallow channels 992.

Another modification to the CFPCRs involves making grooves between temperature zones to increase the resistance to lateral heat conduction between zones to improve thermal isolation between reaction zones as shown in FIG. 36A (Chen et al., "Temperature Distribution Effects on Micro-CFPCR Performance," *Biomed. Microdevices* 10(2): 141-152 (2008), which is hereby incorporated by reference in its entirety). The graph of FIG. 36B shows the relative intensity of amplification efficiency as a function of reaction time using a device with and without grooves. The presence of the grooves notably enhances amplification efficiency at the shorter reaction times.

FIG. 37 shows the results of ANSY simulations and depicts the effects of different linear flow rates (mm/s) on the temperature distribution of a fluid plug moving into an isothermal zone for a continuous flow thermal cycler (see Hashimoto et al., "Rapid PCR in a Continuous Flow Device," *LOC* 4:638-45 (2004); Chen et al., "Electrokinetically Synchronized Polymerase Chain Reaction Microchip Fabricated in Polycarbonate," *Anal. Chem.* 77:658-66 (2005), which are hereby incorporated by reference in their entirety). In the present case, the thermal reaction modeled was a PCR with three temperature zones, 95° C., 67° C. and 72° C. Along the x-axis is plotted the distance the plug travels into the isothermal zone. As can be seen, faster linear velocities result in the inability to reach the 95° C. (denaturation) zone. Shown to the right is a gel image of CF-PCR products generated from λ-DNA template for both a 1,000 bp and 500 bp product. The absence of a band at 1,000 bp for this 20-cycle PCR is because the linear velocity employed (4 mm/s) has exceeded the kinetic rate of building a 1,000 bp amplicon using Taq polymerase; the band at 500 bp is present because sufficient time has been allotted to build this amplicon.

In summary, unique advantages of CFPCRs compared to batch-type thermal reactors are: (1) better thermal management, providing extremely short reaction times; (2) the number of cycles or the time of the thermal reaction can be controlled by the length of the reaction channel and/or the linear transport rate of sample through the reactor zone; and (3) the heaters and the thermal sensors can be positioned off-module to provide a simple and low-cost fluidic bio-processor appropriate for one-time use applications as required for diagnostics. The thermal cycler process produces PCR products in the least amount of processing time published to-date. In addition, the CF process can be used in LDRs and other thermally-based reactions.

Figure 38:
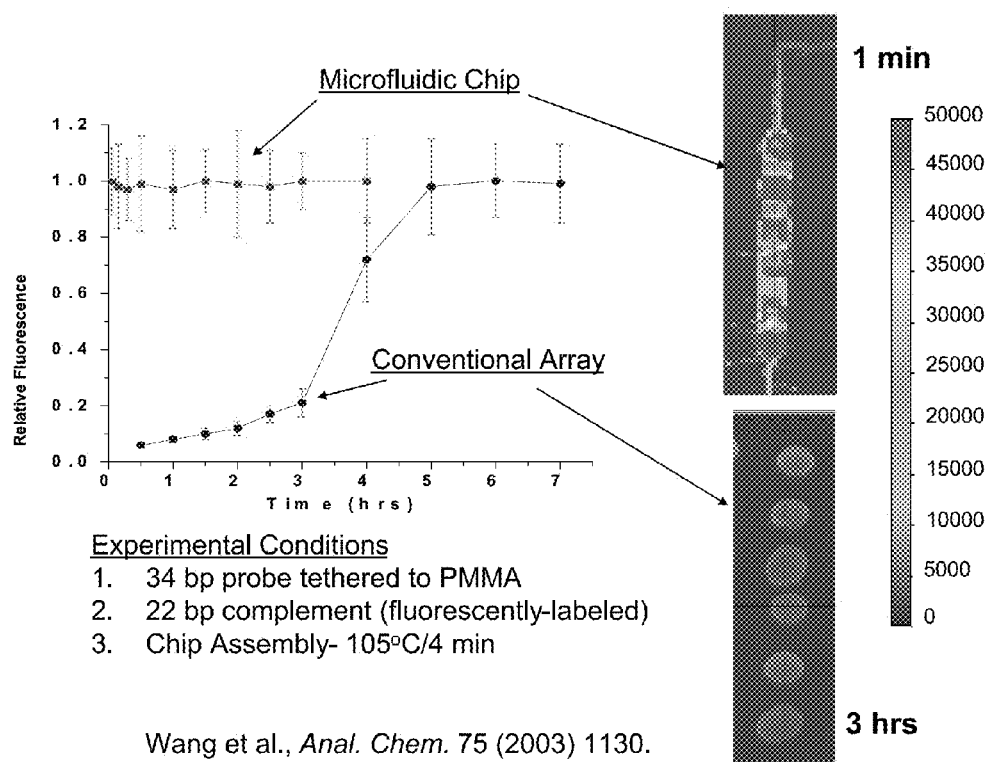
FIG. 38 is a comparison of the hybridization kinetics between a fluorescently labeled oligonucleotide probe and it complementary PMMA oligonucleotide probe tethered to the surface of a microfluidic chip or a conventional PMMA array surface (Wang et al., "Microarrays Assembled in Microfluidic Chips Fabricated from Poly(methyl methacrylate) for the Detection of Low-Abundant DNA Mutations," *Anal. Chem.* 75(5):1130-40 (2003), which is hereby incorporated by reference in its entirety).

Microfluidic-based DNA hybridization array modules, including DNA microarrays and universal arrays, have been constructed into microfluidic channels that are made from a thermoplastic (Wang et al., "Microarrays Assembled in Microfluidic Chips Fabricated from Poly(methyl methacrylate) for the Detection of Low-Abundant DNA Mutations," *Anal. Chem.* 75(5):1130-40 (2003), which is hereby incorporated by reference in its entirety). The advantage of configuring arrays in microfluidic channels is that it can significantly reduce the processing time by minimizing diffusional bottlenecking. FIG. 38 is a graph comparing the hybridization kinetics between a fluorescently labeled oligonucleotide probe and its complementary PMMA oligonucleotide probe tethered to the surface of a microfluidic chip or a conventional PMMA array surface (Wang et al., "Microarrays Assembled in Microfluidic Chips Fabricated from Poly(methyl methacrylate) for the Detection of Low-Abundant DNA Mutations," *Anal. Chem.* 75(5):1130-40 (2003), which is hereby incorporated by reference in its entirety). The fluorescent intensities obtained from oligonucleotide hybridization in the microfluidic channel was saturated at the first time point assessed (i.e., ~5 minutes), whereas the time required for fluorescence intensity saturation on the PMMA array surface was much greater (~5 hours). The forced flow of target solution over the probe-tethered surface of the microfluidic channel provides enhanced mass transfer of targets to the surface-immobilized probes reducing hybridization time. In addition, the small volume of the hybridization chamber afforded by the microfluidic channel configuration reduces the diffusional distances required for target to reach the surface probes.

In one embodiment of the present invention, oligonucleotide primer sets for carrying out the nucleic acid amplification methods (i.e., snakeHE and grass primers) of the present invention are immobilized on the array modules to facilitate cluster amplification and solid-phase sequencing of target nucleotide sequences. These can also be immobilized onto the surface of waveguides as well to allow for excitation of the entire array.

Figure 39:
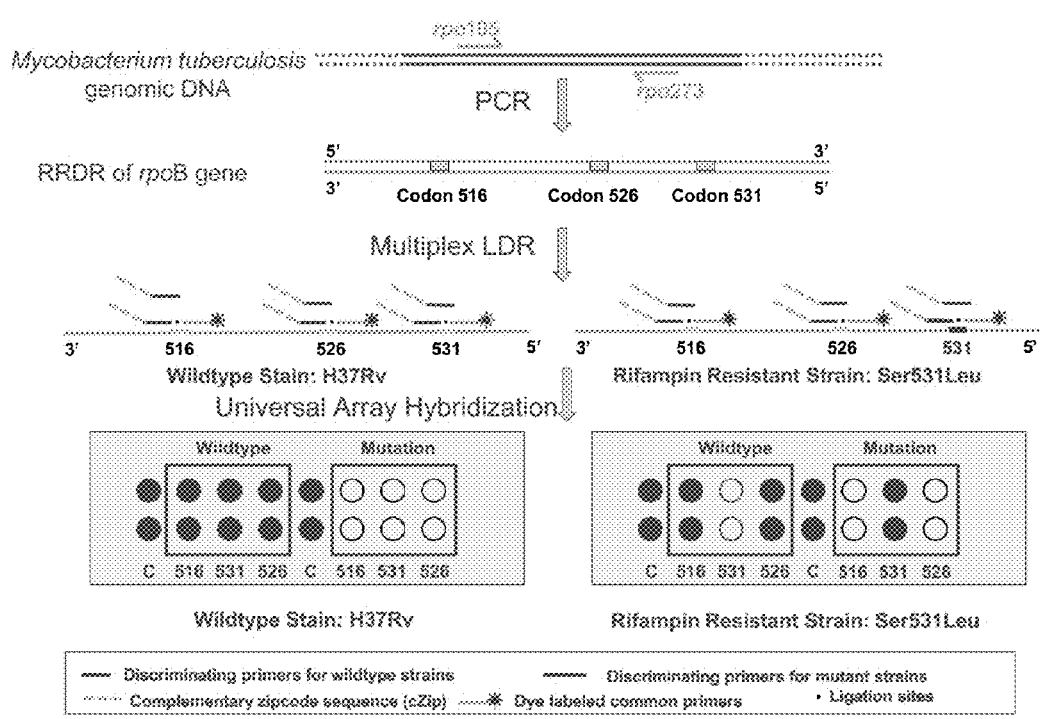
FIG. 39 is a schematic of the modular-based micro-system used for genotyping clinical samples and detecting drug resistance mutations in *Mycobacterium tuberculosis*. This assay strategy involved the use of a PCR and an LDR followed by universal array detection of the sequence variations.
Figure 40:
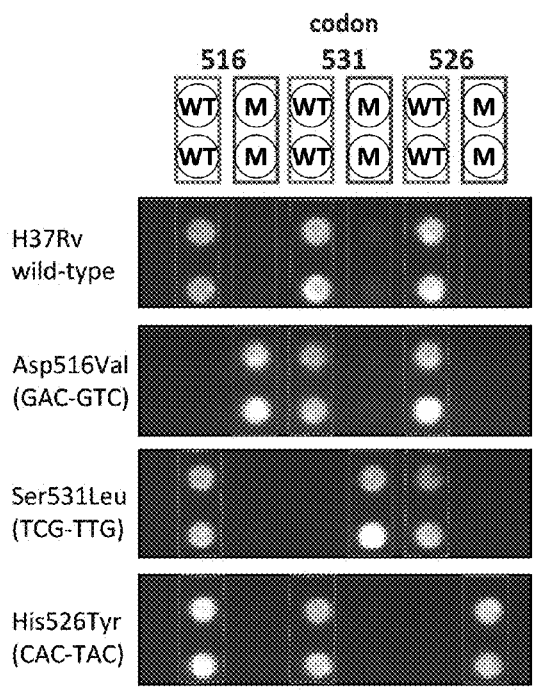
FIG. 40 shows the data generated using the modular-based micro-system of the present invention for genotyping clinical samples and detecting drug resistance mutations in *Mycobacterium tuberculosis*.

As an example of using this modular design approach for building integrated systems for molecular analyses, a polymer and modular-based micro-system for genotyping clinical samples, or detecting drug resistance mutations in *Mycobacterium tuberculosis* has been developed. The assay strategy employed involved the use of a PCR and an LDR followed by universal array detection of the sequence variations (see FIG. 39). The assay can allow for screening multiple mutations and reading out the results using the universal array with evanescent excitation. While the example shows the screening for sequence variations in *Mycobacterium tuberculosis*, primer sequences can be reprogrammed to screen for any target. The entire DNA processing is carried out using a polymer fluidic bio-processor, which consists of operational steps for cell lysis, solid-phase extraction of DNA, PCR amplification, LDR for identifying the mutations, and readout using the universal programmable array. The system provided complete automation of sample processing and generated high quality answers in less than 15 min, compared to nearly 11 hours required using conventional bench-top instruments (see FIG. 40). Results for the detection of sequence variations in *Mycobacterium tuberculosis* samples are shown using the system depicted in FIG. 40.

Another aspect of the present invention involves the integration of the array devices themselves and/or the integrated microfabricated modules and construction of a new sequencing/diagnostics instrument for both discovery and clinical applications. Operation of the automated DNA sequencing instrument requires integrated control of electronic, optical, thermal and hydraulic elements. The instrument will be fully autonomous and provide easy access to the fluidic modules to allow replacement of these modules following processing due to the need for performing diagnostic sequencing. There are several sub-systems that will be developed to operate the fluidic modules and extract data as well as process it, which will all be controlled by the operator via an intelligent graphical user interface (GUI). Mechanical hardware will also be required, including, mounting gigs for the fluidic bio-processor, reagent reservoirs, rack mounts for the electronic boards and optical hardware, optical hardware for large area, high resolution imaging and mounts for the fluidic plumping. The subsystems and their requirements are detailed below.

Fluidic sub-system: The fluidic sub-system requires fluidic control hardware, including valves and pumps, with standard input/output configurations using off-chip and/or on-chip elements. These control elements must easily interface to the fluidic modules and will dispense the appropriate volumes of reagents at the desired times during any sequencing run. Sample input strategies must provide the ability to accept any type of clinical sample and minimize sample contamination issues between diagnostic sequencing runs. Finally, software for automated control of the fluid handling system including the necessary graphical user interface (GUI) during a sequencing run must be provided.

Thermal processing hardware and software: All thermal energy required for the thermal cycling reactions, such as PCR and/or LDR or DNA amplifications, will be provided by a heating stage located directly on the instrument. After insertion of the fluidic bio-processor into the instrument, the fluidic bio-processor can be pressed against the heater surface to provide good thermal contact. The heating stage will consist of Kapton film heaters attached to copper blocks of the required thickness to provide a uniform heat flux and temperature distribution to maximize thermal reaction efficiency. Necessary temperatures for the thermal reactions will be spatially localized over the fluidic bio-processor and sensed by thermocouples positioned inside the copper blocks. The control hardware and software will provide simple operator input into the system for selecting the temperatures required for the thermal reactions. The control software will contain feedback loops for monitoring temperatures ($\pm 1°$ C.) and minimizing over-shoot.

The optical sub-system: The optical sub-system will contain control circuitry for the large area imaging CCD as well as image processing software to recognize clusters and read spectral data from low-density spots following nucleotide addition steps. Control hardware for aligning the pillared-array with the large area imaging CCD pixels is also required. This will include automated focusing by piezo-driven stages to provide sharp images over the entire imaging field. Multi-color hardware/software will score each nucleotide base added in a single image at high speed.

The electrical sub-system: This system will require an Instrument Control Unit (ICU) that will have an on-board electronic microprocessor that communicates with all electronic sub-systems (digital-to-analog and analog-to-digital converters, stepper motor drivers, temperature monitors, etc.) and coordinates their operation. The ICU will be designed to generate internal timing signals for the control and synchronization of time sensitive events without requiring operator intervention. The host computer software will include a GUI that can be customized for a particular operating environment. For normal use, a turn-key interface will be implemented that leads the user through the required setup and operating steps with robust bound checking and error detection.

The electronic hardware will likely require >1,000 individual discrete functional integrated circuits (IC) on a dozen or more printed circuit boards. In addition, the largest arrays will generate hundreds of millions of DNA sequence base data entries every few minutes. High-density programmable logic devices will replace ICs where possible to reduce the cost of the instrument without sacrificing data acquisition rates and data processing speed. These devices are called Field Programmable Gate Arrays (FPGA) and are readily available at relatively low-cost from a number of manufacturers. Modern FPGAs contain the equivalent of hundreds to millions of individual logic gates all within a single integrated circuit package. Since most of the interconnections are done internally to the FPGA, signal propagation times are much shorter than conventional IC approaches.

The various aspects of the present invention, including the methods of target nucleotide sequence amplification and sequencing, target nucleotide sequence capture, enrichment, and identification, and devices and instruments described above are designed to address a number of clinical and research DNA sequencing needs, including (i) whole genome sequencing such as, de novo assembly or whole genome re-sequencing; (ii) re-sequencing of PCR amplicons or targeted regions of the genome; (iii) low frequency mutation identification and profiling; (iv) promoter methylation detection and screening to identify cancer; (v) genetic variation identification (e.g., SNP genotyping, copy number variation, copy changes in tumors that predict outcome); (vi) gene expression analysis, including whole genome RNA profiling and expression studies using degraded RNA from stored samples (e.g., formalin-fixed, paraffin-embedded tissue samples); and (vii) gene regulation studies, including whole genome small RNA discovery and quantification, genome wide measurements of protein-nucleic acid interactions, and genome wide DNA methylation profiling.

The various aspects of the present invention are also useful for identifying individuals at risk of getting cancer. There is a genetic basis for certain types of cancer. For example, a new form of genetic cancer, known as "autozygosity", which arises as a consequence of endogamy (marrying within one's ethnic or religious groups), has recently been discovered. In addition, recent studies suggest that copy number variations (CNV) in certain genes may be responsible for certain inherited diseases. The methods and instruments of the present invention can be used to determine the presence of both autozygosity and CNVs by studying the DNA of 100 individuals with early cancer. The entire genome will be sequenced at low coverage (5-fold), allowing a rough draft genome from 4 to 8 individuals/instrument/day to be obtained. This will allow mapping of additional cancer genes in candidate regions, which will then be re-sequenced at a deeper level of coverage to identify cancer-causing mutations. Approximately 1,200 cancer genes (about 5-fold higher than previously thought) have already been identified. The array devices and amplification method of the present invention will allow for very low-cost sequencing to find the inherited mutations in individuals who may be at risk. The methods and instruments described herein, including a microfabricated device containing a unique DNA array, will specifically capture and sequence the exons and surrounding intronic regions of these 1,200 genes, as well as additional genes to identify sequence or copy number variation.

An alternative approach to using gene-specific primers on an array is to capture the gene-specific regions in liquid. Although there are a number of approaches to do so, they all have limitations. In accordance with the methods of the present invention described supra, gene-specific primers are either ligated or extended on the correct target to create a longer biotinylated capture sequence. This process allows for removal of the unincorporated biotinylated nucleotides or primers, and capture of the desired targets in a microfabricated device. Simple denaturation releases the target, and it is now suitable for sequencing.

In another embodiment, the methods and instruments of the present invention are used to identify cancer in an individual at an earlier and more treatable stage. The most convenient test to find early hidden cancer is one that identifies appropriate markers in a blood sample. Alternatively, the sample can be a biopsy, bodily fluid, or captured tumor cells. The molecular analysis of 161 primary colon tumors for mutations and promoter methylation silencing revealed 88% of tumors had mutations, 70% had cancer-specific methylation, and combined 94% had at least one change, suggesting that nucleic acid-based tests will likely require a multiplexed panel of both mutation and methylation biomarkers.

The technology of the present invention is suitable for enriching target nucleotide sequences prior to characterization of methylation status. Identification of the cancer specific methylation changes can be detected in the enriched target sequences by solid phase sequencing. Characterization of the cancer-specific methylation changes can also be carried out as described in U.S. Pat. No. 7,358,048 to Barany et al., which is hereby incorporated by reference in its entirety. Both mutation and methylation changes may be screened at a sensitivity of up to 1 in 100,000, enabling detection of early, hidden, and more treatable cancer.

The methods and instruments of the present invention are also useful for identifying tumor markers that predict outcome and guide treatment towards more effective and less toxic drugs. Commercial tests are now available to predict the likelihood of recurrence in breast cancer patients, but the accuracy of these tests is 80% or less. Using methods and instrumentation described herein, a 69-gene expression set that provides an accuracy of 94% in predicting a favorable outcome has been developed. When this gene expression data is combined with mutational status known as "MSI" and a specific cancer gene promoter methylation status, specificity is improved to 97%. By using a "four dimensional" profiling approach (gene expression, DNA copy number, promoter methylation, and gene mutations), changes in cancer gene pathways within individual tumors have been identified that would predict response to a new generation of gene-specific drugs.

In general, for all cancers, the process of identifying tumor specific changes, especially those correlating with outcome, requires building an atlas of molecular profiles in at least 100-200 tumors of a given type. To achieve this, new approaches for "n-dimensional" profiling need to be developed and can be developed using the methods and instruments described herein. For the discovery phase, deep genomic profiling, using paired-end sequencing of both direct fragments (2K-5K) as well as sequencing of linking libraries (10K) may be performed simultaneously on the large 576 million to 2.3 billion address DNA array to generate 200-400 billion bases of raw data. This will identify >99% of cancer-specific point mutations, short insertions/deletions, all copy number variations, autozygosity, common and inherited predisposing SNPs. Since the platform described herein amplifies and sequences much longer gene fragments, other genomic structure abnormalities such as loss of heterozygosity (LOH), loss or gain of chromosomal arms or regions thereof, transversions and translocations that occurred often in the tumor may also be examined.

For discovery of new splice variants or fusion genes in the tumor transcriptome, after reverse-transcribing mRNA, cDNA products are fragmented and ultra-long paired-end sequencing of such fragments as shown in FIGS. 8-9 is used. This will identify >99% of splice variant transcripts as well as identify translocations. A more sophisticated approach and one that is uniquely amenable to the microfabricated devices described herein is to initially separate high-quality RNA by size, prior to generating cDNA fragments. This would assist in determining the precise exons used in each splice variant transcript. There is a growing body of literature to suggest tumors have aberrant splice variants, some of which may drive tumor progression, and these are often excellent targets for gene-specific therapies, as they are lacking in normal tissue. Once a transcriptome atlas is created of the most frequent or clinically significant variants identified in a particular tumor class, gene-specific capture methods may be used for more directed sequencing combined with standard transcriptome profiling of tags on the 3' end of transcripts.

A unique tool for epigenetic profiling, termed "Methyl-tag", involves sequencing to determine methylation status of over 98% of CpG islands. The technique, which is depicted in FIGS. 11-13, is based on bisulfite conversion of AciI recognition sites (ubiquitous in CpG islands but uncommon elsewhere in the genome), which retain their asymmetric recognition sequence if methylated in the GCGG but not the CCGC orientation. After bisulfite conversion and two rounds of random-primer replication to remove methylated cytosines and uracils, a cocktail of linkers and ligase converts CpG islands into a set of fragments uniquely tagged with two different universal sequences. Millions of tags are then sequenced on the instrument of the present invention. Methylated sites are then mapped back to the known human genome sequence. Likewise, miRNA copy numbers will be determined by ligating on linkers, followed by sequencing across the miRNA using standard protocols. This will provide a deep database of molecular changes that influence transcript activity.

The methods and instruments of the present invention are also useful for determining gene expression signatures that predict disease recurrence (i.e., cancer recurrence), and signatures that predict response to specific pharmaceutical treatments. For a given tumor type, data will be collected from 500 patients with both primary and metastatic disease, and tissue will be processed to obtain pathological data. The samples will be profiled using the methods and instruments of the present invention, for digital mRNA, mutational, CNV, LOH, methylation, and miRNA results, which will be linked to the clinical data for developing molecular signatures of cancer recurrence. Prototype bioinformatic tools required to analyze these large data sets have been developed. Once signatures are validated on an additional 300 patients, those identified as non-responders would be placed into appropriate clinical trials or novel therapies based on the molecular lesions.

Figure 41:
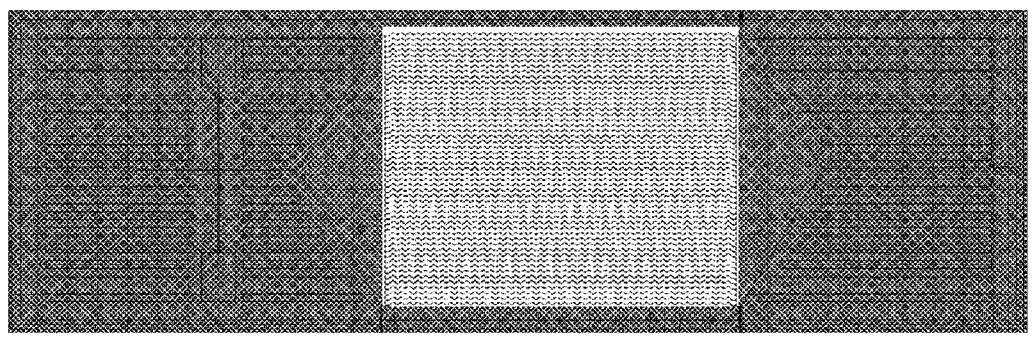
FIG. 41 is a schematic of a polymeric high-throughput microsampling unit (HTMSU) that selectively and specifically isolates small numbers of circulating tumor cells from a patient sample through an antibody mediated capture process (Adams et al., "Highly Efficient Circulating Tumor Cell Isolation from Whole Blood and Label-Free Enumeration Using Polymer-Based Microfluidics with an Integrated Conductivity Sensor," *J. Am. Chem. Soc.* 130(27):8633-41 (2008), which is hereby incorporated by reference in its entirety).
Figure 42:
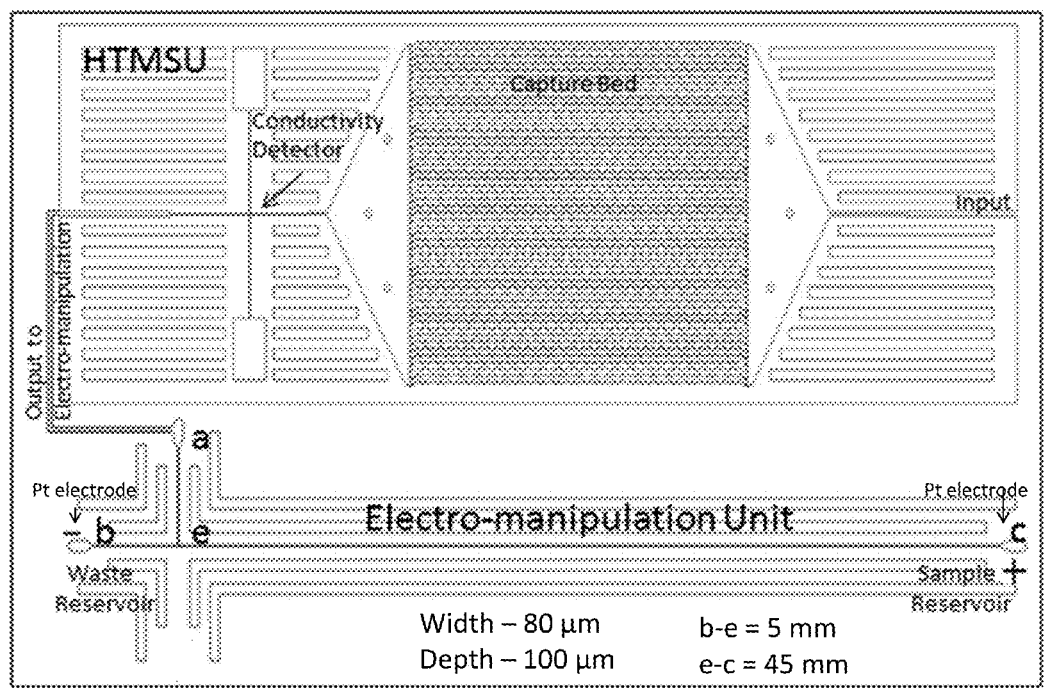
FIG. 42 is a schematic of the polymeric HTMSU as shown in FIG. 41 with an electromanipulation unit. The capture bed consists of a series of 51 curvilinear channels (30 μm wide and 150 μm deep). The electromanipulation unit contains 80 μm wide, 100 μm deep, and 5 cm long linear channels that facilitate the isolation and enrichment of the small numbers of circulating tumor cells found in a biological sample. The cells are introduced into the electromanipulation unit at port (a), which serves as the entrance port. Port (a) is connected to a "T" junction labeled (e). Exit (b) serves as the sample waste reservoir, while reservoir (c) is the cell receiving reservoir (see Dharmasiri et al., "High Throughput Selection, Enumeration, Electrokinetic Manipulation, and Molecular Profiling of Low-Abundance Circulating Tumor Cells Using a Microfluidic System," *Anal. Chem.* 83:2301-09 (2011), which is hereby incorporated by reference in its entirety).
Figures 43A, 43B, 43C:
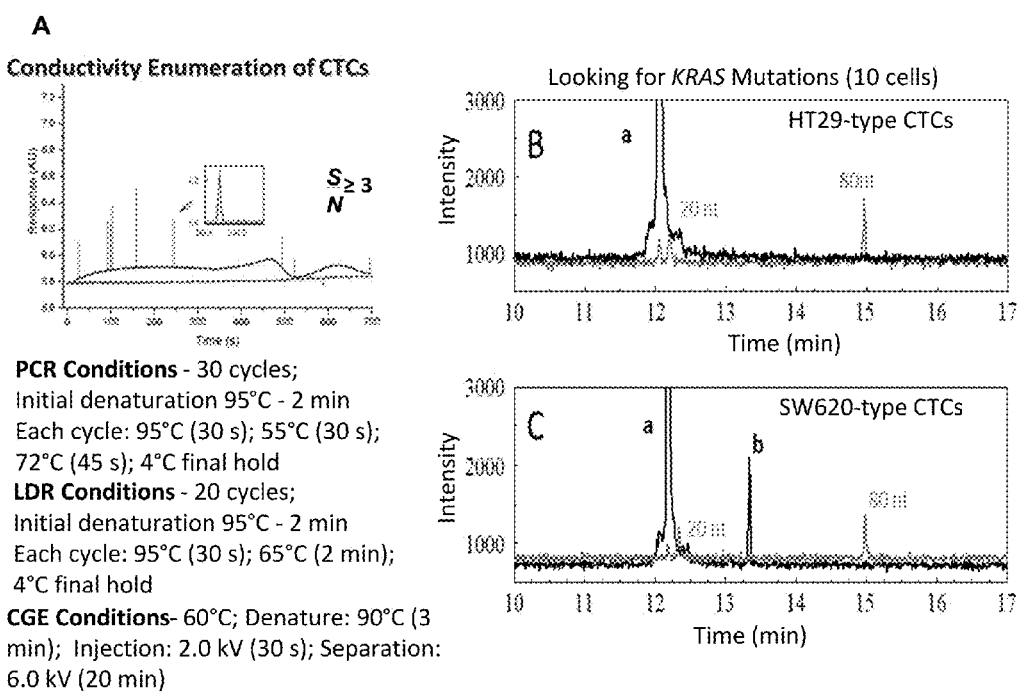
FIGS. 43A-43C show the conductivity enumeration of circulating tumor cells (CTCs).

The methods and instruments of the present invention are also useful for identifying those who do not need painful and toxic chemotherapy, while also identifying specific patients who would benefit from chemotherapy or more targeted therapies. Early recurrence can be identified, allowing for more effective intervention, using a novel polymer-based microfluidic device that can selectively and specifically isolate exceedingly small numbers of circulating tumor cells (CTCs) through a monoclonal antibody (mAB) mediated process by sampling large input volumes (>1 mL) of whole blood directly in short time periods (<10 min), see FIG. 41 (see also, U.S. Patent Publication No. 2009/0074637 to Murphy et al., Adams et al., "Highly Efficient Circulating Tumor Cell Isolation From Whole Blood and Label-Free Enumeration Using Polymer-Based Microfluidics with an Integrated Conductivity Sensor," *JACS* 130:8633-41 (2008), which are hereby incorporated by reference in their entirety). The CTCs are concentrated into small volumes (190 nL) and the number of cells captured are read quantitatively using electrokinetic techniques to direct the cells into a receiving reservoir to concentrate the cells nearly 1,000-fold. This is achieved without labeling the cells; but rather by releasing the captured cells and using an integrated conductivity sensor for enumeration (see FIG. 42 and Dharmasiri et al., "High Throughput Selection, Enumeration, Electrokinetic Manipulation, and Molecular Profiling of Low-Abundance Circulating Tumor Cells Using a Microfluidic System," Anal. Chem. 83:2301-09 (2011). The microfluidic device contains a series of high-aspect ratio microchannels (35 µm width×150 µm depth) that are replicated in poly(methyl methacrylate) (PMMA) from a metal mold master. The microchannel walls are covalently decorated with mABs directed against circulating tumor cells over-expressing the epithelial cell adhesion molecule (EpCAM). This microfluidic device can accept inputs of whole blood, and its CTC capture efficiency can be highly quantitative (>97%) by designing capture channels with the appropriate widths and heights. The simplicity in manufacturing the device and its ease of operation makes it attractive for clinical applications requiring one-time use operation. The utility of this device for isolating other circulating tumor cells, such as tumor cells shed into circulation from colorectal cancer patients, has also been demonstrated. Finally, DNA from such captured cells has been isolated and the presence of K-ras mutations in certain cell types confirmed (in this case, the SW620 cell line, which harbors K-ras mutations, see FIG. 43). Conversely, colorectal tumor cells found in circulation that do not present K-ras mutations were also successfully genotyped (see FIG. 43, HT-29 cells).

EXAMPLES

Figure 44:
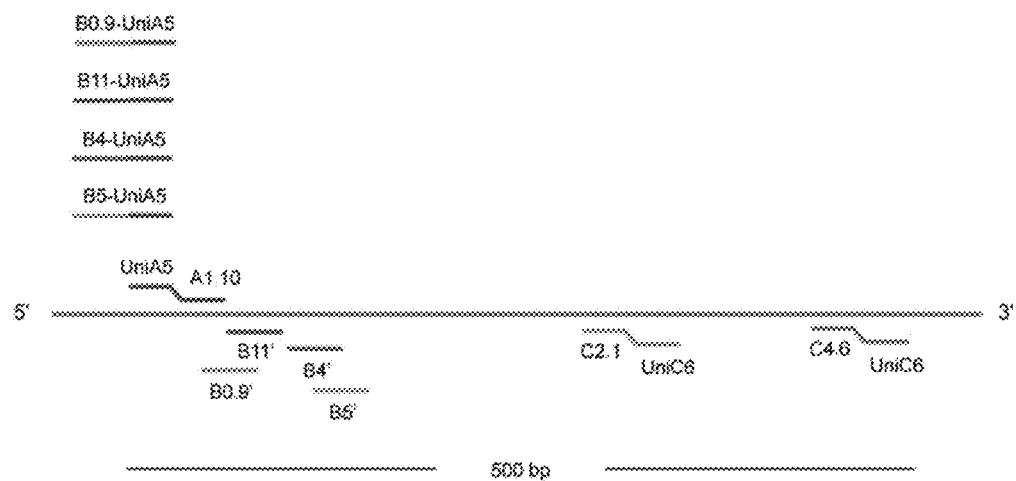
FIG. 44 shows the genomic region in the human p53 gene between exon 5 and exon 6 that is detected using the solution and solid phase amplification methods of the present invention.

The following examples are provided to illustrate embodiments of the present invention but they are by no means intended to limit its scope Example 1—p53 Sample Preparation A genomic region in human p53 gene between exon 5 and exon 6 was amplified using solution-phase and solid-surface methods of the present invention. FIG. 44 shows the sequence of the region between exon 5 and exon 6 of the p53 gene and the location of the primers within this region. These DNA templates were prepared from normal human lymphocyte genomic DNA, followed by a series of first-stage PCR, dilution, and second-stage PCR to derive the final templates. FIGS. 45-47 are tables showing the sequences for the p53 probe primers, solid phase primers, and template primers used in these Examples.

At the first PCR stage, four forward primers A1-B11 Bridge, A1-B12 Bridge, A1-B13 Bridge, or A1-B14 Bridge were tested in conjunction with a reverse primer p53Ex5-6_R to determine the most effective forward PCR primer. The pairing between A1-B11 Bridge and p53Ex5-6_R primers was the top choice since this pair showed the most abundant PCR amplicons. The PCR mixture (50 µl) contained 20 mM Tricine, 16 mM $(NH_4)_2SO_4$(pH 8.7), 2.5 mM $MgCl_2$, 0.2 mM dNTP, 0.4 µM primers, 2 ng/µl genomic DNA, 0.5 µ/µl AmpliTaq Gold™ DNA polymerase. The PCR procedure included a pre-denaturation step at 95° C. for 10 minutes, 35 cycles of three-step amplification with each cycle consisting of denaturation at 94° C. for 30 seconds, annealing at 63° C. for 1 minute and extension at 72° C. for 1 minute. PCR products were visualized by electrophoresis in 1.8% agarose gel.

The second-stage PCR was carried out using 1 µl of a million-fold dilution of the first-stage PCR products, with the nine primer pairs shown in Table 4 below. The PCR mixture (50 µl) contained 20 mM Tricine, 16 mM $(NH_4)_2SO_4$(pH 8.7), 2.5 mM $MgCl_2$, 0.2 mM dNTP, 0.4 µM primers, 2 ng/ul genomic DNA, 0.5 µ/µl AmpliTaq Gold™ DNA polymerase. The PCR procedure included a pre-denaturation step at 95° C. for 10 minutes, 35 cycles of three-step amplification with each cycle consisting of denaturation at 94° C. for 30 seconds, annealing at 63° C. for 1 minute and extension at 72° C. for 1 minute. PCR products were visualized by electrophoresis in a 1.8% agarose gel

TABLE 4

Primer Pairs for Second Stage PCR

| | |
|---|---|
| UniA5-A1.10 | UniC6-C4.1 |
| UniA5-A1.10 | UniC24-C4.1 |
| UniA27-A1.10 | UniC6-C4.1 |
| UniA21-A1.10 | UniC24-C4.1 |
| UniA22-A1.10 | UniC24-C4.1 |
| UniA23-A1.10 | UniC24-C4.1 |
| UniA5-A1.10 | UniC6-C2.1 |
| UniA22-A1.10 | UniC24-C2.1 (short template) |
| UniA23-A1.10 | UniC24-C2.1 (short template) |

UniC6-C4.1 and UniC24-C4.1 are reverse primers used to generate PCR fragments around 500 bp. UniC6-C2.1 and UniC24-C2.1 are reverse primers used to generate PCR fragments around 200 bp. The PCR products were purified to remove excess primers by passing Microcon YM-30 filters three times. The final PCR products were subject to an additional million-fold dilution before using as the templates for solution-phase and solid-surface amplifications.

Example 2—Solution-Phase PCR Amplification

Three DNA templates were selected in the initial solution-phase amplifications. For each template, the various sets of PCR primers of Table 5 below were chosen to determine optimal condition for amplification. Thus, a total of eight reactions with 50 µl each were established.

The solution-phase PCR (50 µl) contained 1×Pyrophage 3137 buffer (pH8.8) plus enzyme stabilizer, 0.4 mM dNTP, 0.2 µM primers, 2 µl of a million-fold diluted templates, 0.5 M betaine, 2 mM $MgSO_4$, 0.1 µ/µl 3137 DNA polymerase (exonuclease minus). The reactions were carried out in 30 cycles PCR consisted of 90° C. for 10 seconds, 55° C. for 1 minute, and 68.5° C. for 1 minute. The amplification products were analyzed by electrophoresis in 1.8% agarose gel.

TABLE 5

Solution Phase PCR Templates, Primers, and Products

| Template | Primer 1 | Primer 2 | Product (lane in gels of FIG. 57) |
|---|---|---|---|
| UniA5_A1.10/ UniC6-C4.1 | NH2-T20-spacer-UniA5 | NH2-T15-PC-spacer-UniC6 (PC: photo-cleavage) | 2, 10 |
| | T5-spacer-B5-UniA5 | NH2-T15-PC-spacer-UniC6 | 3, 11 |
| | T5-spacer-B5-UniA5HE | NH2-T15-PC-spacer-UniC6 | 4, 12 |
| UniA22-A1.10/ UniC24-C4.1 | $NH_2$-T20-spacer-UniA22Lg | $NH_2$-T20-PC-spacer-UniC24Lg | 5, 13 |
| | T5-spacer-B5-UniA22 | $NH_2$-T20-PC-spacer-UniC24Lg | 6, 14 |
| | T5-spacer-B5-UniA22HE | $NH_2$-T20-PC-spacer-UniC24Lg | 7, 15 |

TABLE 5-continued

Solution Phase PCR Templates, Primers, and Products

| Template | Primer 1 | Primer 2 | Product (lane in gels of FIG. 57) |
|---|---|---|---|
| UniA23-A1.10, UniC24-C4.1 | T5-spacer-B5-UniA23 | NH$_2$-T20-PC-spacer-UniC24Lg | 8, 16 |
| | T5-spacer-B5-UniA23HE | NH$_2$-T20-PC-spacer-UniC24Lg | 9, 17 |

Each of the eight 50 µl reactions was equally divided to serve as experiments and controls, and the effects of Eva Green, betaine, primer B, and template size were assessed as described below.

For each 25 µl experiment, 0.6 µl of 20×Eva green was added. A total of 16 reactions were carried out under the same PCR conditions described above. The amplification results were visualized on a 1.8% agarose gel. No apparent difference of amplification efficiency was found among each template/primer set.

For each 25 µl experiment, 0.25 M betaine was added. Experiments were repeated to further test 0.5 M and 1 M betaine conditions. A total of 32 reactions were carried out under the same PCR conditions described above. The amplification results were visualized on a 1.8% agarose gel as shown in the top and bottom panels of FIG. 48. The agarose gel shown in the bottom panel of FIG. 48 shows more consistent and higher product yield with the addition of 0.25 M betaine to the reaction mixture.

For each 25 µl experiment, 0.4 µM B primer was added. A total of 16 reactions were carried out under the same PCR conditions described above. The amplification results were visualized on a 1.8% agarose gel. No apparent difference of amplification efficiency was found in the presence and absence B primer.

Short (200 bp) and regular (500 bp) templates were added to each 25 µl experiment and control, respectively. A total of 16 reactions were carried out under the same PCR conditions described above. The amplification results were visualized on a 1.8% agarose gel. The intensity of amplification products are compared with short templates and regular template in the presence or absence of B primer.

Figure 48:
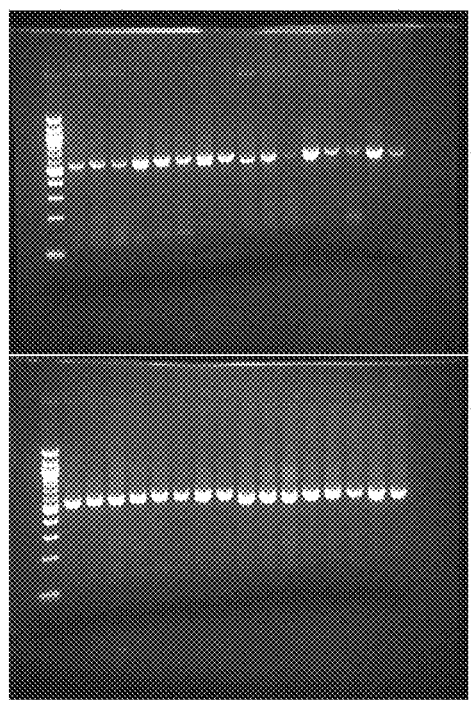
FIG. 48 shows p53 amplification products generated using the amplification methods of the present invention visualized by gel electrophoresis.

FIG. 48 shows amplification products generated using the various primers and reaction products described above. Lanes 2-9 of the gel in the top panel of FIG. 48 were generated under the standard reaction conditions described above, while lanes 2-9 of the bottom panel were generated in reaction conditions that included 0.25 betaine. Products shown in lanes 10-17 in the top panel were generated under reaction conditions that included the addition of the B11 primer, and products in lanes 10-17 of the bottom panel were generated in reactions that included 0.25 betaine and the B11 primer.

Solution phase amplification behaves differently than solid amplification. Using the strand-displacing thermophilic 3172 exo-minus polymerase under standard conditions, varying yields were observed as shown in the top panel of FIG. 48. As predicted, the ability of Snake HE primers to hairpin back on themselves and form full-length hairpin products reduces the overall yield of products under standard amplification conditions (FIG. 48, lanes 4, 7, & 9 in top panel). This is more evident when adding the B11 primer, which mimics the "Grass" design (FIG. 48, lanes 12, 15, & 17 in top panel). By optimizing the amplification conditions including using 0.25M betaine in the buffer, excellent yields are obtained under all conditions, with even better yields when adding the B11 grass primer (FIG. 48, bottom panel).

Figures 49A, 49B:
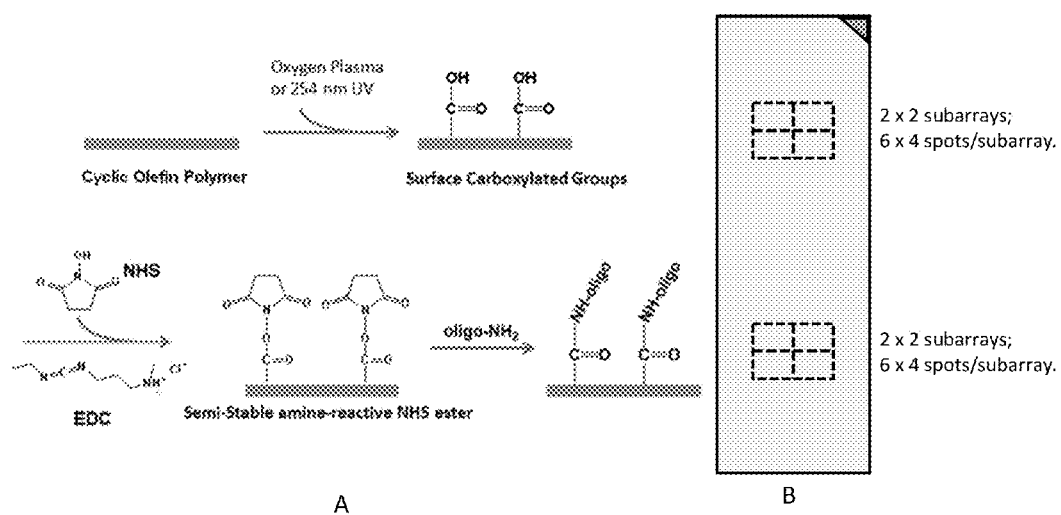
FIGS. 49A-49B are a schematics of the immobilization of amino-modified oligonucleotides onto activated Zeonor® 1420R COP (Cyclo Olefin Polymer) slides via click chemistry (FIG. 49A) and PCR primer arrays spotted onto 1×3 Zeonor® 1420R COP slides (FIG. 49B).
Figure 50A:
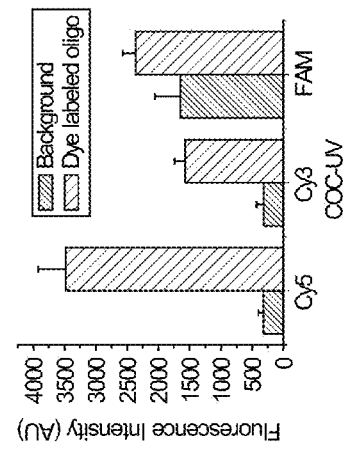
FIGS. 50A-50D show the results of selective activation of cyclic olefin copolymer (COC) using UV exposure or an oxygen plasma. Both methods generate surface carboxylic acids that can be used for the immobilization of amine-terminated oligonucleotides.
Figure 50B:
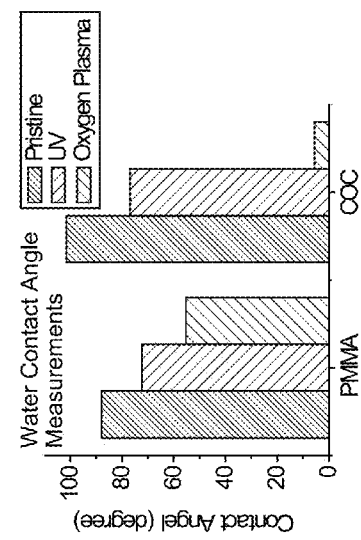
Figure 50C:
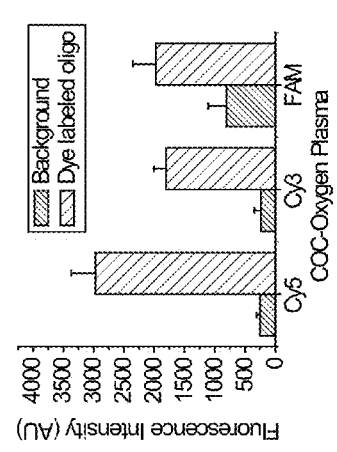
Figure 50D:
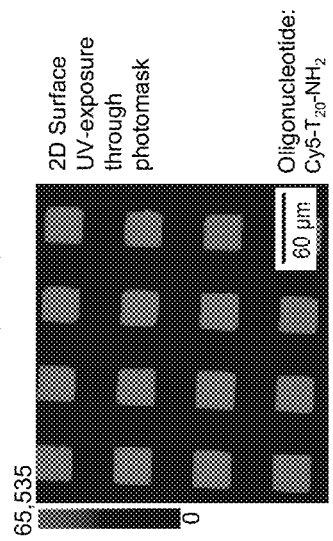

Example 3—Surface Activation and Primer Immobilization Procedures on a Polymer Surface The 5' amino modified primers for solid phase PCR were immobilized onto oxygen plasma activated Zeonor® 1420R COP (Cyclo Olefin Polymer) slide surfaces via click chemistry as shown in FIG. 49A (Grabarek and Gergely, "Zero-Length Crosslinking Procedure with the Use of Active Esters," *Analytical Biochemistry,* 185:131-135 (1990); Wang et al., "Microarrays Assembled in Microfluidic Chips Fabricated from Poly(methyl Methacrylate) for the Detection of Low Abundant DNA Mutations," *Analytical Chemistry,* 75:1130-1140 (2003); Xu et al., "Polymer Microfluidic Chips with Integrated Waveguides for Reading Microarrays," *Analytical Chemistry,* 79:9007-9013 (2007), which are hereby incorporated by reference in their entirety). Surface carboxylic acids were generated by placing COP slides in the vacuum chamber of a Technics Series 800 micro reactive ion etcher (Surplus Process Equipment Corp., Santa Clara, Calif.) for 2 min using a 250 mTorr oxygen pressure and 50 W radio frequency. Then, the COP slides were functionalized using 50 mg/mL 1-ethyl-3-(3-dimethylaminopropyl) carbodiimide hydrochloride (EDC) and 5 mg/mL N-hydroxysuccinimide (NETS) in MES (2-(N-morpholino) ethanesulfonic acid) buffer (pH=6.0) for 10 min to form succinimidyl ester intermediates, which can react with amino modified oligonucleotide primers to form a stable amide bond. The amino modified primers were dissolved in 0.02 M Na$_2$HPO$_4$/Na$_3$PO$_4$ buffer (pH=9.0) to a final concentration of 50 µM and were dispensed onto COP slides using a Piezorray™ noncontact microarray printing system (Perkin Elmer, Boston, Mass.). The dispensed volume of each spot was 0.33±0.03 nL, and the spots were ~150 µm in diameter. The pattern in which each test array was spotted is shown in FIG. 49B. After incubation in a humidified chamber at room temperature for 4 hours, the spotted COP slides were thoroughly washed with 0.1% sodium dodecyl sulfate (SDS) to remove non-specifically absorbed oligonucleotides. The unreacted succinimidyl ester intermediates were finally capped using 50 mM ethanolamine in 20 mM PBS (pH=7.4) for 10 minutes. To reduce non-specific absorption of polymerase, the COP slides were blocked using 0.5% ultrapure BSA in 20 mM PBS (pH=7.4) for 10 minutes and stored at 4° C. for future amplification runs.

FIG. 50 shows the results of selective activation of cyclic olefin copolymer (COC) using UV exposure or oxygen plasma. As shown, both techniques allow the covalent attachment of DNA primers to only those areas of the polymer exposed to the activating source, either UV light or an oxygen plasma. In both cases, surface carboxylic acids are generated on the surface that can be subsequently reacted with amine-terminated oligonucleotides using EDC/NHS coupling chemistry. FIG. 50A shows sessile water contact angles following UV or plasma oxidation (the smaller contact angle is indicative of a higher coverage of surface carboxylate groups). FIG. 50B displays a scanning fluorescence microscope image of a COC surface exposed to UV light through a photomask and subsequently reacted with amine terminated oligonucleotides (blue squares show the activated areas or those areas exposed to the UV radiation). FIG. 50C displays a bar graph indicating areas of the COC surface of non-UV activated areas (background) and UV activated areas of COC that were treated with an amine-terminated oligonucleotide bearing either Cy3, Cy5 or FAM labeling dye. FIG. 50D is the same as FIG. 50C except the COC surface was plasma treated.

Example 4—Evaluation of Cleavage Chemistry

Primer array #L2 (FIG. 51) was designed to evaluate the cleavage chemistry. Primers in columns 1 and 2 of the array layout have photocleavable linkers, which can be photocleaved by exposure to 365 nm UV light (see U.S. Pat. No. 7,057,031 to Olejnik et al., and Olejnik et al., "Photocleavable Biotin Derivatives: A Versatile Approach for the Isolation of Biomolecules," *Proc. Nat'l Acad. Sci. USA*, 92:7590-7594 (1995), which are hereby incorporated by reference in their entirety). Primers in columns 3, 4 and 5 of the array layout shown in FIG. 51 have dUTPs within their sequences, which can be enzymatically cleaved by USER™ (Uracil-Specific Excision Reagent) enzyme (NEB, Ipswich, Mass.) (U.S. Pat. No. 7,435,572 to Bitinaite et al., which is hereby incorporated by reference in its entirety). Primers in rows 1, 2, and 3 are the forward primer UniA, reverse primer UniC and the mixture of forward primer UniA and reverse primer UniC, respectively. Primers in control row 4 are 5'-Cy3-T20-amino-3', 5'-Cy5-T20-amino-3' and a non-related sequence 5'-amino-zip1, respectively.

The PCR mixture (75 µL) consisted of 3 µL of 1/100 diluted templates (UniA5-A1.10+UniC6-C4.1.), 1×Pyrophage 3137 PCR buffer (pH=8.8) with thermal protectant, 3 mM $MgSO_4$, 0.25 M Betaine, 400 µM of each dNTP, 0.2% ultrapure BSA and 0.1 U/µL Pyrophage 3137 exo-polymerase. PCR mixture (65 µL) was filled into a solid phase PCR reaction chamber assembled by sealing a 65 µL GeneFrame® (Abgene, Rochester, N.Y.) gasket to a Zeonor® 1420R COP slide immobilized with a combination of PCR primers (see Example 1). The PCR procedure included a pre-denaturation step at 91.5° C. for 20 seconds, followed by 40 cycles of thermal cycling with each cycle consisting of denaturation at 91.5° C. for 5 seconds and at 90° C. for 15 seconds, annealing at 52° C. for 5 seconds and 55° C. for 60 seconds, and extension at 70° C. for 5 seconds and at 68° C. for 60 seconds. The thermal cycling was performed using a TC-412 thermal cycler (Techne, Burlington, N.J.) equipped with a flat plate for in situ PCR. After thermal cycling, the Gene-Frame® gasket was removed and the COP slide was washed with 0.1% SDS for 5 minutes. A denaturation step was performed by incubating the COP slide in an ultra pure water bath at 97° C. for 1 minute. Successful solid phase PCRs were confirmed by multiple sequence specific hybridizations using fluorescent dye (Cy3) labeled probes (see FIG. 45).

Figures 52A, 52B, 52C, 52D:
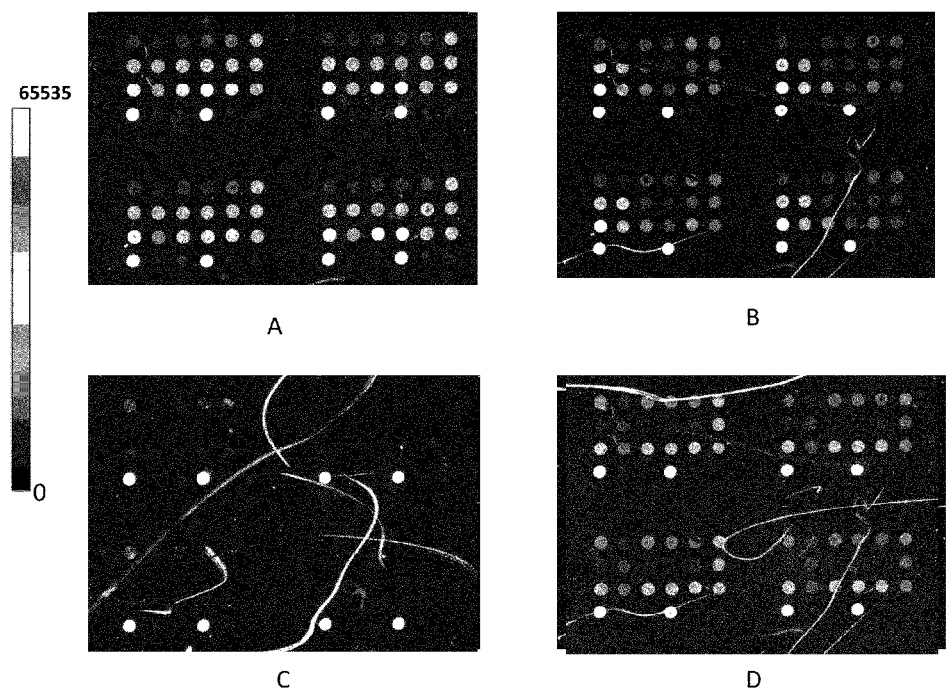
FIGS. 52A-52D are fluorescence images acquired after multiple steps of hybridization of probe sequences to array #L2.

The first hybridization step was performed by incubating the PCR amplified primer arrays in 50 µL of 100 nM forward primer (a mixture of 23For and 24ForB, see FIG. 45) in 8×SSC buffer at 65° C. for 90 minutes. After hybridization, the COP slide was rinsed briefly in 4×SSC and washed in 2×SSC and 0.1% SDS at 60° C. for 5 minutes. Fluorescence images were acquired using a ScanArray Express® (Perkin Elmer, Boston, Mass.) microarray scanner and are shown in FIG. 52A. Fluorescence signals were observed from spots in rows 2 and 3, resulting from the hybridization of the Cy3 labeled forward probe to surface bound PCR products extended from the reverse primers. Fluorescence signals from spots in row 3 (mixture of forward primer UniA and reverse primer UniC) were higher than those from spots in row 2 (reverse primer UniC only), indicating that successful surface amplification generated significantly larger amounts of products than did surface extension only. Surface extension is a process in which only surface immobilized primers are extended by the polymerase when DNA templates in solution repeatedly hybridize to them. Surface amplification is a process in which surface bound replicas of DNA templates can hybridize to immobilized primers in their vicinity and form additional replicas of DNA templates. Successful surface amplification is crucial for generating clonal amplification clusters for subsequent sequencing.

The second hybridization step was performed after the removal of the reverse strands of the PCR products by cleaving the dUTPs in the reverse primers using USER™ (Uracil-Specific Excision Reagent) enzyme (NEB, Ipswich, Mass.). USER™ enzyme is a mixture of uracil DNA glycosylase (UDG) and the DNA glycosylase-lyase Endonuclease VIII. UDG catalyses the release of free uracil from uracil-containing DNA, forming an abasic (apyrimidinic) site while leaving the phosphodiester backbone intact. The lyase activity of Endonuclease VIII breaks the phosphodiester backbone at the 3' and 5' sides of an abasic site so that base-free deoxyribose is released. The USER™ cleavage was performed by incubating the arrays in 50 µL of 2×TE buffer containing 2 µL of USER™ enzyme (1 U/µL) at 37° C. for 15 minutes. Following a denaturation step by incubating the COP slide in an ultra pure water bath at 97° C. for 1 minute, the hybridization, washing and imaging followed the same procedures described in the forward probe hybridization with the resulting fluorescence image shown in FIG. 52B. The fluorescence signals from spots in rows 2 and 3, columns 3 to 5 decreased significantly compared to those from the same spots in FIG. 52A, indicating successful removal of reverse strands of PCR products through the enzymatic cleavage of dUTPs.

The third hybridization step was performed after the removal of the reverse strands of the PCR products by cleaving the photocleavable linkers in the reverse primers using UV illumination. The photocleavage was performed by exposing the arrays to 365 nm UV light for 10 minutes using a CL-1000 UV Crosslinker (UVP, Cambridge, England). Following a denaturation step by incubating the COP slide in an ultra pure water bath at 97° C. for 1 minute, the hybridization, washing, and imaging following procedures described in the first hybridization with the resulting fluorescence image shown in FIG. 52C. The fluorescence signals from spots in rows 2 and 3, columns 1 and 2 decreased significantly compared to those from the same spots in FIG. 52A, indicating successful removal of reverse strands of the PCR products by photo cleavage of the photocleavable linkers.

Following a denaturation step by incubating the COP slide in an ultra pure water bath at 97° C. for 1 minute, a final hybridization, washing, and imaging steps followed the procedures described in the first hybridization except that the reverse hybridization probes (23Rev and 24RevB, see FIG. 45) were used to replace the forward hybridization probes. The fluorescence image is shown in FIG. 52D. Fluorescence signals were observed for spots in rows 1 and 3, resulting from the hybridization of the cy3 labeled reverse probes to the surface bound PCR products extended from the forward primers. The fluorescence intensities from spots in FIG. 52D were only slightly lower than those from the spots shown in FIG. 52A, indicating significant amounts of surface bound DNA replicas were intact after multiple steps of denaturation, hybridization, and cleavage. Fluorescence signals from spots in row 3 (mixture of forward primer UniA and reverse primer UnivC) were higher than those from spots in row 2 (forward primer UniA only) indicating that successful surface amplification generated a significantly greater amount of PCR products then did surface extension.

Example 5—Evaluation of Hairpin/Mismatch and Hairpin/Extension Primers

Primer array #10E, as shown in FIG. 53, was designed to evaluate primer hairpin/extension design. Primers in rows 1, 2 and 3 are regular PCR primers, hairpin/mismatch primers and hairpin/extension primers, respectively. Primers in columns 1 to 6 are forward primer only (column 1), reverse primer only (column 2), mixture of forward and reverse primers (column 3), mixture of forward, reverse and B primers (column 4), mixture of forward, reverse, and D primers (column 5), and mixture of forward, reverse, B, and D primers (column 6). All reverse primers and D primers have photocleavable linkers, which can be photocleaved by 365 nm UV light. Primers in control row 4 are 5'-Cy3-T20-amino-3', 5'-Cy5-T20-amino-3' and a non-related sequence 5'-amino-zip1, respectively.

The PCR reaction mixture (75 μL) consisted of 3 μL of 1/100 diluted templates (UniA23-A1.10+UniC24-C2.1), 1×Pyrophage 3137 PCR buffer (pH=8.8) with thermal protectant, 3 mM MgSO$_4$, 0.25 M Betaine, 400 μM of each dNTP, 0.2% ultrapure BSA and 0.1 U/μL Pyrophage 3137 exo-polymerase. PCR mixture (65 μL) filled a solid phase PCR reaction chamber assembled by sealing a 65 μL Gene-Frame® (Abgene, Rochester, N.Y.) gasket to a Zeonor® 1420R COP slide immobilized with a combination of PCR primers (Example 1). The PCR procedure included a pre-denaturation step at 91.5° C. for 20 seconds, followed by 40 cycles of thermal cycling with each cycle consisting of denaturation at 91.5° C. for 5 seconds and at 90° C. for 15 seconds, annealing at 52° C. for 5 seconds and at 55° C. for 60 seconds, and extension at 70° C. for 5 seconds and at 68° C. for 60 seconds. The thermal cycling was performed using a TC-412 thermal cycler (Techne, Burlington, N.J.) equipped with a flat plate for in situ PCR. After thermal cycling, the Gene-Frame® gasket was removed and the COP slide was washed with 0.1% SDS for 5 minutes. Then, a denaturation step was performed by incubating the COP slide in an ultra pure water bath at 97° C. for 1 minute. Successful solid phase PCR was confirmed by multiple sequence specific hybridizations using fluorescent dye (Cy3) labeled probes (FIG. 45).

Figures 54A, 54B, 54C:
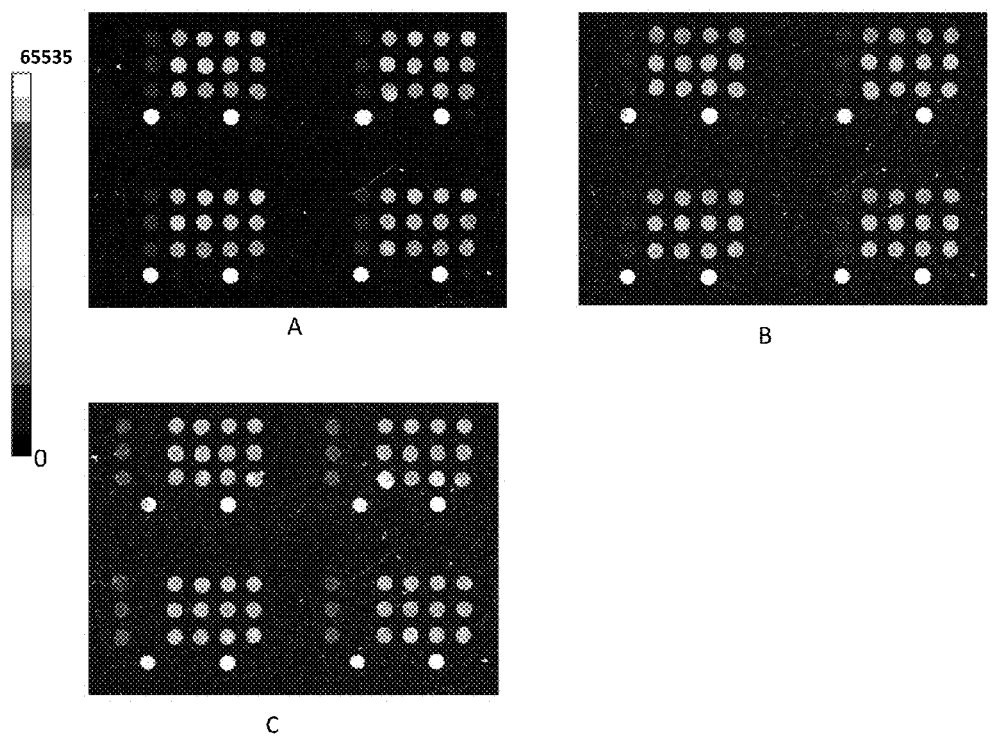
FIGS. 54A-54C are fluorescence images acquired after multiple steps of hybridization of probe sequences to array #10E.
Figure 55C:
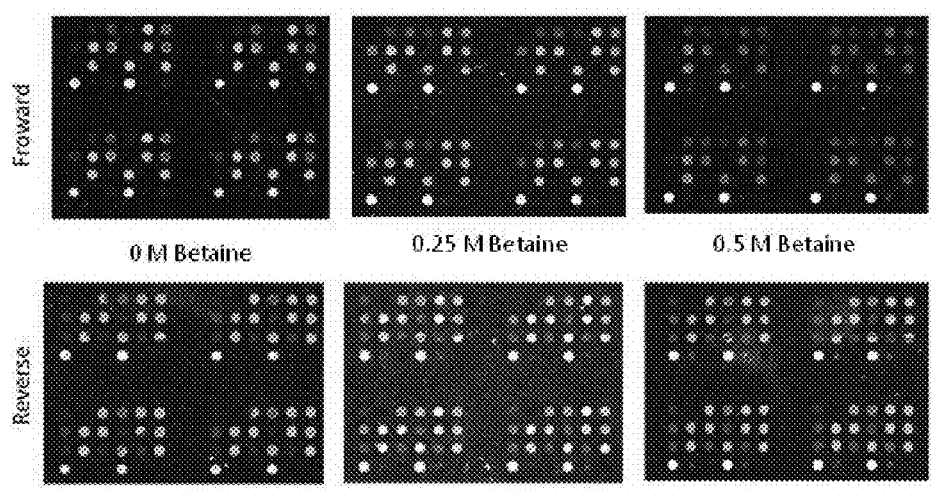

The first hybridization step was performed by incubating the PCR amplified arrays in 50 μL of 100 nM forward primers (a mixture of 23For and 24ForB, see FIG. 45) in 8×SSC buffer at 65° C. for 90 minutes. After hybridization, the COP slide was rinsed briefly in 4×SSC and washed in 2×SSC, 0.1% SDS at 60° C. for 5 minutes. The fluorescence image was acquired using a ScanArray Express® (Perkin Elmer, Boston, Mass.) microarray scanner and is shown in FIG. 54A. Fluorescence signals were observed from spots in columns 2 to 6, resulting from the hybridization of cy3 labeled forward probes to the PCR product extended from the reverse primers. Fluorescence signals from spots in columns 3 to 6 (mixture of forward primer UniA, reverse primer UniC, and B and/or D primers) were much higher than those from spots in column 2 (reverse primer UniC only) indicating that successful surface amplification generated significantly more PCR products than did surface extension. Fluorescence intensities from spots in rows 2 and 3 were higher than those from spots in row 1, indicating the hairpin design facilitates the surface amplification compared to PCR primers not containing these hairpin structures. Fluorescence intensities from spots in row 3 were higher than those from spots in row 2, indicating that hairpin/extension design facilitates surface amplification compared to hairpin/mismatch design under these conditions.

The second hybridization step was performed after the removal of reverse strands of the PCR products by cleaving photocleavable linkers in the reverse primers using UV illumination. The photocleavage was performed by exposing the arrays to 365 nm UV light for 10 minutes using CL-1000 UV Crosslinker (UVP, Cambridge, England). Following a denaturation step by incubating the COP slide in an ultra pure water bath at 97° C. for 1 minute, the hybridization, washing and imaging steps followed the procedures described in the first hybridization. The fluorescence image is shown in FIG. 54B. The overall fluorescence signals decreased significantly compared to those in FIG. 54A, indicating successful removal of reverse strands of PCR products by photocleavage of photocleavable linkers.

Following a denaturation step by incubating the COP slide in an ultra pure water bath at 97° C. for 1 minute, the third hybridization, washing, and imaging steps followed the procedure described in the first hybridization except that the reverse hybridization probes (23Rev and 24RevB, see FIG. 45) were used in place of the forward hybridization probes. The fluorescence image is shown in FIG. 54C. Fluorescence signals were observed from spots in columns 1 and 3 to 6, resulting from the hybridization of Cy3 labeled reverse probes to the PCR product extended from the forward primers. Fluorescence signals from spots in columns 3 to 6 (mixture of forward primer UniA, reverse primer UnivC, and B and/or D primers) were much higher than those from spots in column 1 (forward primer UniA only) indicating that successful surface amplification generated significantly more PCR products than did surface extension. The overall fluorescence intensities from spots in FIG. 54C were comparable to those from spots in FIG. 54A, indicating significant amounts of surface bound DNA replicas were intact after the multiple step procedure of denaturation, hybridization and cleavage.

Example 6—Evaluation of the Structures and Position of Hairpin Primers on Amplification Primer array #14G was designed to evaluate a variety of primer hairpin design structures at different locations and of different lengths (FIGS. 55-59). FIGS. 55-59 differ in array layout with regard to control well placement (compare FIGS. 55 and 56). All reverse primers have a dUTP in their sequence, which can be enzymatically cleaved by USER™ (Uracil-Specific Excision Reagent) enzyme (NEB, Ipswich, Mass.). Primers in the control row are 5'-Cy3-T20-amino-3', 5'-Cy5-T20-amino-3' and a non-related sequence 5'-amino-zip1, respectively.

The PCR reaction mixture (75 μL) consisted of 3 μL of a 1/1000 dilution of input templates (UniA5-A1.10+UniC6-C4.1.), 1×Pyrophage 3137 PCR buffer (pH=8.8) with thermal protectant, 3 mM MgSO$_4$, 400 μM of each dNTP, 0.2% ultrapure BSA, 0.1 U/μL Pyrophage 3137 exo-polymerase, and different concentrations of Betaine (0 M, 0.25 M, and 0.5 M). Sixty-five μL of PCR mixture was filled into a solid phase PCR reaction chamber assembled by sealing a 65 μL Gene-Frame® (Abgene, Rochester, N.Y.) gasket to a COP slide immobilized with different combinations of PCR primers (see Example 1). The PCR procedure included an initial hybridization/extension step consisting of 2 cycles of denaturation at 91.5° C. and hybridization/extension at 55° C. for 15 minutes followed by 40 cycles of thermal cycling with each cycle consisting of denaturation at 91.5° C. for 5 seconds and at 90° C. for 15 seconds, annealing at 52° C. for 5 seconds and at 55° C. for 60 seconds and extension at 70° C. for 5 seconds and at 68° C. for 60 seconds. The thermal cycling was performed using a TC-412 thermal cycler (Techne, Burlington, N.J.) equipped with a flat plate for in situ PCR. After thermal cycling, the Gene-Frame® gasket was removed and the COP slide was washed with 0.1% SDS for 5 minutes. Then, a denaturation procedure was performed by incubating the COP slide in an ultra pure water bath at 97° C. for 1 minute. Successful solid phase PCR was confirmed by multiple sequence specific hybridizations using fluorescent dye (Cy3) labeled probes (see FIG. 45).

The first hybridization step was performed by incubating the PCR amplified arrays in 50 µL of 100 nM forward primers (a mixture of 23For and 24ForB, see FIG. 45) dissolved in 8×SSC buffer at 65° C. for 90 minutes. After hybridization, the COP slide was rinsed briefly in 4×SSC and washed in 2×SSC, 0.1% SDS at 60° C. for 5 minutes. The fluorescence image was acquired by a ScanArray Express® (Perkin Elmer, Boston, Mass.) microarray scanner and was quantified using ScanArray Express software. FIG. 55B shows the results of hybridization of the forward probe (schematic of array layout shown in FIG. 55A). The intensity of signal is displayed by color: weak (blue, green, yellow, orange, red, white) saturation The results demonstrate that the SnakeHE primer design (spots 8, 11, 14, 16, & 18) gives stronger signal than the Snake primer design (spot 5), or standard PCR primer design (spot 3). Further, in contrast to the liquid results, use of the B11 primer does not improve yields (spot 4, 6, 9, & 12).

Figures 57A, 57B:
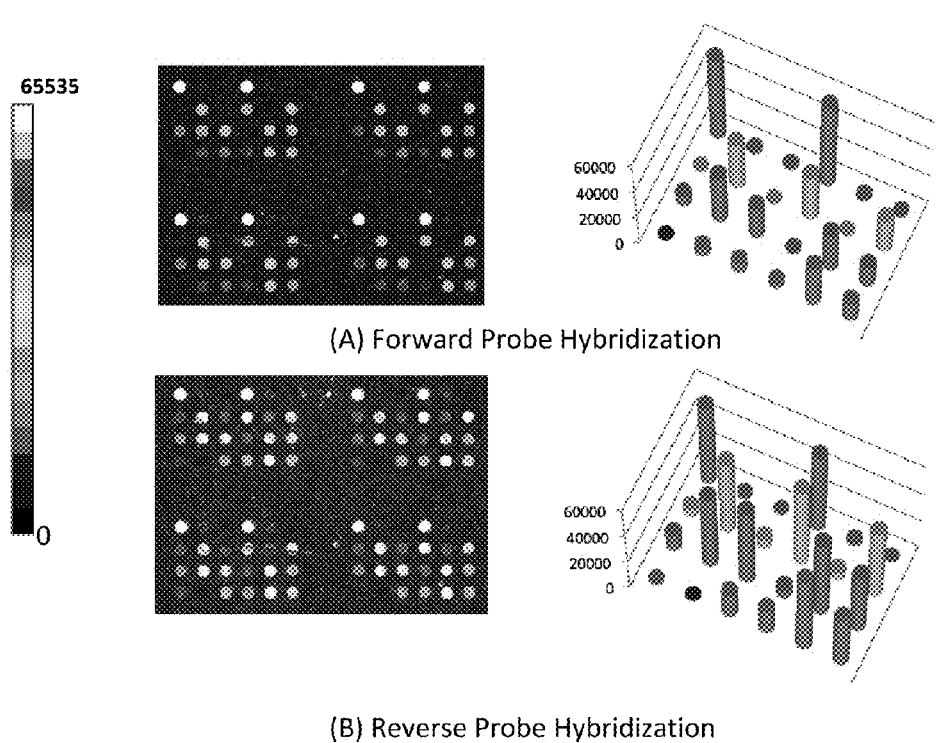
FIGS. 57A-57B show the fluorescence images and the quantification results of forward probe (FIG. 57A) and reverse probe (FIG. 57B) hybridization following solid phase amplification on COC substrate.
Figure 58A:
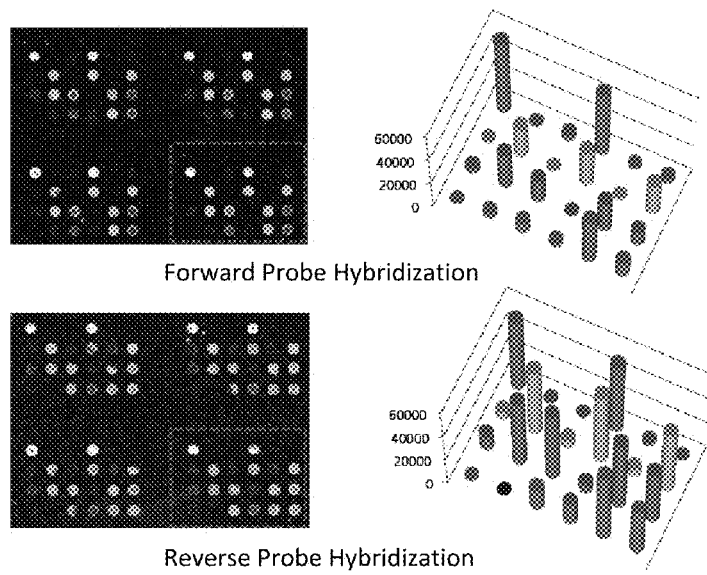
Figure 58B:
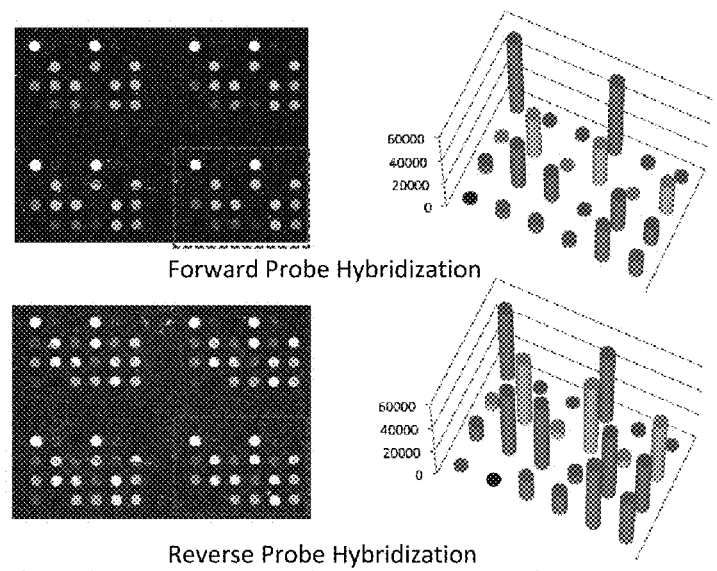
Figure 59A:
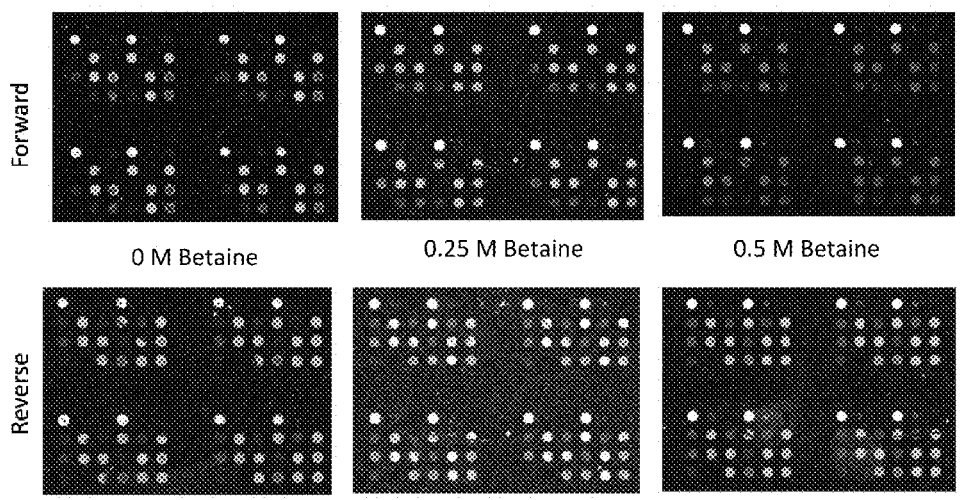

The second hybridization step was carried out after the reverse strand of the PCR product extended from the primers containing dUTPs were cleaved by USER™ (Uracil-Specific Excision Reagent) enzyme (NEB, Ipswich, Mass.). The USER™ cleavage was performed by incubating the arrays in 50 µL of 2×TE buffer containing 2 µL of USER™ enzyme (1 U/µL) at 37° C. for 15 minutes. Following a denaturation step by incubating the COP slide in an ultra pure water bath at 97° C. for 1 minute, hybridization, washing and imaging following procedures described in the first hybridization example except that the reverse hybridization probes (23Rev and 24RevB, see FIG. 45) were used to replace the forward hybridization probes. The fluorescence image and the quantification results are shown in FIG. 57A (forward probe) and FIG. 57B (reverse probe) (array layout shown in FIG. 56).

The above results are extended to demonstrate excellent yields in amplification, when hybridizing with both the forward and reverse strands. Results on the solid surface using different concentrations of betaine demonstrate that 0.25M betaine provided the highest yields (FIG. 58B) compared to 0M (FIG. 58A) and 0.5M betaine (FIG. 58C) (see also FIG. 55C), in several cases saturating the detector at those positions. Quantitation of the spotted arrays that were subjected to solid phase PCRs using 0 M, 0.25 M and 0.5 M betaine concentrations (arrays shown in FIGS. 58A-58C and 59A) generated the fluorescent intensity data provided in FIG. 59B. These results verify the best yields for solid surface amplification were when using the Snake HE design, and the exact nature of the primer sequence and distance between the A and B sequence has some influence on yield.

Example 7—Extensions/Terminations with Cy5 Labeled ddGTP

Primer array #14G-2 is shown in FIG. 60. All reverse primers had a dUTP in its sequence, which allowed it to be enzymatically cleaved by USER™ (Uracil-Specific Excision Reagent) enzyme (NEB, Ipswich, Mass.). Primers in the control row were 5'-Cy3-T20-amino-3', a non-related sequence 5'-amino-zip3 and Temp4.1. The PCR reaction mixture (75 µL) consisted of 3 µL of 1/1000 diluted templates (UniA5-A1.10+UniC6-C4.1.), 1×Pyrophage 3137 PCR buffer, pH=8.8) with thermal protectant, 0.25 M betaine, 3 mM MgSO$_4$, 400 µM of each dNTP, 0.2% ultrapure BSA and 0.1 U/µL Pyrophage 3137 exo-polymerase. Sixty-five µL of the PCR mixture was filled into a solid phase PCR reaction chamber assembled by sealing a 65 µL Gene-Frame® (Abgene, Rochester, N.Y.) gasket to a COP slide immobilized with different combinations of PCR primers (Example 1). The PCR procedure included an initial hybridization/extension step consisting of 2 cycles of denaturation at 91.5° C. and hybridization/extension at 55° C. for 15 minutes, followed by 40 cycles of thermal cycling with each cycle consisting of denaturation at 91.5° C. for 5 seconds and at 90° C. for 15 seconds, annealing at 52° C. for 5 seconds and at 55° C. for 60 seconds and extension at 70° C. for 5 seconds and at 68° C. for 60 seconds. The thermal cycling was performed using a TC-412 thermal cycler (Techne, Burlington, N.J.) equipped with a flat plate for in situ PCR. After thermal cycling, the Gene-Frame® gasket was removed and the COP slide was washed with 0.1% SDS for 5 minutes.

The reverse strands of the PCR product extended from the primers containing dUTPs were cleaved by USER™ (Uracil-Specific Excision Reagent) enzyme (NEB, Ipswich, Mass.). The USER™ cleavage was performed by incubating the arrays in 50 µL of 2×TE buffer containing 2 µL of USER enzyme (1 U/µL) at 37° C. for 15 minutes. After cleavage, the reverse strand was denatured by incubating the COP slide in an ultra pure water bath at 97° C. for 1 minute.

The extension mixture (25 µL) consisted of 1× ThermoPol Reaction Buffer (20 mM Tris-HCl, 10 mM (NH$_4$)$_2$SO$_4$, 10 mM KCl, 2 mM MgSO$_4$, 0.1% Triton X-100, pH 8.8 @ 25° C.), 2U Therminator™ II DNA Polymerase (NEB, Ipswich, Mass.), 1 µM 5'-Cy3-23R extension primer, 1 µM Cy5-ddGTP and either with or without 5 µM dTTP. Gardner and Jack, "Determinants of Nucleotide Sugar Recognition in an Archaeon DNA Polymerase," *Nucleic Acids Research*, 27:2545-2553 (1999); Gardner and Jack, "Acyclic and Dideoxy Terminator Preferences Denote Divergent Sugar Recognition by Archaeon and Taq DNA Polymerases," *Nucleic Acids Research*, 30:605-613 (2002); and Seo et al., "Four-Color DNA Sequencing by Synthesis on a Chip Using Photocleavable Fluorescent Nucleotides," *Proc. Nat'l Acad. Sci.*, 102:5926-5931 (2005), which are hereby incorporated by reference in their entirety.

The template and primer sequences are:

```
Template:
                                        (SEQ ID NO: 29)
3'. . . CGGAGTGTTGGAGGCAGTACACGACACT. . .5'

Primer(23R)
                                        (SEQ ID NO: 30)
5'-Cy3-GCCTCACAACCTCCGTCATGTGCTG
```

Figures 61A, 61B:
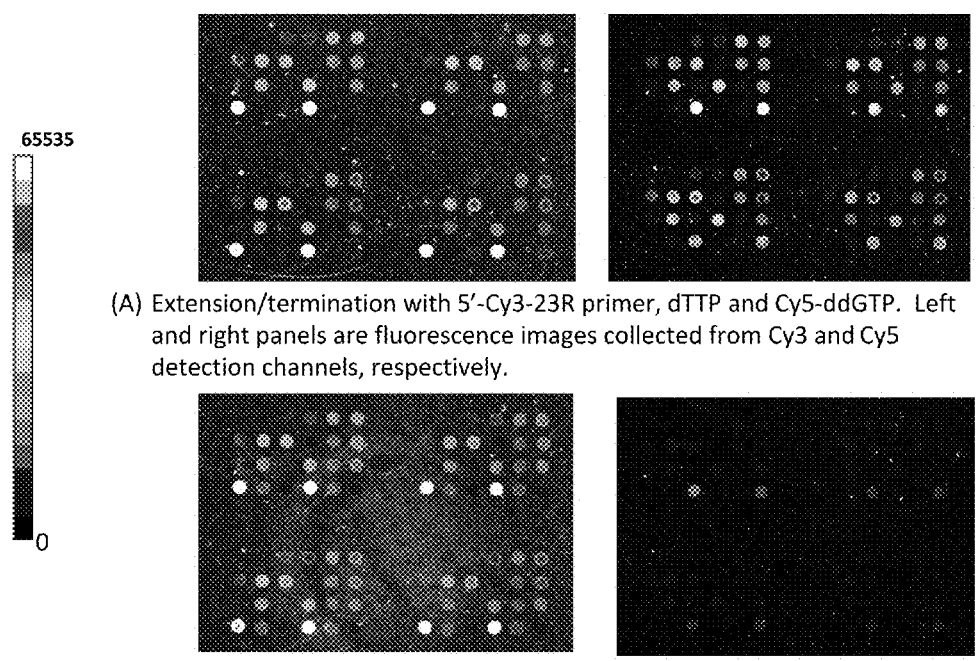
FIGS. 61A-61B are fluorescence images acquired after extension/termination reactions.

The first extension base is T and the second extension/termination base is G (underlined). The extension/termination results are shown in FIGS. 61A-61B. When the extension/termination mixture contained both dTTP and Cy5-ddGTP, fluorescence signals were observed in both the Cy3 channel (from primer) and the Cy5 channel (from extension/termination) as shown in FIG. 61A. When the extension/termination mixture contained Cy5-ddGTP only (no dTTP), fluorescence signals were observed in the Cy3 channel (from primer) but were barely seen in the Cy5 channel (from extension/termination) as shown in FIG. 61B. These results indicated that the surface amplified PCR products could be successfully used in sequence specific extension/termination reactions.

Example 8—SU-8 Micropillar Fabrication

SU-8 2005 micropillars were fabricated on a 500 μm thick quartz substrate, using front or back (via Cr mask) SU-8 exposure. The SU-8 fabrication process followed the following procedure: Approximately 5 mL of SU-8 was applied to a quartz wafer. Spin coating was performed at 2,000 rpm for 30 seconds resulting in a film thickness of ~4.9±0.2 μm. A pre-bake step was carried out for 1 min at 70° C. and 2 min at 100° C. on a hotplate. The substrates were exposed in a mask aligner through the optical mask at 110-130 mJ/cm². A post-exposure bake was performed with the same parameters as for the pre-bake, the wafers were developed in SU-8 developer for 2 min and rinsed with isopropyl alcohol. To allow for final cross-linking and to eliminate residual solvent, a hard-bake step was carried out at 150° C. for 10 min. Resulting structures consisted of an array (4×4 mm) of pillars in 128 squares as shown in FIG. 15C. Each square area contained 1 million 2×5 μm pillars as shown in the SEM images of FIGS. 15A and 15B.

Example 9—Oligonucleotide Attachment to SU-8 Surfaces

Figures 62A, 62B:
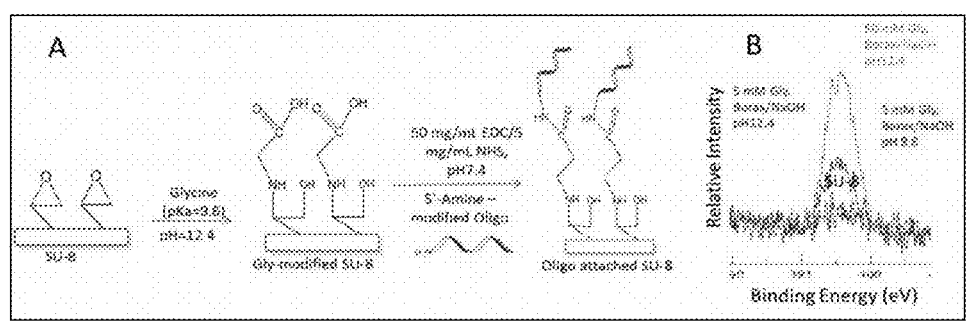
FIGS. 62A-62B show oligonucleotide attachment to SU-8 surfaces utilizing free epoxy rings present on the SU-8 surface.
Figure 63A:
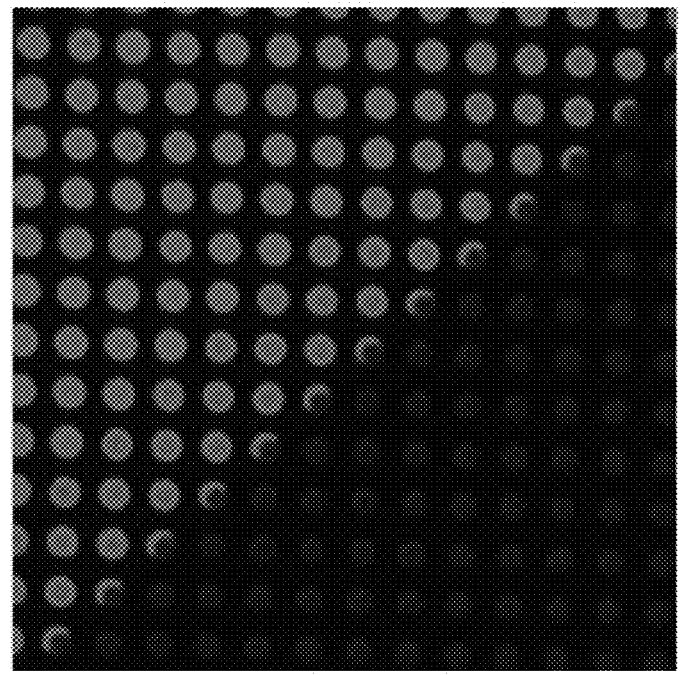
FIG. 63A shows a confocal fluorescence image of Cy-3/NH$_2$-modified oligonucleotides covalently attached to SU-8 micropillars via the glycine cross-linker.
Figure 63B:
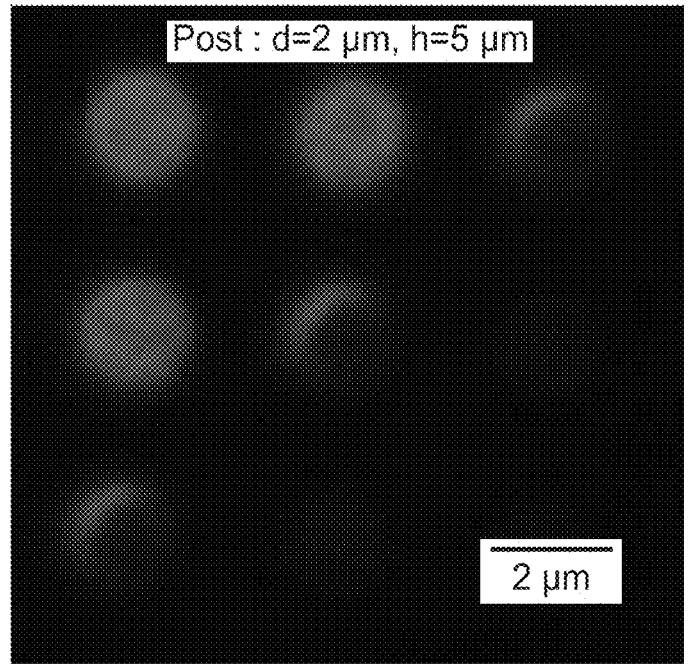
FIG. 63B shows another confocal fluorescence image of Cy-3/NH$_2$-modified oligonucleotides covalently attached to SU-8 micropillars via the glycine cross-linker.

Various attachment chemistries were tested for attachment of oligonucleotides to the SU-8 surfaces. The first of these involved direct attachment via condensation of primary amine groups with the free epoxy rings present on SU-8. This method uses amine-modified oligonucleotide for covalent attachment. Alternatively, oligonucleotide attachment was achieved using glycine or alanine as a cross-linker and amine-modified oligonucleotides as shown in the schematic of FIG. 62A. X-ray photoelectron spectroscopy results of pristine and glycine modified SU-8 attachment is shown in FIG. 62B. FIG. 63A-63B show confocal fluorescence images of Cy3 $NH_2$ modified oligonucleotides attached to SU-8 micropillars via the glycine crosslinker.

Oligonucleotide attachment to the SU-8 surface was also achieved using amine PEG Carboxyl $NH_2$-$(PEG)_4COOH$ as crosslinker and an amine modified primer. $NH2$-$(PEG)_4$ COOH (1-2 mM) in 0.2 M $Na_2CO_3$ (pH 11.4) was attached to the SU-8 either flat or posted surface, followed by EDC/NHS coupling of amine-modified primers to the NHS ester.

Figure 64A:
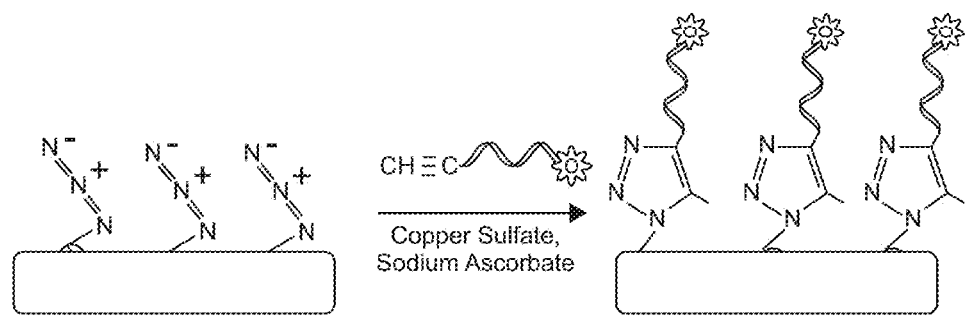
FIGS. 64A-64B show oligonucleotide attachment to SU-8 surface utilizing click chemistry.
Figure 64B:
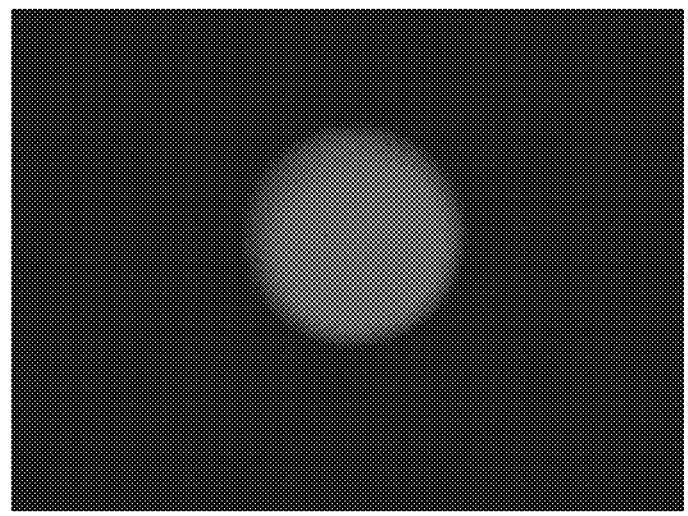

Finally, oligonucleotide attachment to SU-8 surface can be achieved utilizing Click Chemistry via amine-PEG-azide as crosslinker and Hexynyl modified oligonucleotide (see schematic of FIG. 64A). SU-8 was modified with (1 mM) $NH_2$-$(PEG)_4$-$N_3$ in 0.2 M $Na_2CO_3$ (pH 11.4) while Hexynyl-modified oligonucleotides were attached to the surface (50 μM) in $Cu^{+2}$ and sodium ascorbate. The excess of surface azides are blocked with L-homopropargylglycine (HPG) in $Cu^{+2}$ and sodium ascorbate solution. FIG. 64B is a confocal fluorescence image of Cy3-labeled oligonucleotide attached to SU-8 micropillars surface via "click chemistry".

Figure 65:
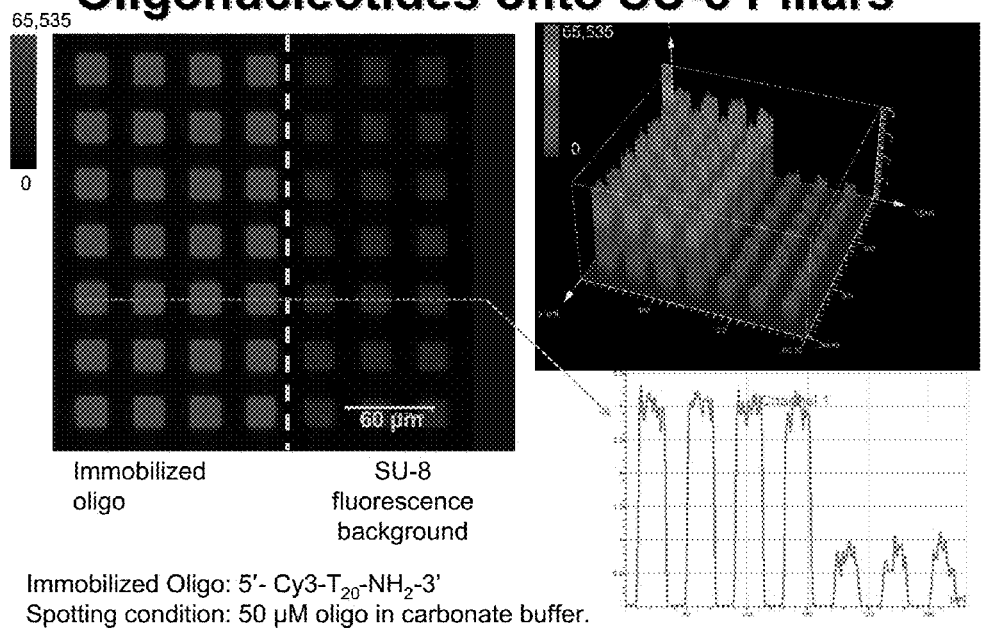
FIG. 65 show the immobilization of Cy-3 labeled oligonucleotides onto SU-8 pillars of a device of the present invention.
Figure 66:
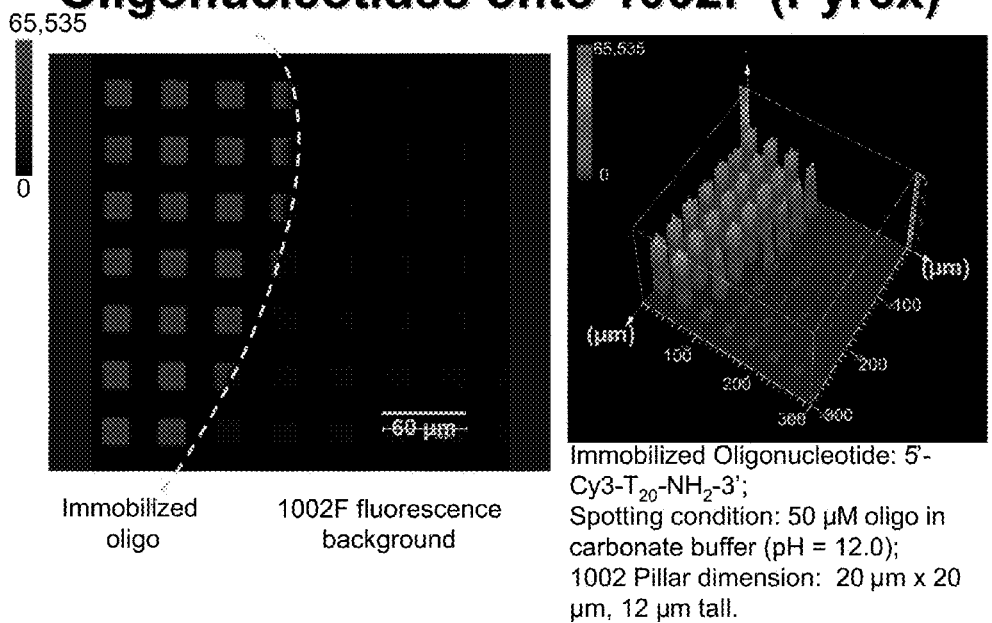
FIG. 66 shows the covalent immobilization of Cy-3 labeled oligonucleotides onto 1002F pillars of a device of the present invention.
Figure 67:
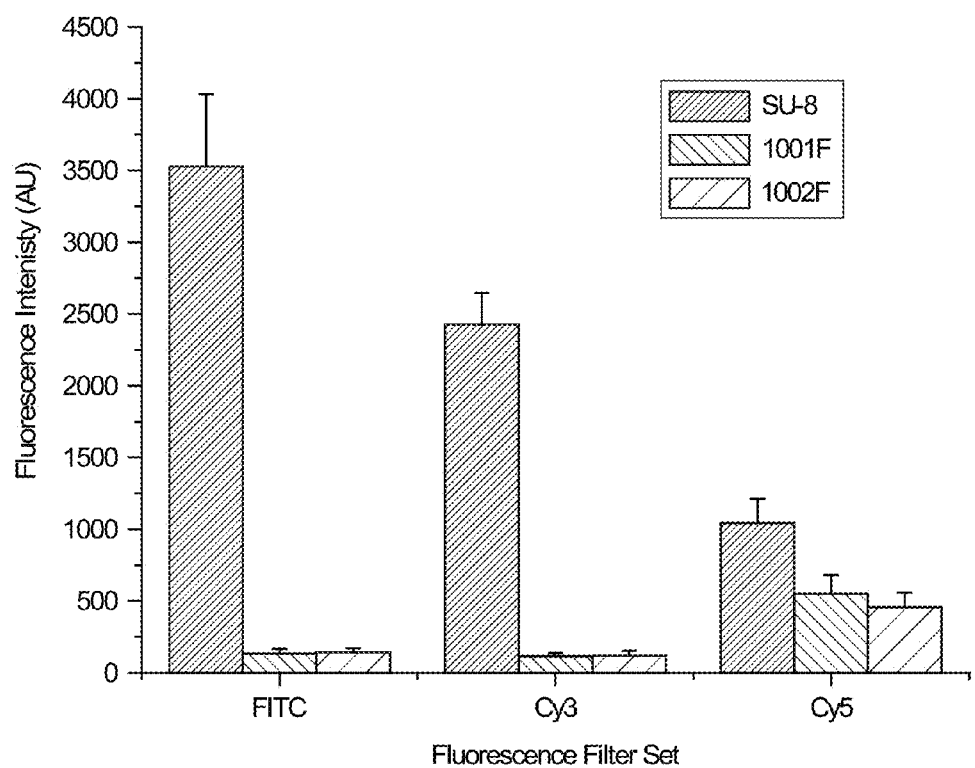
FIG. 67 is a graph showing the background fluorescence levels of SU-8, 1001F, and 1002F photoresists.

FIGS. 65 and 66 show the immobilization of cy3-labeled oligonucleotides onto SU-8 and 1002F pillar surfaces, respectively. SU-8 displays autofluorescence, especially when excited at an excitation wavelength appropriate for Cy3 type fluorescent labels, as seen in the fluorescence images of FIG. 65 (right side of each image). However, other negative tone resists can be used, such as 1001F and 1002F, that show similar properties as SU-8, but do not display autofluorescence. FIG. 67 is a graph showing a comparison of background fluorescence levels of SU-8, 1001F, and 1002F. 1001F and 1002F are also commercially available epoxide-based negative tone resists. Both materials can be functionalized in similar fashions as SU-8.

Example 10—Clonal Amplification on COC Surface and SU-8 Micropillars

The primers $NH_2$-T20-spacer-B5-UniA5HE and $NH_2$-T20-spacer-UniC6dU, each at 50 μM, were spotted onto the activated COC surface. $NH_2$-T20-spacer-UniC6dU had a dUTP in its sequence, which could be enzymatically cleaved by USER™ (Uracil-Specific Excision Reagent) enzyme (NEB, Ipswich, Mass.).

Figure 68A:
FIGS. 68A-68B are fluorescence micrographs showing solid phase amplification on COC surfaces.
Figure 68B:

The initial hybridization/extension consisted of 2 cycles of denaturation at 91.5° C. and hybridization/extension at 55° C. for 15 min in a PCR reaction mixture (75 μL) consisting of 3 μL of 1/1000 and 1/10,000 diluted templates (UniA5-A1.10+UniC6-C4.1.), 1×Pyrophage 3137 PCR buffer(pH=8.8) with thermal protectant, 3 mM $MgSO_4$, 400 μM of each dNTP, 0.2% ultrapure BSA, 0.25M Betaine and 0.1 U/μL Pyrophage 3137 exo-polymerase. Sixty-five μL of the PCR mixture was filled into a solid phase PCR reaction chamber assembled by sealing a 65 μL Gene-Frame® (Abgene, Rochester, N.Y.) gasket. The solid phase amplification was performed in the same PCR mixture except that no template was added. Forty-cycles of thermal cycling consisted of denaturation at 91.5° C. for 5 s and at 90° C. for 15 s, annealing at 52° C. for 5 s and at 55° C. for 60 s, and finally, extension at 70° C. for 5 s and at 68° C. for 60 s. The thermal cycling was performed using a TC-412 thermal cycler (Techne, Burlington, N.J.) equipped with a flat plate for in situ PCR. After thermal cycling, the Gene-Frame® gasket was removed and the COC slide was washed with 0.1% SDS for 5 min. Then, a denaturation procedure was performed by incubating the COC slide in ultrapure water at 97° C. for 1 min. Following a USER™ (Uracil-Specific Excision Reagent; NEB, Ipswich, Mass.) cleavage step, the hybridization step was performed by incubating the PCR amplified arrays in 50 μL of 100 nM forward probing primer (a mixture of 23F and 24F, see FIG. 45) dissolved in 8×SSC buffer at 65° C. for 90 min. After hybridization, the COC slide was rinsed briefly in 4×SSC and washed in 2×SSC, 0.1% SDS at 60° C. for 5 min. The fluorescence images were acquired using an epi-fluorescence microscope and are shown in FIGS. 68A and 68B. The formation of clusters on the surface and the reduced numbers of clusters from 10e3 to 10e4 dilution were observed (compare FIGS. 68A and 68B, respectively), which indicated clonal surface amplification.

A mixture of primers $NH_2$-T20-spacer-B5-UniA5HE and $NH_2$-T20-spacer-UniC6dU, each at 50 μM, were spotted on $NH_2$—$PEG_4$-COOH (Pierce Inc) modified SU-8 pillars fabricated on a quartz plate. $NH_2$-T20-spacer-UniC6dU had a dUTP in its sequence, which could be enzymatically cleaved by USER™ (Uracil-Specific Excision Reagent) enzyme (NEB, Ipswich, Mass.).

Figure 69A:
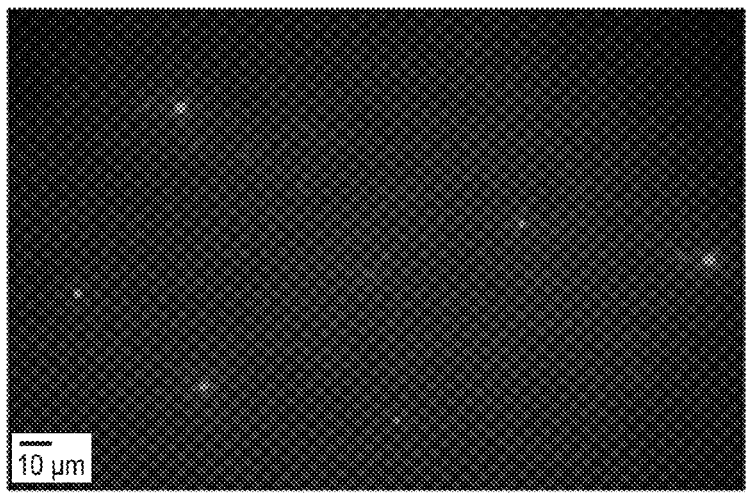
FIGS. 69A-69C show surface amplification of DNA templates from SU-8 micropillars patterned photolithographically on a quartz substrate.
Figure 69B:
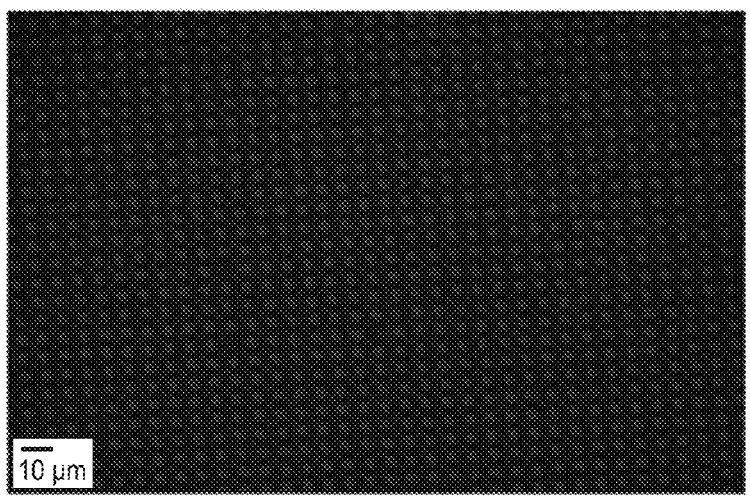
Figure 69C:
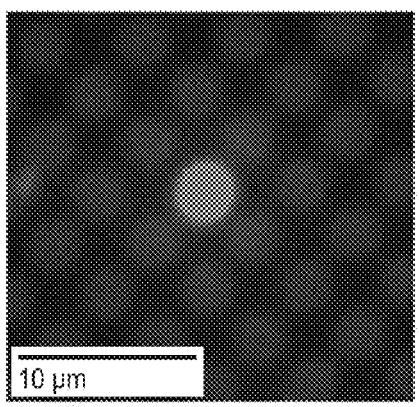

The initial hybridization/extension consisted of 2 cycles of denaturation at 91.5° C. and hybridization/extension at 55° C. for 15 min in a PCR reaction mixture (25 μL) consisting of 1 μL of 1/10e7 diluted templates (UniA5-A1.10+UniC6-C4.1.), 1×Pyrophage 3137 PCR buffer (pH=8.8) with thermal protectant, 3 mM $MgSO_4$, 400 μM of each dNTP, 0.2% ultrapure BSA, 0.25M Betaine and 0.1 U/μL Pyrophage 3137 exo-polymerase. Twenty-five μL of PCR mixture was filled into a solid phase PCR reaction chamber assembled by sealing a 25 µL Gene-Frame® (Abgene, Rochester, N.Y.) gasket to the quartz plate containing the SU-8 pillars. The solid phase amplification was performed in the same PCR mixture except that no template was added. Forty-cycles of thermal cycling consisted of denaturation at 91.5° C. for 5 s and at 90° C. for 15 s, annealing at 52° C. for 5 s and at 55° C. for 60 s, and extension at 70° C. for 5 s and at 68° C. for 60 s. The thermal cycling was performed using a TC-412 thermal cycler (Techne, Burlington, N.J.) equipped with a flat plate for in situ PCR. After thermal cycling, the Gene-Frame® gasket was removed and the slide was washed with 0.1% SDS for 5 min. Then, a denaturation procedure was performed by incubating the quartz slide containing the SU-8 micropillars in ultra pure water at 97° C. for 1 min. Following a USER™ cleavage step, the hybridization step was performed by incubating the PCR amplified arrays in 50 µL of 100 nM forward probing primers (a mixture of 23F and 24F, see table x) dissolved in 8×SSC buffer at 65° C. for 90 min. After hybridization, the quartz slide containing the SU-8 micropillars was rinsed briefly in 4×SSC and washed in 2×SSC, 0.1% SDS at 60° C. for 5 min. The fluorescence images were acquired using an epi-fluorescence microscope and are shown in FIGS. 69A and 69C. The randomly bright microposts indicated that each micropost served as a microreactor for clonal surface amplification. No fluorescence signal was observed after a denaturation procedure as shown in FIG. 69B.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for identifying one or more of a plurality of target nucleotide sequences in a sample comprising:
providing a sample potentially containing one or more target nucleotide sequences and/or complements thereof, each target nucleotide sequence comprising a first, second, and third target portion, wherein the second target portion is between the first and third target portions;
providing one or more oligonucleotide primer sets, each set characterized by (a) a first oligonucleotide primer comprising a first primer portion complementary to the first target portion and a second primer portion that is the same as the second target portion, wherein the second primer portion is 5' to the first primer portion, and (b) a second oligonucleotide primer comprising a third primer portion that is the same as the third target portion;
providing a first polymerase;
blending the sample, the oligonucleotide primer sets, and the first polymerase to form a polymerase extension reaction mixture;
subjecting the polymerase extension reaction mixture to a hybridization treatment, wherein the first and third primer portions of the first and second oligonucleotide primers, respectively, hybridize to their respective complementary portions of the target nucleotide sequence or complement thereof, and an extension treatment, wherein the hybridized oligonucleotide primers extend to form primary primer extension products;
denaturing the primary primer extension products from the target nucleotide sequences and complements thereof;
providing a second polymerase;
blending the polymerase extension reaction mixture after said subjecting it to the hybridization treatment and the extension treatment and the second polymerase to form a polymerase amplification reaction mixture;
subjecting the polymerase amplification reaction mixture to one or more polymerase amplification reaction cycles comprising a denaturation treatment, wherein hybridized nucleic acid sequences are separated, a hybridization treatment, wherein the first and third primer portions of the first and second oligonucleotide primers, respectively, hybridize to their respective complementary portions of the primary primer extension products and an extension treatment, wherein hybridized oligonucleotide primers extend to form first oligonucleotide primer extension products and second oligonucleotide primer extension products; and
subjecting the first and/or second oligonucleotide primer extension products to a sequencing reaction to identify the presence of one or more target nucleotide sequences in the sample.

2. The method of claim 1, wherein said providing a sample comprises:
appending one or more first, second, and/or third target portions, or complements thereof, to remaining parts of the one or more target nucleotide sequences, or complements thereof.

3. The method of claim 2, wherein the first, second, and third target portions, or complements thereof, are appended to the remaining parts of the one or more target nucleotide sequences, or complements thereof, using an enzyme selected from the group consisting of ligases, polymerases, recombinases, terminal transferases, endonucleases, DNA repair enzymes, and reverse transcriptases.

4. The method of claim 1, wherein one or both of the first and second oligonucleotide primers in each primer set is attached to a solid support.

5. The method of claim 4 further comprising:
repeating one or more times said providing a second polymerase, said blending to form a polymerase amplification reaction mixture, and said subjecting the polymerase amplification reaction mixture to one or more polymerase amplification reaction cycles, to amplify the first and second oligonucleotide primer extension products prior to said subjecting the first and/or second oligonucleotide primer extension products to the sequencing reaction to identify the presence of one or more target nucleotide sequences in the sample.

6. The method of claim 4, wherein the solid support comprises a plurality of pillars.

7. The method of claim 6, wherein one or both of the oligonucleotide primers in an oligonucleotide primer set are attached to the pillar surfaces, but not to surfaces of the solid support between the pillars.

8. The method of claim 1 further comprising:
denaturing the target nucleotide sequences from their complements in the sample prior to said subjecting the polymerase extension reaction mixture to the hybridization and the extension treatment.

9. The method of claim 5, wherein the second polymerase exhibits strand displacement activity.

10. The method of claim 5, wherein the first oligonucleotide primer extension products comprise the first primer portion, the second primer portion, a third portion that is complementary to the third primer portion, and a fourth portion that is complementary to the second primer portion.

11. The method of claim 5, wherein the second oligonucleotide primer extension products comprise a first portion that is complementary to the first primer portion, a second portion that is complementary to the second primer portion, the third primer portion, and a fourth portion that is the same as the second primer portion, wherein the fourth portion is 5' to the second portion.

12. The method of claim 11, wherein the second oligonucleotide primer extension products hairpin by hybridization between the second and fourth portions, said hairpin extending from its 3' end to form full-length hair-pinned second oligonucleotide primer extension products.

13. The method of claim 12, wherein the first primer portion of the first oligonucleotide primers hybridize to their complementary sequence on the full-length hair-pinned second oligonucleotide primer extension products and extend to make first oligonucleotide primer extension products while displacing part of the full-length hair-pinned second oligonucleotide primer extension products having the same sequence.

14. The method of claim 13 further comprising:
cleaving second oligonucleotide primer extension products from the solid support.

15. The method of claim 14 further comprising:
providing third oligonucleotide primers, each third oligonucleotide primer comprising a fifth primer portion complementary to a fifth portion of the first oligonucleotide primer extension products, wherein said third oligonucleotide primer is attached to the solid support;
providing fourth oligonucleotide primers, each fourth oligonucleotide primer comprising a sequence complementary to a region of the first oligonucleotide primer extension product;
providing a polymerase and a ligase;
blending the first oligonucleotide primer extension products, the third oligonucleotide primers, the fourth oligonucleotide primers, the polymerase, and the ligase to form an extension-ligation mixture;
subjecting the extension-ligation mixture to a hybridization treatment, wherein the third and fourth oligonucleotide primers hybridize to their complementary regions on the first oligonucleotide primer extension products, and an extension-ligation treatment, wherein the hybridized fourth oligonucleotide primers extend to form complements of a portion of the first oligonucleotide primer extension product and ligate to the fifth primer portion of hybridized third oligonucleotide primers to form ligation extension products; and
cleaving the first oligonucleotide primer extension products from the solid support, wherein said ligation extension products are subjected to said sequencing reaction to identify the presence of one or more target nucleotide sequences in the sample.

16. The method of claim 14, wherein said cleaving occurs at a uracil that is 3' to the third primer portion of the second oligonucleotide primer extension products, leaving the third primer portion of the second oligonucleotide primer extension products attached to the solid support with a phosphate on the 3' ends.

17. The method of claim 16 further comprising:
providing a kinase that selectively hydrolyzes 3' phosphate groups;
providing a third polymerase that contains 5' to 3' exonuclease activity and lacks strand-displacing activity;
blending the solid support containing the first oligonucleotide primer extension products, the third primer portions of the cleaved second oligonucleotide primer extension products having a phosphate on their 3' ends, the kinase, and the third polymerase to form a kinase-polymerase mixture;
subjecting the kinase-polymerase mixture to a hybridization treatment, wherein the third primer portion of the cleaved second oligonucleotide primer extension products hybridize to the first oligonucleotide primer extension products, and a kinase-polymerase treatment, wherein the phosphate on the 3' end of each hybridized third primer portion of the cleaved second oligonucleotide primer extension products is excised and extended to form kinase-polymerase extension products, said kinase-polymerase extension products each comprising a first portion that is complementary to the first primer portion, a second primer portion and a third oligonucleotide primer portion; and
cleaving the first oligonucleotide primer extension products from the solid support, wherein the kinase-polymerase extension products are subjected to said sequencing reaction to identify the presence of one or more target nucleotide sequences in the sample.

18. The method of claim 17, wherein said cleaving comprises endonuclease digestion of the second primer portion of the first oligonucleotide primer extension product.

19. The method of claim 13 further comprising:
removing the first oligonucleotide primer extension products from the solid support and
digesting a portion of the hairpinned second oligonucleotide primer extension products to form single stranded second oligonucleotide primer extension products, wherein said single stranded second oligonucleotide primer extension products are subjected to said sequencing reaction to identify the presence of one or more target nucleotide sequences in the sample.

20. The method of claim 19, wherein said digesting comprises:
providing nucleotide analogue primers, said primers comprising a sequence that is complementary to the first portion of the second oligonucleotide primer extension products;
hybridizing the nucleotide analogue primers to the first portion of the second oligonucleotide primer extension products;
providing an exonuclease enzyme having 3' to 5' activity on double stranded DNA; and
digesting the second oligonucleotide primer extension products 3' to the first portion of said extension products.

21. A method for identifying one or more of a plurality of target nucleotide sequences, said method comprising:
providing a sample potentially containing one or more target nucleotide sequences, and/or complements thereof, each target nucleotide sequence comprising a first, second, and third target portion, wherein the second target portion is between the first and third target portions;
providing one or more oligonucleotide primer sets, each set characterized by (a) a first oligonucleotide primer comprising a first primer portion that is the same as the first target portion and a second primer portion that is complementary to the second target portion, wherein the second primer portion is 5' to the first primer portion, and (b) a second oligonucleotide primer comprising a third primer portion that complementary to the third target portion and a fourth primer-specific portion, wherein the fourth primer-specific portion is 5' to the third primer portion;
providing a first polymerase;
blending the sample, the oligonucleotide primer sets, and the first polymerase to form a polymerase extension reaction mixture;
subjecting the polymerase extension reaction mixture to a hybridization treatment, wherein the first and third primer portions of the first and second oligonucleotide primers, respectively, hybridize to their respective complementary portions of the target nucleotide sequence, or complement thereof, and an extension treatment, wherein the hybridized oligonucleotide primers extend to form primary primer extension products;

denaturing the primary primer extension products from the target nucleotide sequences and/or complements thereof;

providing a second polymerase;

blending the polymerase extension reaction mixture after said subjecting it to the hybridization treatment and the extension treatment and the second polymerase to form a polymerase amplification reaction mixture;

subjecting the polymerase amplification reaction mixture to one or more polymerase amplification reaction cycles comprising a denaturation treatment, wherein hybridized nucleic acid sequences are separated, a hybridization treatment, wherein the first and third primer portions of the first and second oligonucleotide primers, respectively, hybridize to their respective complementary portions of the primary primer extension products and an extension treatment, wherein the hybridized oligonucleotide primers extend to form first oligonucleotide primer extension products and second oligonucleotide primer extension products; and subjecting the first and/or second oligonucleotide primer extension products to a sequencing reaction to identify the presence of one or more target nucleotide sequences in the sample.

22. The method of claim 1, wherein said sequencing reaction is a solid-phase sequencing reaction.

23. The method of claim 1, wherein said sequencing reaction is selected from the group consisting of a fluorescent primer hybridization reaction, a molecular beacon hybridization reaction, a primer extension reaction, a 5'-3' exonuclease reaction, a ligase detection reaction, a ligase chain reaction, a pyrosequencing reaction, a fluorescence-based sequencing-by-synthesis reaction, a fluorescence-based sequencing-by-ligation reaction, an ion-based sequencing-by-synthesis reaction, and an ion-based sequencing-by-ligation reaction.

24. The method of claim 21, wherein said sequencing reaction is a solid-phase sequencing reaction.

* * * * *

UNITED STATES PATENT AND TRADEMARK OFFICE
CERTIFICATE OF CORRECTION

| | | |
|---|---|---|
| PATENT NO. | : 9,670,540 B2 | Page 1 of 1 |
| APPLICATION NO. | : 14/234011 | |
| DATED | : June 6, 2017 | |
| INVENTOR(S) | : Barany et al. | |

It is certified that error appears in the above-identified patent and that said Letters Patent is hereby corrected as shown below:

In the Specification

Column 1 at Lines 11-14, delete "This invention was made with government support under grant number 1U01AI075470 awarded by the National Institutes of Allergy and Infectious Diseases. The government has certain rights in this invention." and insert -- This invention was made with government support under Grant Number AI075470 awarded by the National Institutes of Health. The Government has certain rights in the invention. --

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*